United States Patent
Ma et al.

(10) Patent No.: US 11,723,271 B2
(45) Date of Patent: Aug. 8, 2023

(54) ORGANIC COMPOUND, AND ELECTRONIC COMPONENT AND ELECTRONIC DEVICE THEREFOR

(71) Applicant: Shaanxi Lighte Optoelectronics Material Co., Ltd., Xi'an (CN)

(72) Inventors: Tiantian Ma, Xi'an (CN); Lei Yang, Xi'an (CN); Linlin Hu, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 18/011,941

(22) PCT Filed: Dec. 16, 2021

(86) PCT No.: PCT/CN2021/138848
§ 371 (c)(1),
(2) Date: Dec. 21, 2022

(87) PCT Pub. No.: WO2022/156445
PCT Pub. Date: Jul. 28, 2022

(65) Prior Publication Data
US 2023/0200234 A1    Jun. 22, 2023

(30) Foreign Application Priority Data

Jan. 22, 2021 (CN) .......................... 202110090733.9
Feb. 9, 2021 (CN) .......................... 202110181958.5

(51) Int. Cl.
*H10K 85/60* (2023.01)
*C07D 487/04* (2006.01)
(Continued)

(52) U.S. Cl.
CPC ....... *H10K 85/6572* (2023.02); *C07D 487/04* (2013.01); *C07D 519/00* (2013.01);
(Continued)

(58) Field of Classification Search
CPC . H10K 85/6572; C07D 487/04; C07D 519/00
See application file for complete search history.

(56) References Cited

U.S. PATENT DOCUMENTS

| 11,611,045 | B2 * | 3/2023 | Yang | H10K 85/6574 |
| 2009/0105488 | A1 * | 4/2009 | Cheng | C09K 11/06 |
| | | | | 548/440 |

(Continued)

FOREIGN PATENT DOCUMENTS

| CN | 102596950 A | 7/2012 |
| CN | 107623073 A | 1/2018 |

(Continued)

OTHER PUBLICATIONS

International Search Report from corresponding International Application No. PCT/CN2021/138848, dated Mar. 17, 2021, 5 pages with translation.

(Continued)

*Primary Examiner* — Caleb E Henry
(74) *Attorney, Agent, or Firm* — Tucker Ellis LLP

(57) ABSTRACT

An organic compound, and an electronic component and an electronic device using same, and the organic compound has a structure as shown in a formula A, a formula B, a formula D or a formula F. Ar is selected from substituted or unsubstituted aryl with 6 to 30 carbon atoms and substituted or unsubstituted heteroaryl with 3 to 30 carbon atoms, and Het is selected from substituted or unsubstituted nitrogen-containing heteroaryl with 2 to 20 carbon atoms, and the nitrogen-containing heteroaryl at least contains two N atoms. The organic compound of the present disclosure can significantly reduce a driving voltage of a device and increase a service life of the device; and in addition, the organic compound of the present disclosure can further improve an efficiency of the device.

(Continued)

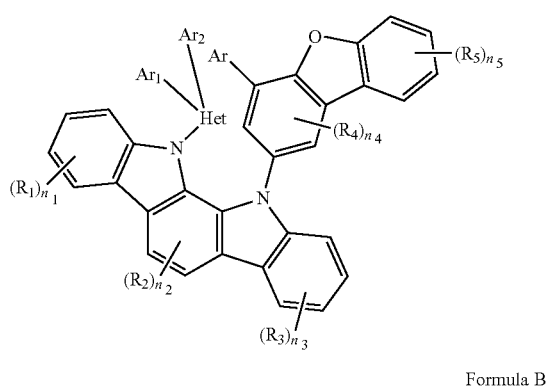

Formula A

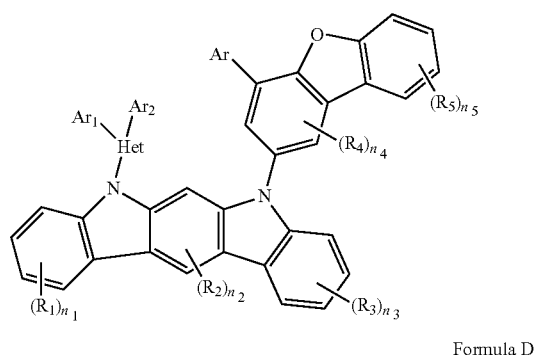

Formula B

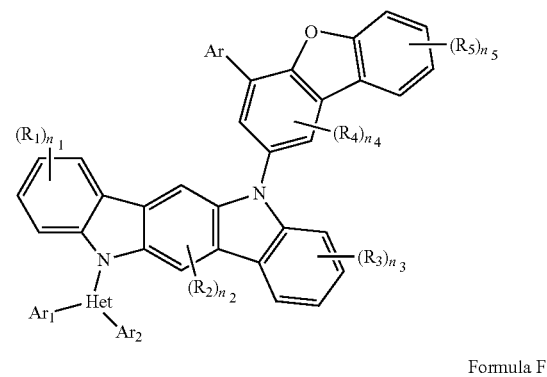

Formula D

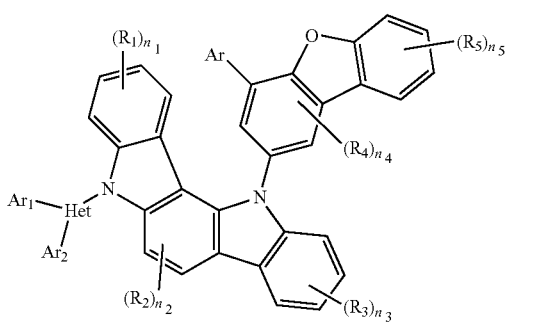

Formula F

(51) Int. Cl.
 *C07D 519/00* (2006.01)
 *C09K 11/06* (2006.01)
 *H10K 50/11* (2023.01)

(52) U.S. Cl.
 CPC ............ *C09K 11/06* (2013.01); *H10K 85/654* (2023.02); *H10K 85/6574* (2023.02); *C09K 2211/1018* (2013.01); *H10K 50/11* (2023.02)

(56) References Cited

U.S. PATENT DOCUMENTS

| | | | |
|---|---|---|---|
| 2015/0236267 A1* | 8/2015 | Hiroaki | H10K 50/156 257/40 |
| 2016/0181542 A1* | 6/2016 | Kawamura | C09K 11/025 585/27 |
| 2018/0248127 A1 | 8/2018 | Lee | |
| 2018/0309057 A1* | 10/2018 | Ikeda | H10K 50/171 |
| 2018/0309081 A1* | 10/2018 | Ikeda | H10K 50/81 |
| 2018/0331304 A1 | 11/2018 | Ma | |
| 2019/0010256 A1* | 1/2019 | Lee | C08F 10/02 |
| 2019/0393430 A1 | 12/2019 | Park | |
| 2020/0203621 A1* | 6/2020 | Kim | C07D 403/10 |
| 2022/0089610 A1 | 3/2022 | Mo | |

FOREIGN PATENT DOCUMENTS

| | | |
|---|---|---|
| CN | 108084081 A | 5/2018 |
| CN | 108794482 A | 11/2018 |
| CN | 109422768 A | 3/2019 |
| CN | 109791997 A | 5/2019 |
| CN | 110294703 A | 10/2019 |
| CN | 110785863 A | 2/2020 |
| CN | 110903290 A | 3/2020 |
| CN | 111149229 A | 5/2020 |
| CN | 111269219 A | 6/2020 |
| CN | 111377937 A | 7/2020 |
| CN | 111463352 A | 7/2020 |
| CN | 111943941 A | 11/2020 |
| CN | 112939985 A | 6/2021 |
| CN | 113061136 A | 7/2021 |
| KR | 20180010166 A | 1/2018 |
| KR | 20190069083 A | 6/2019 |
| KR | 20200001439 A | 1/2020 |
| TW | 202031646 A | 9/2020 |
| WO | 2017078403 A1 | 5/2017 |

OTHER PUBLICATIONS

Duan, Lu-meng, "Synthesis and Characterization of a Novel Indolocarbazole Compound", dated Sep. 2020, 5 pages with translation.

* cited by examiner

ORGANIC COMPOUND, AND ELECTRONIC COMPONENT AND ELECTRONIC DEVICE THEREFOR

CROSS REFERENCE TO RELATED APPLICATIONS

The present disclosure claims the priority of the Chinese patent application No. CN202110090733.9 filed on Jan. 22, 2021 and the Chinese patent application No. CN202110181958.5 filed on Feb. 9, 2021, and the contents of the Chinese patent applications are hereby incorporated by reference in their entirety as a part of the present disclosure.

TECHNICAL FIELD

The present disclosure relates to the technical field of organic materials, in particular to an organic compound, and an electronic component and an electronic device therefor.

BACKGROUND

With the development of an electronic technology and the progress of material science, an application range of electronic components for realizing electroluminescence or photoelectric conversion is wider and wider. Such electronic component generally includes a cathode and an anode which are arranged oppositely, and a functional layer arranged between the cathode and the anode. The functional layer is composed of a multiple of organic or inorganic film layers, and generally includes an energy conversion layer, a hole transport layer disposed between the energy conversion layer and the anode, and an electron transport layer disposed between the energy conversion layer and the cathode.

Taking an organic electroluminescent device as an example, it generally includes an anode, a hole transport layer, an electroluminescent layer serving as an energy conversion layer, an electron transport layer and a cathode which are sequentially stacked. When a voltage is applied to the cathode and the anode, an electric field is generated between the two electrodes, under the action of the electric field, the electrons on the cathode side move to the electroluminescent layer, while the holes on the anode side move to the electroluminescent layer, so the electrons and the holes are combined in the electroluminescent layer to form excitons, and the excitons are in an excited state and release energy outwards, which in turn makes the electroluminescent layer emit light outward.

At present, during the use of the organic electroluminescent device, problems of luminous efficiency reduction, service life shortening and the like occur, which will lead to the decline of the performance of the organic electroluminescent device.

SUMMARY

Aiming at the above problems in the prior art, the present disclosure aims to provide an organic compound, and an electronic component and an electronic device using the same. The organic compound can be used in an organic electroluminescent device, and can improve performance of the device.

In order to realize the above purpose, in a first aspect, the present disclosure provides an organic compound, having a structure as shown in a formula A, a formula B, a formula D or a formula F:

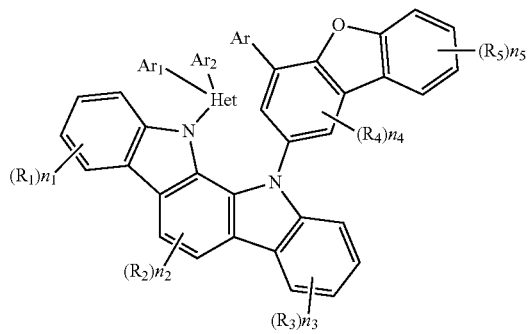

Formula A

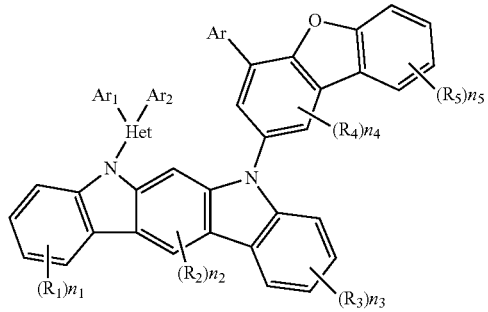

Formula B

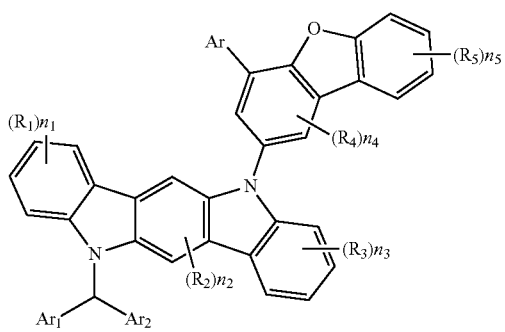

Formula D

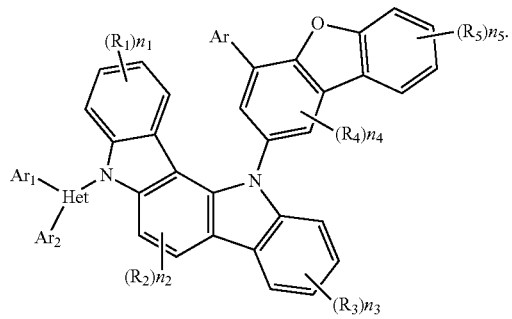

Formula F

Ar is selected from substituted or unsubstituted aryl with 6 to 30 carbon atoms and substituted or unsubstituted heteroaryl with 3 to 30 carbon atoms.

Het is selected from substituted or unsubstituted nitrogen-containing heteroaryl with 2 to 20 carbon atoms, and the nitrogen-containing heteroaryl at least contains two N atoms.

$Ar_1$ and $Ar_2$ are each independently selected from hydrogen, substituted or unsubstituted aryl with 6 to 30 carbon atoms, and substituted or unsubstituted heteroaryl with 3 to 20 carbon atoms.

$R_1$, $R_2$, $R_3$, $R_4$ and $R_5$ are the same or different, and are each independently selected from deuterium, fluorine, cyano, alkyl with 1 to 10 carbon atoms, aryl with 6 to 20 carbon atoms, and heteroaryl with 3 to 30 carbon atoms; $n_1$ represents the number of $R_1$ and is selected from 0, 1, 2, 3 or 4, when $n_1$ is greater than 1, any two $R_1$ are the same or different, and alternatively, two adjacent $R_1$ form a ring; $n_2$ represents the number of $R_2$ and is selected from 0, 1 or 2, when $n_2$ is greater than 1, any two $R_2$ are the same or different, and alternatively, two adjacent $R_2$ form a ring; $n_3$ represents the number of $R_3$ and is selected from 0, 1, 2, 3 or 4, when $n_3$ is greater than 1, any two $R_3$ are the same or different, and alternatively, two adjacent $R_3$ form a ring; $n_4$ represents the number of $R_4$ and is selected from 0, 1 or 2, when $n_4$ is greater than 1, any two $R_4$ are the same or different, and alternatively, two adjacent $R_4$ form a ring; and $n_5$ represents the number of $R_5$ and is selected from 0, 1, 2, 3 or 4, when $n_5$ is greater than 1, any two $R_5$ are the same or different, and alternatively, two adjacent $R_5$ form a ring.

Substituents in the Het, the Ar, the $Ar_1$ and the $Ar_2$ are each independently selected from deuterium, a halogen group, cyano, heteroaryl with 3 to 15 carbon atoms, aryl with 6 to 15 carbon atoms, trialkylsilyl with 3 to 12 carbon atoms, triarylsilyl with 18 to 20 carbon atoms, alkyl with 1 to 10 carbon atoms, deuterated alkyl with 1 to 10 carbon atoms, haloalkyl with 1 to 10 carbon atoms, cycloalkyl with 3 to 10 carbon atoms, heterocycloalkyl with 2 to 10 carbon atoms, alkoxy with 1 to 10 carbon atoms, alkylthio with 1 to 10 carbon atoms, aryloxy with 6 to 15 carbon atoms, arylthio with 6 to 15 carbon atoms, and phosphinyloxy with 6 to 15 carbon atoms.

In a second aspect, the present disclosure provides an electronic component, including an anode and a cathode which are oppositely arranged, and a functional layer arranged between the anode and the cathode. The functional layer contains the organic compound described in the first aspect of the present disclosure.

In a third aspect, the present disclosure provides an electronic device, including the electronic component described in the second aspect of the present disclosure.

The compound of the present disclosure has a structure formed by the combination of an electron-deficient aza-aryl group, an electron-rich indolocarbazole group and dibenzofuran. The electron-deficient aza-aryl group and the electron-rich indolocarbazole group respectively have high electron and hole injection and transport properties, such that a material molecular structure is bipolar and suitable for a luminescent layer in an organic electroluminescent device. At the same time, the 2-position of the dibenzofuranyl is directly connected to a nitrogen atom of the indolocarbazole group, which improves the energy transfer efficiency to the guest molecule while effectively maintaining the high first triplet state energy level of the compound, and can effectively enhance the luminescence efficiency of the device. The substitution of aryl or heteroaryl at the 4-position of dibenzofuranyl can not only improve the material carrier mobility and the energy transfer efficiency, but also effectively improve the stability of the molecular structure, thus effectively reducing the driving voltage of the device and increasing the device lifetime.

Other features and advantages of the present disclosure will be described in detail in the subsequent specific implementation part.

BRIEF DESCRIPTION OF THE DRAWINGS

The drawings are used to provide a further understanding of the present disclosure and constitute a part of the specification, and are used to explain the present disclosure together with the following specific implementations, but do not constitute limitations on the present disclosure. In the drawings.

Figure 1:
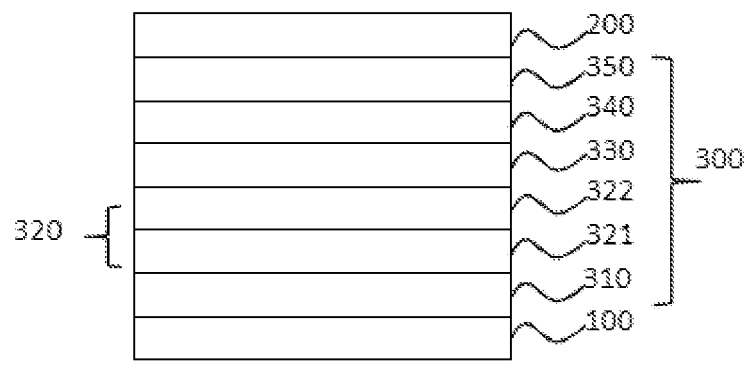
FIG. 1 is a schematic structural diagram of an organic electroluminescent device according to one implementation of the present disclosure.

DESCRIPTION OF REFERENCE NUMERALS 100, anode; 200, cathode; 300, functional layer; 310, hole injection layer; 320, hole transport layer; 321, first hole transport layer; 322, second hole transport layer; 330, organic luminescent layer; 340, electron transport layer; and 350, electron injection layer.

DETAILED DESCRIPTION

The specific implementations of the present disclosure are described in detail below in combination with the drawings. It should be understood that the specific implementations described herein are merely used to illustrate and interpret the present disclosure, but not to limit the present disclosure.

In a first aspect, the present disclosure provides an organic compound, having a structure as shown in a formula A, a formula B, a formula D or a formula F:

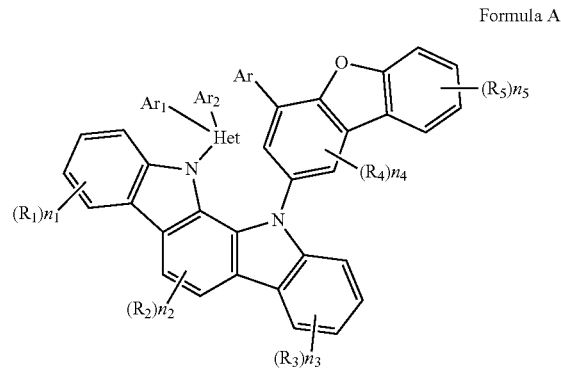

Formula A

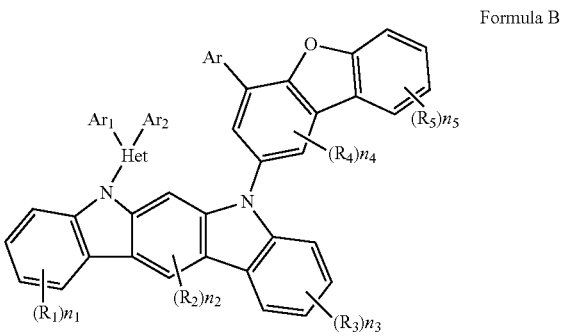

Formula B

-continued

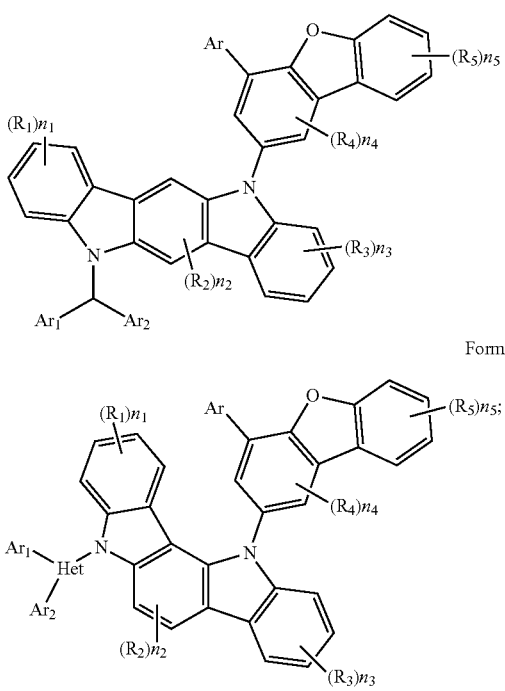

Formula D

Formula F wherein, Ar is selected from substituted or unsubstituted aryl with 6 to 30 carbon atoms and substituted or unsubstituted heteroaryl with 3 to 30 carbon atoms;

Het is selected from substituted or unsubstituted nitrogen-containing heteroaryl with 2 to 20 carbon atoms, and the nitrogen-containing heteroaryl at least contains two N atoms;

$Ar_1$ and $Ar_2$ are each independently selected from hydrogen, substituted or unsubstituted aryl with 6 to 30 carbon atoms, and substituted or unsubstituted heteroaryl with 3 to 20 carbon atoms;

$R_1$, $R_2$, $R_3$, $R_4$ and $R_5$ are the same or different, and are each independently selected from deuterium, fluorine, cyano, substituted or unsubstituted alkyl with 1 to 10 carbon atoms, substituted or unsubstituted aryl with 6 to 20 carbon atoms, and substituted or unsubstituted heteroaryl with 3 to 30 carbon atoms;

$n_1$ represents the number of $R_1$ and is selected from 0, 1, 2, 3 or 4, when $n_1$ is greater than 1, any two $R_1$ are the same or different, and alternatively, two adjacent $R_1$ form a ring.

In the present disclosure, when two adjacent $R_1$ form the ring, the ring is a saturated or unsaturated 6- to 14-membered ring.

$n_2$ represents the number of $R_2$ and is selected from 0, 1 or 2, when $n_2$ is greater than 1, any two $R_2$ are the same or different, and alternatively, two adjacent $R_2$ form a ring.

In the present disclosure, when two adjacent $R_2$ form the ring, the ring is a saturated or unsaturated 6- to 14-membered ring.

$n_3$ represents the number of $R_3$ and is selected from 0, 1, 2, 3 or 4, when $n_3$ is greater than 1, any two $R_3$ are the same or different, and alternatively, two adjacent $R_3$ form a ring.

In the present disclosure, when two adjacent $R_3$ form the ring, the ring is a saturated or unsaturated 6- to 14-membered ring.

$n_4$ represents the number of $R_4$ and is selected from 0, 1 or 2, when $n_4$ is greater than 1, any two $R_4$ are the same or different, and alternatively, two adjacent $R_4$ form a ring.

$n_5$ represents the number of $R_5$ and is selected from 0, 1, 2, 3 or 4, when $n_5$ is greater than 1, any two $R_5$ are the same or different, and alternatively, two adjacent $R_5$ form a ring.

Preferably, $n_4$ and $n_5$ are each independently selected from 0.

Substituents in the Het, the Ar, the $Ar_1$ and the $Ar_2$ are each independently selected from deuterium, a halogen group, cyano, heteroaryl with 3 to 15 carbon atoms, aryl with 6 to 15 carbon atoms, trialkylsilyl with 3 to 12 carbon atoms, triarylsilyl with 18 to 20 carbon atoms, alkyl with 1 to 10 carbon atoms, deuterated alkyl with 1 to 10 carbon atoms, haloalkyl with 1 to 10 carbon atoms, cycloalkyl with 3 to 10 carbon atoms, heterocycloalkyl with 2 to 10 carbon atoms, alkoxy with 1 to 10 carbon atoms, alkylthio with 1 to 10 carbon atoms, aryloxy with 6 to 15 carbon atoms, arylthio with 6 to 15 carbon atoms, and phosphinyloxy with 6 to 15 carbon atoms.

In the present disclosure, connection sites of dibenzofuran are shown in a formula

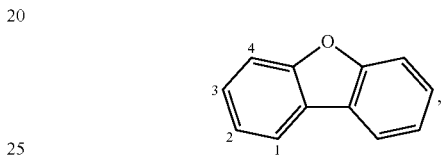

and 1, 2, 3 and 4 represent possible connection sites.

In the present disclosure, the term "alternative" and "alternatively" means that the subsequently described event or environment may, but does not to occur, and the description includes an occasion where the event or environment occurs or does not occur. For example, "alternatively, two adjacent substituents form a ring" means that the two substituents may form a ring but do not have to form a ring, including: a situation that the two adjacent substituents form the ring and a situation that the two adjacent substituents do not form the ring.

In the present disclosure, "alternatively, two adjacent $R_i$ form a ring" means that any two adjacent $R_i$ may form a ring and may not form a ring. For example, when two adjacent $R_i$ form a ring, the ring may be a saturated or unsaturated 6- to 14-membered ring, such as a benzene ring, a naphthalene ring, a phenanthrene ring, etc., but not limited to this.

Preferably, the organic compound is selected from a compound shown in a formula A.

In one embodiment of the present disclosure, two adjacent $R_1$ form a benzene ring.

In one embodiment of the present disclosure, two adjacent $R_2$ form a benzene ring.

In one embodiment of the present disclosure, two adjacent $R_3$ form a benzene ring.

In the present disclosure, the description of "each . . . is independently", " . . . is respectively and independently" and " . . . is independently selected from" can be exchanged, and should be understood in a broad sense, which means that in different groups, the specific options expressed between the same signs do not influence each other, or in a same group, the specific options expressed between the same signs do not influence each other. For example, the meaning of

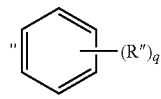

Q-1

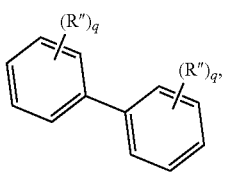

Q-2 where each q is independently 0, 1, 2 or 3, and each R" is independently selected from hydrogen, deuterium, fluorine and chlorine" their meanings are: a formula Q-1 indicates that a benzene ring has q substituents R", each R" can be the same or different, and the options of each R" do not influence each other; and a formula Q-2 indicates that every benzene ring of biphenyl has q substituents R", the number q of the substituents R" on the two benzene rings can be the same or different, each R" can be the same or different, and the options of each R" do not influence each other.

In the present disclosure, the term such as "substituted or unsubstituted" means that a functional group defined by the term may have or do not have a substituent (hereinafter, the substituent is collectively referred to as $R_x$ in order to facilitate description). For example, the "substituted or unsubstituted aryl" refers to aryl having the substituent $R_x$ or unsubstituted aryl. The above substituent, namely $R_x$ may be deuterium, a halogen group, cyano, heteroaryl with 3 to 15 carbon atoms, aryl with 6 to 15 carbon atoms, trialkylsilyl with 3 to 12 carbon atoms, triarylsilyl with 18 to 20 carbon atoms, alkyl with 1 to 10 carbon atoms, deuterated alkyl with 1 to 10 carbon atoms, haloalkyl with 1 to 10 carbon atoms, cycloalkyl with 3 to 10 carbon atoms, heterocycloalkyl with 2 to 10 carbon atoms, alkoxy with 1 to 10 carbon atoms, alkylthio with 1 to 10 carbon atoms, aryloxy with 6 to 15 carbon atoms, arylthio with 6 to 15 carbon atoms, and phosphinyloxy with 6 to 15 carbon atoms. When two substituents $R_x$ are connected to a same atom, the two substituents $R_x$ may independently exist or may be connected with each other to form a ring with the atom; and when two adjacent substituents $R_x$ exist on the functional group, the two adjacent substituents $R_x$ may independently exist or may be fused with the functional group connected with two adjacent substituents $R_x$ to form a ring.

In the present disclosure, the number of carbon atoms in the substituted or unsubstituted functional group refers to the number of all carbon atoms. For example, if $R_x$ is selected from substituted aryl with 12 carbon atoms, the number of all carbon atoms of the aryl and substituents on the aryl is 12.

In the present disclosure, aryl refers to an optional functional group or substituent derived from an aromatic carbon ring. The aryl may be monocyclic aryl (e.g., phenyl) or polycyclic aryl, in other words, the aryl may be monocyclic aryl, fused aryl, two or more monocyclic aryl conjugatedly connected by carbon-carbon bond, monocyclic aryl and fused aryl which are conjugatedly connected by carbon-carbon bond, and two or more fused aryl conjugatedly connected by carbon-carbon bond. That is, unless otherwise noted, two or more aromatic groups conjugatedly connected by carbon-carbon bond may also be regarded as the aryl of the present disclosure. The aryl does not contain heteroatoms such as B, N, O, S, P, Se and Si. It needs to be noted that biphenyl, terphenyl and fluorenyl are all regarded as aryl in the present disclosure. Specific examples of the aryl include, but are not limited to, phenyl, naphthyl, fluorenyl, anthryl, phenanthryl, biphenyl, terphenyl, benzo[9,10]phenanthryl, pyrenyl, benzofluoranthenyl, chrysenyl and the like. The "substituted or unsubstituted aryl" of the present disclosure may contain 6 to 30 carbon atoms, in some embodiments, the number of carbon atoms in the substituted or unsubstituted aryl may be 6 to 25, in other embodiments, the number of carbon atoms in the substituted or unsubstituted aryl may be 6 to 20. For example, in the present disclosure, the number of carbon atoms of the substituted or unsubstituted aryl may be 6, 12, 13, 14, 15, 18, 20, 24, 25 or 30, and certainly, the number of carbon atoms may also be other numbers, which will not be listed one by one here. In the present disclosure, biphenyl may be understood as aryl substituted with phenyl, and may also be understood as unsubstituted aryl.

In the present disclosure, the substituted aryl may be that one or two or more hydrogen atoms in the aryl are substituted with a group such as a deuterium atom, a halogen group, cyano, aryl, heteroaryl, trialkylsilyl, alkyl, cycloalkyl, alkoxy, and alkylthio. It should be understood that the number of carbon atoms in the substituted aryl refers to the total number of carbon atoms of the aryl and substituents on the aryl, for example, the substituted aryl with 18 carbon atoms means that the total number of carbon atoms of the aryl and substituents is 18.

In the present disclosure, specific examples of aryl as a substituent include, but are not limited to, phenyl, biphenyl, naphthyl, phenanthryl, anthryl, fluorenyl and terphenyl.

In the present disclosure, the heteroaryl refers to a monovalent aromatic ring containing at least one heteroatom in a ring or its derivative, and the heteroatom may be at least one of B, O, N, P, Si, Se and S. The heteroaryl may be monocyclic heteroaryl or polycyclic heteroaryl, in other words, the heteroaryl may be a single aromatic ring system or a multiple of aromatic ring systems conjugatedly connected by carbon-carbon bond, where any one aromatic ring system is one aromatic monocyclic ring or one aromatic fused ring. Illustratively, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridinopyrimidyl, pyridinopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuryl, phenanthrolinyl, isoxazolyl, thiadiazolyl, benzothiazolyl, phenothiazinyl, silafluorenyl, dibenzofuryl and N-arylcarbazolyl (e.g., N-phenylcarbazolyl, N-(1-naphthyl) carbazolyl, N-(2-naphthyl)carbazolyl, N-heteroarylcarbazolyl (e.g., N-pyridylcarbazolyl), N-alkylcarbazolyl (e.g., N-methylcarbazolyl), and the like, but is not limited to thereto. Wherein, thienyl, furyl, phenanthrolinyl, etc. are heteroaryl of the single aromatic ring system, and the N-arylcarbazolyl and N-heteroarylcarbazolyl are heteroaryl of the polycyclic systems conjugatedly connected by carbon-carbon bond. The "substituted or unsubstituted heteroaryl" of the present disclosure may contain 3 to 30 carbon atoms, in some embodiments, the number of carbon atoms in the substituted or unsubstituted heteroaryl may be 3 to 25, in some other embodiments, the number of carbon atoms in the substituted or unsubstituted heteroaryl may be 3 to 20, and in some other embodiments, the number of carbon atoms in the substituted or unsubstituted heteroaryl may be 5 to 20. For example, the number of carbon atoms in the substituted or unsubstituted heteroaryl may further be 3, 4, 5, 7, 12, 13, 18, 20, 24, 25 or 30, and certainly, the number of carbon atoms may also be other numbers, which will not be listed one by one here.

In the present disclosure, the substituted heteroaryl may be that one or two or more hydrogen atoms in the heteroaryl are substituted with a group such as a deuterium atom, a halogen group, cyano, aryl, heteroaryl, trialkylsilyl, alkyl, cycloalkyl, alkoxy, alkylthio and the like. It should be understood that the number of carbon atoms of the substituted heteroaryl refers to the total number of carbon atoms of heteroaryl and substituents on the heteroaryl.

In the present disclosure, specific examples of heteroaryl as a substituent include, but are not limited to, dibenzothienyl, dibenzofuranyl, carbazolyl, indolocarbazolyl, benzimidazolyl, benzoxazolyl and phenanthrolinyl.

In the present disclosure, an unpositioned connecting bond

refers to a single bond extending from a ring system, which means that one end of the connecting bond may be connected with any position in the ring system through which the bond penetrates, and the other end of the connecting bond is connected with the remaining part of a compound molecule.

For example, as shown in the following formula (f), naphthyl represented by the formula (f) is connected with other positions of a molecule through two unpositioned connecting bonds penetrating through a dicyclic ring, and its represented meaning includes any one possible connecting mode as shown in formulae (f-1)-(f-10).

(f)

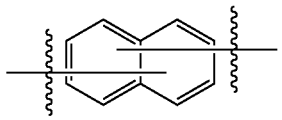

(f-1)

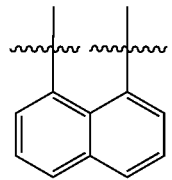

(f-2)

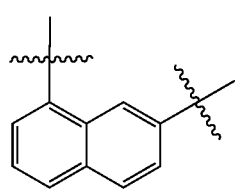

(f-3)

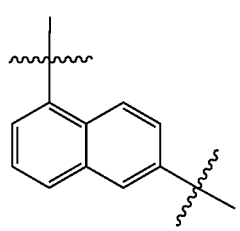

(f-4)

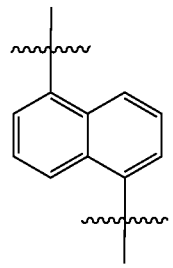

(f-5)

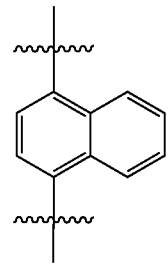

(f-6)

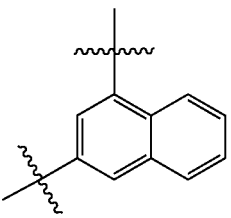

(f-7)

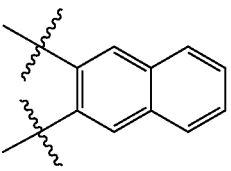

(f-8)

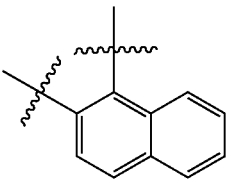

(f-9)

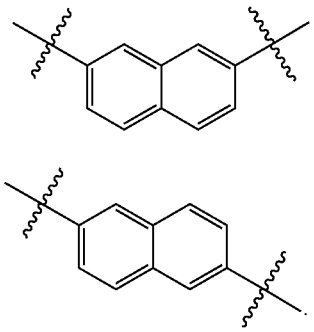

(f-10)

For another example, as shown in the following formula (X'), phenanthryl represented by the formula (X') is connected with other positions of a molecule through one unpositioned connecting bond extending from the middle of a benzene ring on one side, and its represented meaning includes any possible connecting mode as shown in formulae (X'-1)-(X'-4).

connecting bond, and its represented meaning includes any one possible connecting mode as shown in formulae (Y-1)-(Y-7).

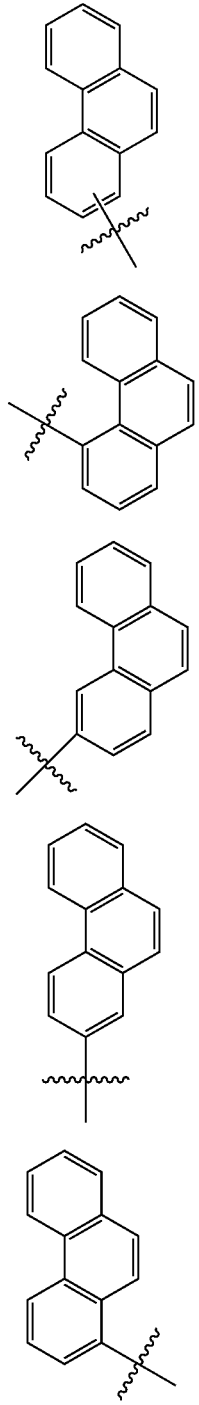

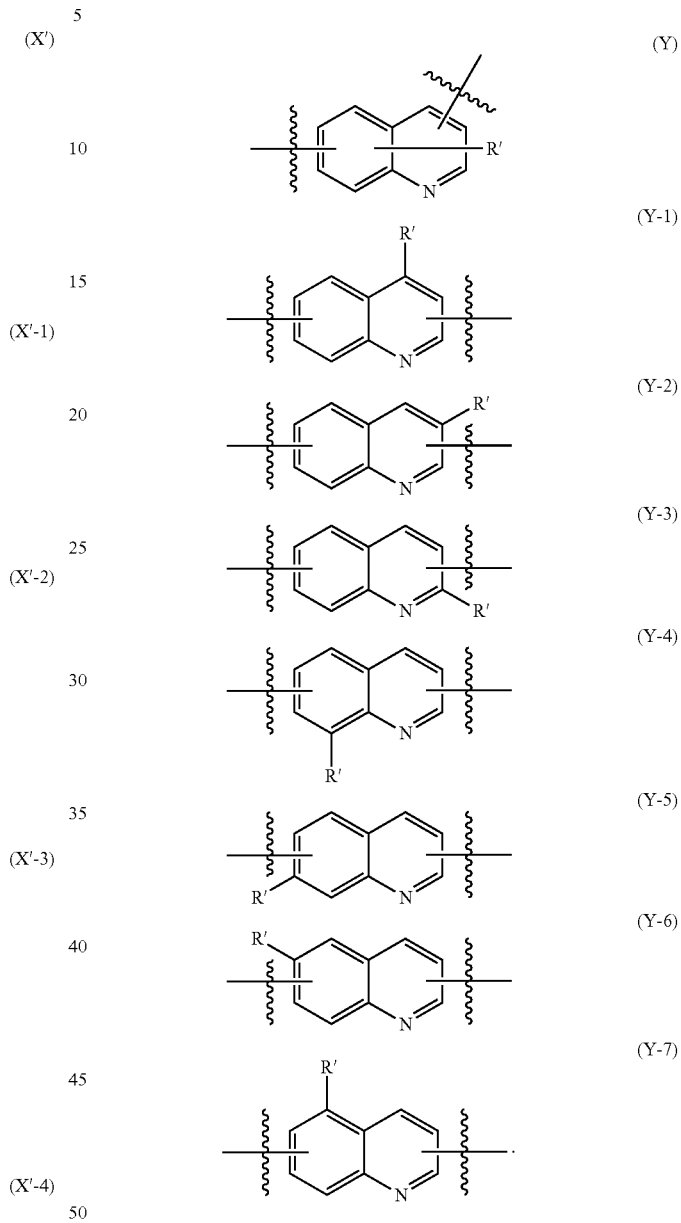

The unpositioned substituent in the present disclosure refers to a substituent connected by a single bond extending from the center of the ring system, which means that the substituent may be connected at any possible position in the ring system. For example, as shown in the following formula (Y), a substituent R' represented by the formula (Y) is connected to a quinoline ring through an unpositioned In the present disclosure, the alkyl with 1 to 10 carbon atoms may include linear alkyl with 1 to 10 carbon atoms and branched alkyl with 1 to 10 carbon atoms, and the number of the carbon atoms, for example, may be 1, 2, 3, 4, 5, 6, 7, 8, 9 and 10. Specific examples of the alkyl with 1 to 10 carbon atoms include, but are not limited to, methyl, ethyl, n-propyl, isopropyl, n-butyl, isobutyl, tert-butyl, n-pentyl, isopentyl, neopentyl, cyclopentyl, n-hexyl, heptyl, n-octyl, 2-ethylhexyl, nonyl, decyl, 3,7-dimethyloctyl and the like.

In the present disclosure, the halogen group may include fluorine, iodine, bromine, chlorine and the like.

In the present disclosure, specific examples of the trialkylsilyl with 3 to 12 carbon atoms include, but are not limited to, trimethylsilyl, triethylsilyl and the like.

In the present disclosure, specific examples of the cycloalkyl with 3 to 10 carbon atoms include, but are not limited to, cyclopentyl, cyclohexyl, adamantyl and the like.

In the present disclosure, specific examples of the deuterated alkyl with 1 to 10 carbon atoms include, but are not limited to, trideuteromethyl.

In one implementation of the present disclosure, $Ar_1$ is selected from hydrogen, substituted or unsubstituted aryl with 6 to 30 carbon atoms, and substituted or unsubstituted heteroaryl with 3 to 20 carbon atoms; and $Ar_2$ is selected from substituted or unsubstituted aryl with 6 to 30 carbon atoms, and substituted or unsubstituted heteroaryl with 3 to 20 carbon atoms.

In one implementation of the present disclosure, $n_1$, $n_2$ and $n_3$ are each independently selected from 0.

In one embodiment of the present disclosure, the Ar is selected from substituted or unsubstituted aryl with 6 to 20 carbon atoms, and substituted or unsubstituted heteroaryl with 5 to 20 carbon atoms.

Preferably, the substituents in the Ar is selected from deuterium, a halogen group, cyano, alkyl with 1 to 5 carbon atoms, aryl with 6 to 12 carbon atoms, heteroaryl with 5 to 12 carbon atoms, trialkylsilyl with 3 to 6 carbon atoms and deuterated alkyl with 1 to 5 carbon atoms.

Specifically, the specific examples of the substituent in the Ar include, but are not limited to, deuterium, fluorine, cyano, methyl, ethyl, n-propyl, isopropyl, tert-butyl, trifluoromethyl, trimethylsilyl, trideuteromethyl, phenyl, naphthyl, biphenyl and carbazolyl.

More preferably, the Ar is selected from substituted or unsubstituted aryl with 6 to 18 carbon atoms and substituted or unsubstituted heteroaryl with 5 to 12 carbon atoms.

In another embodiment of the present disclosure, the Ar is selected from substituted or unsubstituted phenyl, substituted or unsubstituted naphthyl, substituted or unsubstituted biphenyl, substituted or unsubstituted terphenyl, substituted or unsubstituted anthryl, substituted or unsubstituted phenanthryl, substituted or unsubstituted fluorenyl, substituted or unsubstituted pyridyl, substituted or unsubstituted dibenzofuranyl, substituted or unsubstituted dibenzothienyl and substituted or unsubstituted carbazolyl.

In one embodiment of the present disclosure, the Ar is selected from a substituted or unsubstituted group $V_1$, and the unsubstituted group $V_1$ is selected from the group consisting of the following groups:

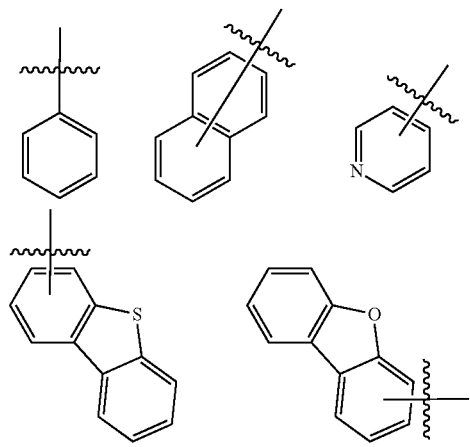

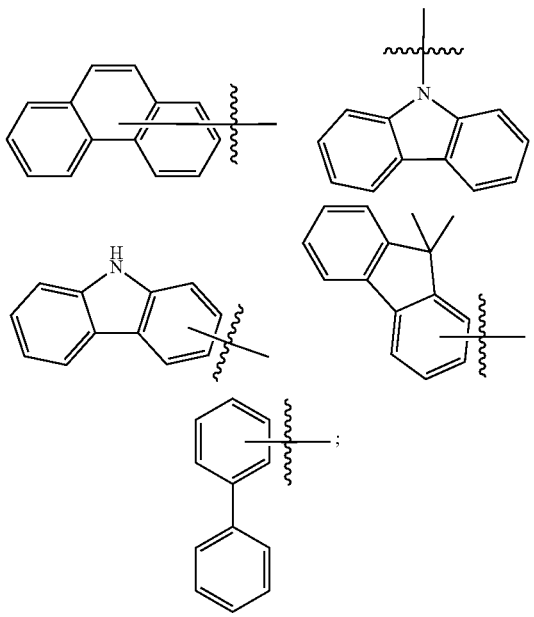

where,

represents a chemical bond; the substituted $V_1$ has one or more substituents, and the substituents on the substituted $V_1$ are each independently selected from deuterium, fluorine, cyano, methyl, ethyl, n-propyl, isopropyl, tert-butyl, trifluoromethyl, trimethylsilyl, trideuteromethyl, phenyl, naphthyl, biphenyl and carbazolyl; and when the number of the substituents in $V_1$ is greater than 1, all the substituents are the same or different.

Optionally, the Ar is selected from the group consisting of the following groups:

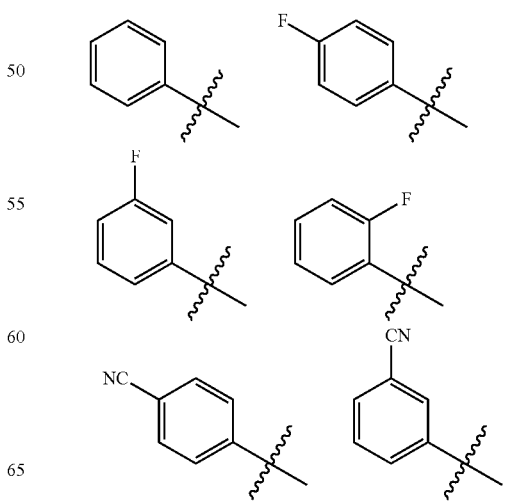

-continued

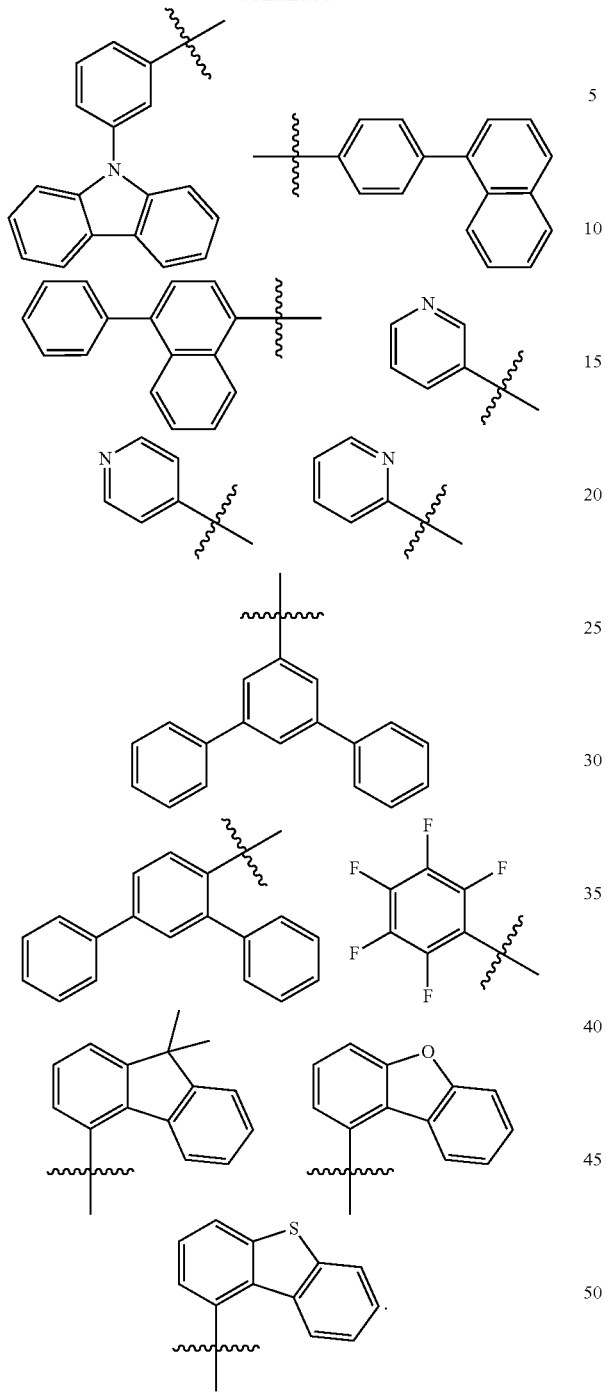

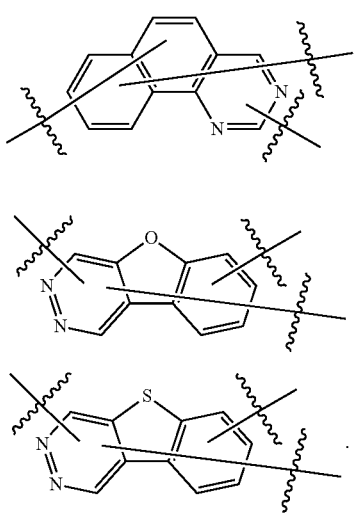

In one embodiment of the present disclosure, the $Ar_1$ and the $Ar_2$ are respectively and independently selected from hydrogen, substituted or unsubstituted aryl with 6 to 20 carbon atoms, and substituted or unsubstituted heteroaryl with 5 to 20 carbon atoms.

Preferably, substituents in the $Ar_1$ and the $Ar_2$ are respectively and independently selected from deuterium, a halogen group, cyano, alkyl with 1 to 5 carbon atoms, aryl with 6 to 12 carbon atoms, and heteroaryl with 5 to 12 carbon atoms.

Specifically, specific examples of the substituents in the $Ar_1$ and $Ar_2$ include, but are not limited to, deuterium, fluorine, cyano, methyl, ethyl, n-propyl, isopropyl, tert-butyl, phenyl, naphthyl, biphenyl and carbazolyl.

In another embodiment of the present disclosure, the $Ar_1$ and the $Ar_2$ are respectively and independently selected from hydrogen, substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted carbazolyl, substituted or unsubstituted dibenzofuranyl, and substituted or unsubstituted dibenzothienyl.

In one embodiment of the present disclosure, the $Ar_1$ and the $Ar_2$ are respectively and independently selected from hydrogen or a substituted or unsubstituted group $V_2$, and the unsubstituted group $V_2$ is selected from the group consisting of the following groups:

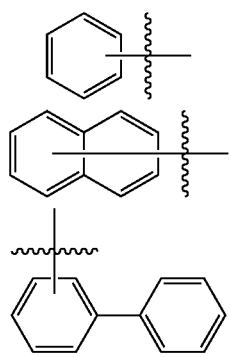

In one embodiment of the present disclosure, the Het is selected from nitrogen-containing heteroaryl with 3 to 12 carbon atoms, and the nitrogen-containing heteroaryl at least contains two N atoms.

In the present disclosure, the nitrogen-containing heteroaryl with 3 to 12 carbon atoms refers to nitrogen-containing heteroaryl with 3, 4, 5, 6, 7, 8, 9, 10, 11 or 12 carbon atoms.

In one embodiment of the present disclosure, the Het is selected from triazinylene, pyrimidylene, quinoxalinylene, quinazolinylene, or the group consisting of the following groups:

-continued

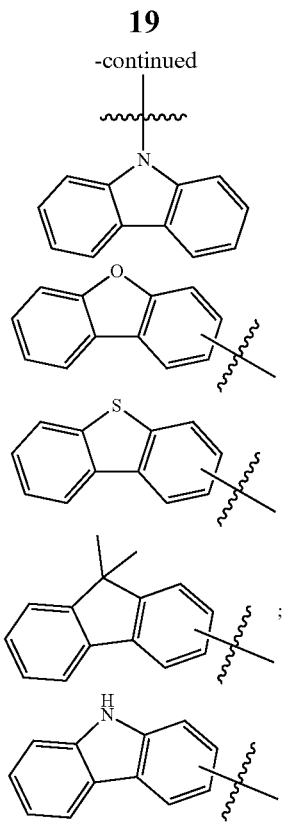

where,

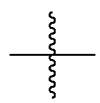

represents a chemical bond; the substituted $V_2$ has one or more substituents, and the substituents in the substituted $V_2$ are each independently selected from deuterium, fluorine, cyano, methyl, ethyl, n-propyl, isopropyl, tert-butyl, phenyl, naphthyl, biphenyl and carbazolyl; and when the number of the substituents in $V_2$ is greater than 1, all the substituents are the same or different.

Optionally, the $Ar_1$ and the $Ar_2$ are respectively and independently selected from the group consisting of the following groups:

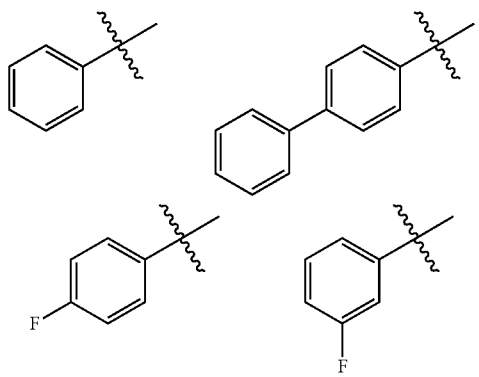

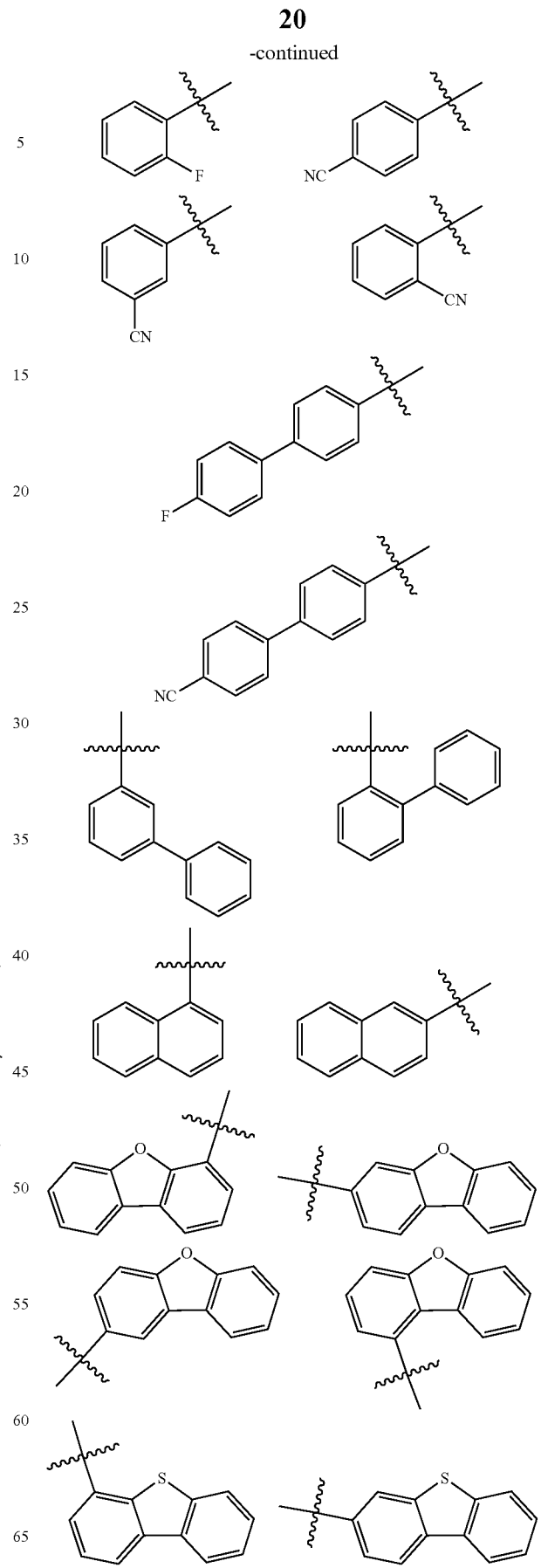

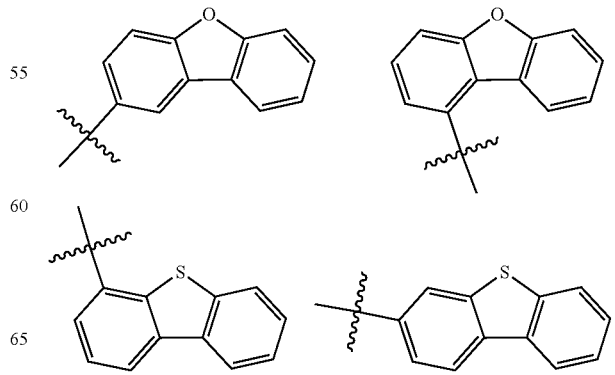

-continued
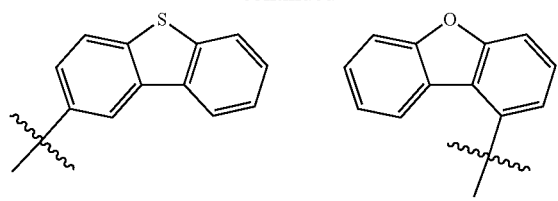
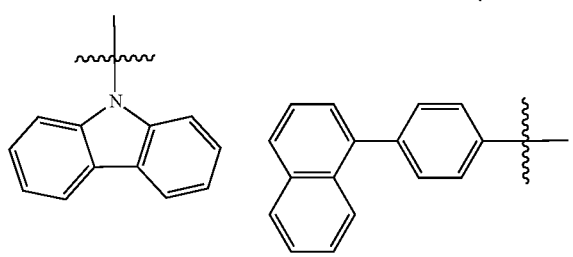
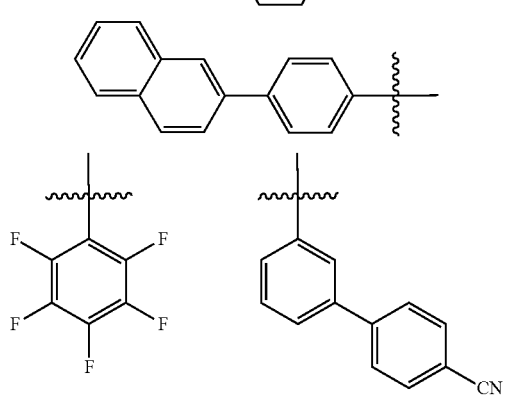
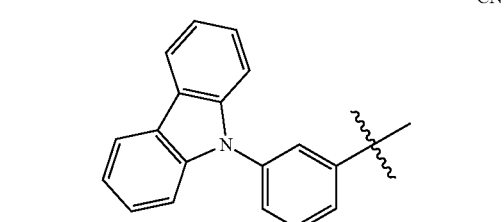
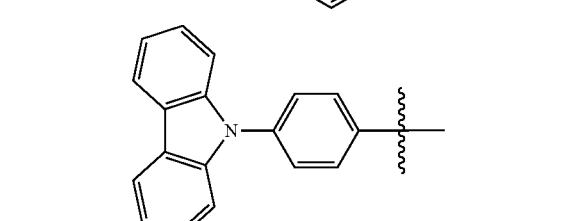
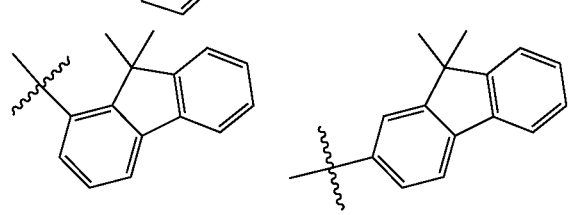
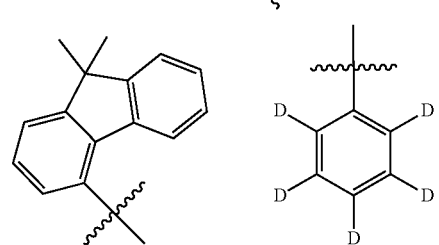
-continued
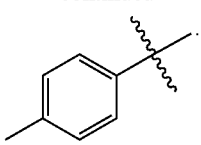
In the present disclosure,
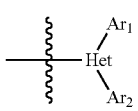
is selected from the group consisting of the following groups:
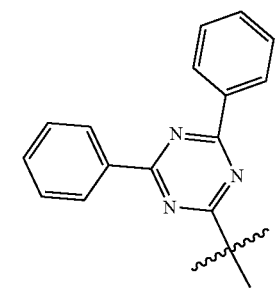
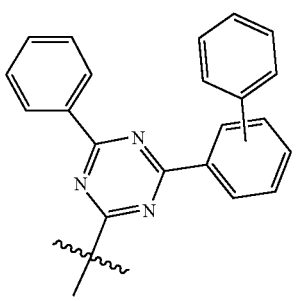
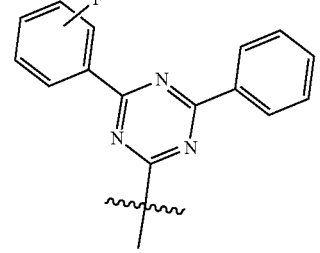
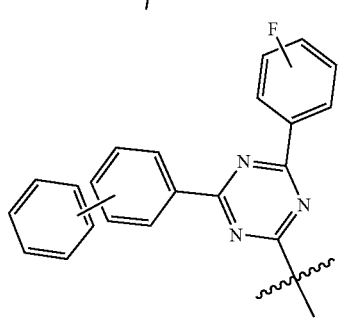

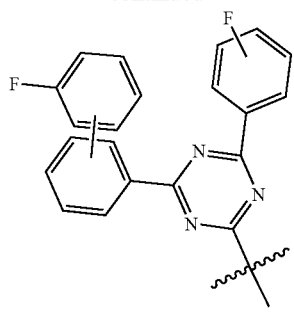
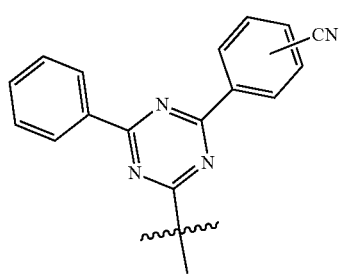
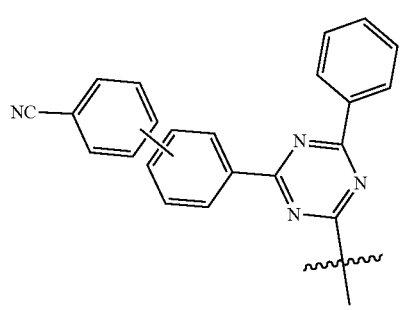
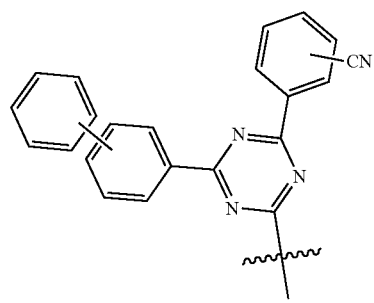
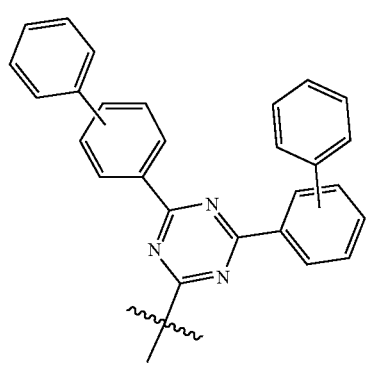
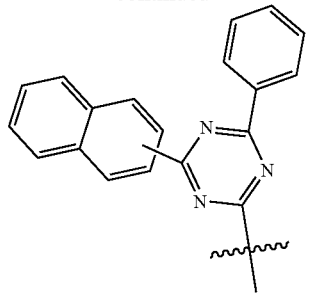
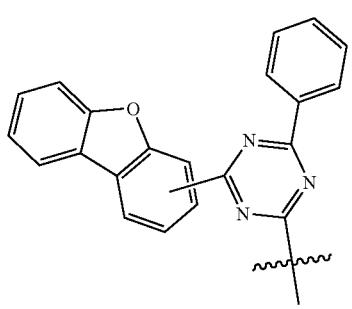
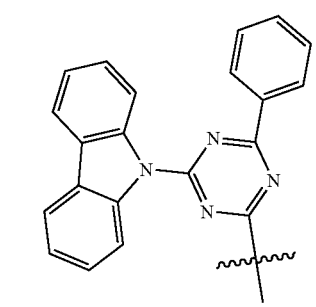
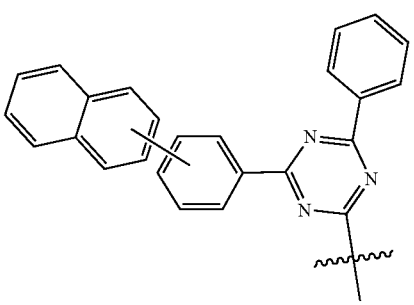
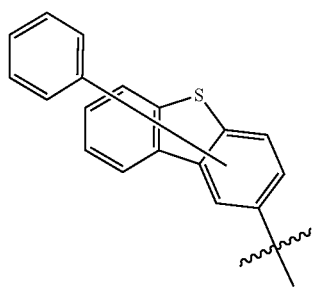

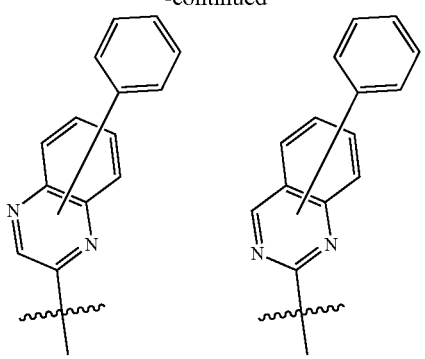
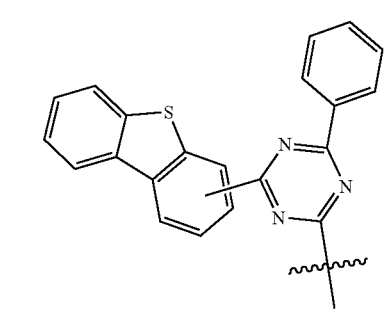
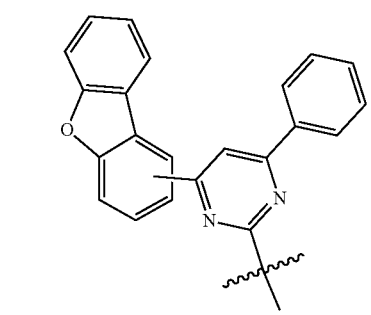
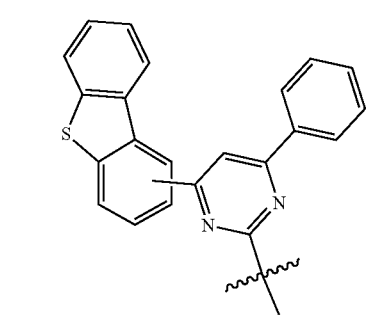
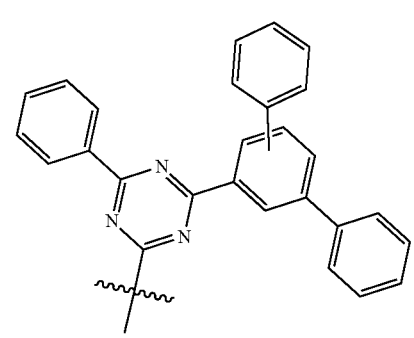
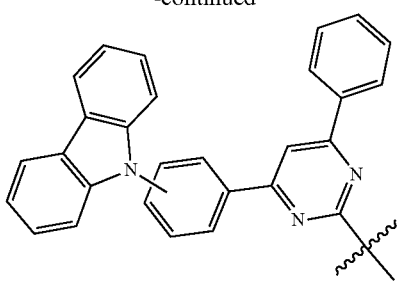
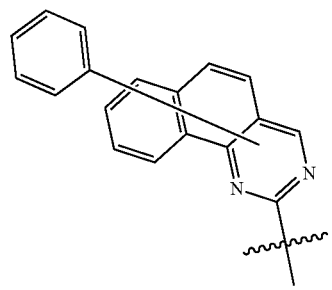
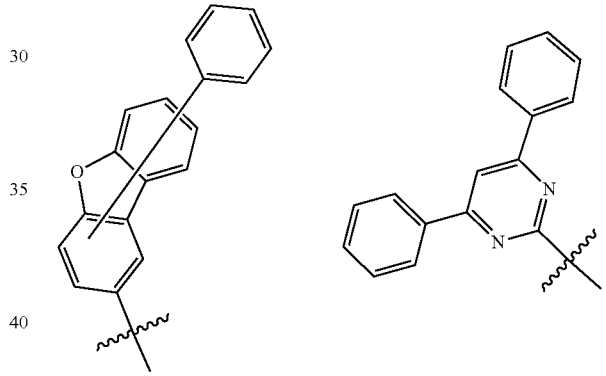
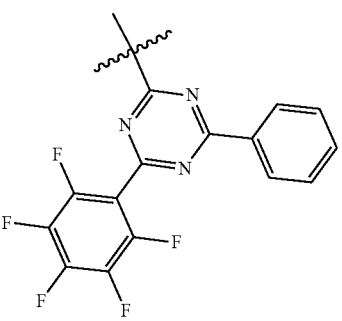
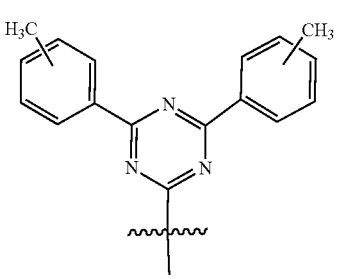

-continued
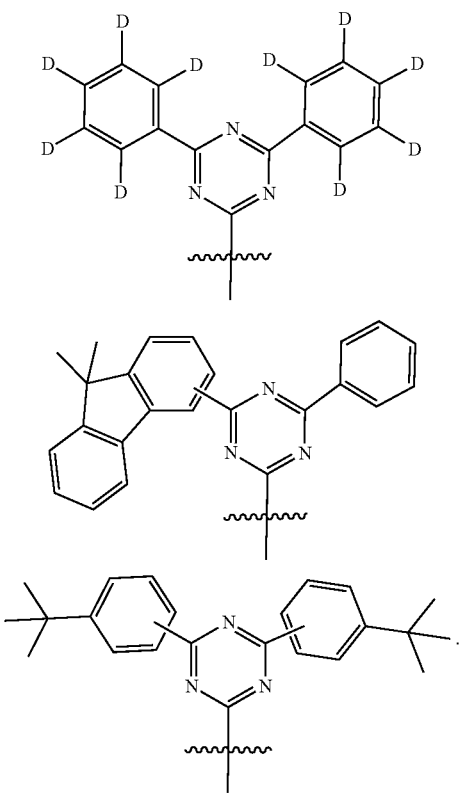
In the present disclosure, optionally,
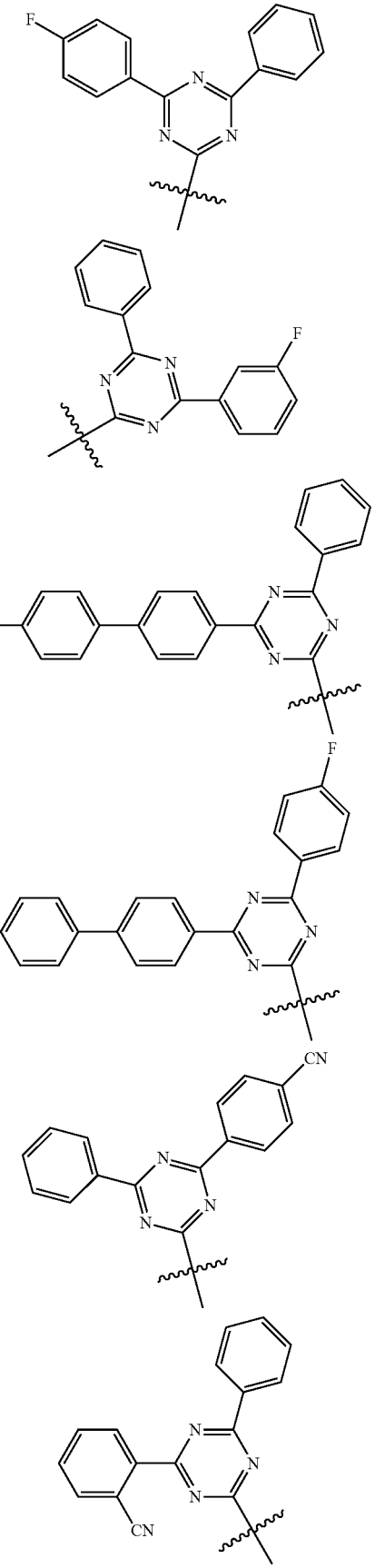
is selected from the group consisting of the following groups:

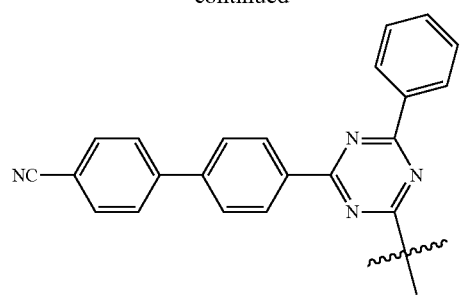
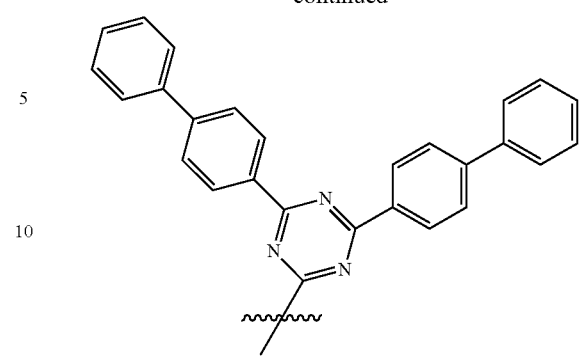
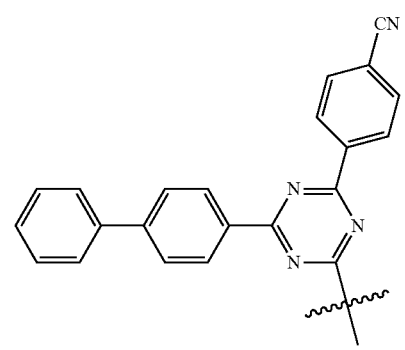
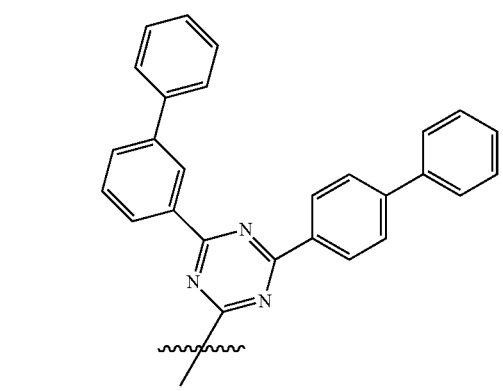
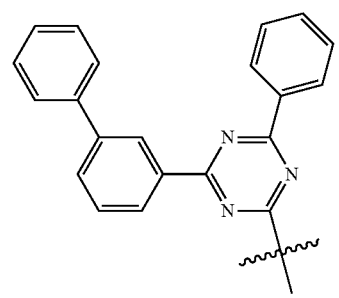
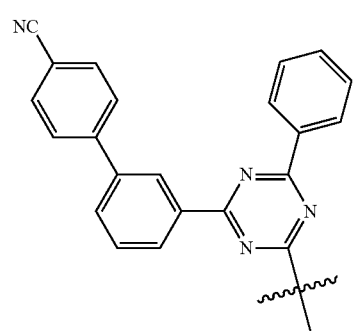
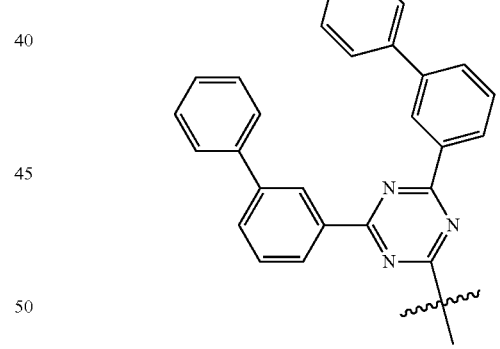
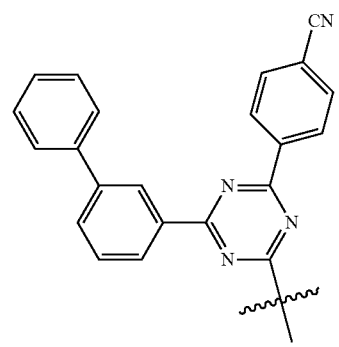
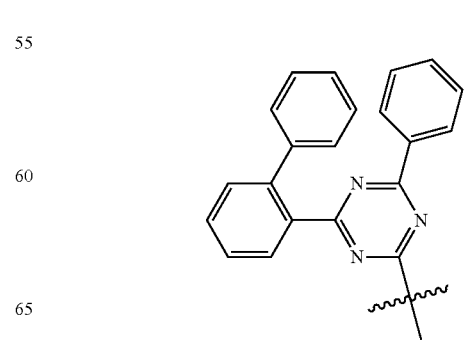

-continued
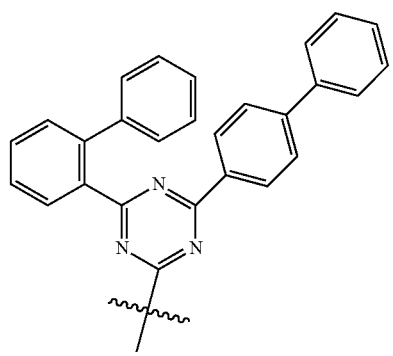
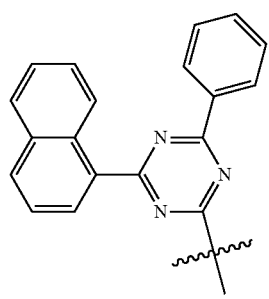
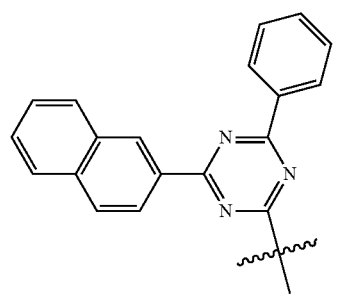
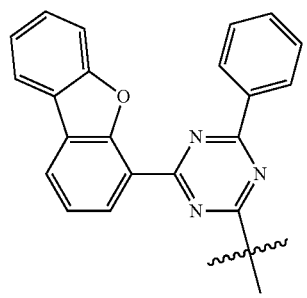
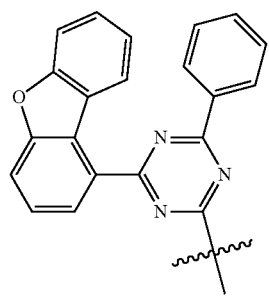
-continued
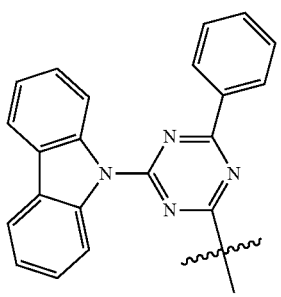
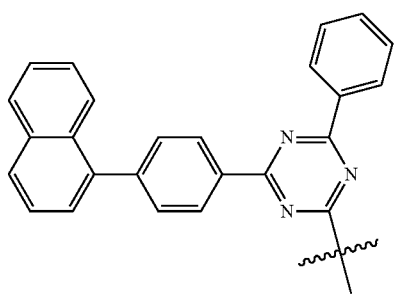
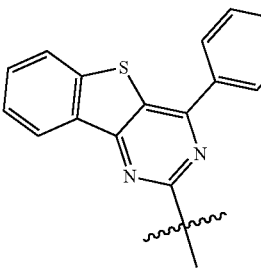
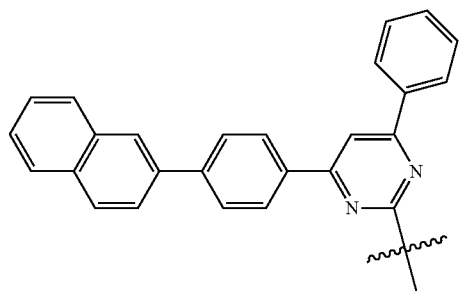
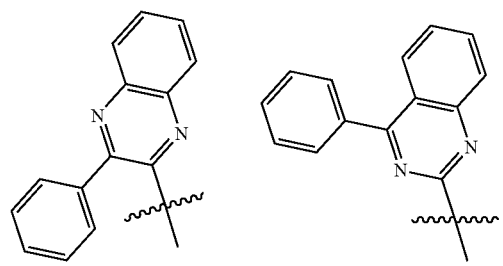
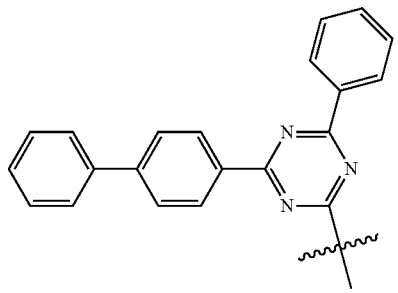

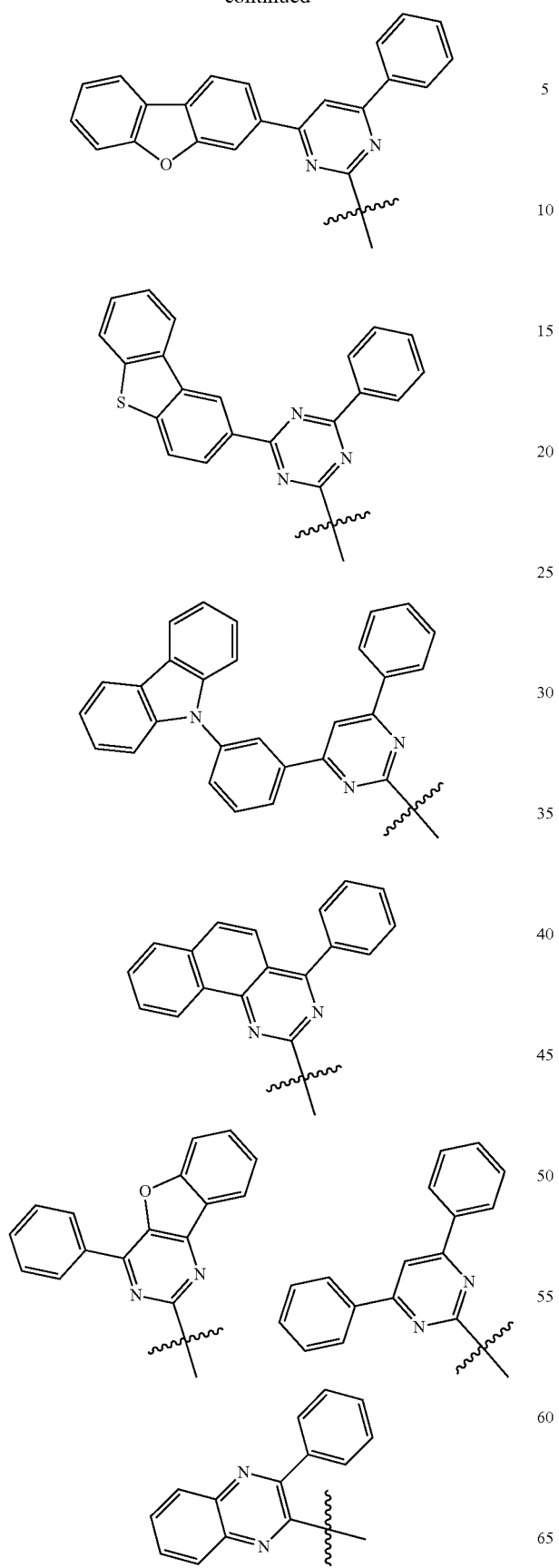
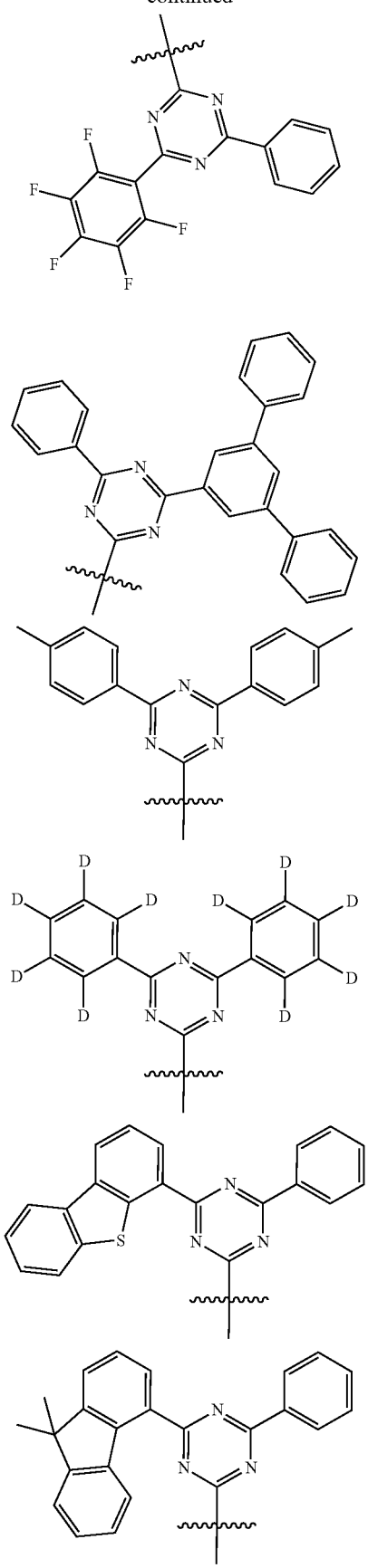

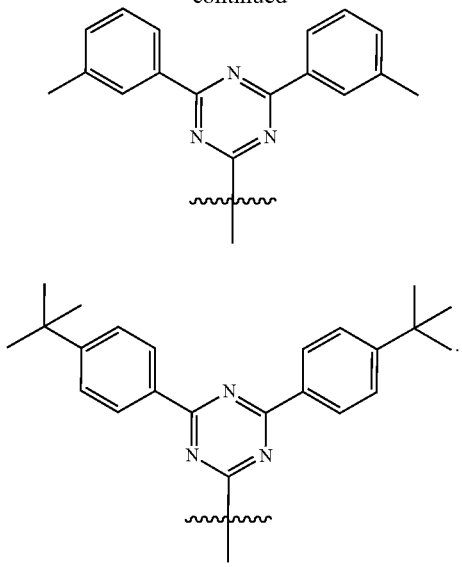
Optionally, two adjacent R₁ form a benzene ring, or two adjacent R₂ form a benzene ring, or two adjacent R₃ form a benzene ring.
In one embodiment of the present disclosure, the organic compound is selected from the group consisting of the following groups:
A1
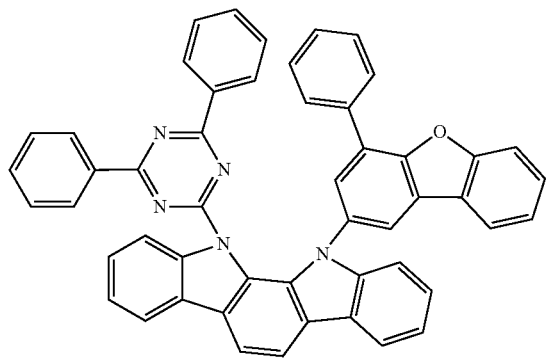
A2
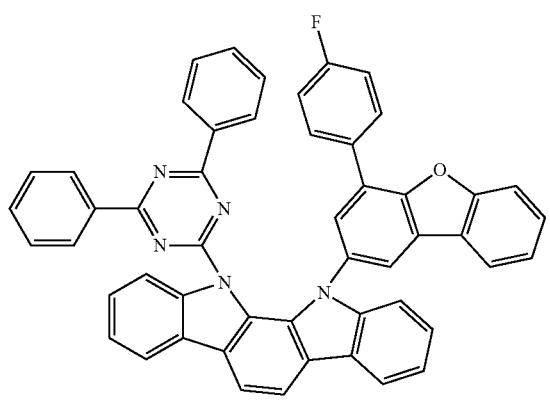
A3
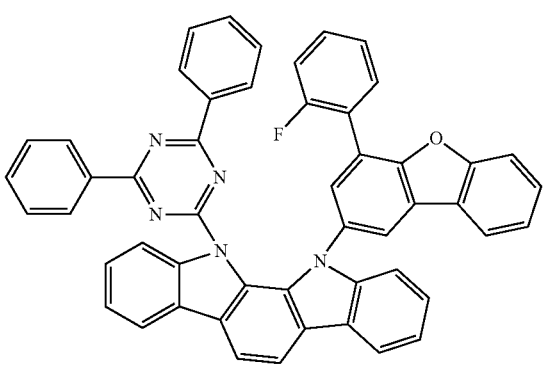
A4
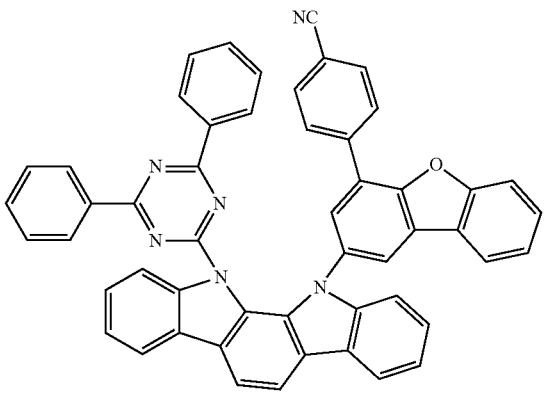
A5
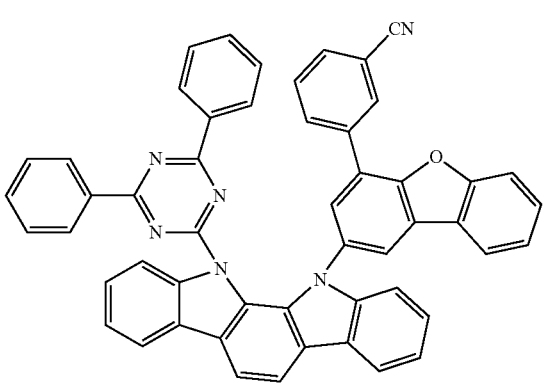
A6

A7
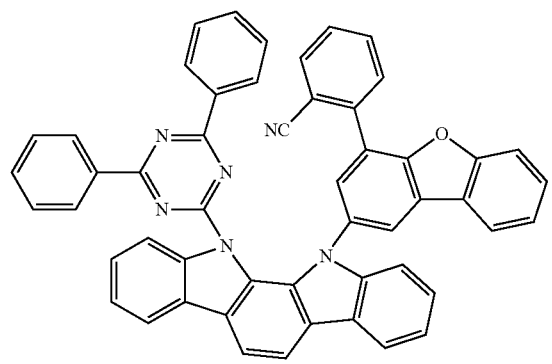
A8
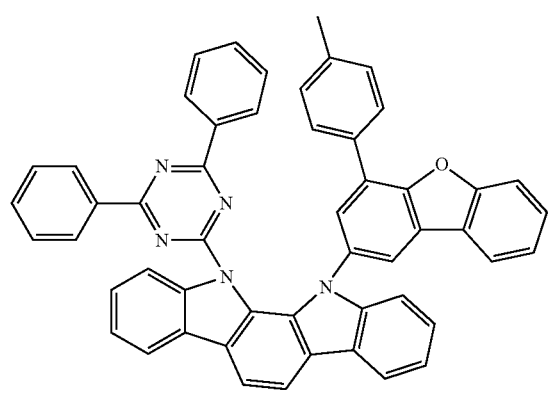
A9
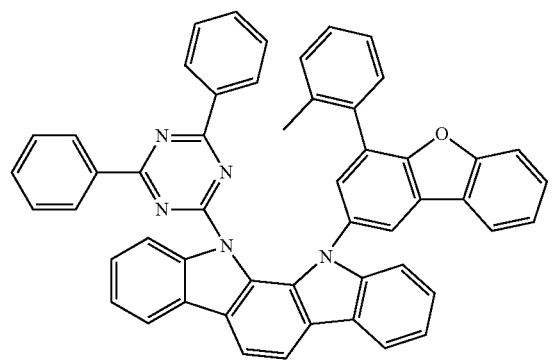
A10
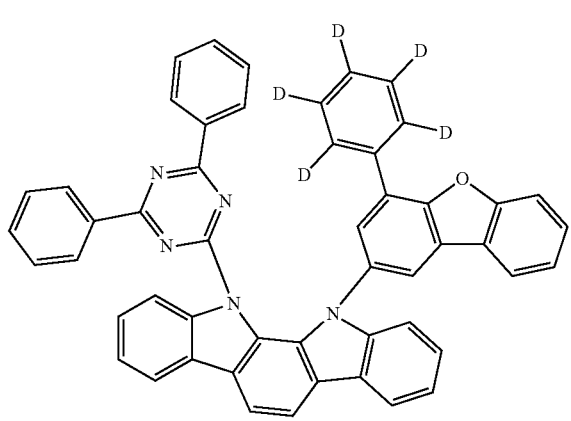
A11
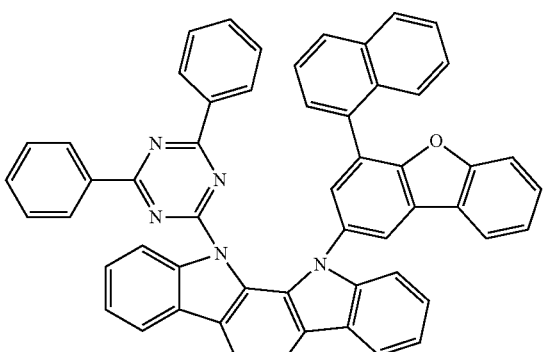
A12
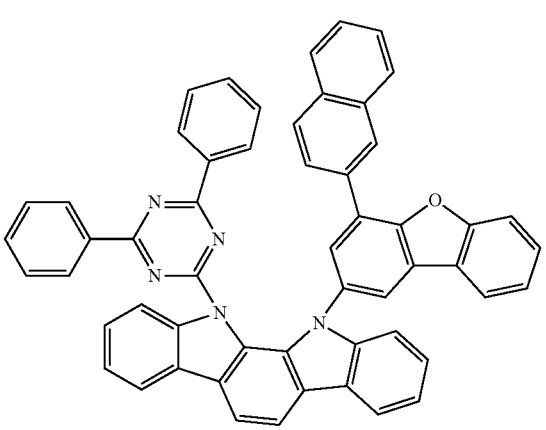
A13
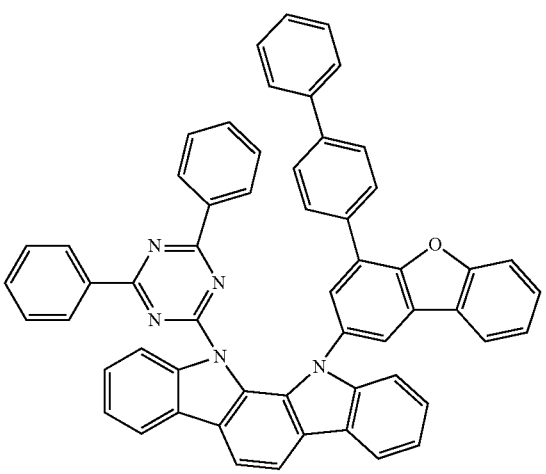

A14
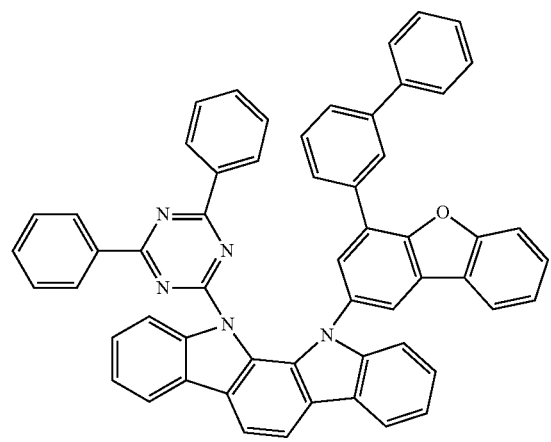
A15
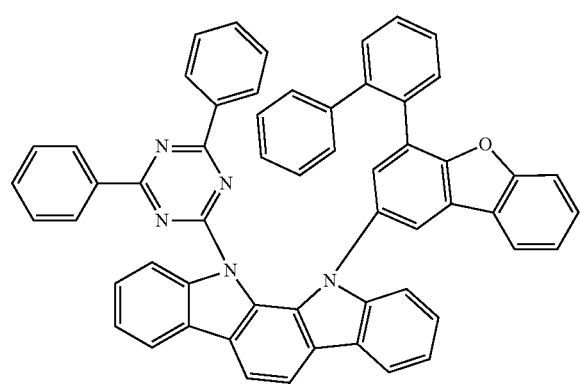
A16
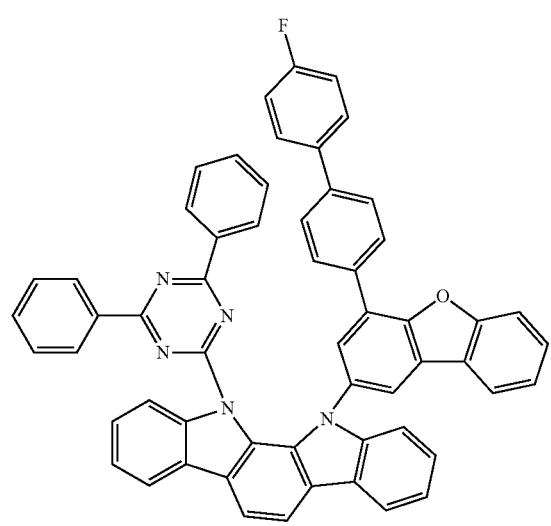
A17
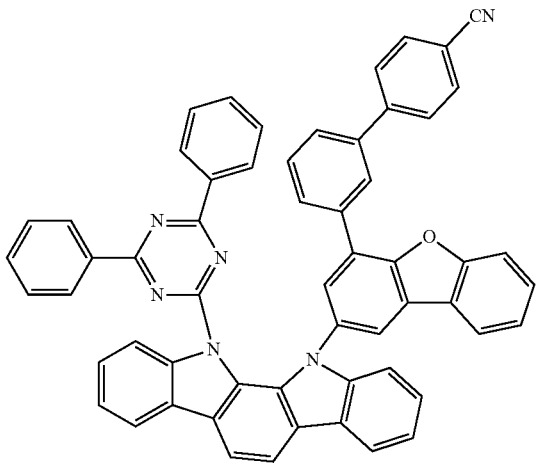
A18
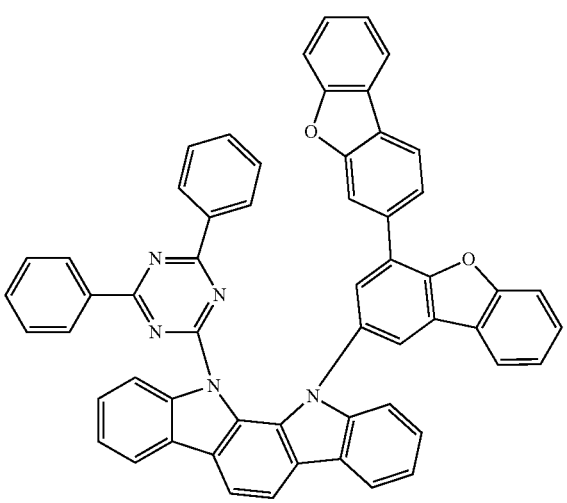
A19
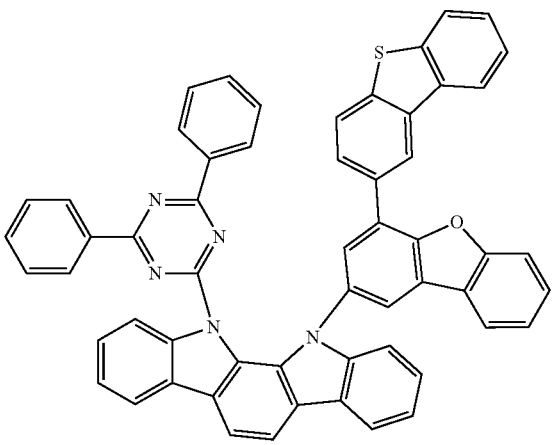

A20
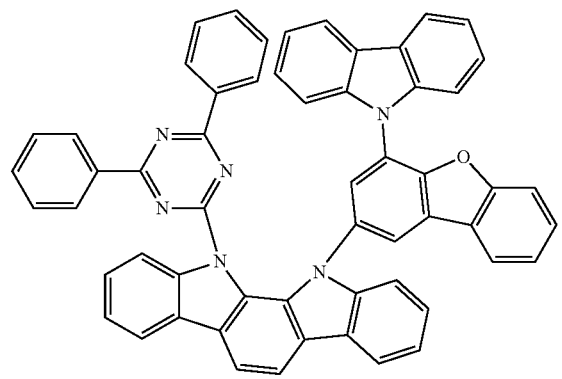
A21
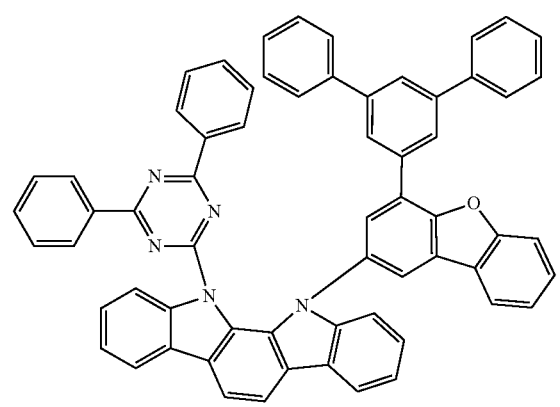
A22
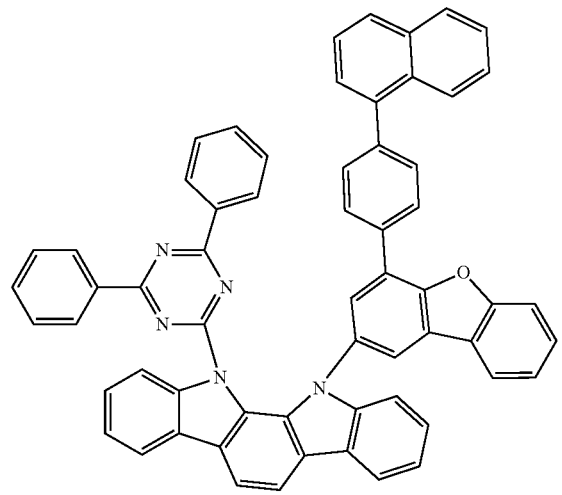
A23
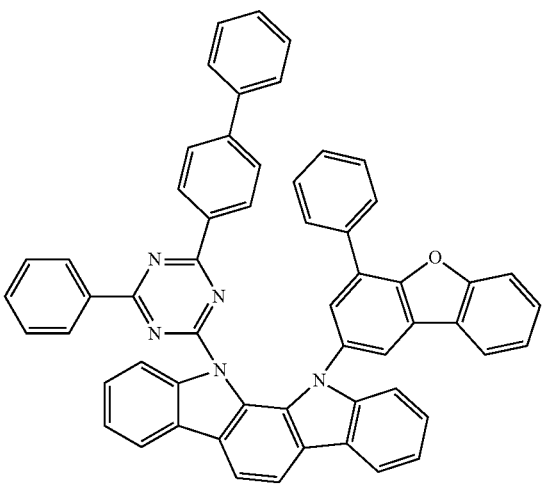
A24
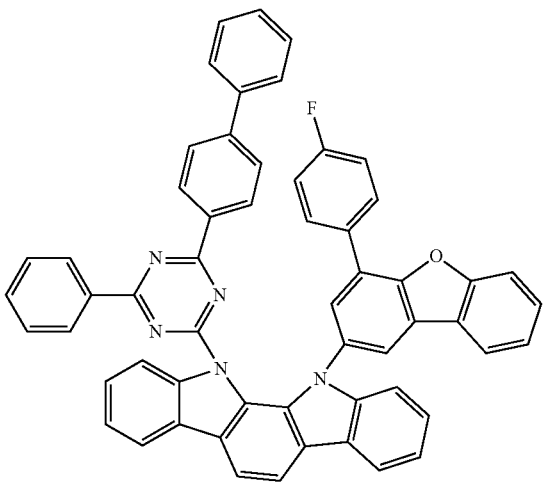
A25
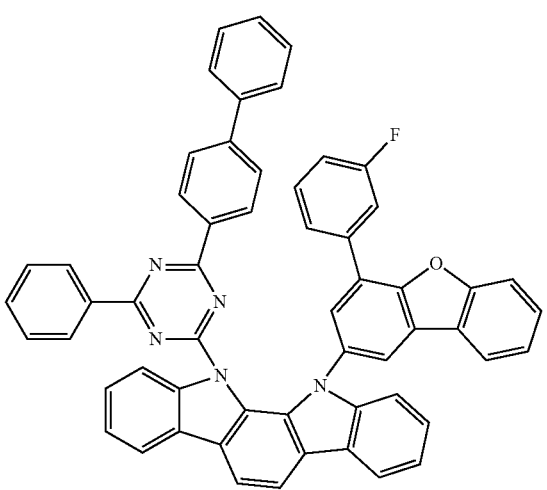

A26
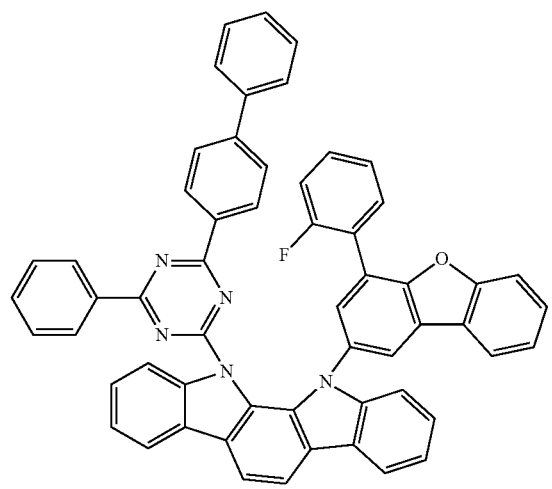
A27
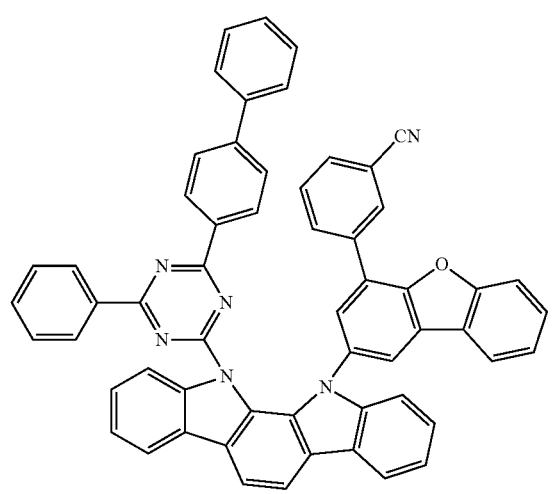
A28
A29
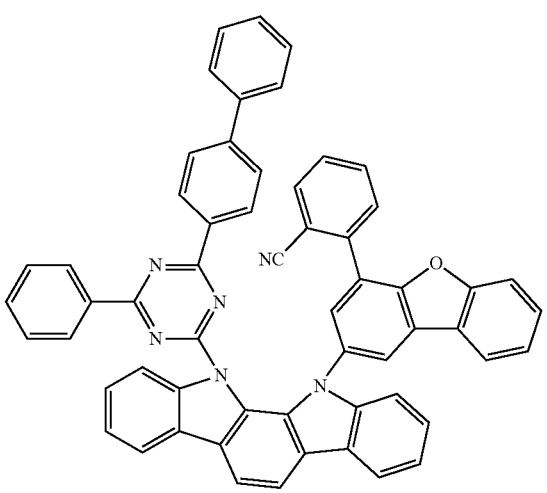
A30
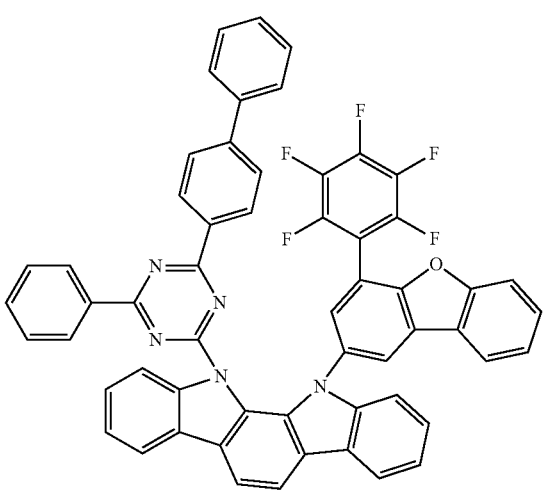
A31

A32
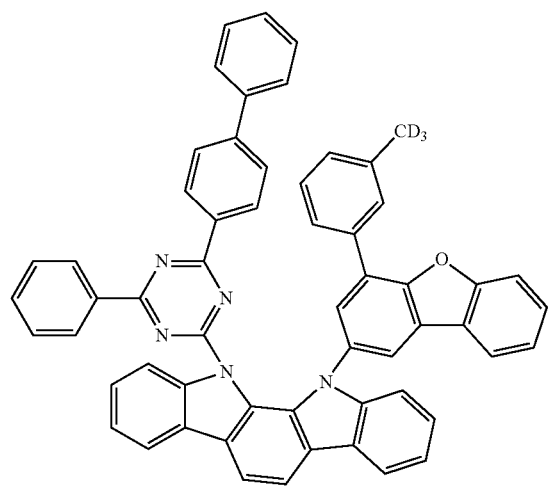
A35
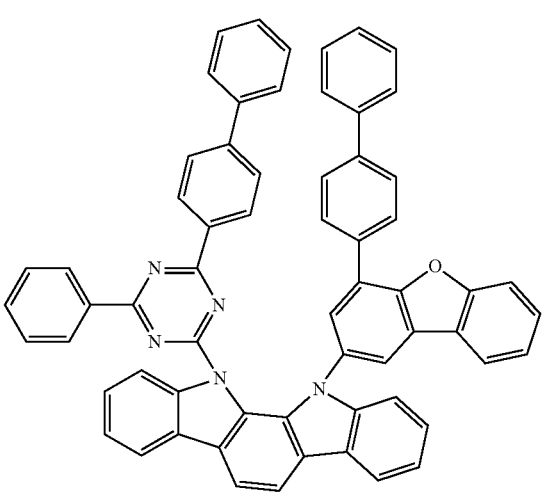
A33
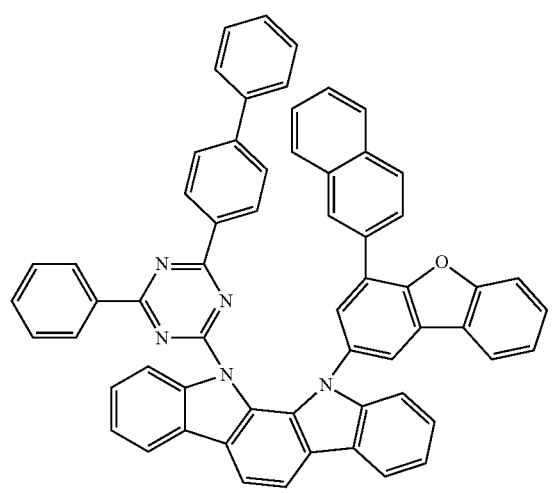
A36
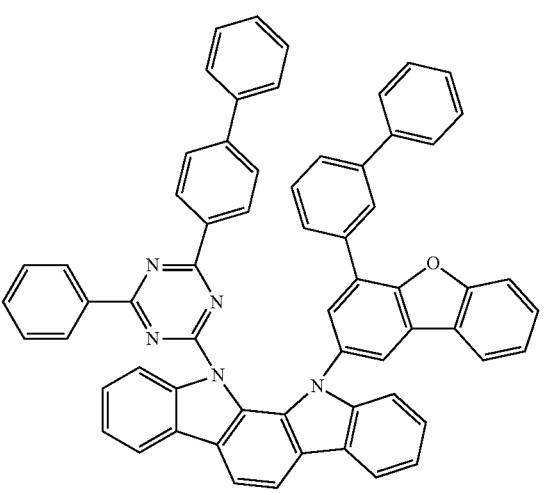
A34
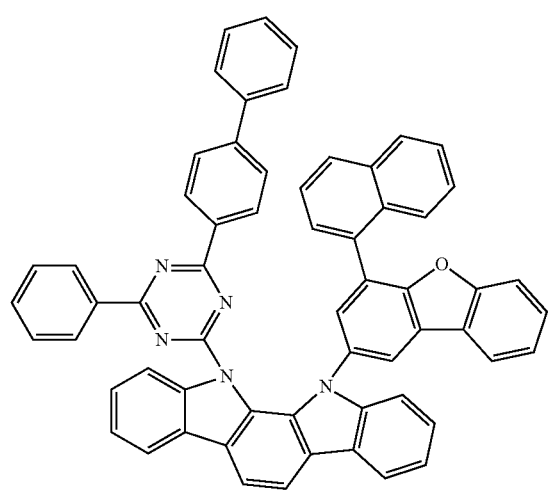
A37
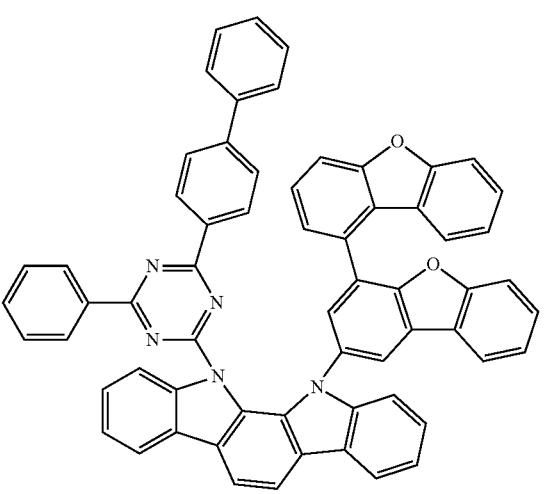

A38
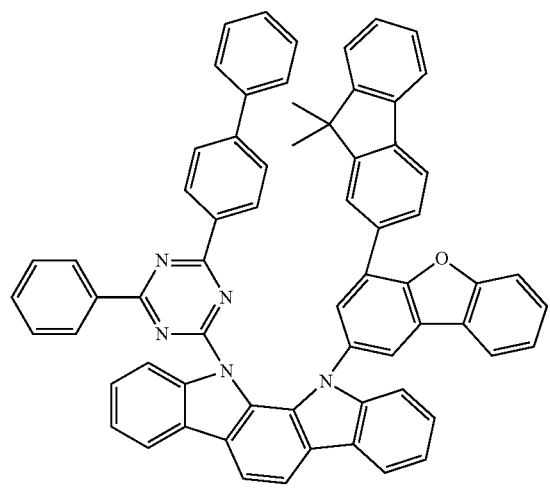
A39
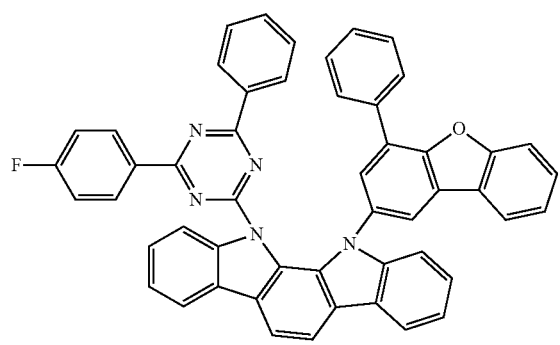
A40
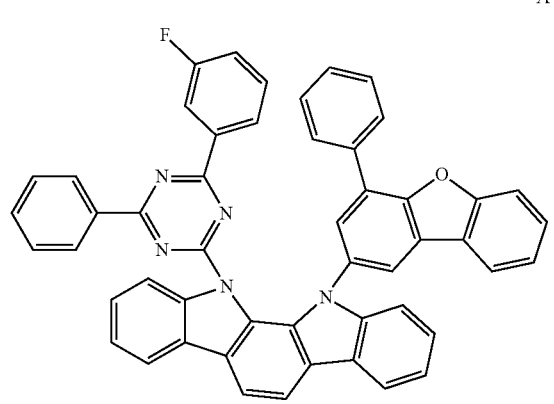
A41
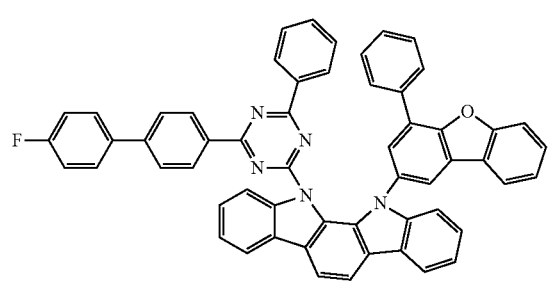
A42
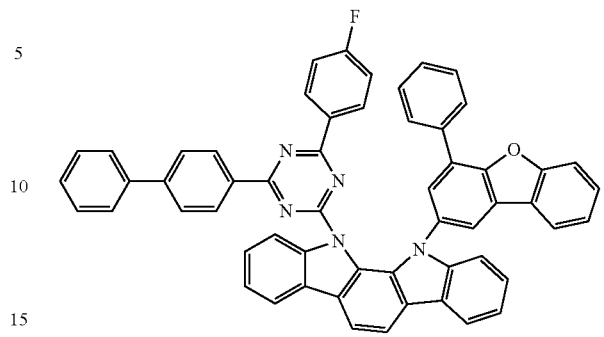
A43
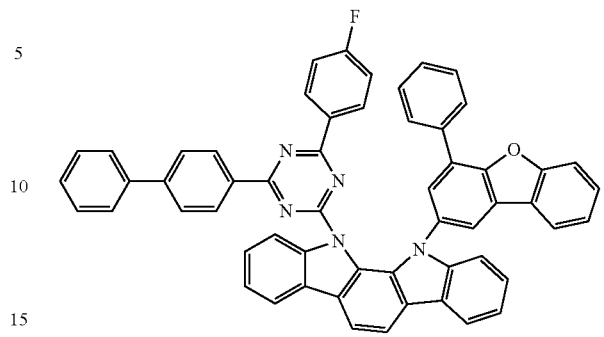
A44
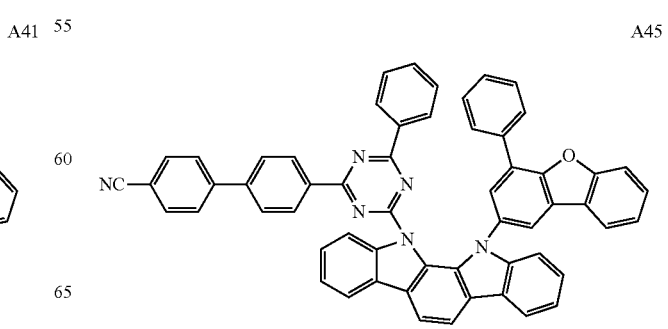
A45
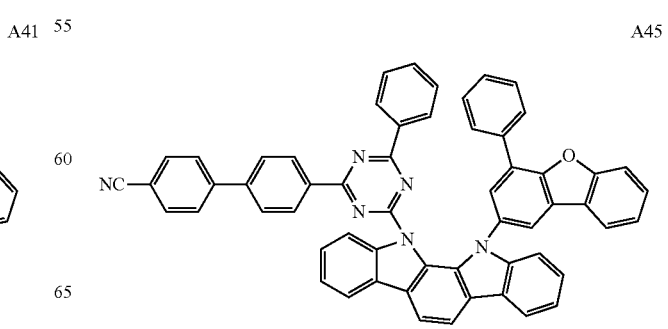

A46
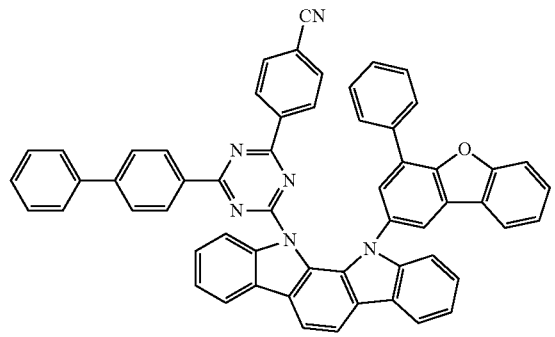
A47
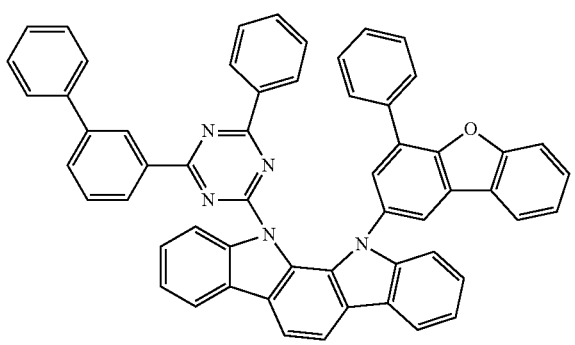
A48
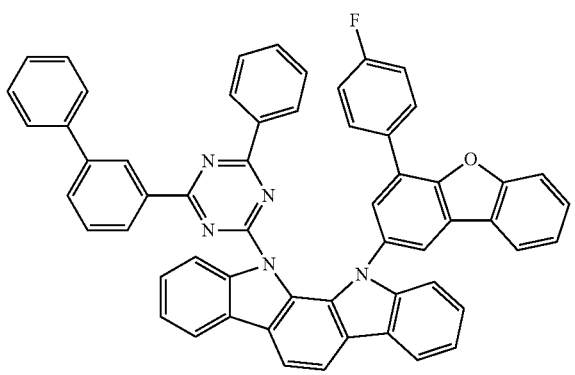
A49
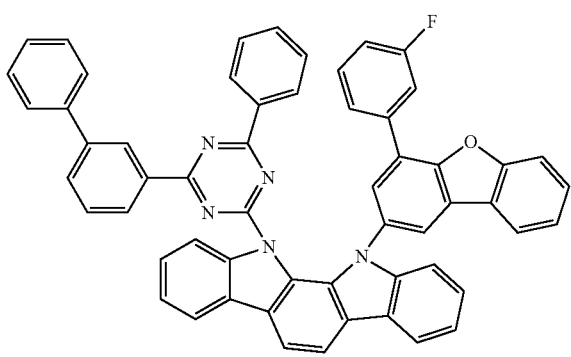
A50
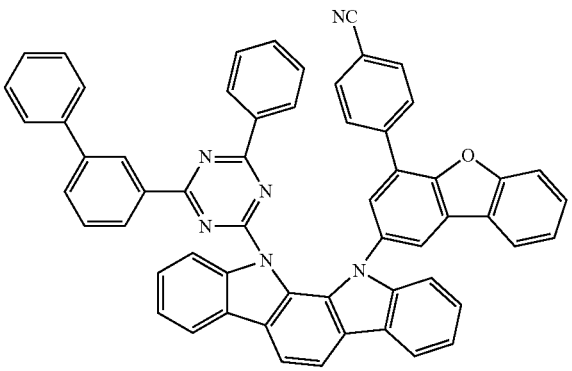
A51
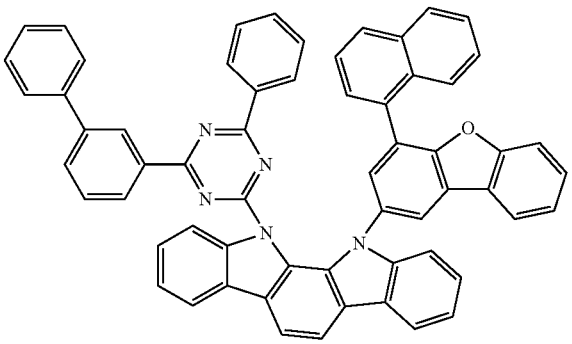
A52
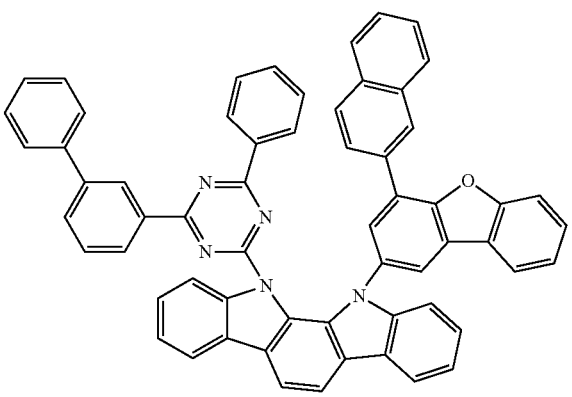
A53
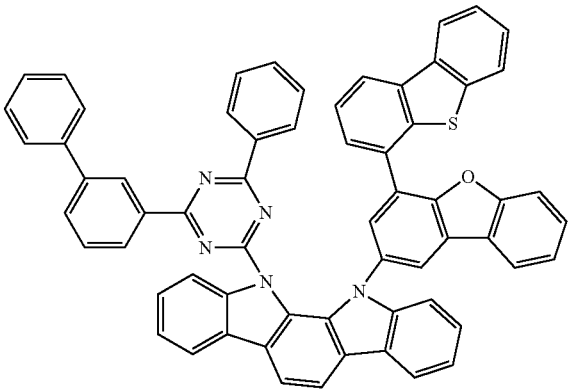

A54
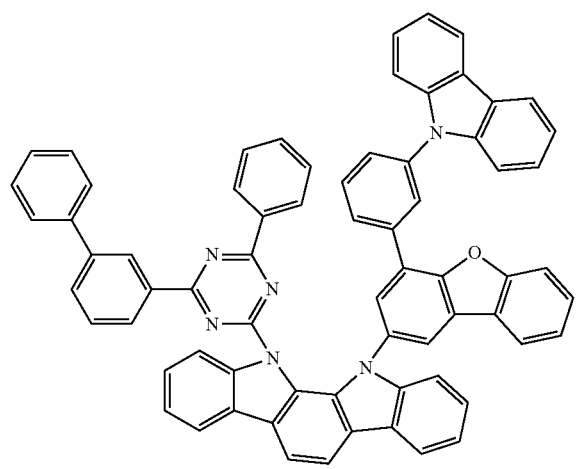
A55
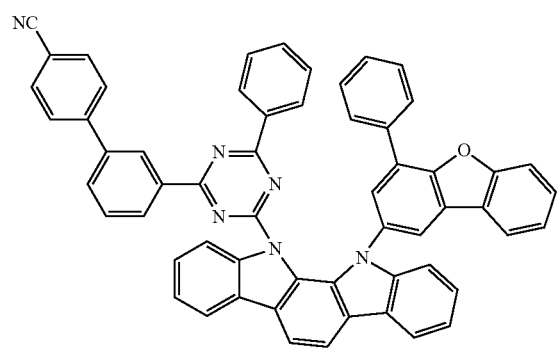
A56
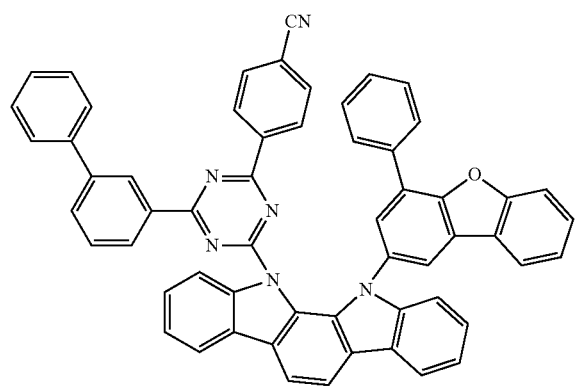
A57
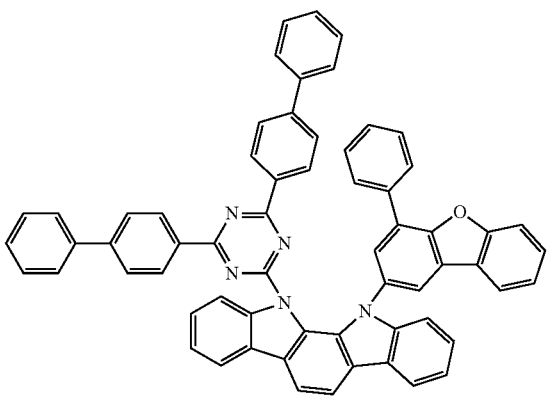
A58
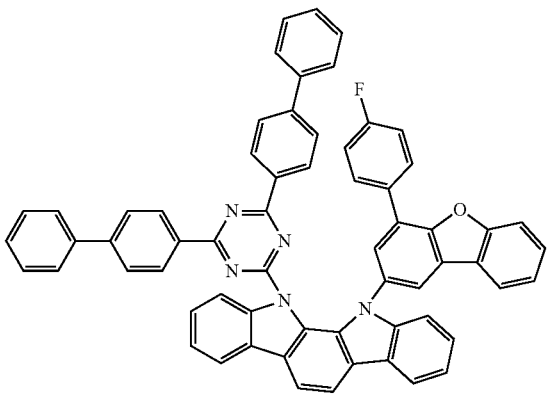
A59
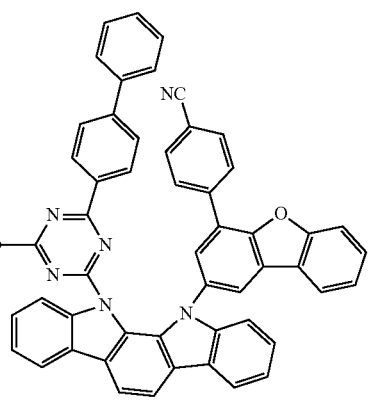

-continued
A60
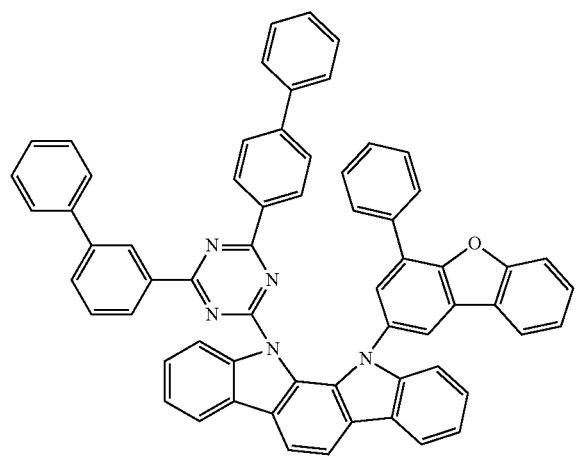
A61
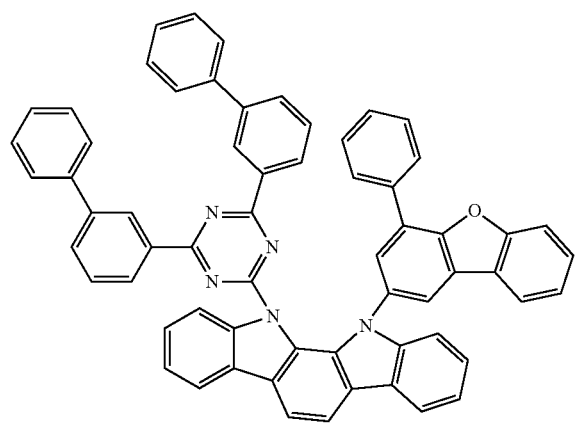
A62
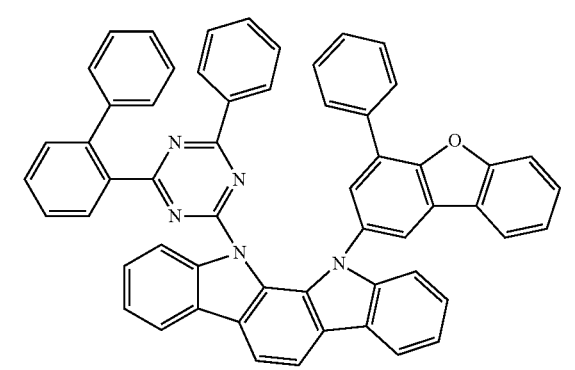
-continued
A63
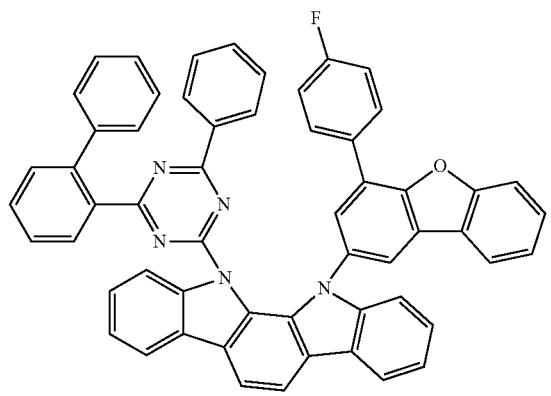
A64
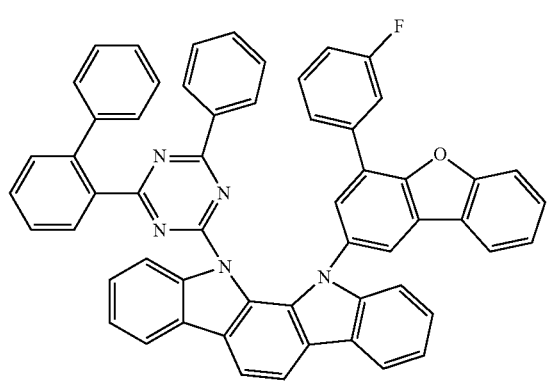
A65
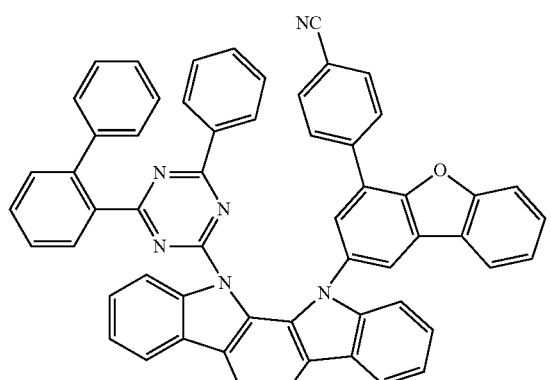
A66
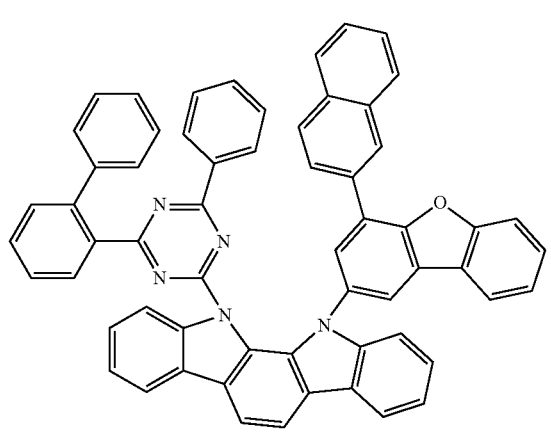

A67
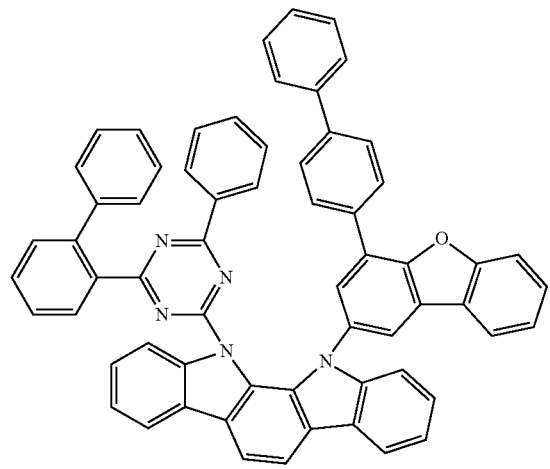
A68
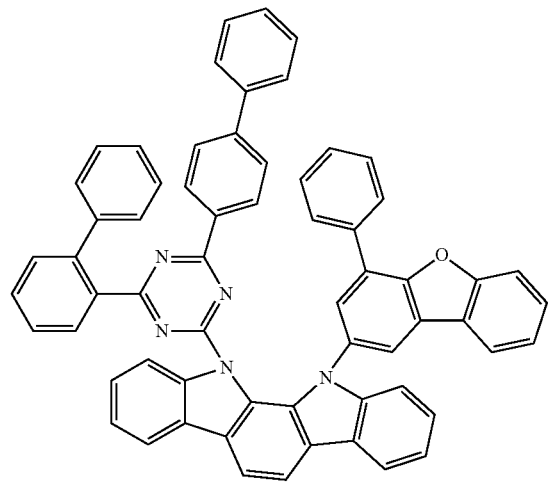
A69
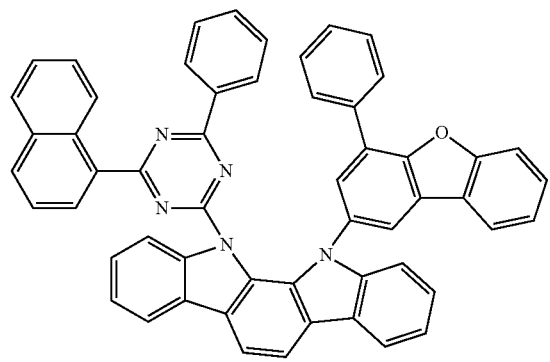
A70
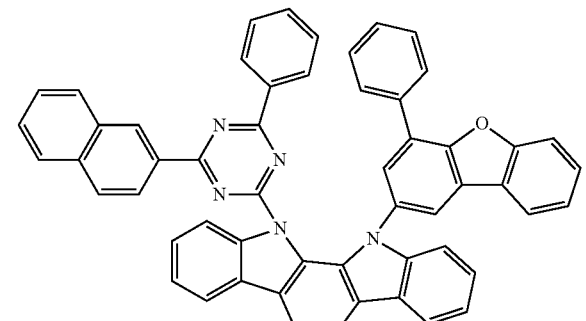
A71
A72
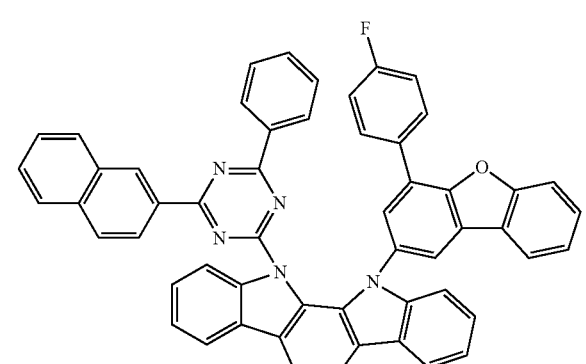
A73
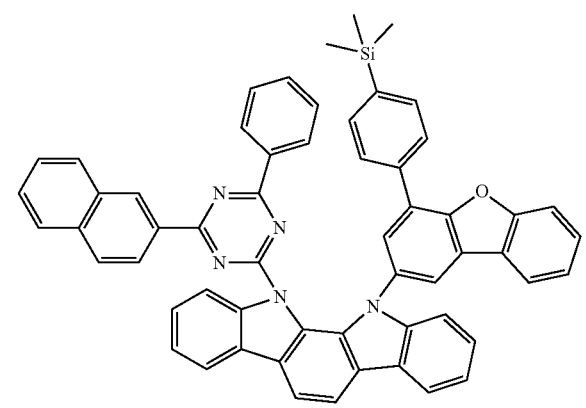

-continued
A74
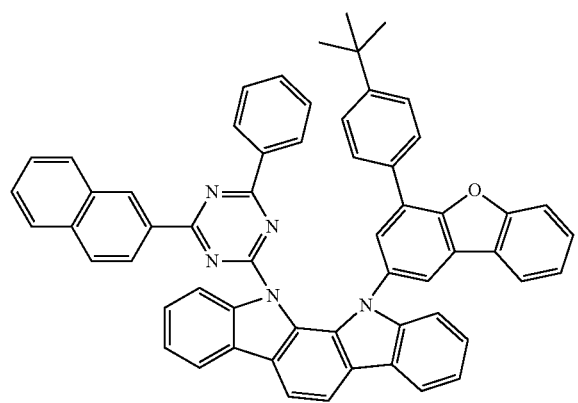
A75
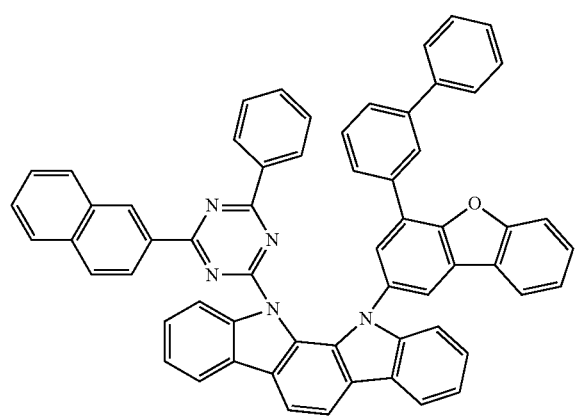
A76
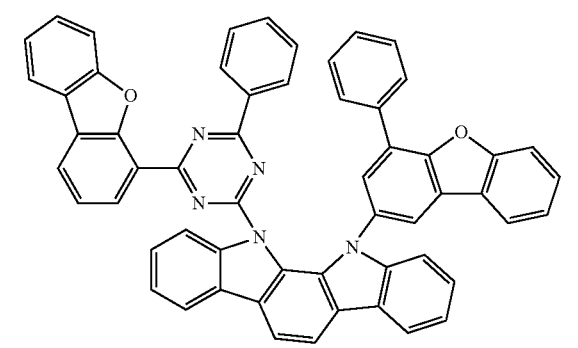
A77
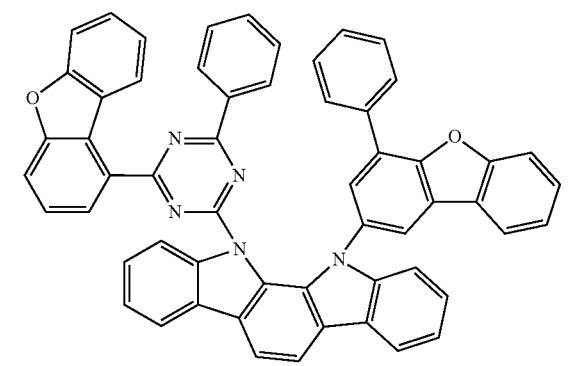
-continued
A78
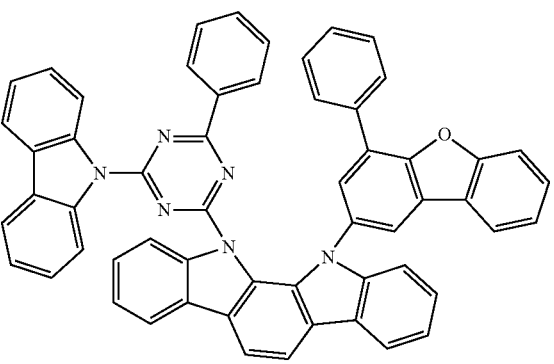
A79
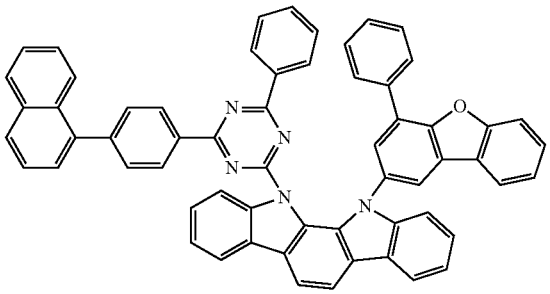
A80
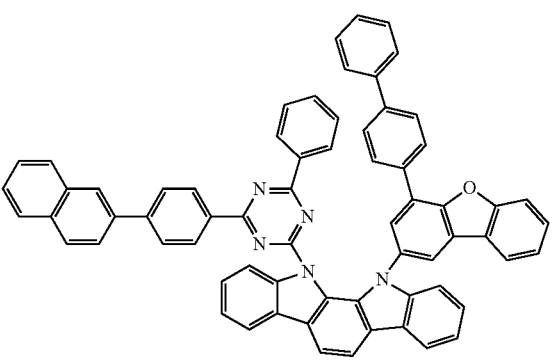
A81
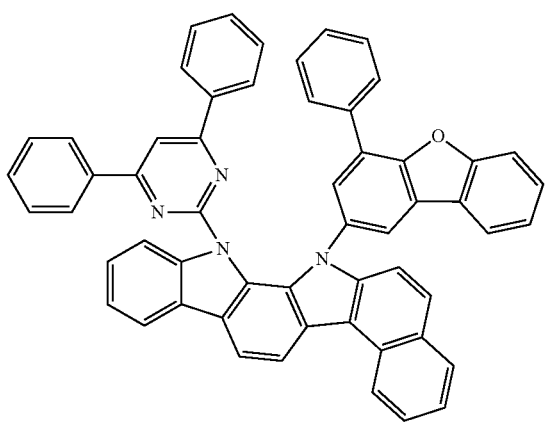

-continued
A82
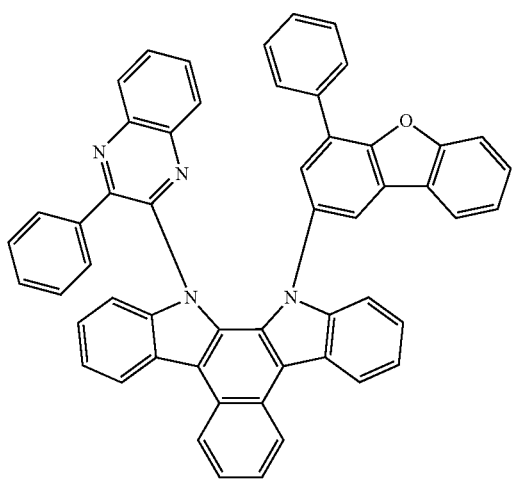
A83
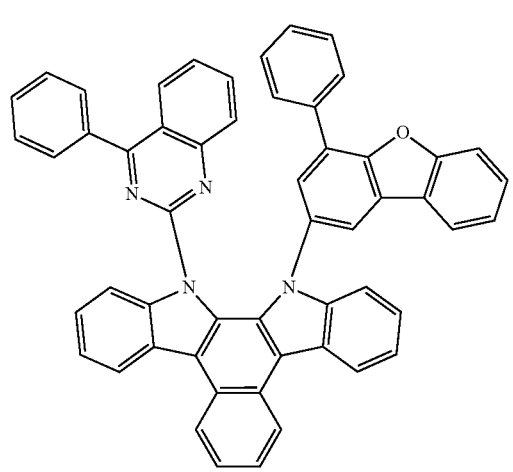
A84
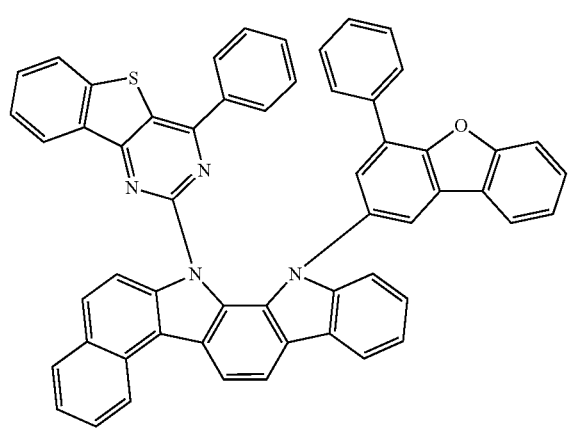
A85
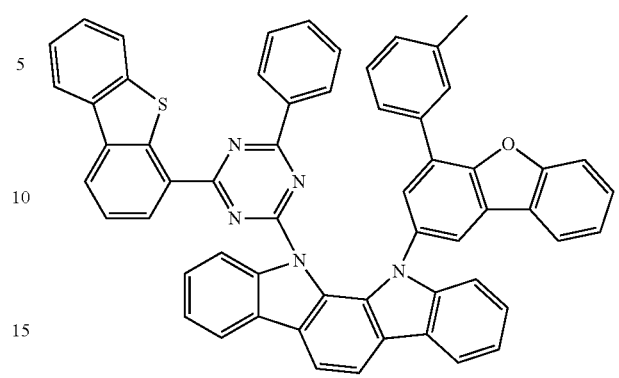
A86
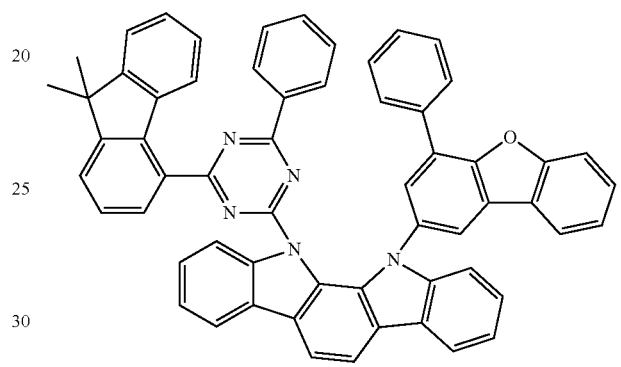
A87
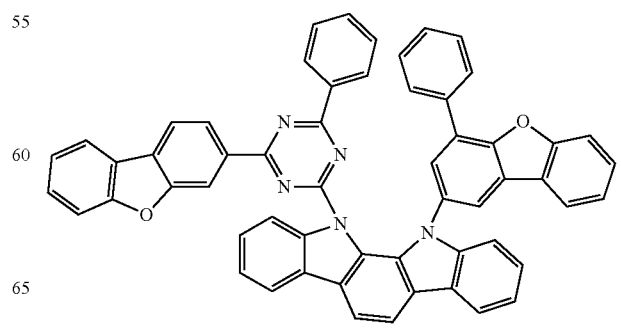
A88

-continued
A89
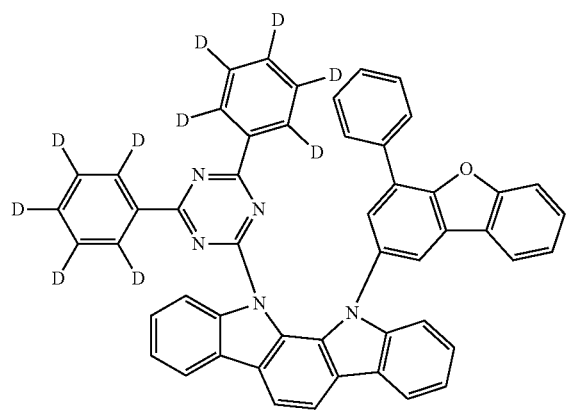
A90
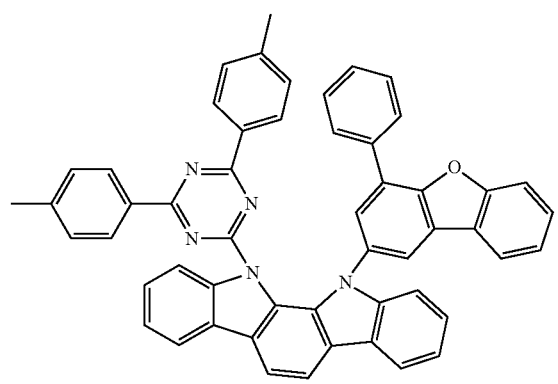
A91
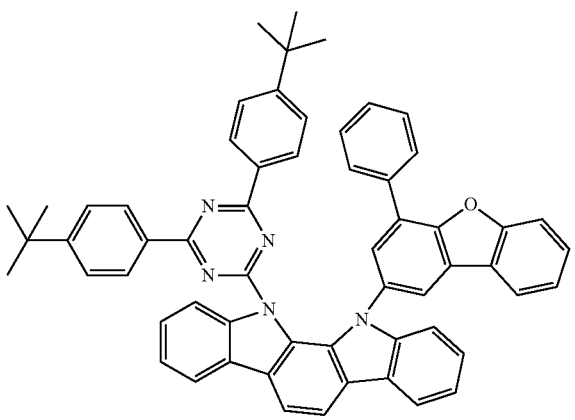
A92
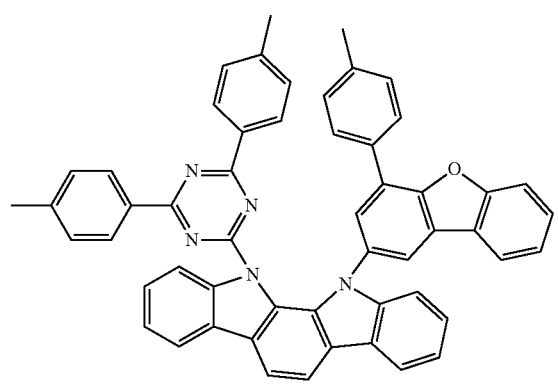
-continued
A93
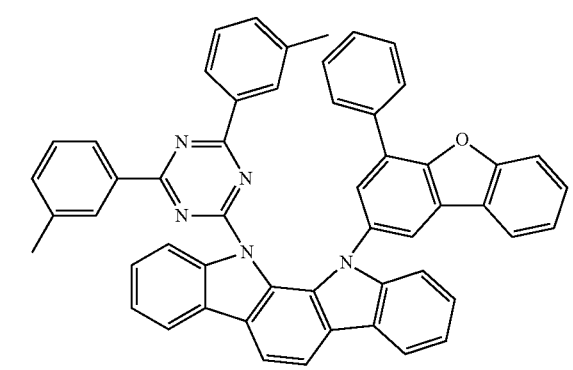
A94
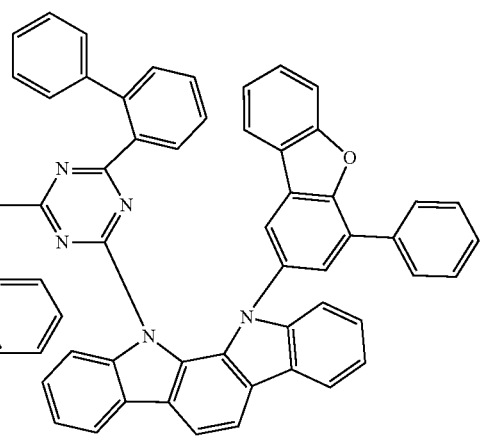
A95
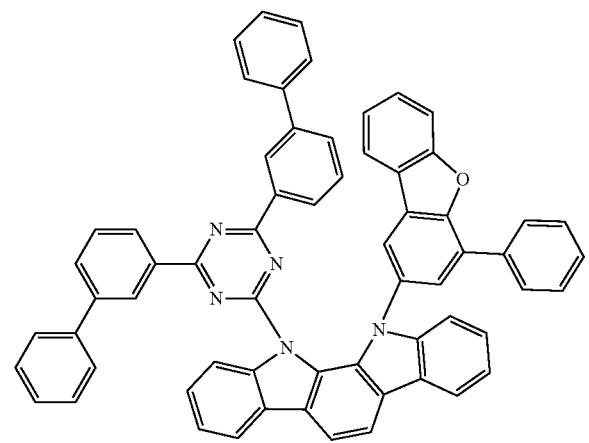

A96
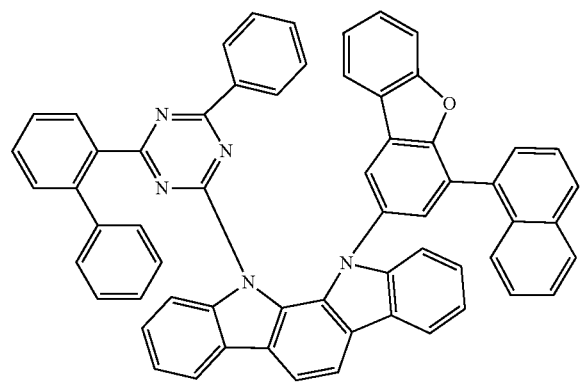
A97
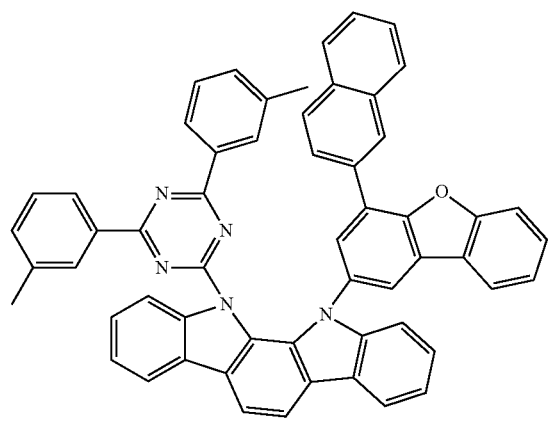
A98
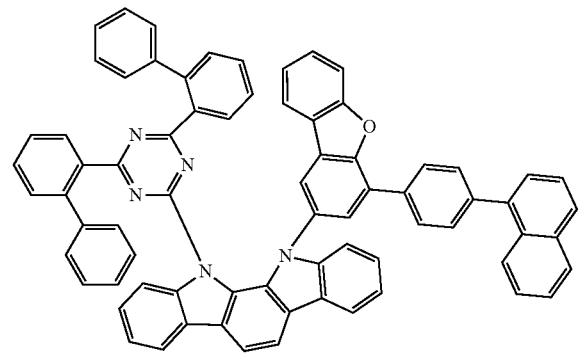
A99
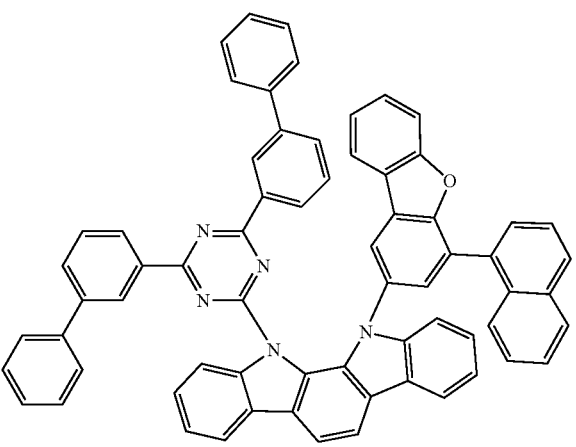
A100
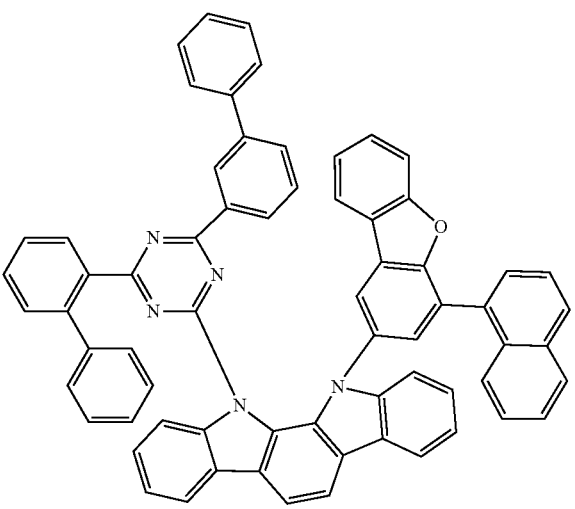
A101
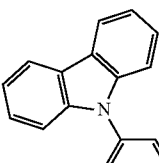

-continued
A102
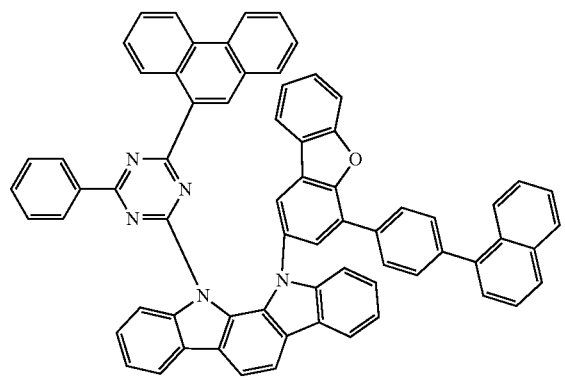
A103
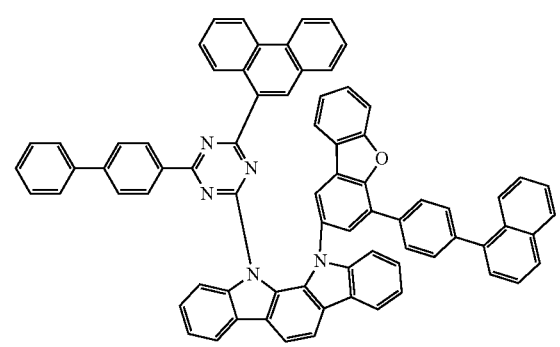
A104
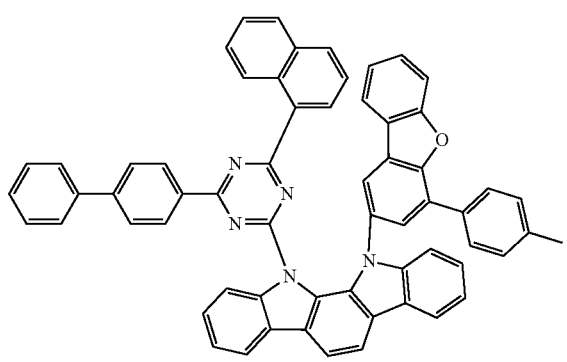
A105
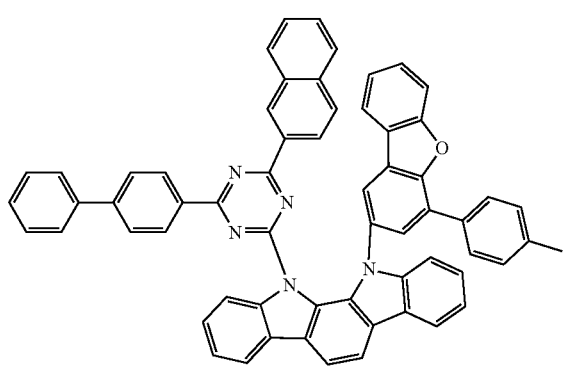
-continued
A106
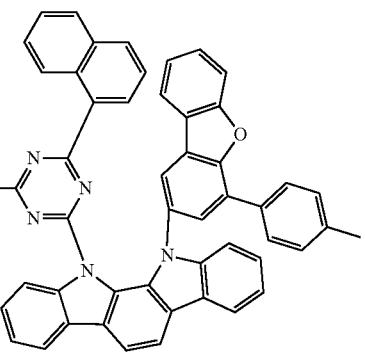
A107
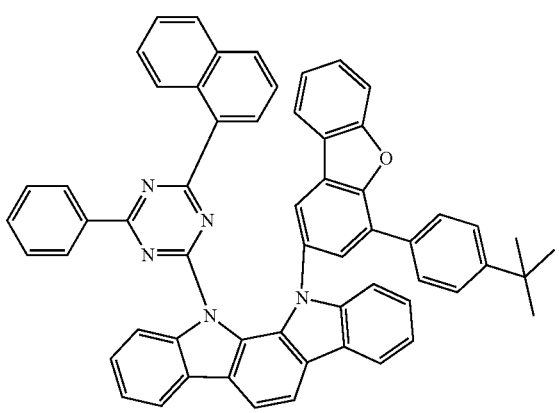
A108
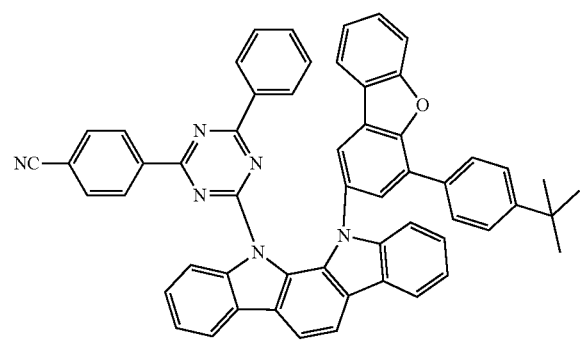
A109
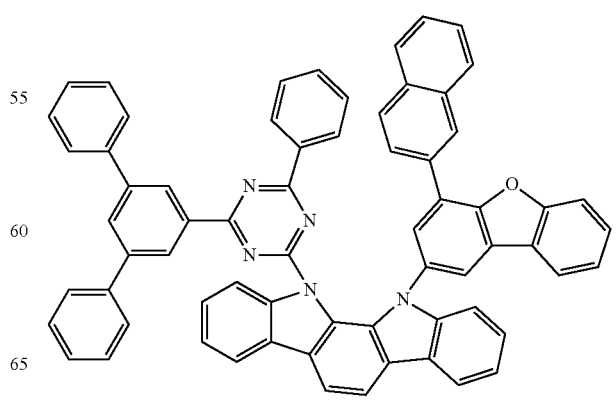

A110
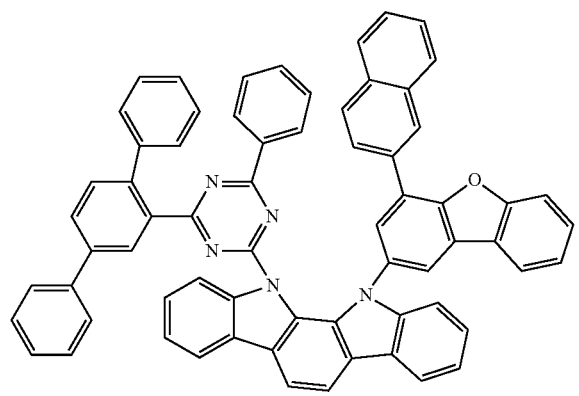
A111
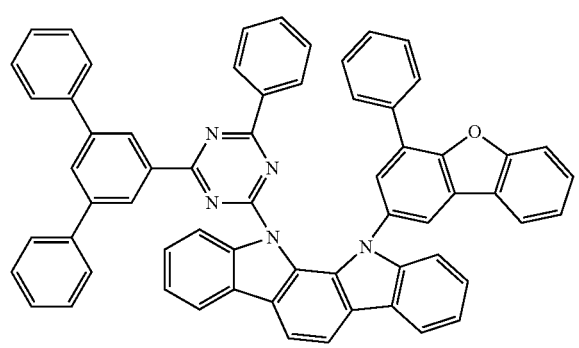
A112
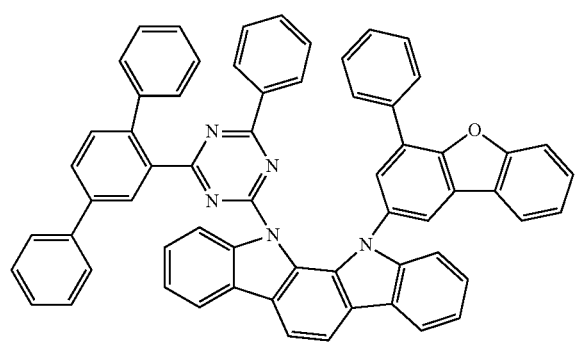
F1
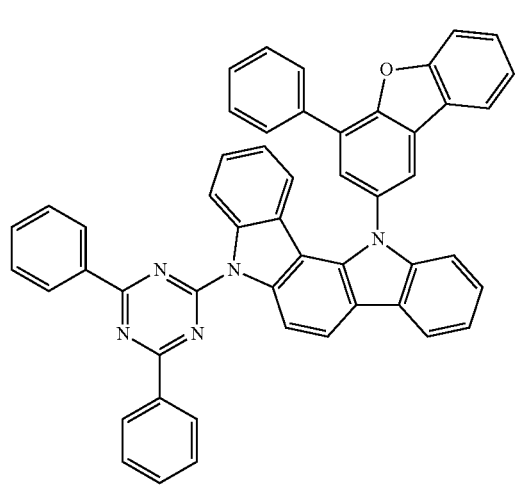
F2
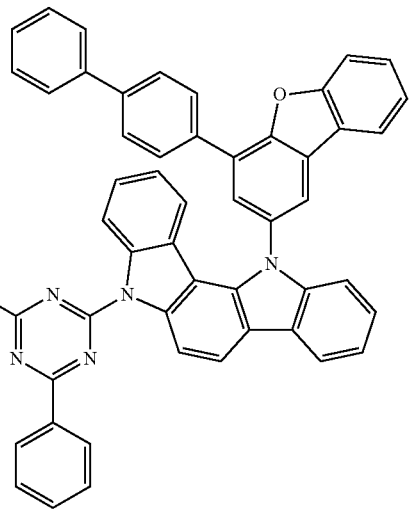
F3
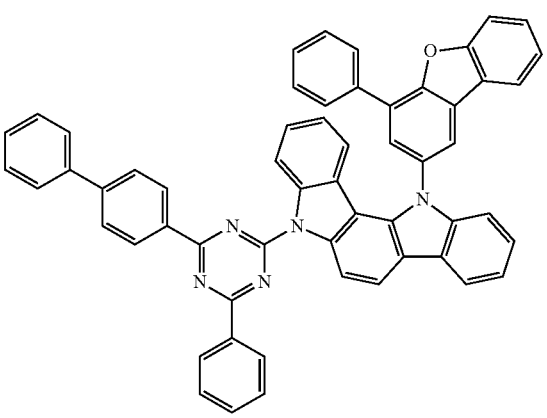
F4
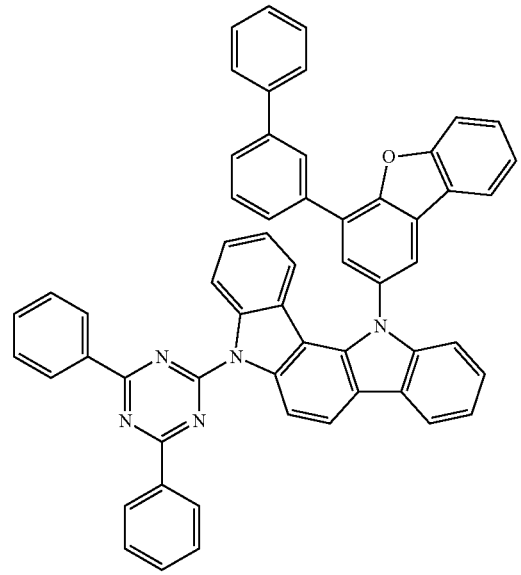

-continued
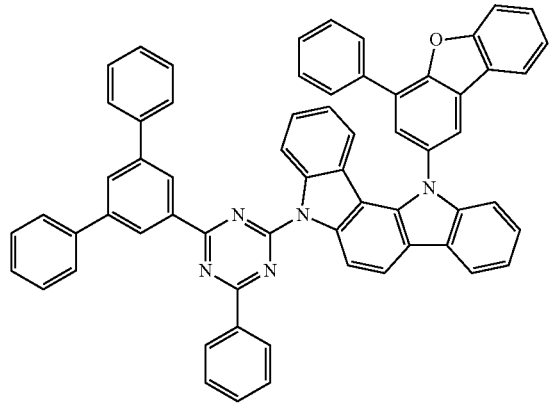
F5
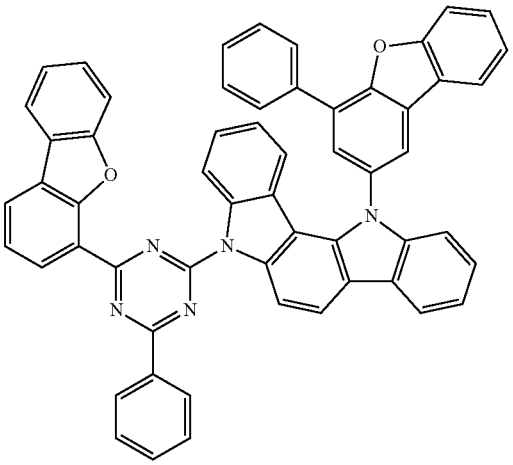
F8
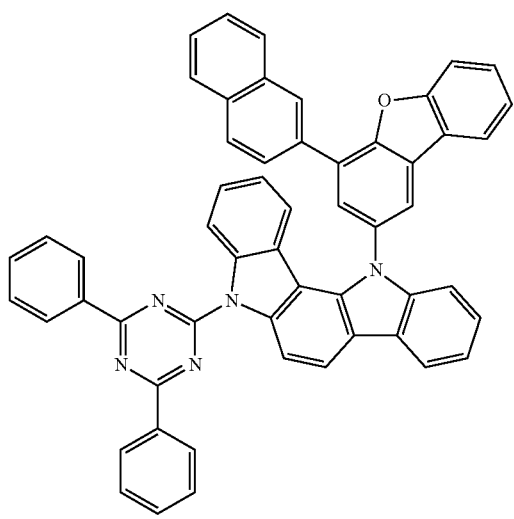
F6
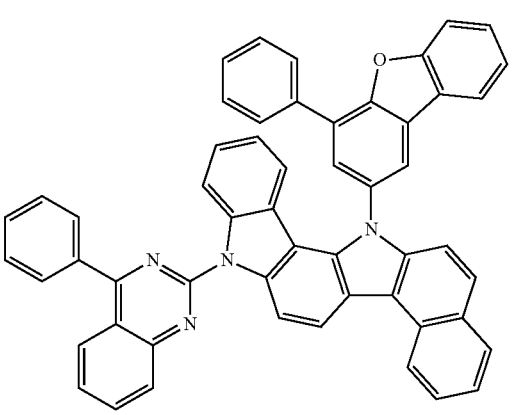
F9
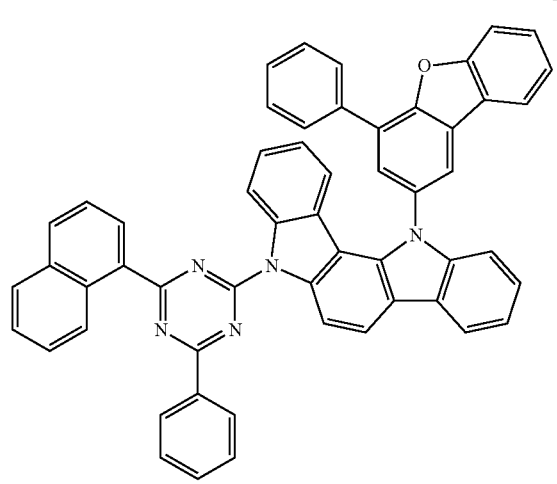
F7
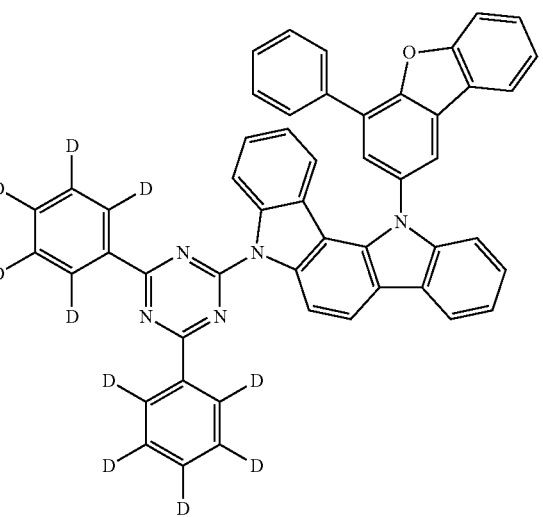
F10

71
-continued
B1
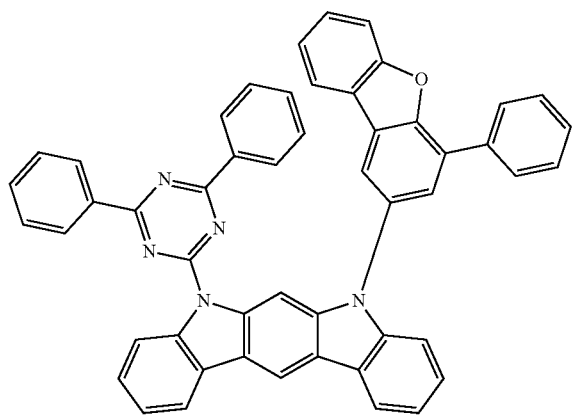
B2
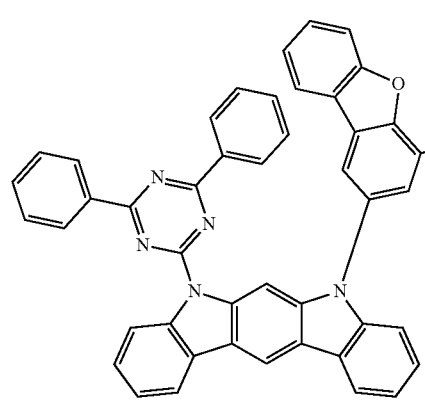
B3
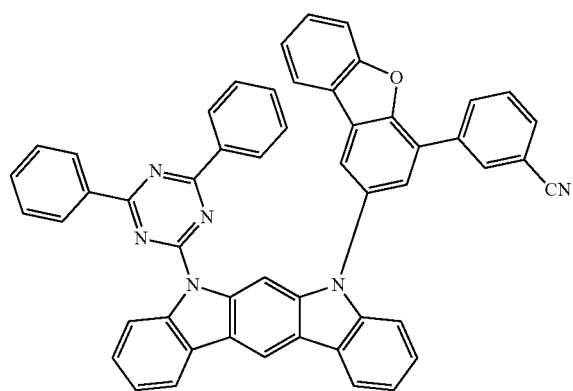
72
-continued
B4
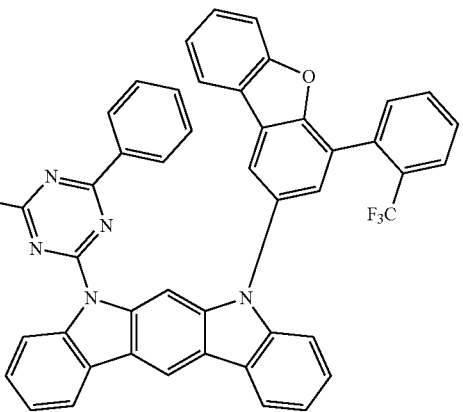
B5
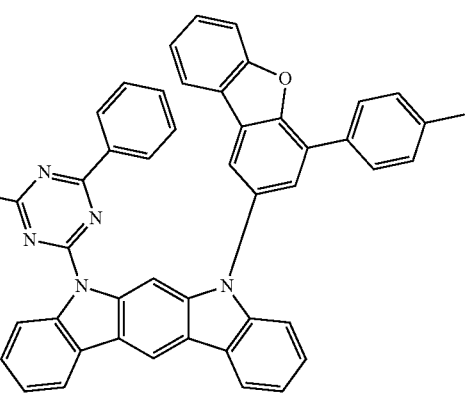
B6
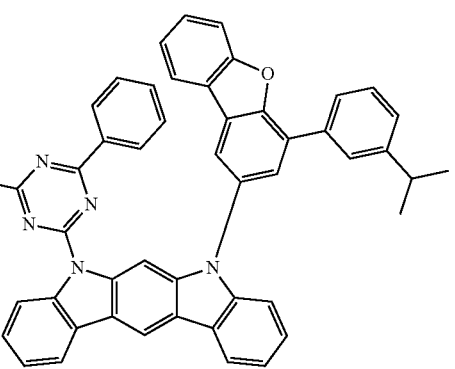
B7
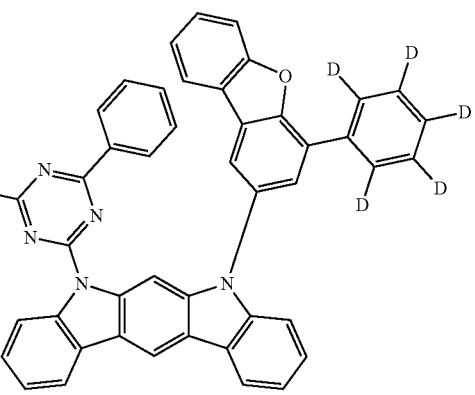

B8
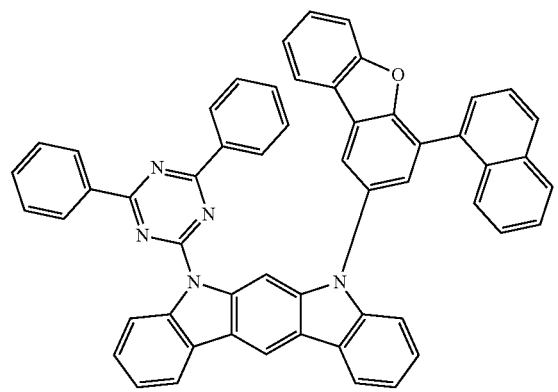
B9
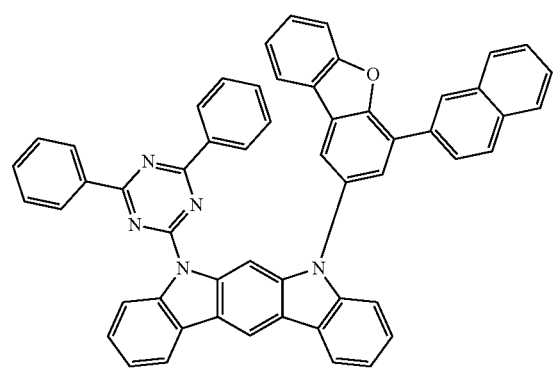
B10
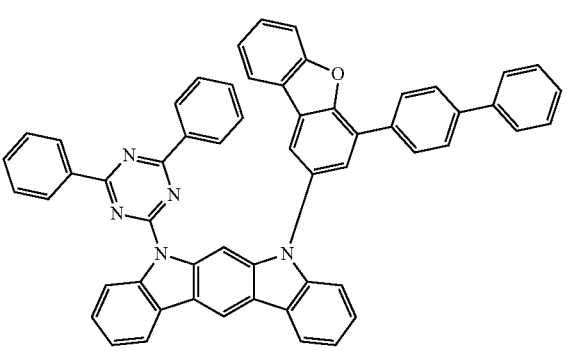
B11
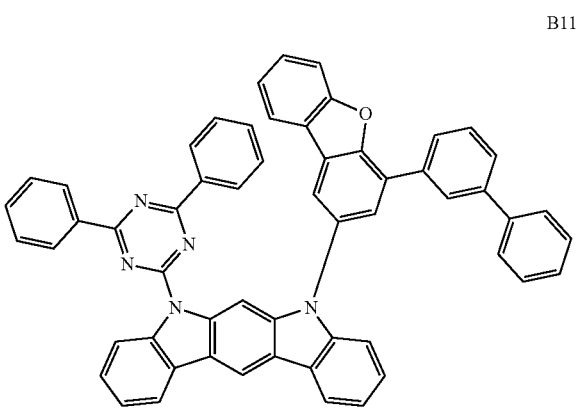
B12
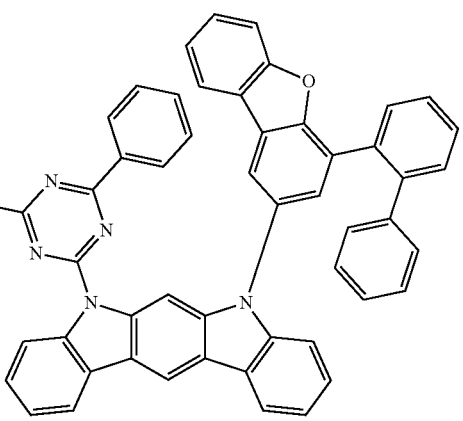
B13
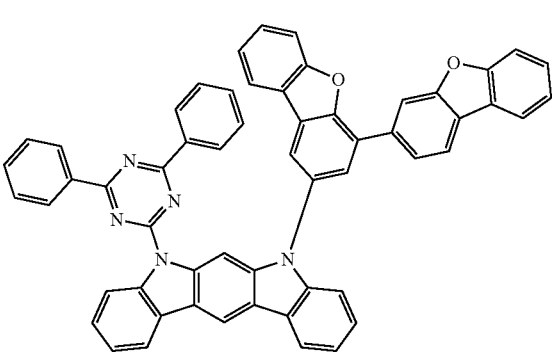
B14
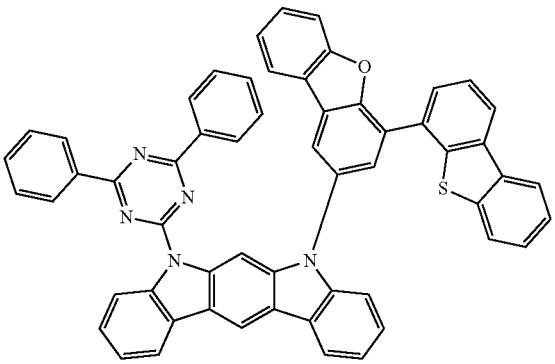
B15
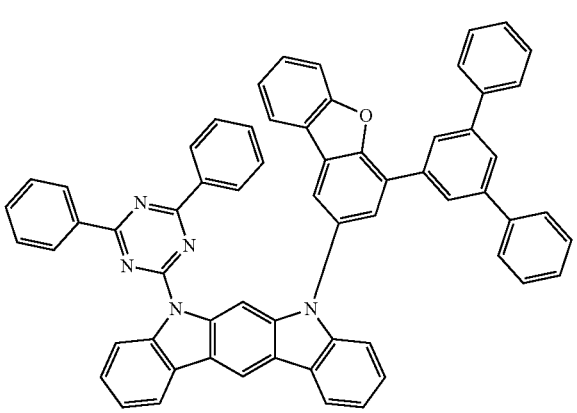

B16
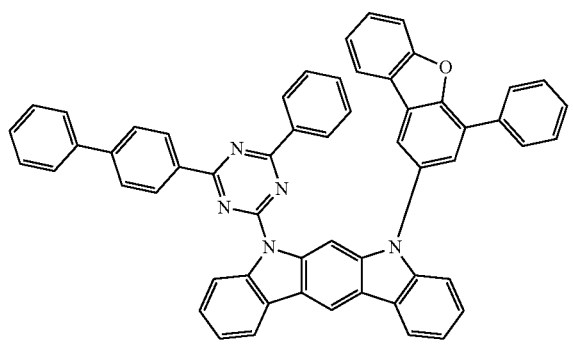
B17
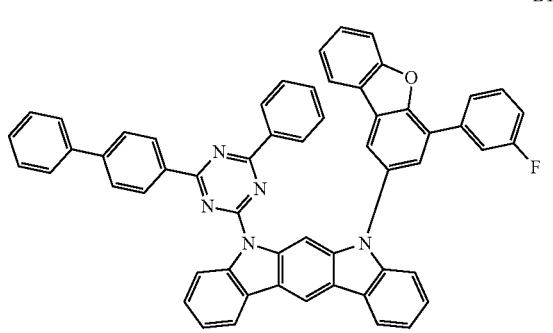
B18
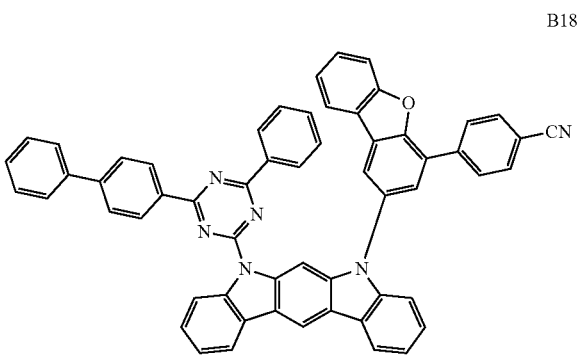
B19
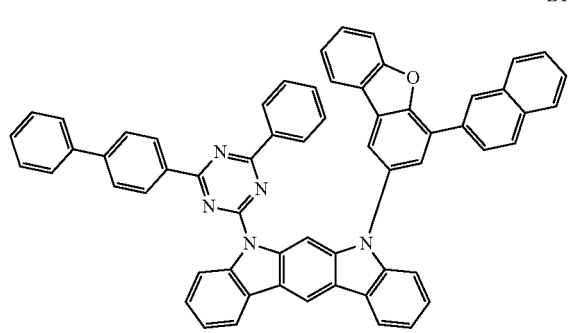
B20
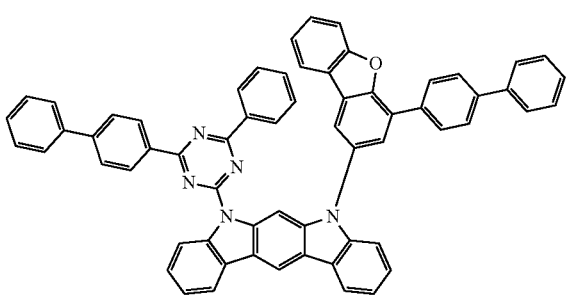
B21
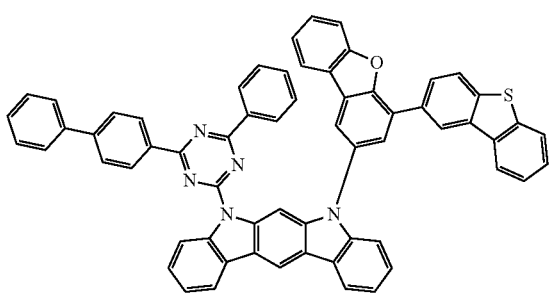
B22
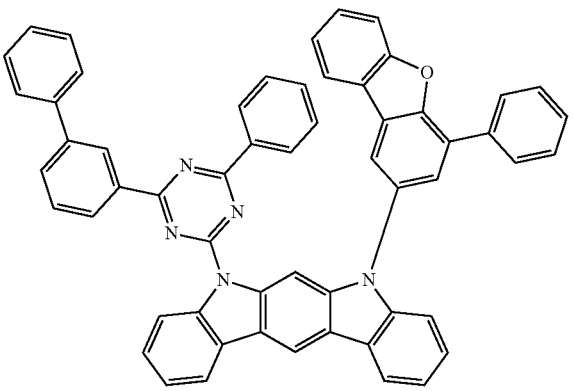
B23
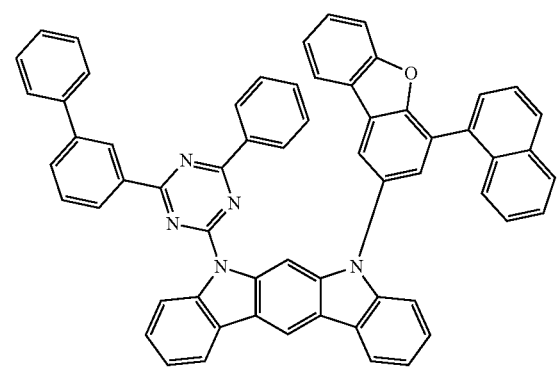

-continued
B24
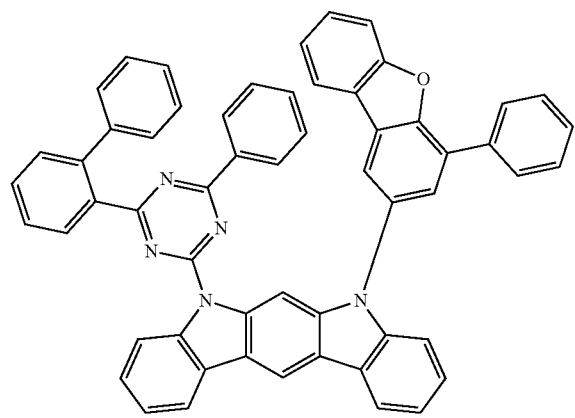
B25
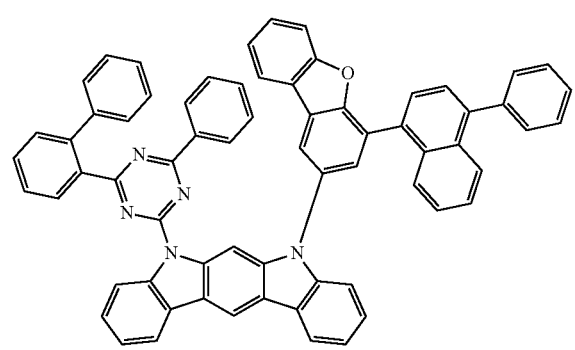
B26
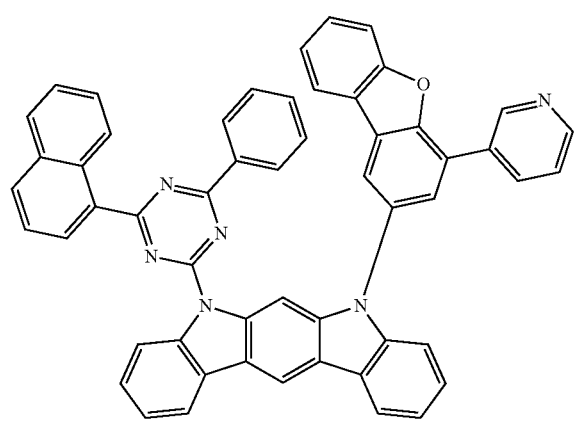
B27
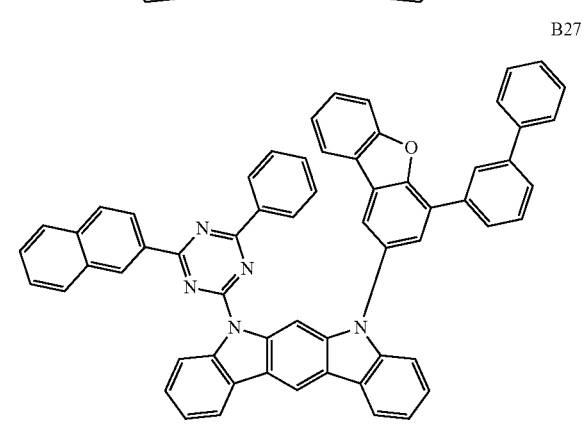
-continued
B28
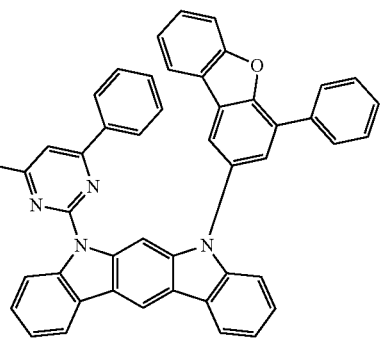
B29
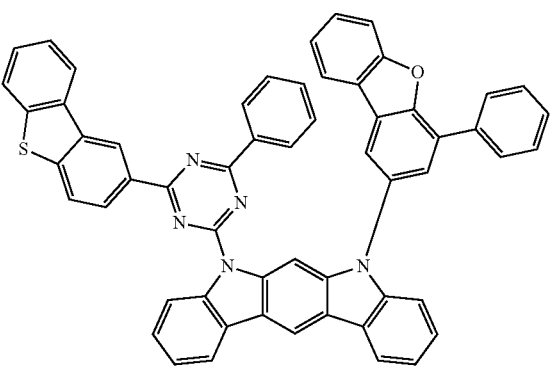
B30
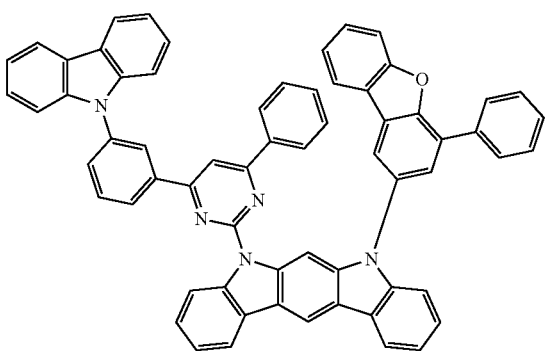
B31
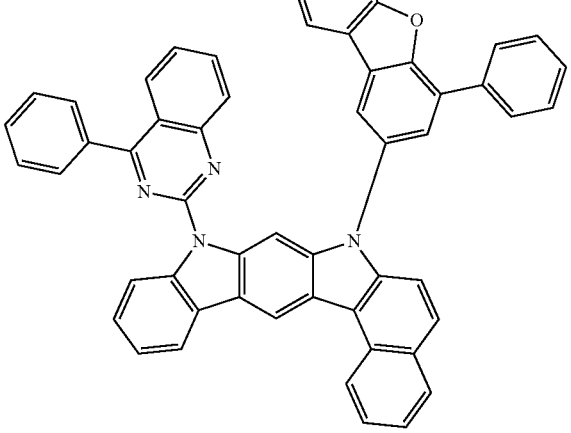

B32
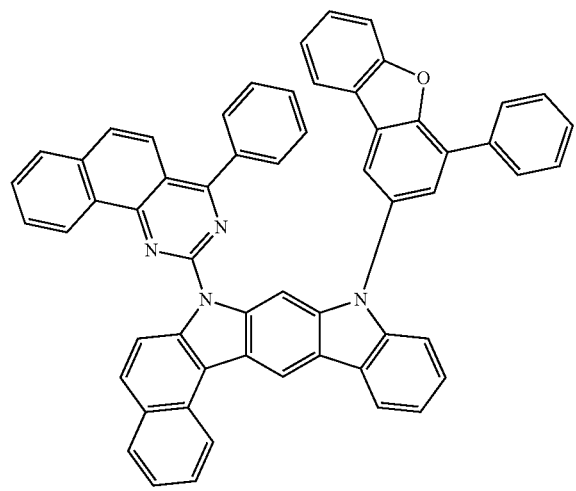
B33
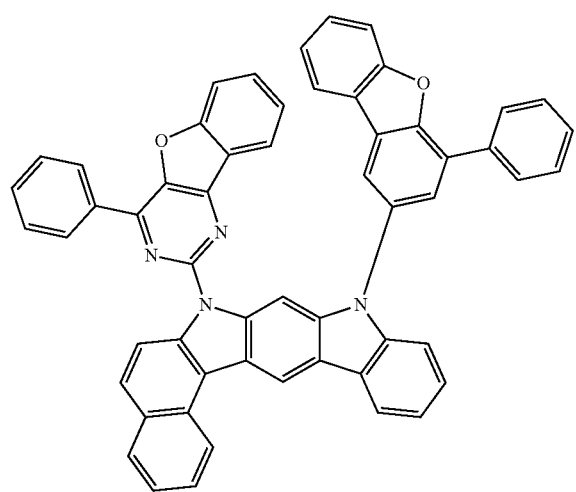
D1
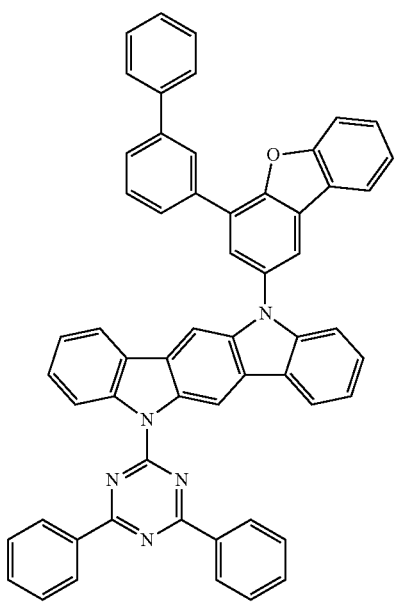
D2
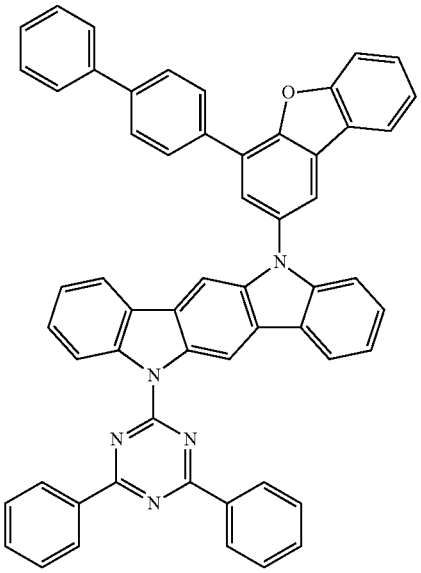
D3
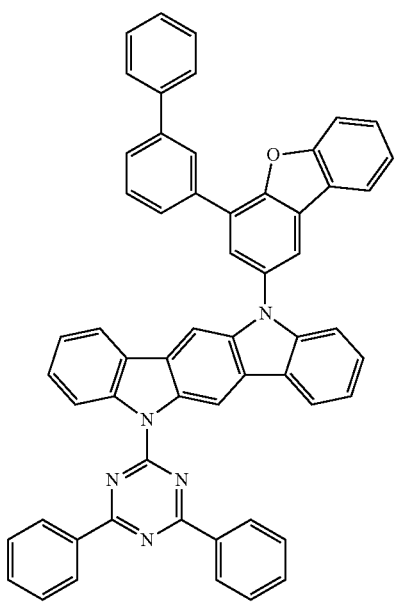

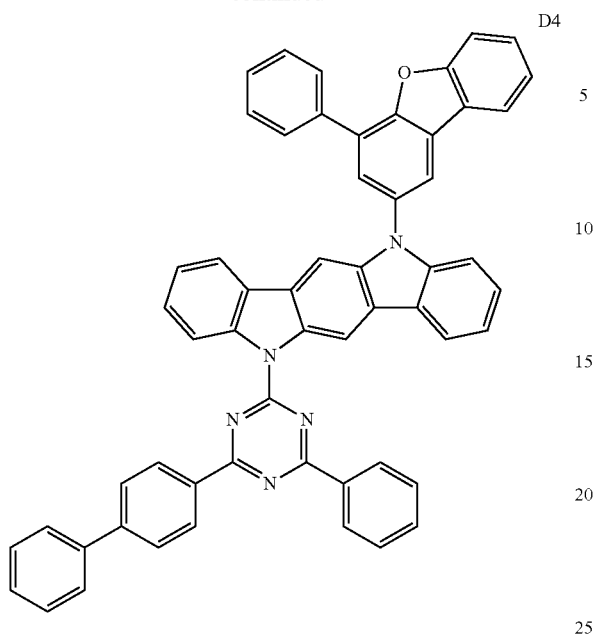
D4
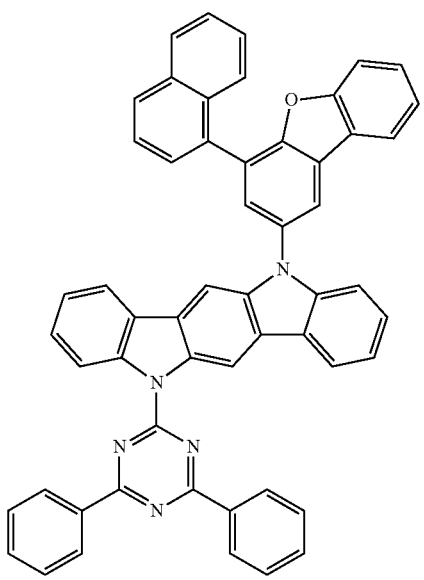
D6
D5
D7
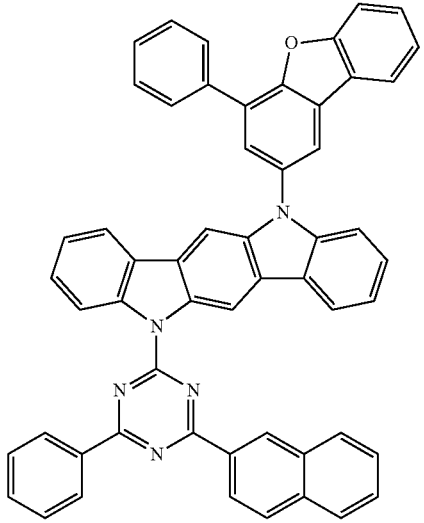

D8
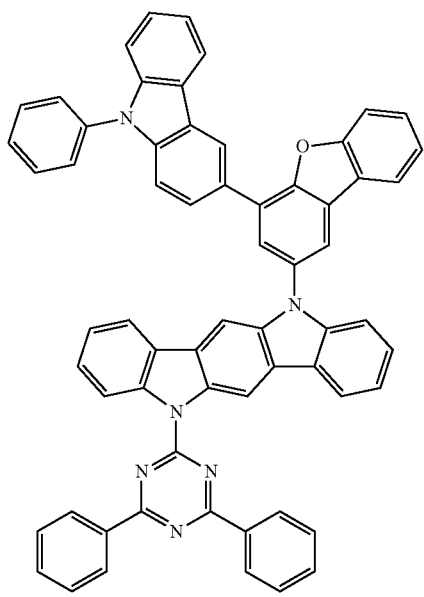
D9
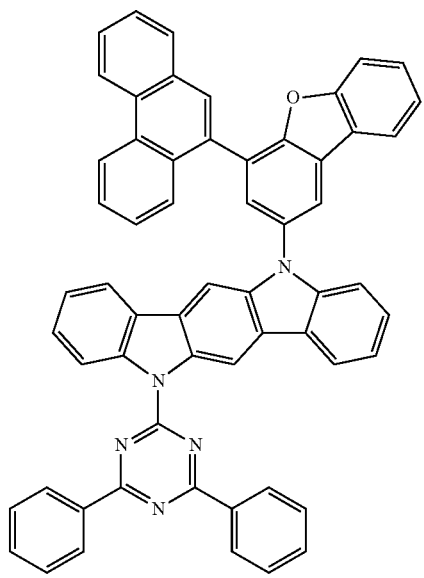
D10
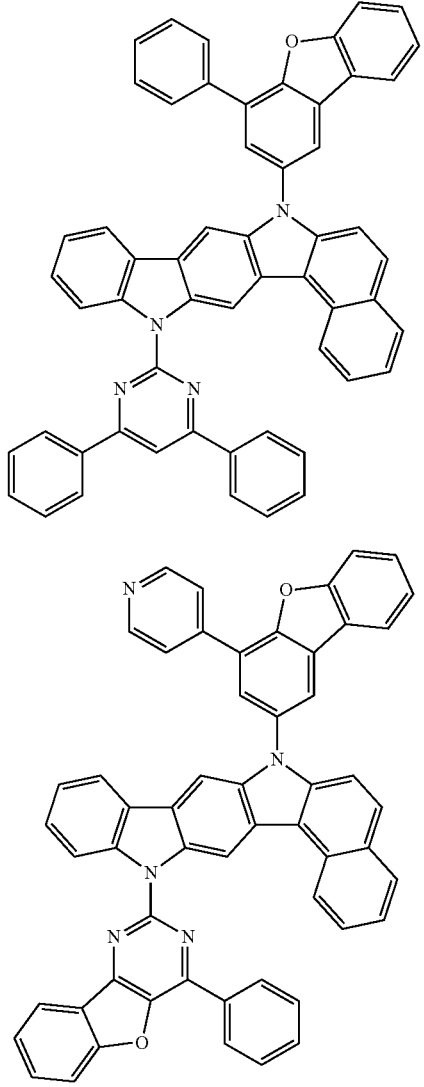
D11
D12
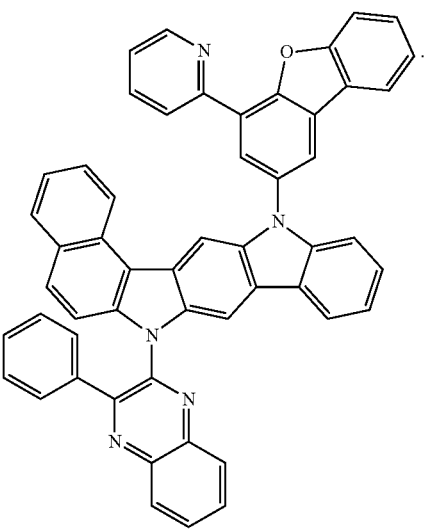
A synthesis method of the provided organic compound is not specially limited by the present disclosure, and those skilled in the art can determine a proper synthesis method according to the organic compound of the present disclosure in combination with a preparation method provided in the synthesis example part. In other words, the synthesis example part of the present disclosure provides a preparation method of the organic compound in an example manner, and the adopted raw materials can be obtained commercially or by a method well known in the field. All the organic compounds provided by the present disclosure can be obtained by those skilled in the art according to these example preparation methods, and all specific preparation methods for preparing the organic compound are no longer detailed here, which should not be understood by those skilled in the art as limiting the present disclosure.

In a second aspect, the present disclosure provides an electronic component, including an anode and a cathode which are oppositely arranged, and a functional layer arranged between the anode and the cathode. The functional layer contains the organic compound described in the first aspect of the present disclosure.

The organic compound provided by the present disclosure can be used for forming at least one organic film layer in the functional layer so as to improve the efficiency characteristic and the service life characteristic of the electronic component.

In one specific embodiment of the present disclosure, the functional layer includes an organic luminescent layer, and the organic luminescent layer includes the organic compound. Generally, the organic luminescent layer may contain a host material and a guest material, and the host material contains the organic compound of the present disclosure.

According to one embodiment of the present disclosure, the electronic component is an organic electroluminescent device, such as a green light device or a red light device. As shown in FIG. 1, the organic electroluminescent device may include an anode 100, a first hole transport layer 321, a second hole transport layer 322, an organic luminescent layer 330 serving as an energy conversion layer, an electron transport layer 340 and a cathode 200 which are sequentially stacked.

Optionally, the anode 100 includes the following anode material, which is preferably a material having a large work function that facilitates hole injection into the functional layer. Specific examples of the anode materials include metals such as nickel, platinum, vanadium, chromium, copper, zinc, and gold, or their alloys; metal oxides such as zinc oxide, indium oxide, indium tin oxide (ITO) and indium zinc oxide (IZO); combined metals and oxides, such as ZnO:Al or $SnO_2$:Sb; or a conductive polymer such as poly(3-methylthiophene), poly[3,4-(ethylene-1,2-dioxy)thiophene] (PEDT), polypyrrole, and polyaniline, but are not limited to thereto. It preferably includes a transparent electrode containing indium tin oxide (ITO) as the anode.

Optionally, the first hole transport layer 321 and the second hole transport layer 322 respectively include one or more hole transport materials, and the hole transport materials may be selected from a carbazole polymer, carbazole connected triarylamine compounds or other types of compounds.

Optionally, the organic luminescent layer 330 may be composed of a single luminescent material, and may also include a host material and a guest material. The host material of the organic luminescent layer 330 may contain the organic compound of the present disclosure. Further optionally, the organic luminescent layer 330 is composed of the host material and the guest material, the holes and electrons injected into the organic luminescent layer 330 may be recombined in the organic luminescent layer 330 to form excitons, the excitons transfer energy to the host material, the host material transfers energy to the guest material, and then the guest material can emit light.

The guest material of the organic luminescent layer 330 may be a compound having a condensed aryl ring or its derivative, a compound having a heteroaryl ring or its derivative, an aromatic amine derivative, or other materials, which is not specially limited in the present disclosure.

According to a specific embodiment, the organic electroluminescent device is a green light device or a red light device, and the organic luminescent layer 330 may be composed of the organic compound provided by the present disclosure; or the organic luminescent layer 330 may be composed of the organic compound provided in the present disclosure and $Ir(piq)_2(acac)$ or GH-p and $Ir(ppy)_3$ together.

The electron transport layer 340 may be of a single-layer structure or a multi-layer structure and may include one or more electron transport materials, and the electron transport materials may be selected from, but are not limited to, a benzimidazole derivative, an oxadiazole derivative, a quinoxaline derivative or other electron transport materials. For example, in one implementation of the present disclosure, the electron transport layer 340 may be composed of ET-01 and LiQ.

In the present disclosure, the cathode 200 may include a cathode material, which is a material with a small work function that facilitates electron injection into the functional layer. Specific examples of the cathode material include, but are not limited to, metals such as magnesium, calcium, sodium, potassium, titanium, indium, yttrium, lithium, gadolinium, aluminum, silver, tin, and lead, or their alloy; or a multi-layer material such as LiF/Al, Liq/Al, $LiO_2$/Al, LiF/Ca, LiF/Al and $BaF_2$/Ca. It is preferable to include a metal electrode containing magnesium and silver as the cathode.

Optionally, as shown in FIG. 1, a hole injection layer 310 may further be arranged between the anode 100 and the first hole transport layer 321, so as to enhance the ability of injecting holes into the first hole transport layer 321. The hole injection layer 310 may be selected from a benzidine derivative, a starburst arylamine compound, a phthalocyanine derivative or other materials, which is not specially limited in the present disclosure. For example, the hole injection layer 310 may be composed of F4-TCNQ.

Optionally, as shown in FIG. 1, an electron injection layer 350 may further be arranged between the cathode 200 and the electron transport layer 340 so as to enhance a ability of injecting electrons into the electron transport layer 340. The electron injection layer 350 may include an inorganic material such as an alkali metal sulfide, and an alkali metal halide, or may include a complex of an alkali metal and an organic substance. For example, the electron injection layer 350 may include LiQ or Yb.

In a third aspect, the present disclosure provides an electronic device containing the electronic component described in the second aspect of the present disclosure.

Figure 2:
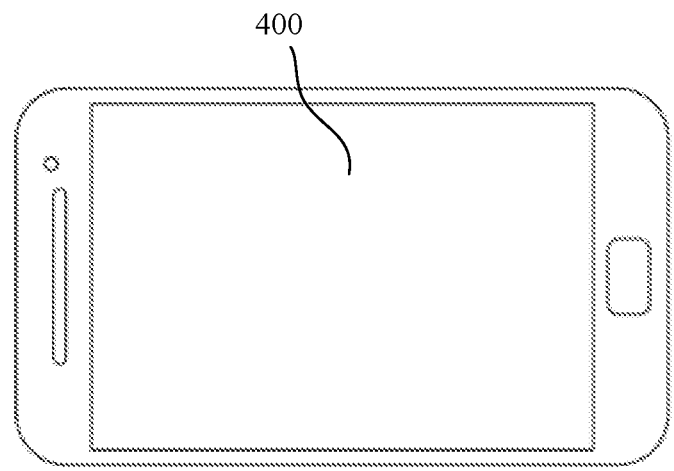
FIG. 2 is a schematic structural diagram of a first electronic device according to one implementation of the present disclosure.

According to one embodiment, as shown in FIG. 2, the electronic device is a first electronic device 400, and the first electronic device 400 includes the above organic electroluminescent device. The first electronic device 400 may, for example, be a display apparatus, a lighting apparatus, an optical communication apparatus or other types of electronic devices, and may include, for example, but is not limited to, a computer screen, a mobile phone screen, a television, electronic paper, an emergency lighting lamp, an optical module and the like.

The compounds in the synthesis method which are not mentioned in the present disclosure are all commercially available raw material products.

An ICP-7700 mass spectrometer is used for analysis and detection of intermediates and compounds in the present disclosure.

A synthesis method of the organic compound of the present disclosure is specifically described below in combination with synthesis examples.

Synthesis of Intermediate IM-i1

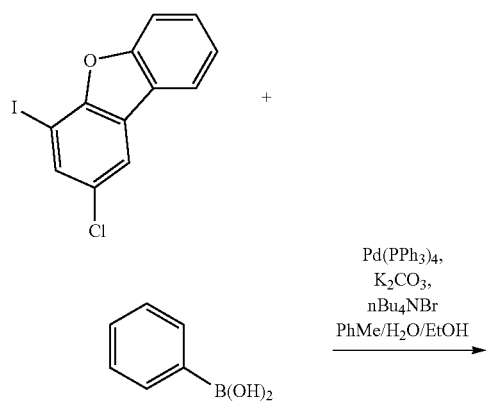

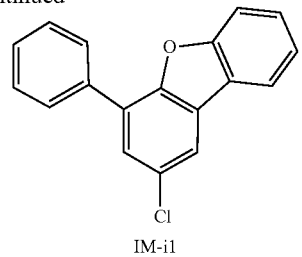

IM-i1

2-chloro-4-iododibenzofuran (30.0 g, 91.3 mmol), phenylboronic acid (12.2 g, 100.4 mmol), tetrakis(triphenylphosphine)palladium (2.1 g, 1.8 mmol), potassium carbonate (25.2 g, 182.6 mmol), tetrabutylammonium bromide (5.9 g, 18.3 mmol), toluene (240 mL), water (60 mL) and ethanol (60 mL) were added into a round-bottom flask, and stirred at 110° C. for a reaction for 6 hours under the protection of nitrogen; when the temperature was cooled to room temperature, the reaction solution was separated after being washed with water, an organic phase was dried with anhydrous magnesium sulfate, and a solvent was removed under reduced pressure to obtain a crude product; and the crude product was purified by silica gel column chromatography using dichloromethane/n-heptane as an eluent to obtain a white solid compound intermediate IM-i1 (21.0 g; 83%).

Referring to the synthesis method of the intermediate IM-i1, a reactant A in Table 1 below is used to replace phenylboronic acid to synthesize an intermediate structure shown in the table below.

TABLE 1

| Intermediate | Reactant A | Structure | Yield |
|---|---|---|---|
| IM-i2 | ![F-C6H4-B(OH)2] | ![structure] | 71% |
| IM-i3 | ![CN-C6H4-B(OH)2] | ![structure] | 65% |

TABLE 1-continued

| Intermediate | Reactant A | Structure | Yield |
|---|---|---|---|
| IM-i4 | 3-biphenylboronic acid | 4-(biphenyl-3-yl)-2-chlorodibenzofuran | 74% |
| IM-i5 | 4'-fluorobiphenyl-4-boronic acid | 4-(4'-fluorobiphenyl-4-yl)-2-chlorodibenzofuran | 68% |
| IM-i6 | naphthalen-1-ylboronic acid | 4-(naphthalen-1-yl)-2-chlorodibenzofuran | 74% |
| IM-i7 | naphthalen-2-ylboronic acid | 4-(naphthalen-2-yl)-2-chlorodibenzofuran | 69% |
| IM-i8 | biphenyl-4-boronic acid | 4-(biphenyl-4-yl)-2-chlorodibenzofuran | 68% |
| IM-i9 | 4-tert-butylphenylboronic acid | 4-(4-tert-butylphenyl)-2-chlorodibenzofuran | 82% |

TABLE 1-continued

| Intermediate | Reactant A | Structure | Yield |
| --- | --- | --- | --- |
| IM-i10 | (HO)₂B-biphenyl | 2-chloro-6-(2-biphenyl)dibenzofuran | 64% |
| IM-i11 | (HO)₂B-pyridin-3-yl | 2-chloro-6-(pyridin-3-yl)dibenzofuran | 57% |
| IM-i12 | phenanthren-1-yl-B(OH)₂ | 2-chloro-6-(phenanthren-1-yl)dibenzofuran | 62% |
| IM-i13 | 3-methylphenyl-B(OH)₂ | 2-chloro-6-(3-methylphenyl)dibenzofuran | 58% |
| IM-i14 | (d5-phenyl)-B(OH)₂ | 2-chloro-6-(d5-phenyl)dibenzofuran | 51% |

Synthesis of Intermediate IM-a1

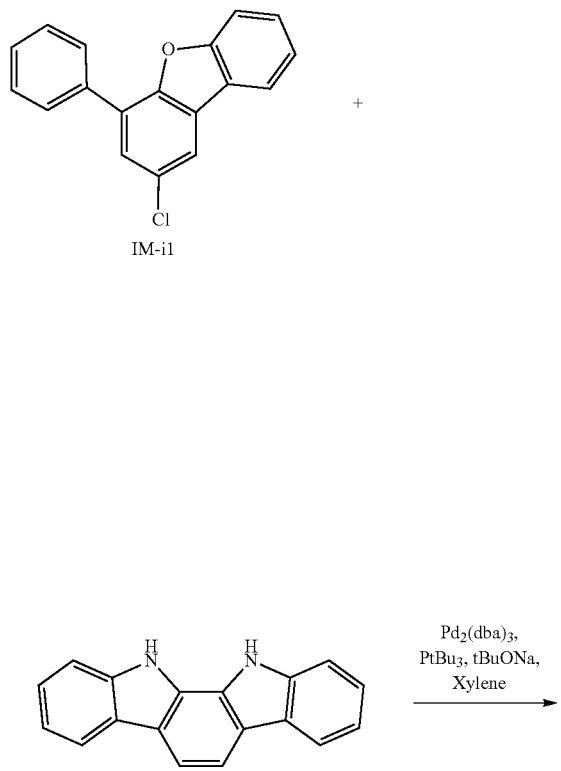

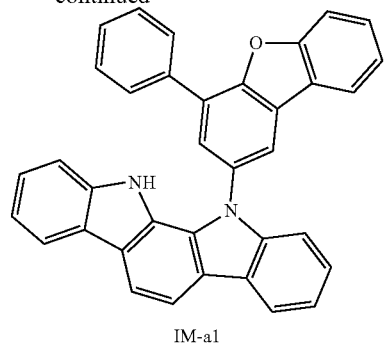

IM-a1

The intermediate IM-i1 (10.0 g, 35.9 mmol), indolo[2,3-a]carbazole (10.1 g, 39.5 mmol), tris(dibenzylideneacetone)dipalladium (0.7 g, 0.7 mmol), tri-tert-butylphosphine (0.3 g, 1.4 mmol), sodium tert-butoxide (5.2 g, 53.8 mmol) and xylene (100 mL) were added into a round-bottom flask, and stirred at 140° C. for a reaction for 10 hours under the protection of nitrogen; when the temperature was cooled to room temperature, the reaction solution was separated after being washed with water, an organic phase was dried with anhydrous magnesium sulfate, and a solvent was removed under reduced pressure to obtain a crude product; and the crude product was purified by silica gel column chromatography using dichloromethane/n-heptane as an eluent to obtain a white solid compound intermediate IM-a1 (11.1 g, 62%).

Referring to the synthesis method of the intermediate IM-a1, a reactant C in Table 2 below is used to replace the intermediate IM-i1, and a reactant B is used to replace indolo[2,3-a]carbazole to synthesize an intermediate structure shown in the table below.

TABLE 2

| Intermediate | Reactant C | Reactant B |
|---|---|---|
| IM-a2 | (3-fluorophenyl dibenzofuran with Cl) | (indolo[2,3-a]carbazole) |
| IM-a3 | (3-cyanophenyl dibenzofuran with Cl) | (indolo[2,3-a]carbazole) |

TABLE 2-continued
IM-a4 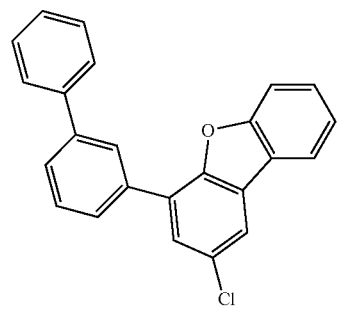 [SMILES: Clc1cc(-c2cccc(-c3ccccc3)c2)c2oc3ccccc3c2c1] 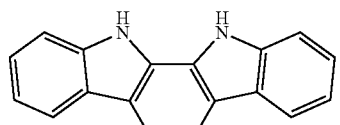
IM-a5 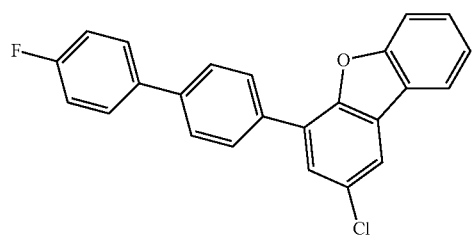 [SMILES: Fc1ccc(-c2ccc(-c3cc(Cl)cc4c3oc3ccccc34)cc2)cc1] 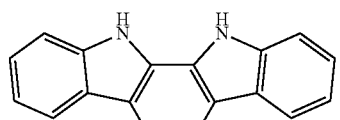
IM-a6 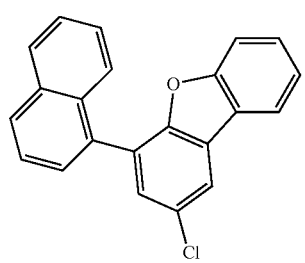 [SMILES: Clc1cc(-c2cccc3ccccc23)c2oc3ccccc3c2c1] 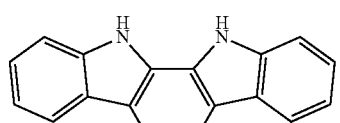
IM-a7 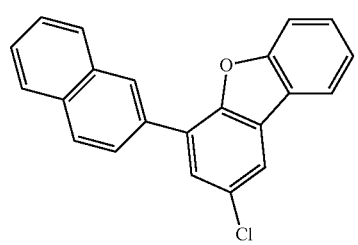 [SMILES: Clc1cc(-c2ccc3ccccc3c2)c2oc3ccccc3c2c1] 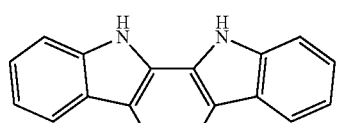
IM-a8 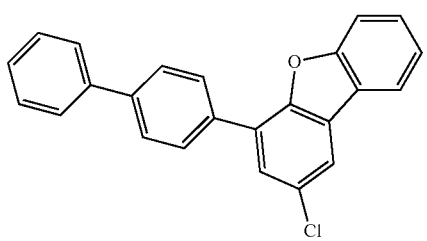 [SMILES: Clc1cc(-c2ccc(-c3ccccc3)cc2)c2oc3ccccc3c2c1] 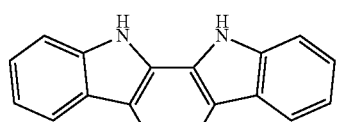
IM-a9 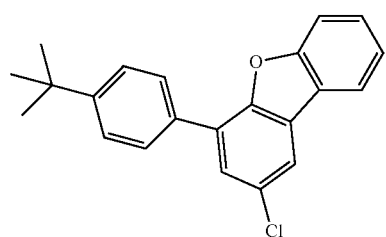 [SMILES: CC(C)(C)c1ccc(-c2cc(Cl)cc3c2oc2ccccc23)cc1] 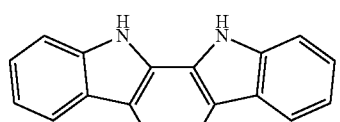

TABLE 2-continued
IM-a11 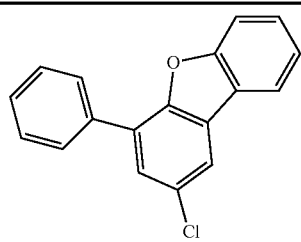 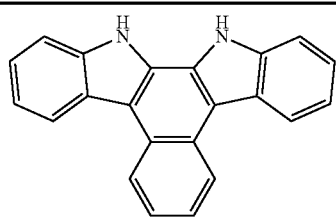
IM-a11 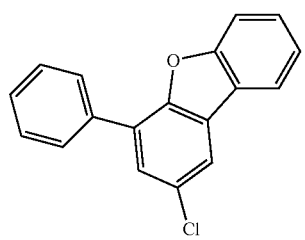 [SMILES: Clc1cc(-c2ccccc2)c2oc3ccccc3c2c1] 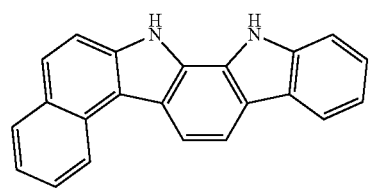 [SMILES: c1ccc2c(c1)ccc1[nH]c3c(ccc4c5ccccc5[nH]c43)c12]
IM-f1 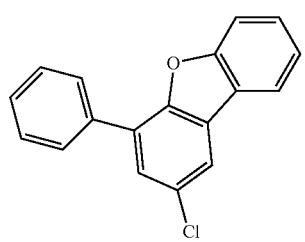 [SMILES: Clc1cc(-c2ccccc2)c2oc3ccccc3c2c1] 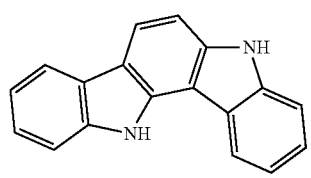 [SMILES: c1ccc2c(c1)[nH]c1c2ccc2[nH]c3ccccc3c21]
IM-g1 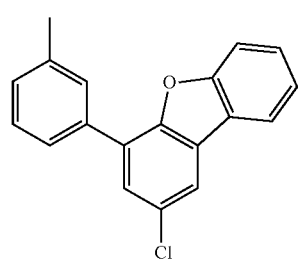 [SMILES: Cc1cccc(-c2cc(Cl)cc3c2oc2ccccc23)c1] 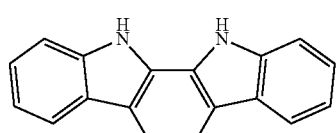
IM-h1 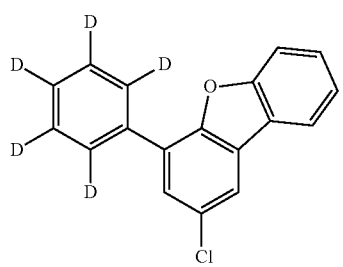 [SMILES: [2H]c1c([2H])c([2H])c(-c2cc(Cl)cc3c2oc2ccccc23)c([2H])c1[2H]] 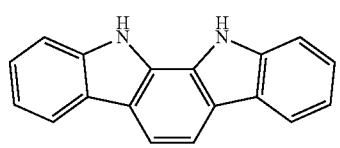 [SMILES: c1ccc2c(c1)[nH]c1c2ccc2c3ccccc3[nH]c21]
| Intermediate | Structure | Yield |
| --- | --- | --- |
| IM-a2 | 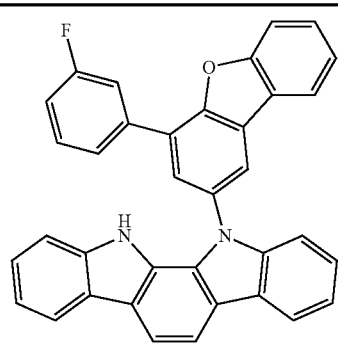 | 72% |

TABLE 2-continued
| | | |
|---|---|---|
| IM-a3 | 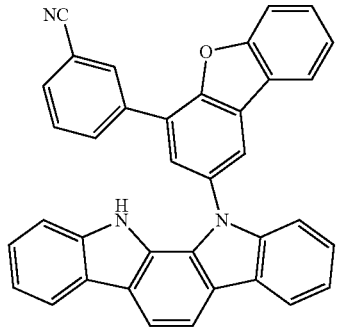 [SMILES: Fc1cccc(-c2cc(-n3c4ccccc4c4ccc5c6ccccc6[nH]c5c43)cc3c2oc2ccccc23)c1] | 62% |
| IM-a4 | 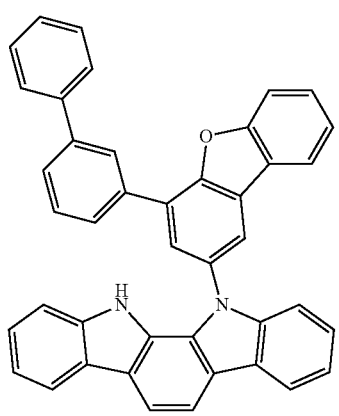 [SMILES: c1ccc(-c2cccc(-c3cc(-n4c5ccccc5c5ccc6c7ccccc7[nH]c6c54)cc4c3oc3ccccc34)c2)cc1] | 48% |
| IM-a5 | 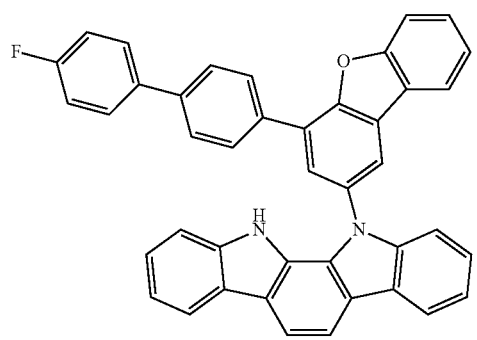 [SMILES: Fc1ccc(-c2ccc(-c3cc(-n4c5ccccc5c5ccc6c7ccccc7[nH]c6c54)cc4c3oc3ccccc34)cc2)cc1] | 59% |
| IM-a6 | 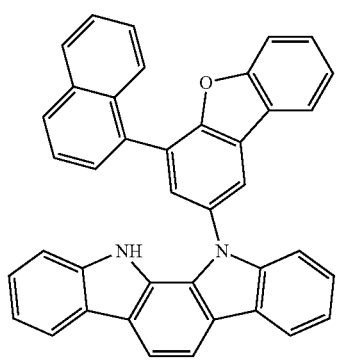 [SMILES: c1ccc2c(-c3cc(-n4c5ccccc5c5ccc6c7ccccc7[nH]c6c54)cc4c3oc3ccccc34)cccc2c1] | 55% |

TABLE 2-continued
| | | |
|---|---|---|
| IM-a7 | 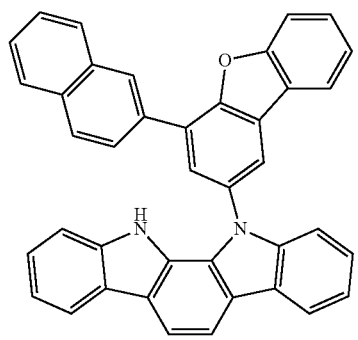 [SMILES: c1ccc2cc(-c3cc(-n4c5ccccc5c5ccc6c7ccccc7[nH]c6c54)cc4c3oc3ccccc34)ccc2c1] | 62% |
| IM-a8 | 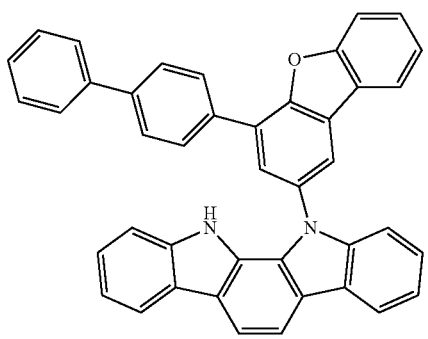 [SMILES: c1ccc(-c2ccc(-c3cc(-n4c5ccccc5c5ccc6c7ccccc7[nH]c6c54)cc4c3oc3ccccc34)cc2)cc1] | 77% |
| IM-a9 | 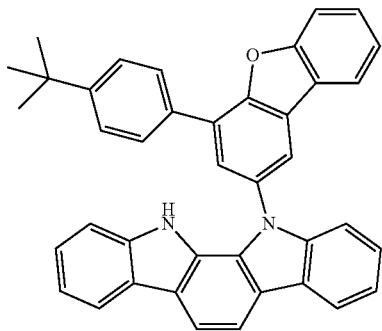 [SMILES: CC(C)(C)c1ccc(-c2cc(-n3c4ccccc4c4ccc5c6ccccc6[nH]c5c43)cc3c2oc2ccccc23)cc1] | 56% |
| IM-a10 | 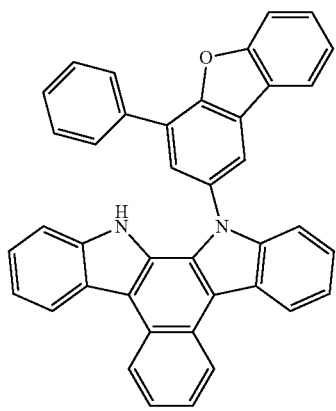 [SMILES: c1ccc(-c2cc(-n3c4ccccc4c4c5ccccc5c5c6ccccc6[nH]c5c43)cc3c2oc2ccccc23)cc1] | 60% |

TABLE 2-continued
| | | |
|---|---|---|
| IM-a11 | 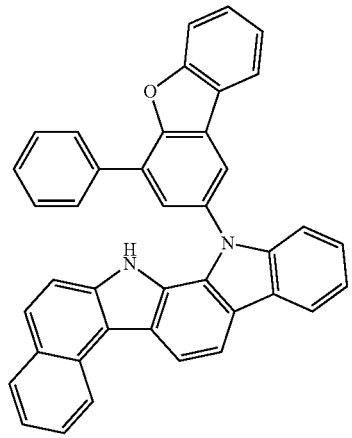 [SMILES: c1ccc(-c2cc(-n3c4ccccc4c4ccc5c([nH]c6ccc7ccccc7c65)c43)cc3c2oc2ccccc23)cc1] | 27% |
| IM-f1 | 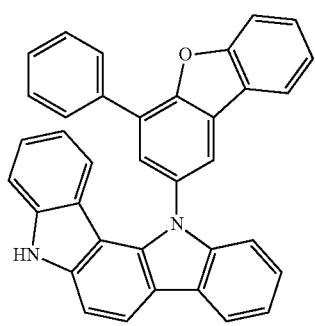 [SMILES: c1ccc(-c2cc(-n3c4ccccc4c4ccc5[nH]c6ccccc6c5c43)cc3c2oc2ccccc23)cc1] | 22% |
| IM-g1 | 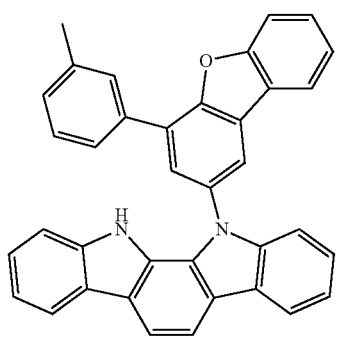 [SMILES: Cc1cccc(-c2cc(-n3c4ccccc4c4ccc5c6ccccc6[nH]c5c43)cc3c2oc2ccccc23)c1] | 39% |
| IM-h1 | 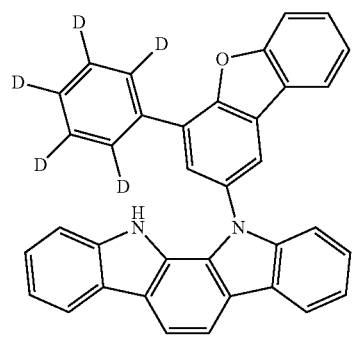 [SMILES: [2H]c1c([2H])c([2H])c(-c2cc(-n3c4ccccc4c4ccc5c6ccccc6[nH]c5c43)cc3c2oc2ccccc23)c([2H])c1[2H]] | 48% |

Synthesis of Intermediate IM-b1

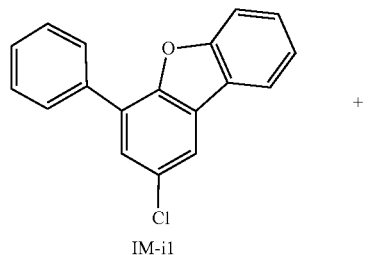

IM-i1

+

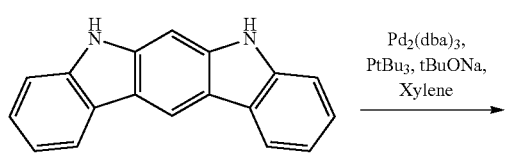

Pd₂(dba)₃,
PtBu₃, tBuONa,
Xylene
⟶

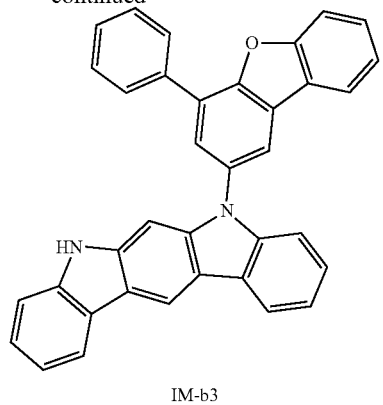

IM-b3

The intermediate I-i1 (10.0 g, 35.9 mmol), 5,7-dihydro-indolo[2,3-B]carbazole (10.1 g, 39.5 mmol), tris(dibenzylideneacetone)dipalladium (0.7 g, 0.7 mmol), tri-tert-butylphosphine (0.3 g, 1.4 mmol), sodium tert-butoxide (5.2 g, 53.8 mmol) and xylene (100 mL) were added into a round-bottom flask, and stirred at 140° C. for 10 hours for a reaction under the protection of nitrogen; when the temperature cooled to room temperature, a reaction solution was separated after being washed with water, an organic phase was dried with anhydrous magnesium sulfate, and a solvent was removed under reduced pressure to obtain a crude product; and the crude product was purified by silica gel column chromatography using dichloromethane/n-heptane as an eluent to obtain a white solid compound intermediate IM-b3 (12.2 g, 68%).

Referring to the synthesis method of the intermediate IM-b3, a reactant C in Table 3 below is used to replace the intermediate IM-i1, and a reactant B is used to replace 5,7-dihydro-indolo[2,3-B]carbazole to synthesize an intermediate structure shown in the table below.

TABLE 3

| Intermediate | Reactant C | Reactant B |
|---|---|---|
| IM-b1 | [structure: 3-cyanophenyl-dibenzofuran-Cl] | [structure: indolo[2,3-b]carbazole] |
| IM-b2 | [structure: biphenyl-dibenzofuran-Cl] | [structure: indolo[2,3-b]carbazole isomer] |

TABLE 3-continued
IM-b4 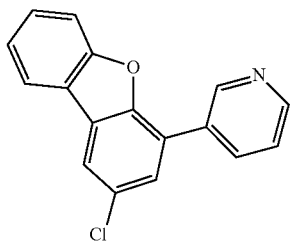 [SMILES: Clc1cc(-c2cccnc2)c2oc3ccccc3c2c1] 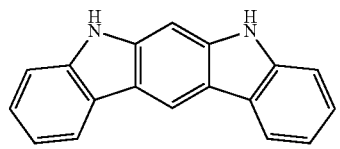 [SMILES: c1ccc2c(c1)[nH]c1cc3[nH]c4ccccc4c3cc12]
IM-b5 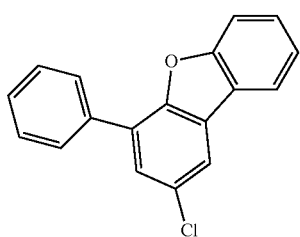 [SMILES: Clc1cc(-c2ccccc2)c2oc3ccccc3c2c1] 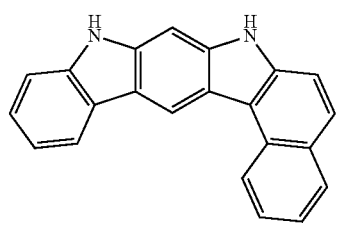 [SMILES: c1ccc2c(c1)ccc1[nH]c3cc4[nH]c5ccccc5c4cc3c12]
IM-b6 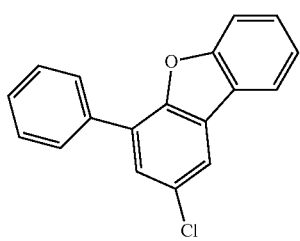 [SMILES: Clc1cc(-c2ccccc2)c2oc3ccccc3c2c1] 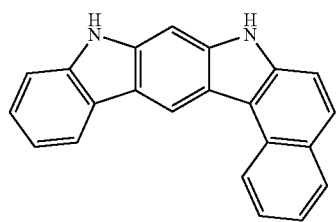 [SMILES: c1ccc2c(c1)ccc1[nH]c3cc4[nH]c5ccccc5c4cc3c12]
IM-d1 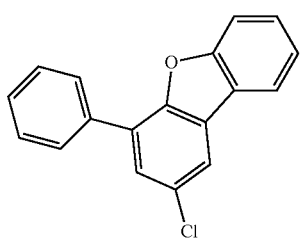 [SMILES: Clc1cc(-c2ccccc2)c2oc3ccccc3c2c1] 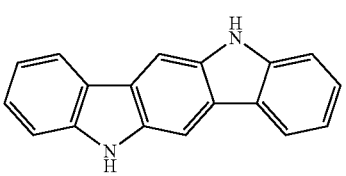 [SMILES: c1ccc2c(c1)[nH]c1cc3c(cc12)[nH]c1ccccc13]
IM-d2 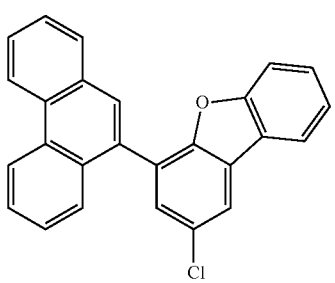 [SMILES: Clc1cc(-c2cc3ccccc3c3ccccc23)c2oc3ccccc3c2c1] 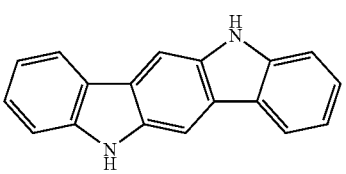 [SMILES: c1ccc2c(c1)[nH]c1cc3c(cc12)[nH]c1ccccc13]
IM-d3 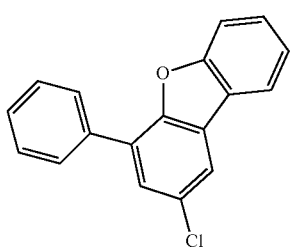 [SMILES: Clc1cc(-c2ccccc2)c2oc3ccccc3c2c1] 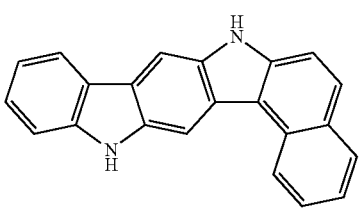 [SMILES: c1ccc2c(c1)ccc1[nH]c3cc4c(cc3c12)[nH]c1ccccc14]

TABLE 3-continued

| Intermediate | Structure | Yield |
|---|---|---|
| IM-b1 | 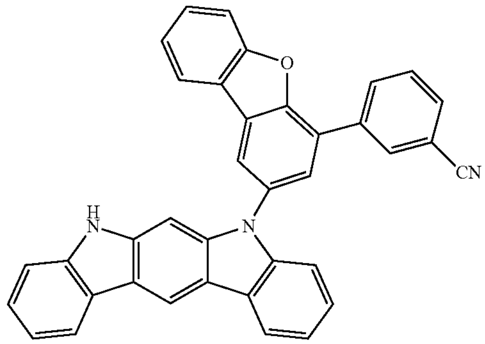 [SMILES: N#Cc1cccc(-c2cc(-n3c4ccccc4c4cc5c(cc43)[nH]c3ccccc35)cc3c2oc2ccccc23)c1] | 54% |
| IM-b2 | 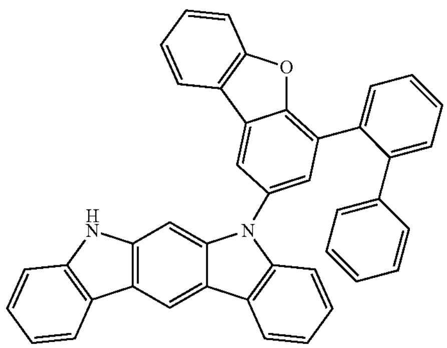 [SMILES: c1ccc(-c2ccccc2-c2cc(-n3c4ccccc4c4cc5c(cc43)[nH]c3ccccc35)cc3c2oc2ccccc23)cc1] | 41% |
| IM-b4 | 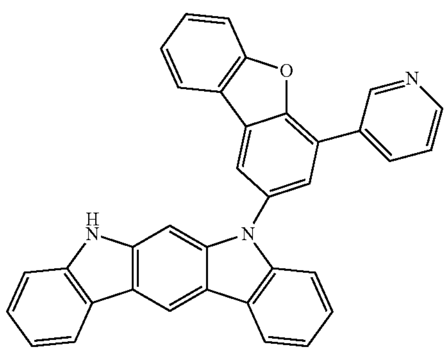 [SMILES: c1cncc(-c2cc(-n3c4ccccc4c4cc5c(cc43)[nH]c3ccccc35)cc3c2oc2ccccc23)c1] | 44% |
| IM-b5 | 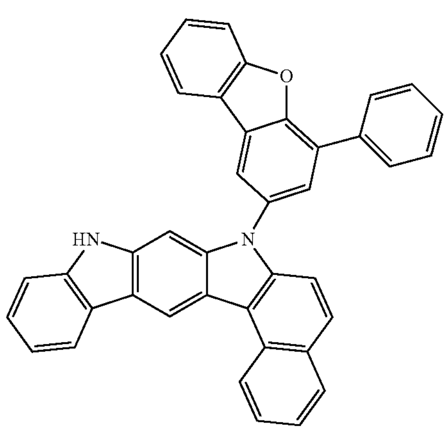 [SMILES: c1ccc(-c2cc(-n3c4cc5[nH]c6ccccc6c5cc4c4c5ccccc5ccc43)cc3c2oc2ccccc23)cc1] | 29% |

TABLE 3-continued
| | | |
|---|---|---|
| IM-b6 | 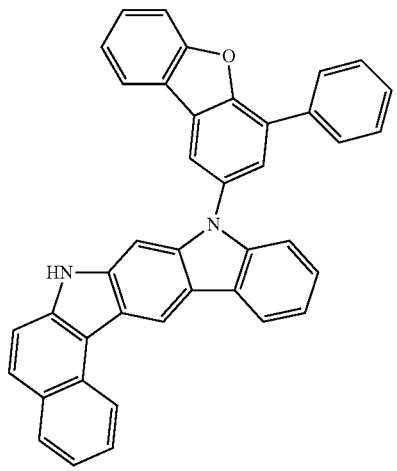 [SMILES: c1ccc(-c2cc(-n3c4ccccc4c4cc5c(cc43)[nH]c3ccc4ccccc4c35)cc3c2oc2ccccc23)cc1] | 33% |
| IM-d1 | 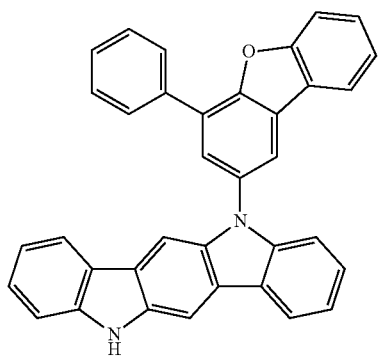 [SMILES: c1ccc(-c2cc(-n3c4ccccc4c4cc5[nH]c6ccccc6c5cc43)cc3c2oc2ccccc23)cc1] | 59% |
| IM-d2 | 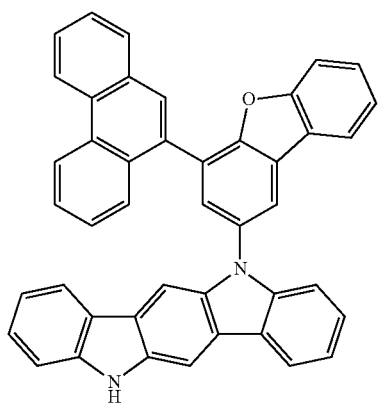 [SMILES: c1ccc2c(c1)cc(-c1cc(-n3c4ccccc4c4cc5[nH]c6ccccc6c5cc43)cc3c1oc1ccccc13)c1ccccc12] | 48% |
| IM-d3 | 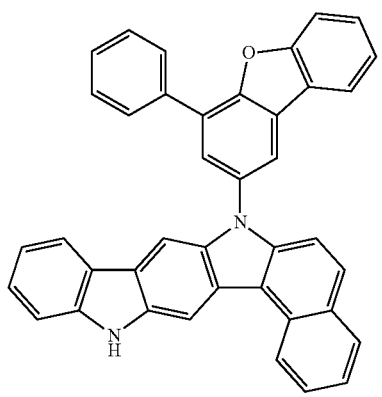 [SMILES: c1ccc(-c2cc(-n3c4cc5c(cc4c4c6ccccc6ccc43)[nH]c3ccccc35)cc3c2oc2ccccc23)cc1] | 31% |

Synthesis of compound A1

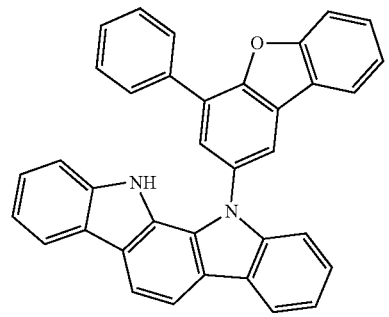

IM-a1

+

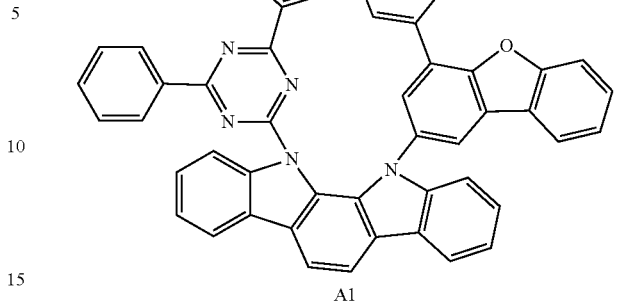

A1

NaH, DMF

The intermediate IM-a1 (6.0 g, 12.0 mmol) and dimethylformamide (60 mL) were added into a round-bottom flask, sodium hydride (0.3 g, 12.0 mmol) was added to the reaction solution at 0° C. under a nitrogen protection condition, and stirred for 1 hour while keeping temperature; then 2-chloro-4,6-diphenyl-1,3,5-triazine (4.8 g, 18.1 mmol) was added into a reaction solution in batches and stirred for 1 hour while keeping temperature, after the temperature was raised to 25° C., and stirring was performed for a reaction for 8 hours; a large amount of deionized water was added into the reaction solution, filtering was performed, and an obtained solid was subjected to drip washing with water and ethanol in sequence and dried to obtain a crude product; and the crude product was purified by silica gel column chromatography using dichloromethane as an eluent, and then an obtained product was purified by recrystallization using toluene to obtain a white solid compound A1 (5.5 g, 63%).

Referring to the synthesis method of the compound A1, a reactant D in Table 4 below is used to replace the intermediate IM-a1, and a reactant E is used to replace 2-chloro-4,6-diphenyl-1,3,5-triazine to synthesize the compound shown in Table 4 below.

TABLE 4

| Compound | Reactant D | Reactant E |
|---|---|---|
| A3 | 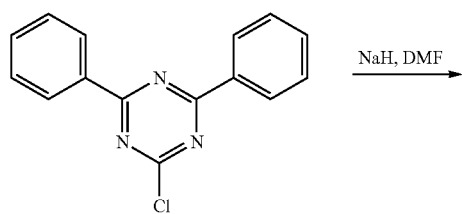 | |

TABLE 4-continued
| | | |
|---|---|---|
| A6 | 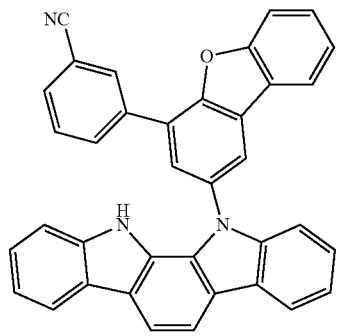 [SMILES: N#Cc1cccc(-c2cc(-n3c4ccccc4c4ccc5c6ccccc6[nH]c5c43)cc3c2oc2ccccc23)c1] | 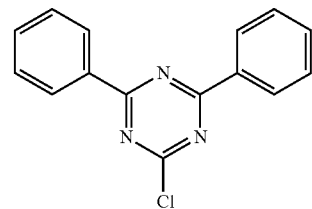 [SMILES: Clc1nc(-c2ccccc2)nc(-c2ccccc2)n1] |
| A14 | 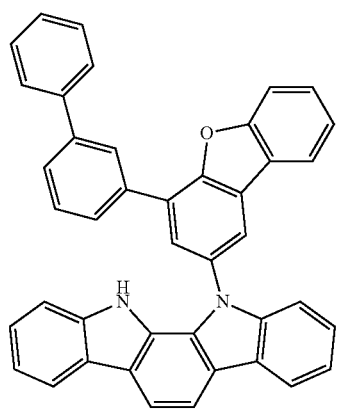 [SMILES: c1ccc(-c2cccc(-c3cc(-n4c5ccccc5c5ccc6c7ccccc7[nH]c6c54)cc4c3oc3ccccc34)c2)cc1] | 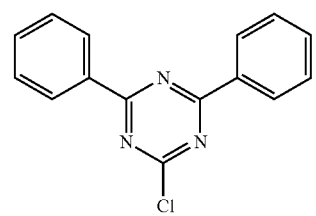 [SMILES: Clc1nc(-c2ccccc2)nc(-c2ccccc2)n1] |
| A16 | 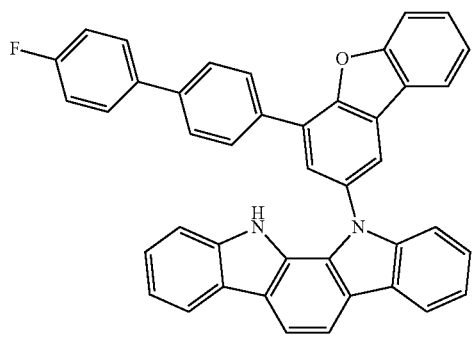 [SMILES: Fc1ccc(-c2ccc(-c3cc(-n4c5ccccc5c5ccc6c7ccccc7[nH]c6c54)cc4c3oc3ccccc34)cc2)cc1] | 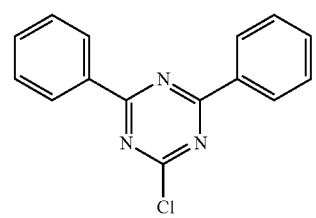 [SMILES: Clc1nc(-c2ccccc2)nc(-c2ccccc2)n1] |
| A23 | 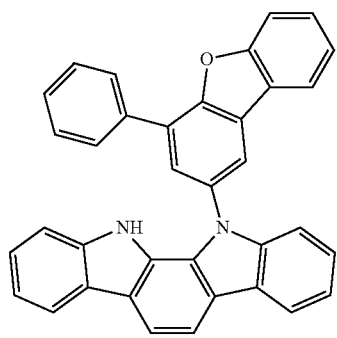 [SMILES: c1ccc(-c2cc(-n3c4ccccc4c4ccc5c6ccccc6[nH]c5c43)cc3c2oc2ccccc23)cc1] | 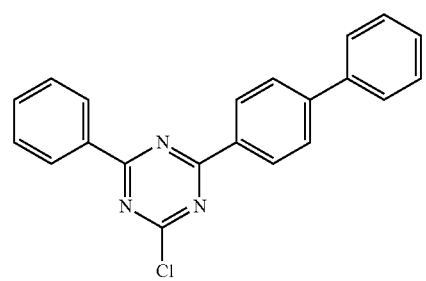 [SMILES: Clc1nc(-c2ccccc2)nc(-c2ccc(-c3ccccc3)cc2)n1] |

TABLE 4-continued
A34 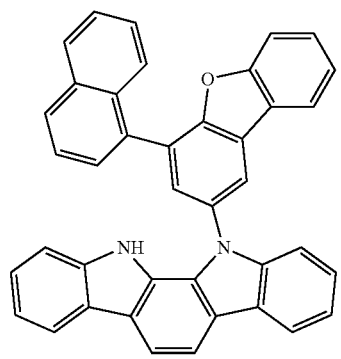 [SMILES: c1ccc2c(-c3cc(-n4c5ccccc5c5ccc6c7ccccc7[nH]c6c54)cc4c3oc3ccccc34)cccc2c1] 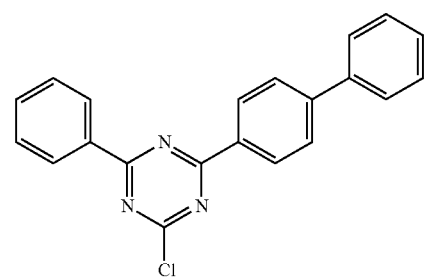 [SMILES: Clc1nc(-c2ccccc2)nc(-c2ccc(-c3ccccc3)cc2)n1]
A39 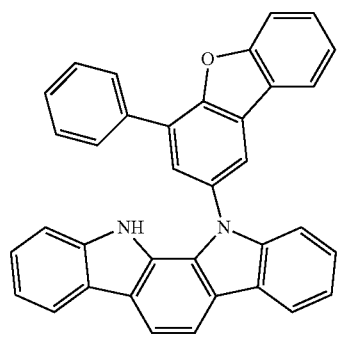 [SMILES: c1ccc(-c2cc(-n3c4ccccc4c4ccc5c6ccccc6[nH]c5c43)cc3c2oc2ccccc23)cc1] 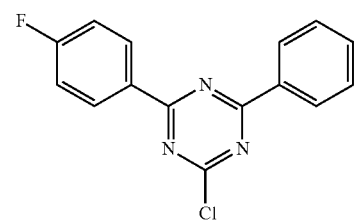 [SMILES: Fc1ccc(-c2nc(Cl)nc(-c3ccccc3)n2)cc1]
A45 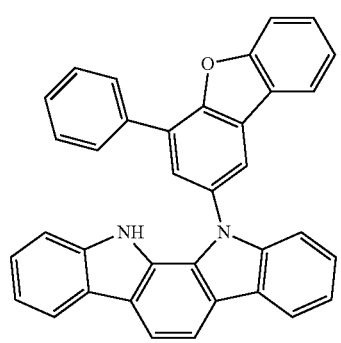 [SMILES: c1ccc(-c2cc(-n3c4ccccc4c4ccc5c6ccccc6[nH]c5c43)cc3c2oc2ccccc23)cc1] 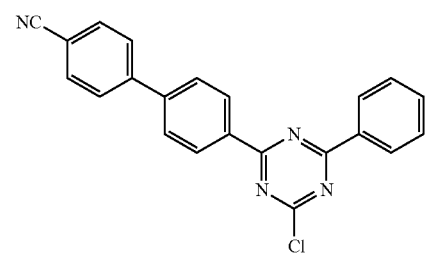 [SMILES: N#Cc1ccc(-c2ccc(-c3nc(Cl)nc(-c4ccccc4)n3)cc2)cc1]
A52 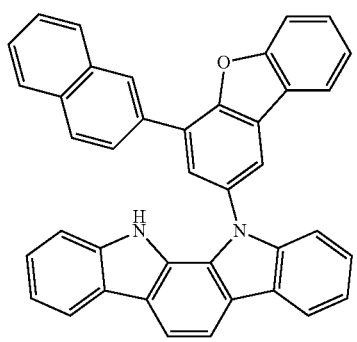 [SMILES: c1ccc2cc(-c3cc(-n4c5ccccc5c5ccc6c7ccccc7[nH]c6c54)cc4c3oc3ccccc34)ccc2c1] 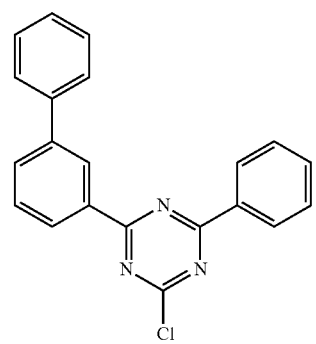 [SMILES: Clc1nc(-c2ccccc2)nc(-c2cccc(-c3ccccc3)c2)n1]

TABLE 4-continued
A57 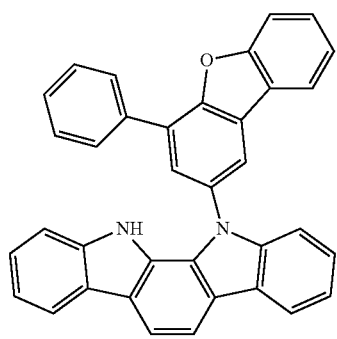 [SMILES: c1ccc(-c2cc(-n3c4ccccc4c4ccc5c6ccccc6[nH]c5c43)cc3c2oc2ccccc23)cc1] 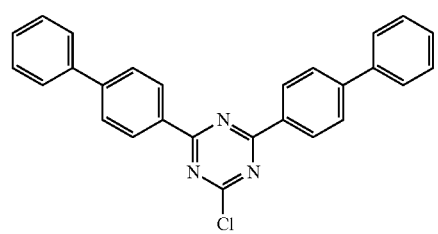 [SMILES: Clc1nc(-c2ccc(-c3ccccc3)cc2)nc(-c2ccc(-c3ccccc3)cc2)n1]
A67 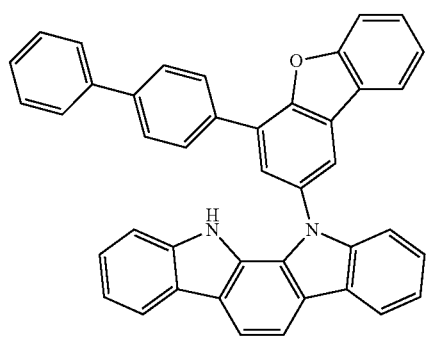 [SMILES: c1ccc(-c2ccc(-c3cc(-n4c5ccccc5c5ccc6c7ccccc7[nH]c6c54)cc4c3oc3ccccc34)cc2)cc1] 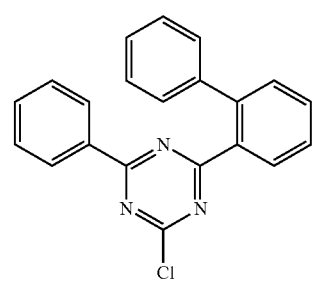 [SMILES: Clc1nc(-c2ccccc2)nc(-c2ccccc2-c2ccccc2)n1]
A74 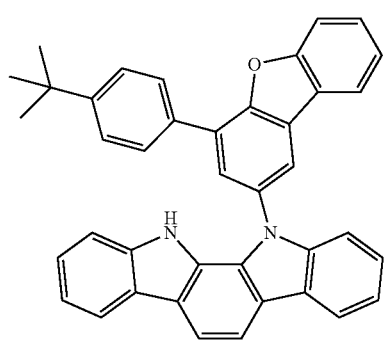 [SMILES: CC(C)(C)c1ccc(-c2cc(-n3c4ccccc4c4ccc5c6ccccc6[nH]c5c43)cc3c2oc2ccccc23)cc1] 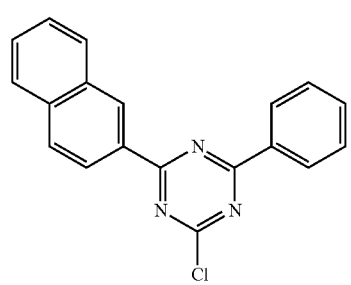 [SMILES: Clc1nc(-c2ccccc2)nc(-c2ccc3ccccc3c2)n1]
A76 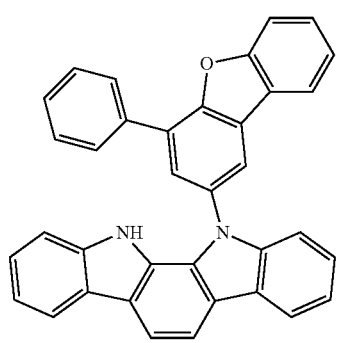 [SMILES: c1ccc(-c2cc(-n3c4ccccc4c4ccc5c6ccccc6[nH]c5c43)cc3c2oc2ccccc23)cc1] 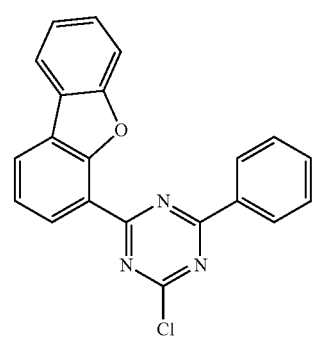 [SMILES: Clc1nc(-c2ccccc2)nc(-c2cccc3c2oc2ccccc23)n1]

TABLE 4-continued
A82 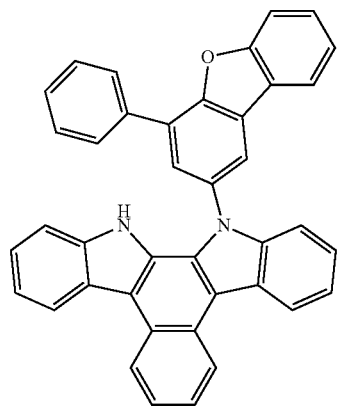 [SMILES: c1ccc(-c2cc(-n3c4ccccc4c4c5ccccc5c5c6ccccc6[nH]c5c43)cc3c2oc2ccccc23)cc1] 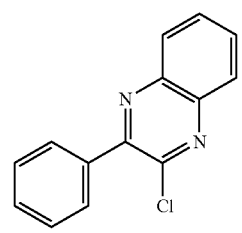 [SMILES: Clc1nc2ccccc2nc1-c1ccccc1]
A84 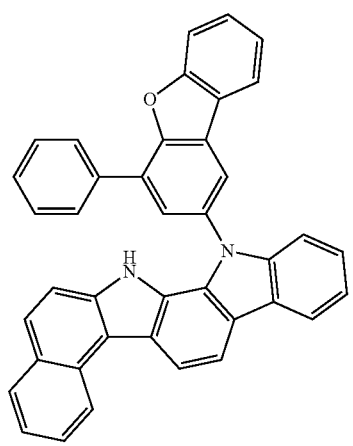 [SMILES: c1ccc(-c2cc(-n3c4ccccc4c4ccc5c([nH]c6ccc7ccccc7c65)c43)cc3c2oc2ccccc23)cc1] 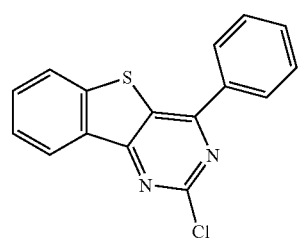 [SMILES: Clc1nc(-c2ccccc2)c2sc3ccccc3c2n1]
F5 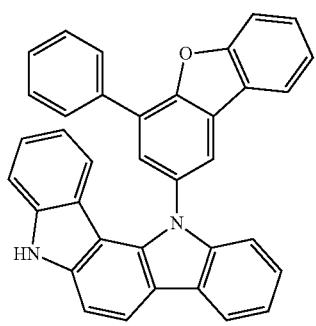 [SMILES: c1ccc(-c2cc(-n3c4ccccc4c4ccc5[nH]c6ccccc6c5c43)cc3c2oc2ccccc23)cc1] 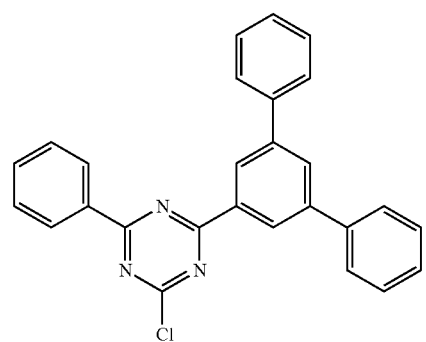 [SMILES: Clc1nc(-c2ccccc2)nc(-c2cc(-c3ccccc3)cc(-c3ccccc3)c2)n1]
F10 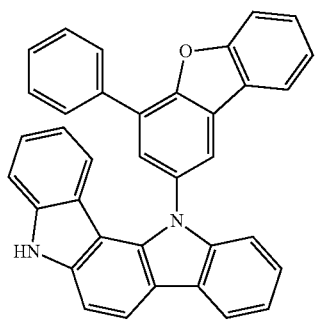 [SMILES: c1ccc(-c2cc(-n3c4ccccc4c4ccc5[nH]c6ccccc6c5c43)cc3c2oc2ccccc23)cc1] 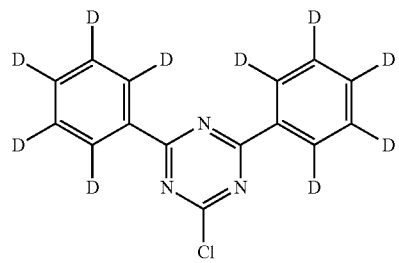 [SMILES: [2H]c1c([2H])c([2H])c(-c2nc(Cl)nc(-c3c([2H])c([2H])c([2H])c([2H])c3[2H])n2)c([2H])c1[2H]]

TABLE 4-continued
| | | |
|---|---|---|
| A85 | 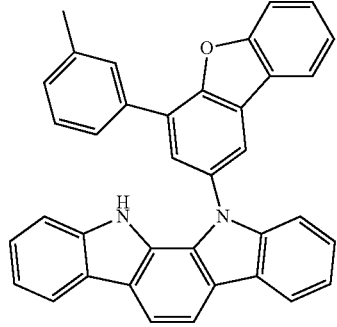 [SMILES: Cc1cccc(-c2cc(-n3c4ccccc4c4ccc5c6ccccc6[nH]c5c43)cc3c2oc2ccccc23)c1] | 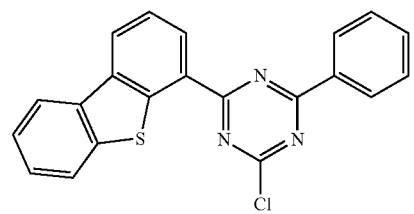 [SMILES: Clc1nc(-c2ccccc2)nc(-c2cccc3c2sc2ccccc23)n1] |
| A79 | 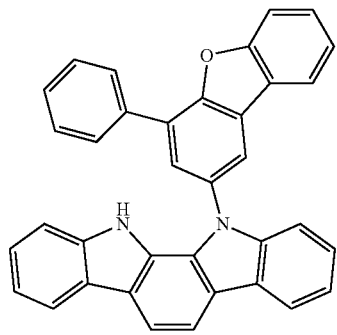 [SMILES: c1ccc(-c2cc(-n3c4ccccc4c4ccc5c6ccccc6[nH]c5c43)cc3c2oc2ccccc23)cc1] | 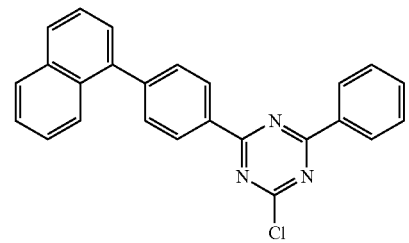 [SMILES: Clc1nc(-c2ccccc2)nc(-c2ccc(-c3cccc4ccccc34)cc2)n1] |
| A86 | 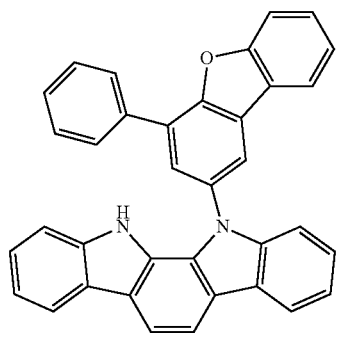 [SMILES: c1ccc(-c2cc(-n3c4ccccc4c4ccc5c6ccccc6[nH]c5c43)cc3c2oc2ccccc23)cc1] | 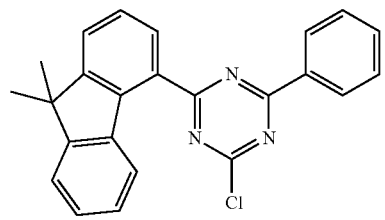 [SMILES: CC1(C)c2ccccc2-c2c(-c3nc(Cl)nc(-c4ccccc4)n3)cccc21] |
| A87 | 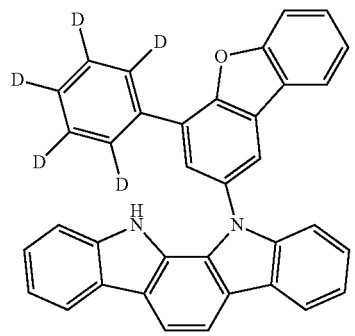 [SMILES: [2H]c1c([2H])c([2H])c(-c2cc(-n3c4ccccc4c4ccc5c6ccccc6[nH]c5c43)cc3c2oc2ccccc23)c([2H])c1[2H]] | 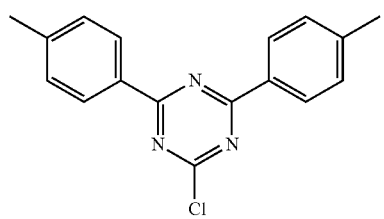 |

TABLE 4-continued
| | | |
|---|---|---|
| A11 | 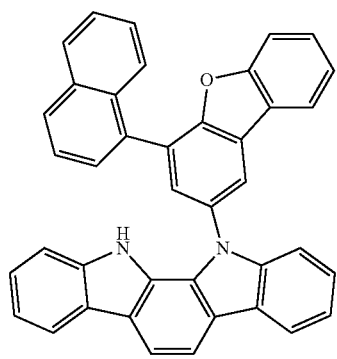 [SMILES: c1ccc2c(-c3cc(-n4c5ccccc5c5ccc6c7ccccc7[nH]c6c54)cc4c3oc3ccccc34)cccc2c1] | 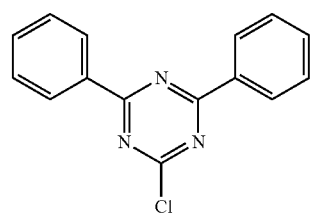 [SMILES: Clc1nc(-c2ccccc2)nc(-c2ccccc2)n1] |
| A88 | 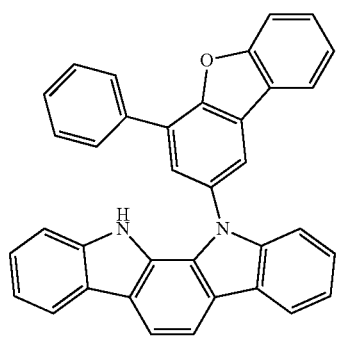 [SMILES: c1ccc(-c2cc(-n3c4ccccc4c4ccc5c6ccccc6[nH]c5c43)cc3c2oc2ccccc23)cc1] | 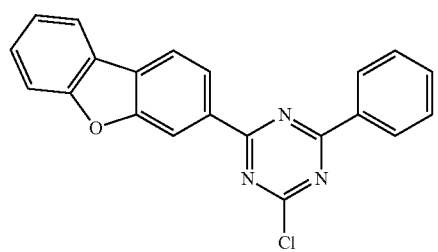 [SMILES: Clc1nc(-c2ccccc2)nc(-c2ccc3c(c2)oc2ccccc23)n1] |
| A43 | 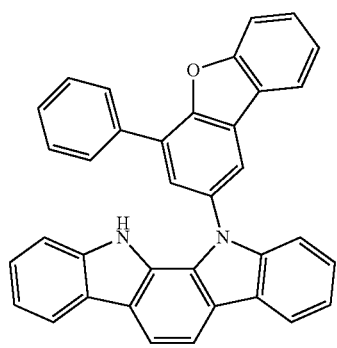 [SMILES: c1ccc(-c2cc(-n3c4ccccc4c4ccc5c6ccccc6[nH]c5c43)cc3c2oc2ccccc23)cc1] | 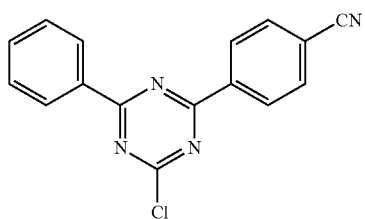 [SMILES: N#Cc1ccc(-c2nc(Cl)nc(-c3ccccc3)n2)cc1] |
| A89 | | 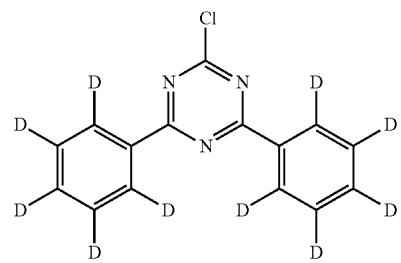 [SMILES: [2H]c1c([2H])c([2H])c(-c2nc(Cl)nc(-c3c([2H])c([2H])c([2H])c([2H])c3[2H])n2)c([2H])c1[2H]] |
| A91 | 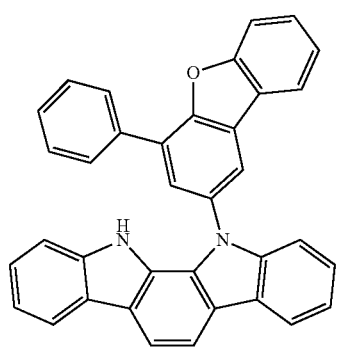 [SMILES: c1ccc(-c2cc(-n3c4ccccc4c4ccc5c6ccccc6[nH]c5c43)cc3c2oc2ccccc23)cc1] | 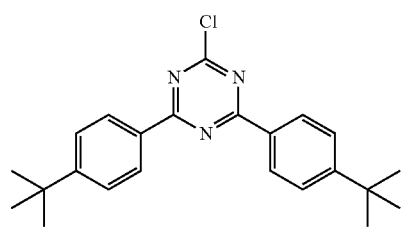 [SMILES: CC(C)(C)c1ccc(-c2nc(Cl)nc(-c3ccc(C(C)(C)C)cc3)n2)cc1] |

TABLE 4-continued
| | | |
|---|---|---|
| A69 | | 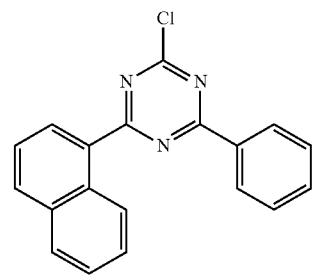 [SMILES: Clc1nc(-c2ccccc2)nc(-c2cccc3ccccc23)n1] |
| A70 | | 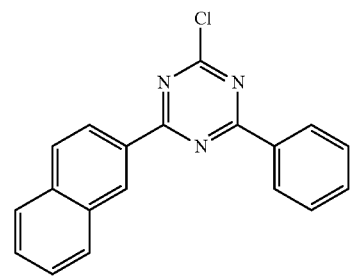 [SMILES: Clc1nc(-c2ccccc2)nc(-c2ccc3ccccc3c2)n1] |
| A109 | 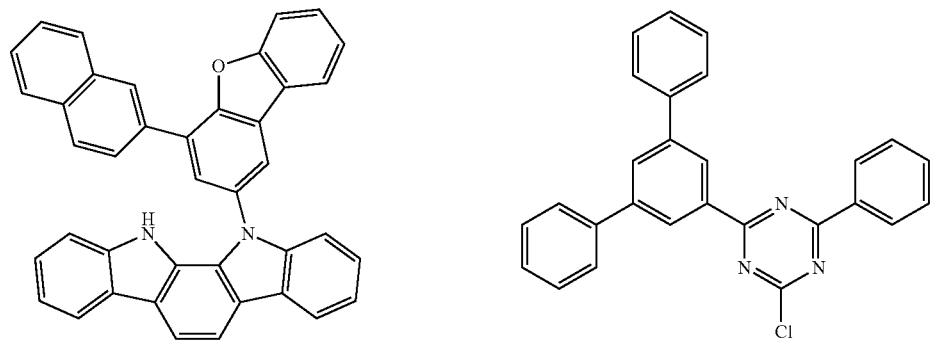 | |
| Compound | Structure | Yield |
|---|---|---|
| A3 | 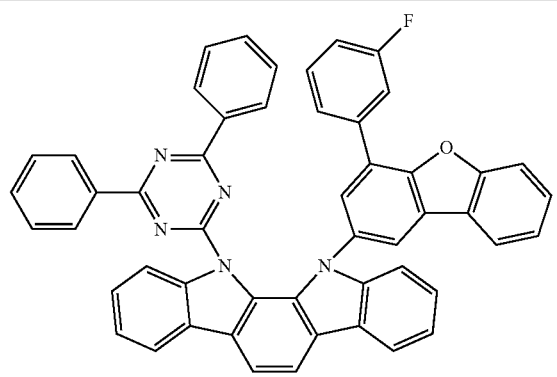 [SMILES: Fc1cccc(-c2cc(-n3c4ccccc4c4ccc5c6ccccc6n(-c6nc(-c7ccccc7)nc(-c7ccccc7)n6)c5c43)cc3c2oc2ccccc23)c1] | 49% |

TABLE 4-continued
| A6 | 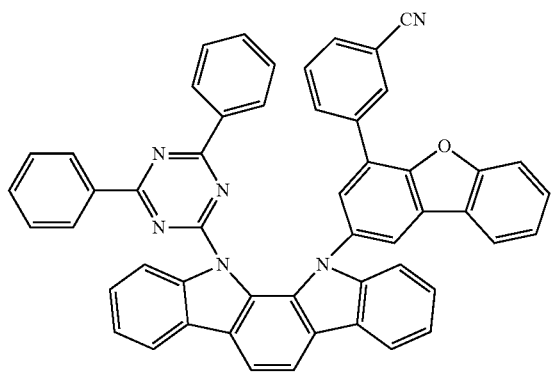 [SMILES: N#Cc1cccc(-c2cc(-n3c4ccccc4c4ccc5c6ccccc6n(-c6nc(-c7ccccc7)nc(-c7ccccc7)n6)c5c43)cc3c2oc2ccccc23)c1] | 59% |
| A14 | 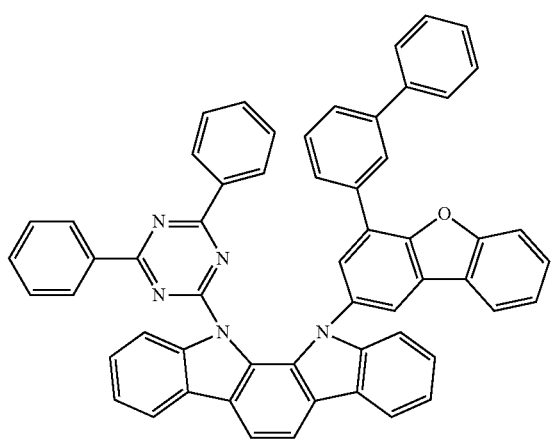 [SMILES: c1ccc(-c2cccc(-c3cc(-n4c5ccccc5c5ccc6c7ccccc7n(-c7nc(-c8ccccc8)nc(-c8ccccc8)n7)c6c54)cc4c3oc3ccccc34)c2)cc1] | 68% |
| A16 | 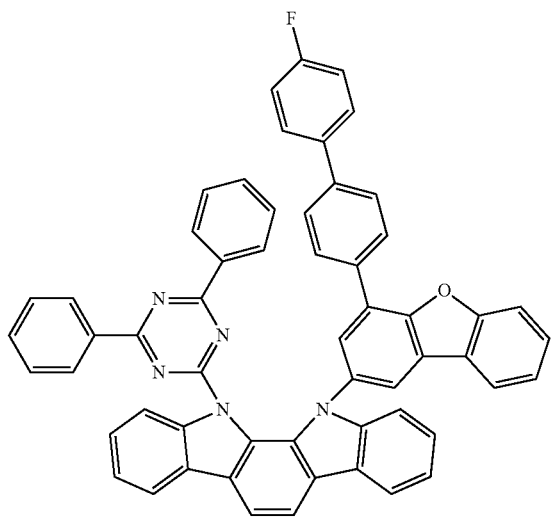 [SMILES: Fc1ccc(-c2ccc(-c3cc(-n4c5ccccc5c5ccc6c7ccccc7n(-c7nc(-c8ccccc8)nc(-c8ccccc8)n7)c6c54)cc4c3oc3ccccc34)cc2)cc1] | 38% |

TABLE 4-continued
A23 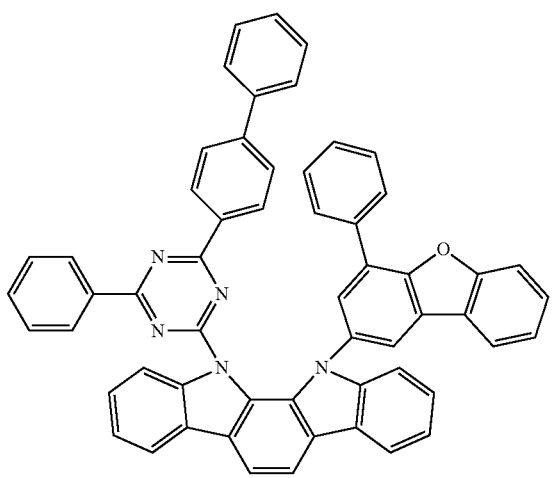 [SMILES: c1ccc(-c2ccc(-c3nc(-c4ccccc4)nc(-n4c5ccccc5c5ccc6c7ccccc7n(-c7cc(-c8ccccc8)c8oc9ccccc9c8c7)c6c54)n3)cc2)cc1] 49%
A34 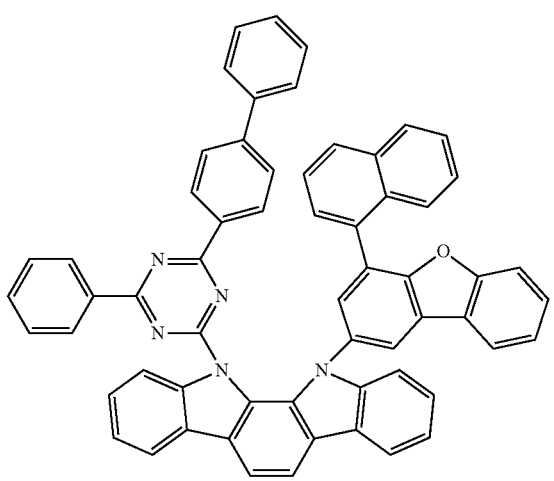 [SMILES: c1ccc(-c2ccc(-c3nc(-c4ccccc4)nc(-n4c5ccccc5c5ccc6c7ccccc7n(-c7cc(-c8cccc9ccccc89)c8oc9ccccc9c8c7)c6c54)n3)cc2)cc1] 42%
A39 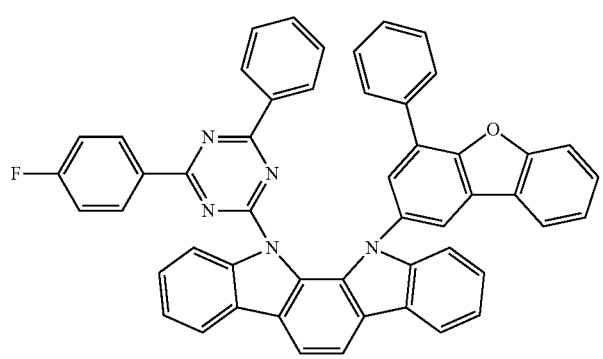 [SMILES: Fc1ccc(-c2nc(-c3ccccc3)nc(-n3c4ccccc4c4ccc5c6ccccc6n(-c6cc(-c7ccccc7)c7oc8ccccc8c7c6)c5c43)n2)cc1] 72%
A45 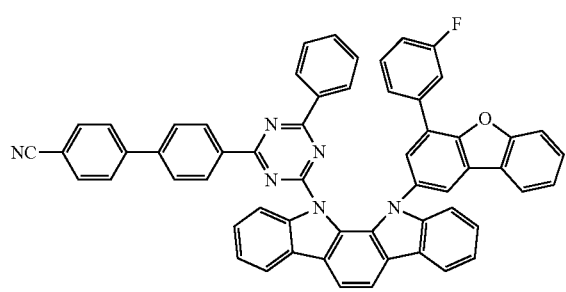 [SMILES: N#Cc1ccc(-c2ccc(-c3nc(-c4ccccc4)nc(-n4c5ccccc5c5ccc6c7ccccc7n(-c7cc(-c8cccc(F)c8)c8oc9ccccc9c8c7)c6c54)n3)cc2)cc1] 53%

TABLE 4-continued
| A52 | 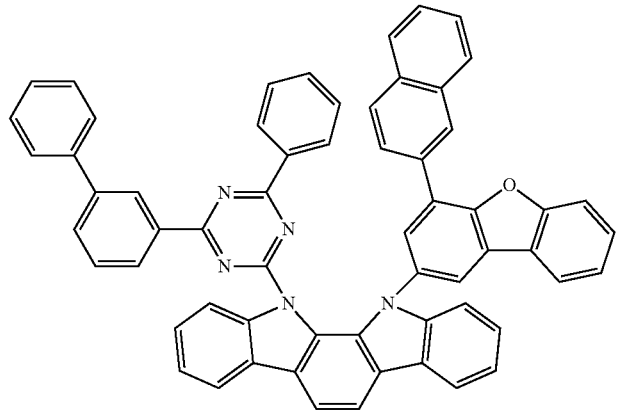 [SMILES: c1ccc(-c2cccc(-c3nc(-c4ccccc4)nc(-n4c5ccccc5c5ccc6c7ccccc7n(-c7cc(-c8ccc9ccccc9c8)c8oc9ccccc9c8c7)c6c54)n3)c2)cc1] | 64% |
| A57 | 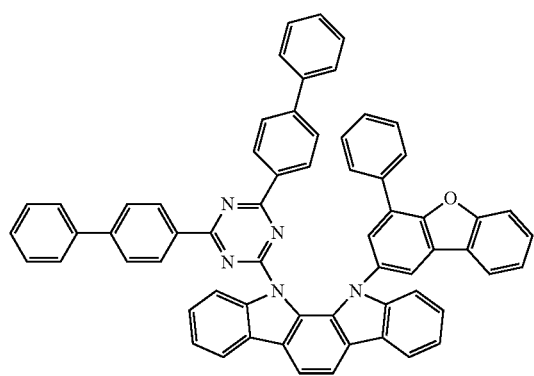 [SMILES: c1ccc(-c2ccc(-c3nc(-c4ccc(-c5ccccc5)cc4)nc(-n4c5ccccc5c5ccc6c7ccccc7n(-c7cc(-c8ccccc8)c8oc9ccccc9c8c7)c6c54)n3)cc2)cc1] | 41% |
| A67 | 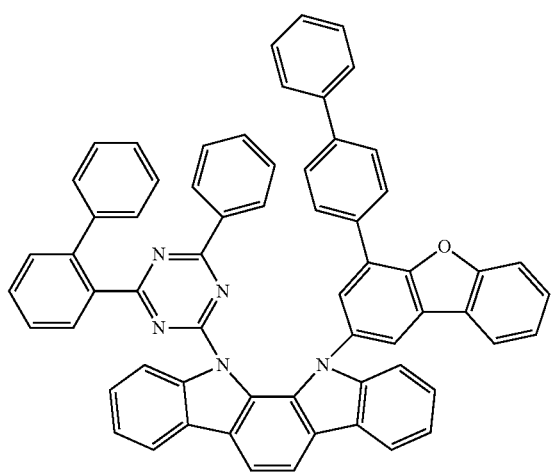 [SMILES: c1ccc(-c2ccc(-c3cc(-n4c5ccccc5c5ccc6c7ccccc7n(-c7nc(-c8ccccc8)nc(-c8ccccc8-c8ccccc8)n7)c6c54)cc4c3oc3ccccc34)cc2)cc1] | 35% |

TABLE 4-continued
| | | |
|---|---|---|
| A74 | 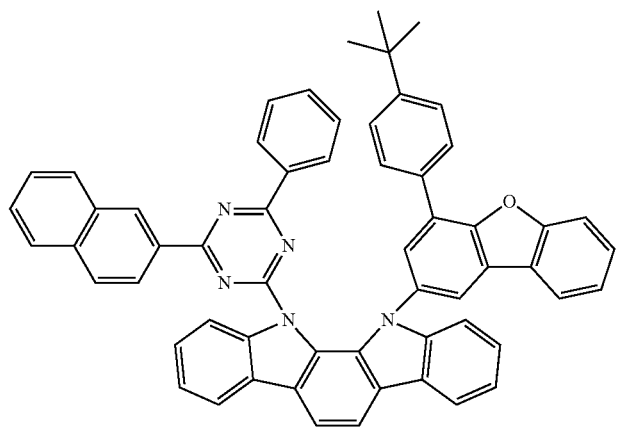 [SMILES: CC(C)(C)c1ccc(-c2cc(-n3c4ccccc4c4ccc5c6ccccc6n(-c6nc(-c7ccccc7)nc(-c7ccc8ccccc8c7)n6)c5c43)cc3c2oc2ccccc23)cc1] | 58% |
| A76 | 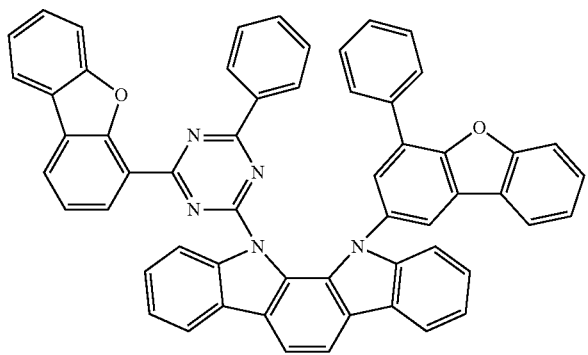 [SMILES: c1ccc(-c2nc(-c3cccc4c3oc3ccccc34)nc(-n3c4ccccc4c4ccc5c6ccccc6n(-c6cc(-c7ccccc7)c7oc8ccccc8c7c6)c5c43)n2)cc1] | 59% |
| A82 | 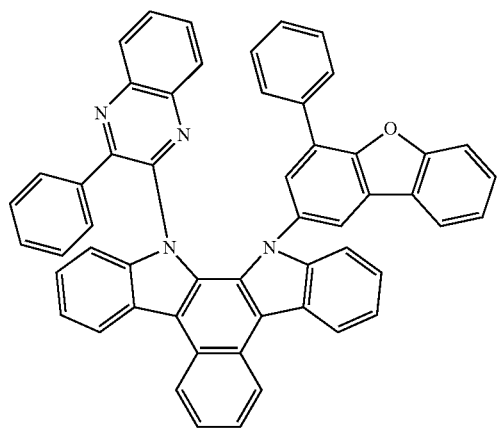 [SMILES: c1ccc(-c2nc3ccccc3nc2-n2c3ccccc3c3c4ccccc4c4c5ccccc5n(-c5cc(-c6ccccc6)c6oc7ccccc7c6c5)c4c32)cc1] | 70% |

TABLE 4-continued
| | | |
|---|---|---|
| A84 | 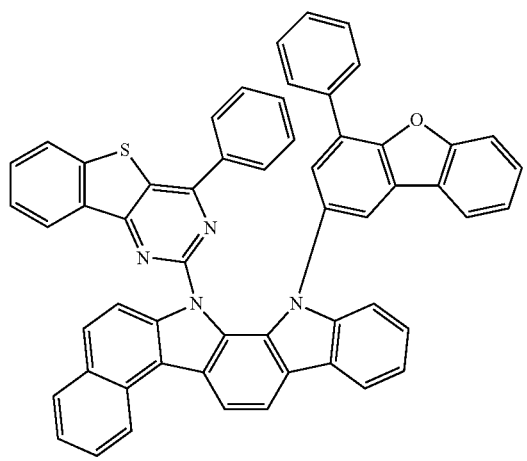 [SMILES: c1ccc(-c2cc(-n3c4ccccc4c4ccc5c6c7ccccc7ccc6n(-c6nc(-c7ccccc7)c7sc8ccccc8c7n6)c5c43)cc3c2oc2ccccc23)cc1] | 71% |
| F5 | 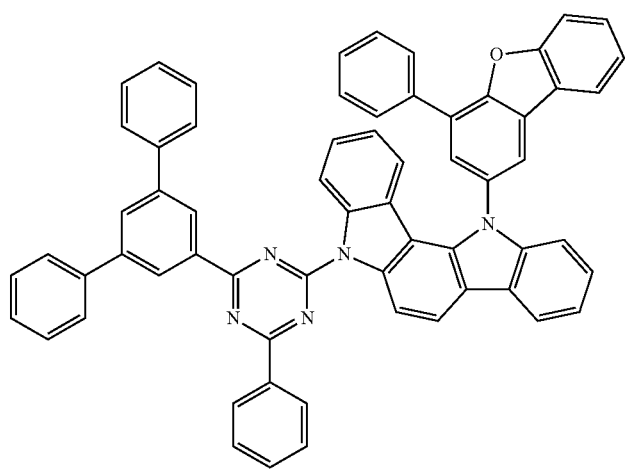 [SMILES: c1ccc(-c2cc(-c3ccccc3)cc(-c3nc(-c4ccccc4)nc(-n4c5ccccc5c5c4ccc4c6ccccc6n(-c6cc(-c7ccccc7)c7oc8ccccc8c7c6)c45)n3)c2)cc1] | 50% |
| F10 | 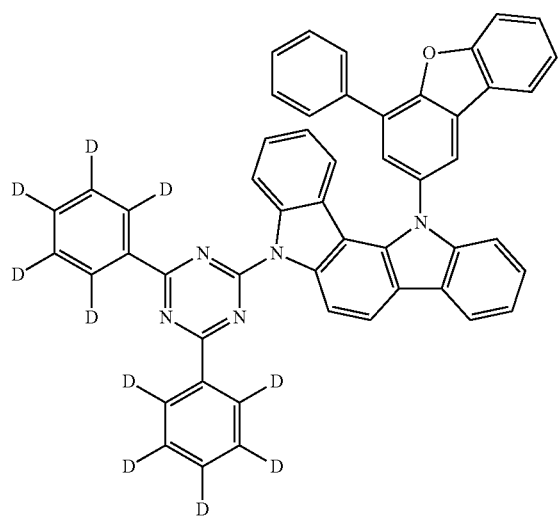 [SMILES: [2H]c1c([2H])c([2H])c(-c2nc(-c3c([2H])c([2H])c([2H])c([2H])c3[2H])nc(-n3c4ccccc4c4c3ccc3c5ccccc5n(-c5cc(-c6ccccc6)c6oc7ccccc7c6c5)c34)n2)c([2H])c1[2H]] | 42% |

TABLE 4-continued
| | | |
|---|---|---|
| A85 | 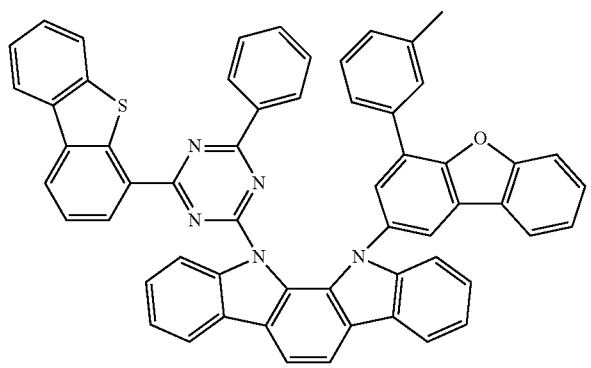 [SMILES: Cc1cccc(-c2cc(-n3c4ccccc4c4ccc5c6ccccc6n(-c6nc(-c7ccccc7)nc(-c7cccc8c7sc7ccccc78)n6)c5c43)cc3c2oc2ccccc23)c1] | 60% |
| A79 | 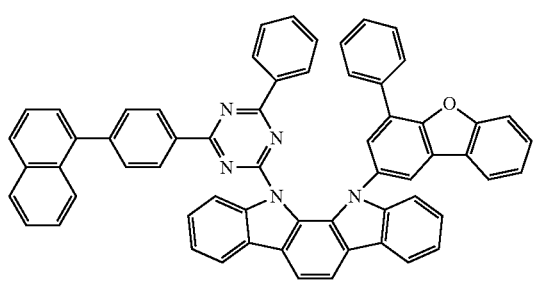 [SMILES: c1ccc(-c2nc(-c3ccc(-c4cccc5ccccc45)cc3)nc(-n3c4ccccc4c4ccc5c6ccccc6n(-c6cc(-c7ccccc7)c7oc8ccccc8c7c6)c5c43)n2)cc1] | 44% |
| A86 | 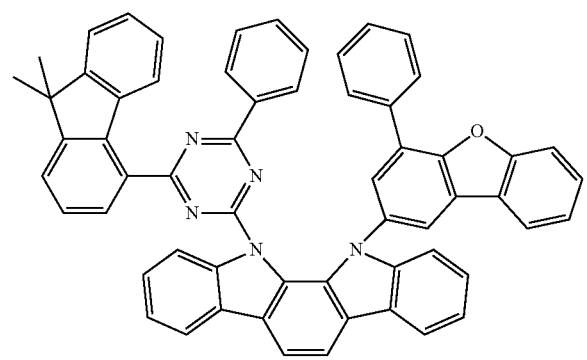 [SMILES: CC1(C)c2ccccc2-c2c(-c3nc(-c4ccccc4)nc(-n4c5ccccc5c5ccc6c7ccccc7n(-c7cc(-c8ccccc8)c8oc9ccccc9c8c7)c6c54)n3)cccc21] | 61% |
| A87 | 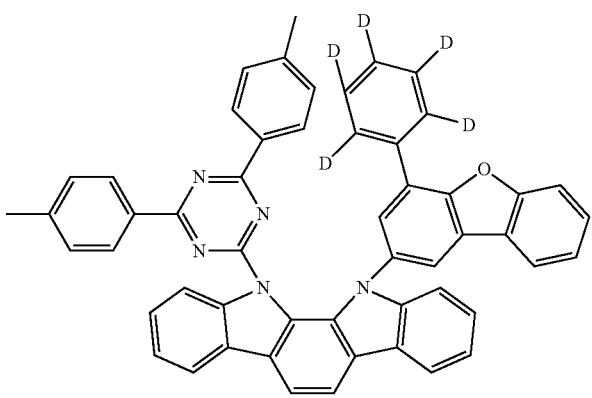 [SMILES: [2H]c1c([2H])c([2H])c(-c2cc(-n3c4ccccc4c4ccc5c6ccccc6n(-c6nc(-c7ccc(C)cc7)nc(-c7ccc(C)cc7)n6)c5c43)cc3c2oc2ccccc23)c([2H])c1[2H]] | 57% |

TABLE 4-continued
| | | |
|---|---|---|
| A11 | 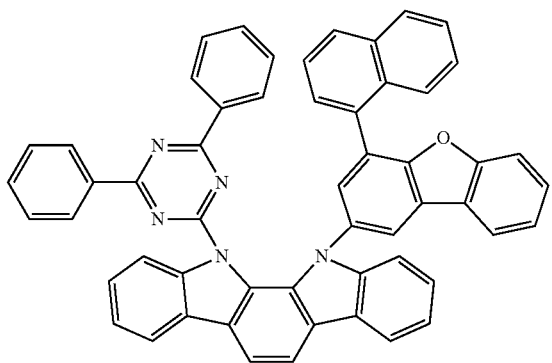 [SMILES: c1ccc(-c2nc(-c3ccccc3)nc(-n3c4ccccc4c4ccc5c6ccccc6n(-c6cc(-c7cccc8ccccc78)c7oc8ccccc8c7c6)c5c43)n2)cc1] | 44% |
| A88 | 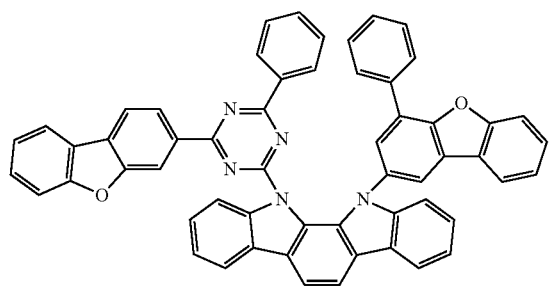 [SMILES: c1ccc(-c2nc(-c3ccc4c(c3)oc3ccccc34)nc(-n3c4ccccc4c4ccc5c6ccccc6n(-c6cc(-c7ccccc7)c7oc8ccccc8c7c6)c5c43)n2)cc1] | 58% |
| A43 | 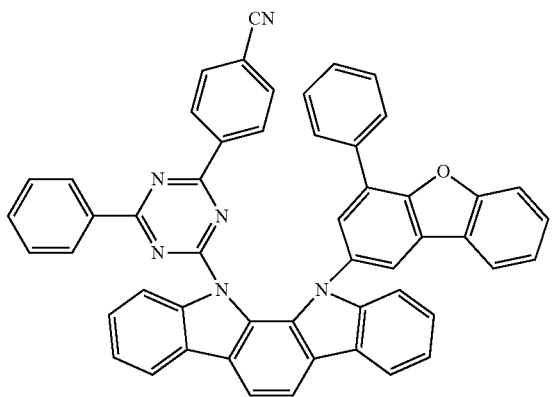 [SMILES: N#Cc1ccc(-c2nc(-c3ccccc3)nc(-n3c4ccccc4c4ccc5c6ccccc6n(-c6cc(-c7ccccc7)c7oc8ccccc8c7c6)c5c43)n2)cc1] | 48% |
| A89 | 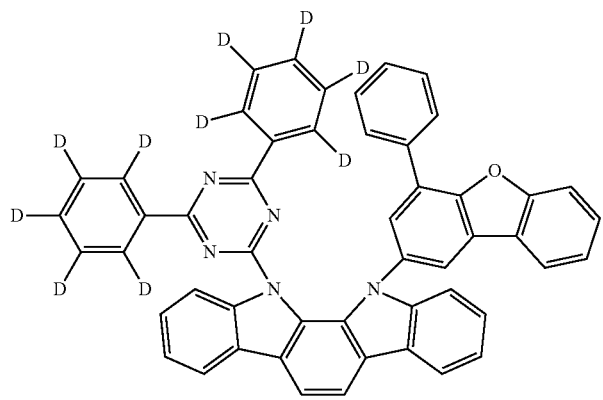 [SMILES: [2H]c1c([2H])c([2H])c(-c2nc(-c3c([2H])c([2H])c([2H])c([2H])c3[2H])nc(-n3c4ccccc4c4ccc5c6ccccc6n(-c6cc(-c7ccccc7)c7oc8ccccc8c7c6)c5c43)n2)c([2H])c1[2H]] | 34% |

TABLE 4-continued
| A91 | 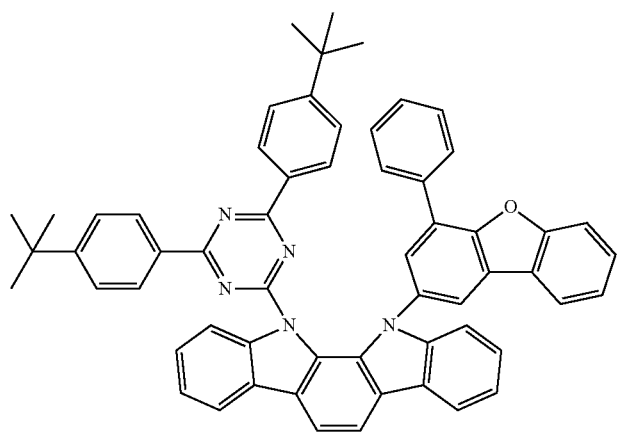 [SMILES: CC(C)(C)c1ccc(-c2nc(-c3ccc(C(C)(C)C)cc3)nc(-n3c4ccccc4c4ccc5c6ccccc6n(-c6cc(-c7ccccc7)c7oc8ccccc8c7c6)c5c43)n2)cc1] | 45% |
| A69 | 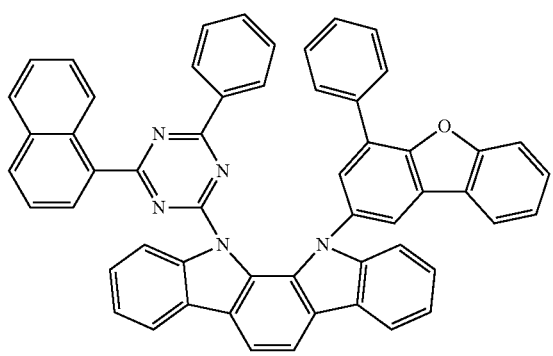 [SMILES: c1ccc(-c2nc(-c3cccc4ccccc34)nc(-n3c4ccccc4c4ccc5c6ccccc6n(-c6cc(-c7ccccc7)c7oc8ccccc8c7c6)c5c43)n2)cc1] | 53% |
| A70 | 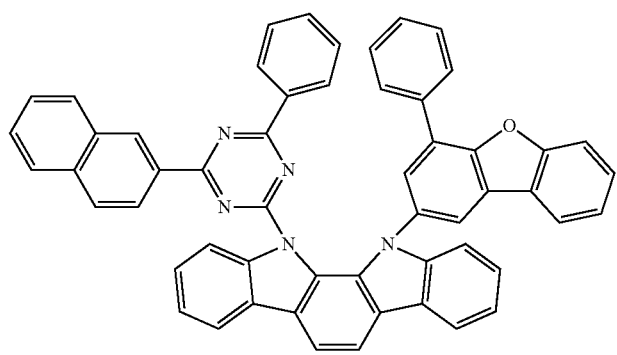 [SMILES: c1ccc(-c2nc(-c3ccc4ccccc4c3)nc(-n3c4ccccc4c4ccc5c6ccccc6n(-c6cc(-c7ccccc7)c7oc8ccccc8c7c6)c5c43)n2)cc1] | 36% |
| A109 | 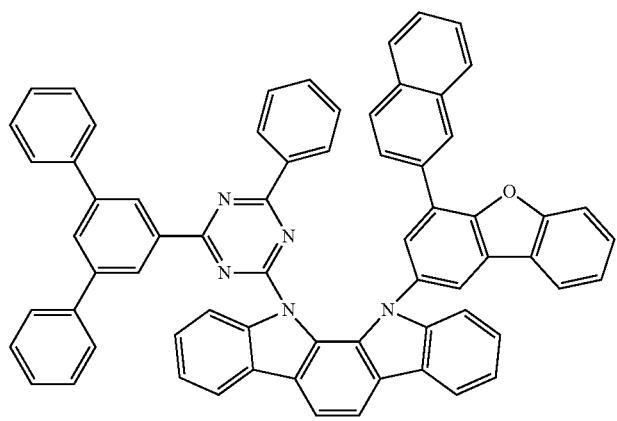 [SMILES: c1ccc(-c2cc(-c3ccccc3)cc(-c3nc(-c4ccccc4)nc(-n4c5ccccc5c5ccc6c7ccccc7n(-c7cc(-c8ccc9ccccc9c8)c8oc9ccccc9c8c7)c6c54)n3)c2)cc1] | 47% |

Mass spectrum data of the above compounds are as shown in Table 5 below.

TABLE 5

| Compound | m/z | Compound | m/z |
|---|---|---|---|
| Compound A1 | m/z = 730.3 [M + H]⁺ | Compound A84 | m/z = 809.2 [M + H]⁺ |
| Compound A3 | m/z = 748.3 [M + H]⁺ | Compound F5 | m/z = 882.3 [M + H]⁺ |
| Compound A6 | m/z = 755.3 [M + H]⁺ | Compound F10 | m/z = 740.3 [M + H]⁺ |
| Compound A14 | m/z = 806.3 [M + H]⁺ | Compound A85 | m/z = 850.3 [M + H]⁺ |
| Compound A16 | m/z = 824.3 [M + H]⁺ | Compound A79 | m/z = 856.3 [M + H]⁺ |
| Compound A23 | m/z = 806.3 [M + H]⁺ | Compound A86 | m/z = 846.3 [M + H]⁺ |
| Compound A34 | m/z = 856.3 [M + H]⁺ | Compound A87 | m/z = 763.3 [M + H]⁺ |
| Compound A39 | m/z = 748.3 [M + H]⁺ | Compound A11 | m/z = 780.3 [M + H]⁺ |
| Compound A45 | m/z = 831.3 [M + H]⁺ | Compound A88 | m/z = 820.3 [M + H]⁺ |
| Compound A52 | m/z = 856.3 [M + H]⁺ | Compound A43 | m/z = 755.3 [M + H]⁺ |
| Compound A57 | m/z = 882.3 [M + H]⁺ | Compound A89 | m/z = 740.3 [M + H]⁺ |
| Compound A67 | m/z = 882.3 [M + H]⁺ | Compound A91 | m/z = 842.4 [M + H]⁺ |
| Compound A74 | m/z = 836.3 [M + H]⁺ | Compound A69 | m/z = 780.3 [M + H]⁺ |
| Compound A76 | m/z = 820.3 [M + H]⁺ | Compound A70 | m/z = 780.3 [M + H]⁺ |
| Compound A82 | m/z = 753.3 [M + H]⁺ | Compound A109 | m/z = 932.3 [M + H]⁺ |

Nuclear magnetism data of the above partial compounds are as shown in Table 6 below.

TABLE 6

| Compound | Nuclear magnetism data |
|---|---|
| A1 | ¹H-NMR (400 MHz, Cl₂D₂): 8.27-8.41 (m, 3H), 8.11-8.22 (m, 2H), 7.94-8.11 (d, 4H), 7.16-7.61 (m, 22H). |
| A23 | ¹H-NMR (400 MHz, Cl₂D₂): 8.27-8.44 (m, 3H), 7.93-8.22 (m, 6H), 7.15-7.73 (m, 26H). |
| A11 | ¹H-NMR (400 MHz, Cl₂D₂): 8.44-8.59 (d, 1H), 8.24-8.42 (m, 3H), 8.15-8.24 (d, 1H), 7.99-8.13 (m, 1H), 7.76-7.89 (d, 2H), 7.03-7.75 (m, 25H). |
| A88 | ¹H-NMR (400 MHz, Cl₂D₂): 8.29-8.44 (m. 3H), 7.98-8.26 (m, 6H), 7.01-7.66 (m, 24H). |

Synthesis of Compound B16

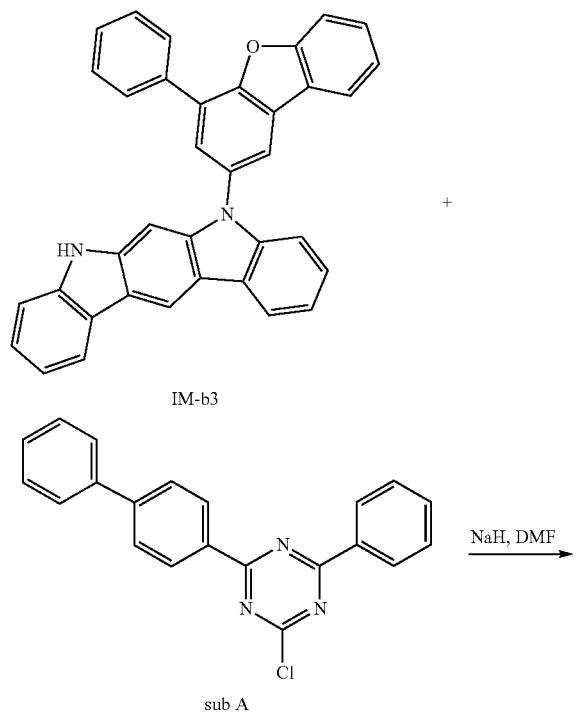

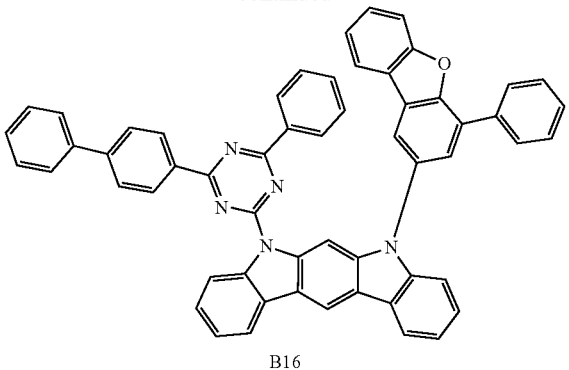

B16

The intermediate IM-b3 (6.0 g, 12.0 mmol) and dimethylformamide (60 mL) were added into a round-bottom flask, sodium hydride (0.3 g, 12.0 mmol) was added at 0° C. under a nitrogen protection condition, and stirred for 1 hour while keeping temperature; then sub A (6.2 g, 18.0 mmol) was added into a reaction solution in batches and stirred for 1 hour while keeping temperature, after the temperature was raised to 25° C., and stirring was performed for a reaction for 8 hours; a large amount of deionized water was added into the reaction solution, filtering was performed, and an obtained solid was subjected to drip washing with water and ethanol in sequence and dried to obtain a crude product; and the crude product was purified by silica gel column chromatography using dichloromethane as an eluent, and then an obtained product was purified by recrystallization using toluene to obtain a white solid compound B16 (6.1 g, 63%).

Referring to the synthesis method of the compound B16, a reactant D in Table 7 below is used to replace the intermediate IM-b3, and a reactant E is used to replace sub A to synthesize the compound shown in Table 7 below.

TABLE 7

| Compound | Reactant D | Reactant E |
| --- | --- | --- |
| B3 | (dibenzofuran-cyanophenyl-indolocarbazole structure) | 2-chloro-4,6-diphenyl-1,3,5-triazine |
| B12 | (dibenzofuran-biphenyl-indolocarbazole structure) | 2-chloro-4,6-diphenyl-1,3,5-triazine |
| B26 | (dibenzofuran-pyridyl-indolocarbazole structure) | 2-chloro-4-naphthyl-6-phenyl-1,3,5-triazine |
| B31 | (dibenzofuran-phenyl-indolocarbazole with naphthyl fusion structure) | 2-chloro-4-phenylquinazoline |

TABLE 7-continued
B32 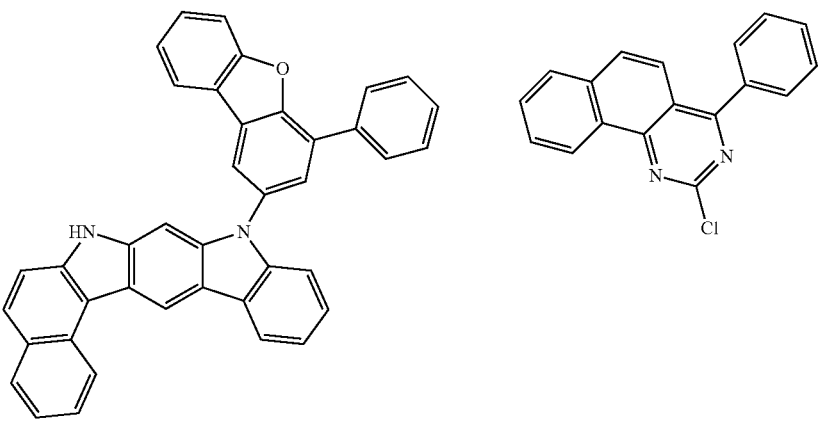
B33 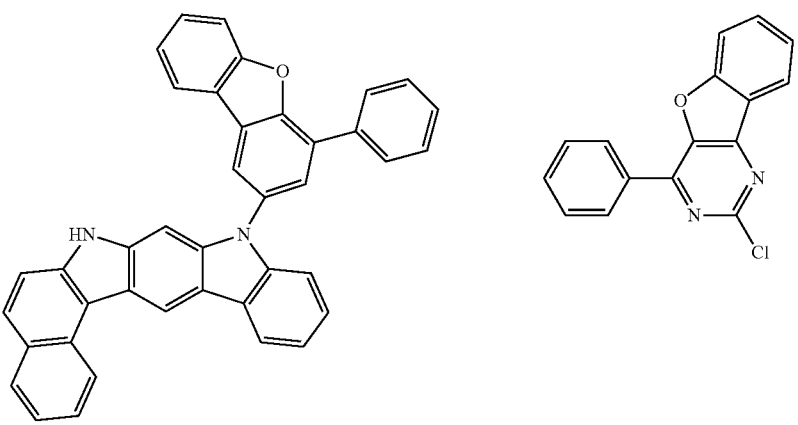
D1 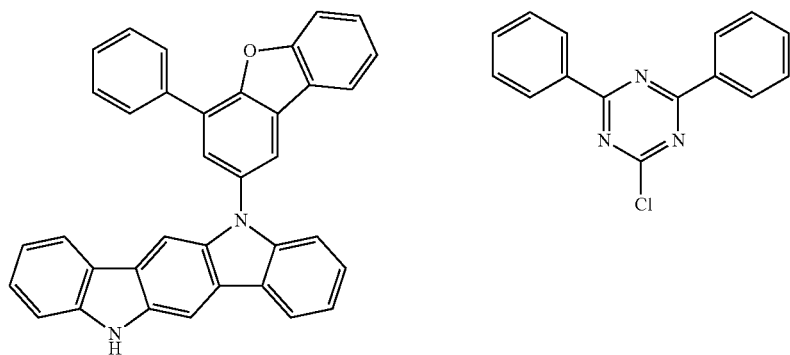
D9 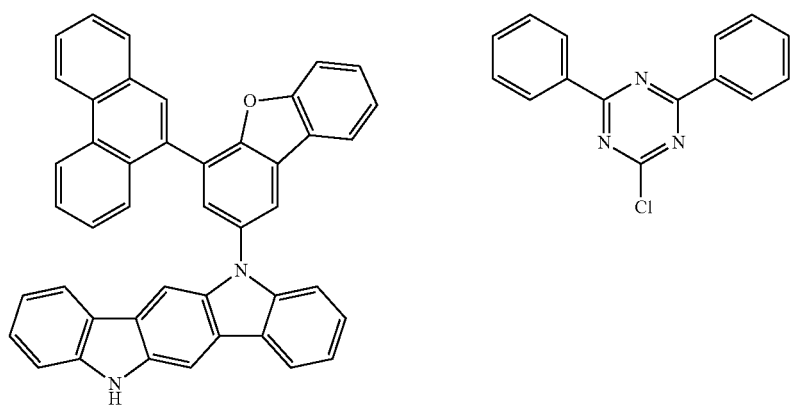

TABLE 7-continued
| D10 | 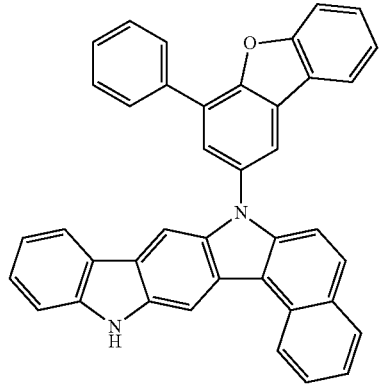 [SMILES: c1ccc(-c2cc(-n3c4cc5c(cc4c4c6ccccc6ccc43)[nH]c3ccccc35)cc3c2oc2ccccc23)cc1] | 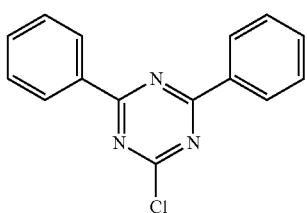 [SMILES: Clc1nc(-c2ccccc2)nc(-c2ccccc2)n1] |
| Compound | Structure | Yield |
|---|---|---|
| B3 | 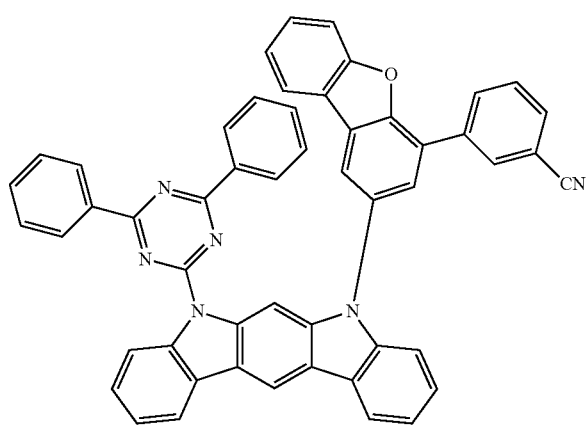 [SMILES: N#Cc1cccc(-c2cc(-n3c4ccccc4c4cc5c6ccccc6n(-c6nc(-c7ccccc7)nc(-c7ccccc7)n6)c5cc43)cc3c2oc2ccccc23)c1] | 58% |
| B12 | 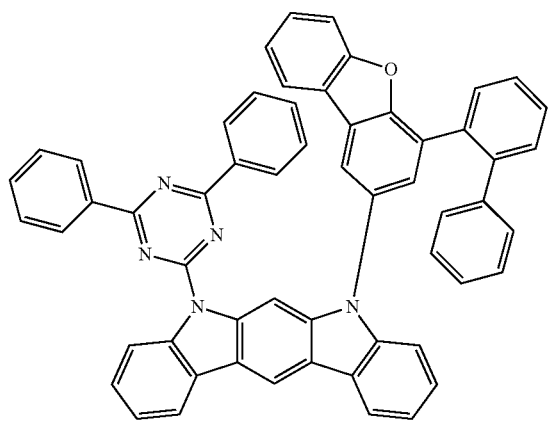 [SMILES: c1ccc(-c2nc(-c3ccccc3)nc(-n3c4ccccc4c4cc5c6ccccc6n(-c6cc(-c7ccccc7-c7ccccc7)c7oc8ccccc8c7c6)c5cc43)n2)cc1] | 45% |

TABLE 7-continued
B26 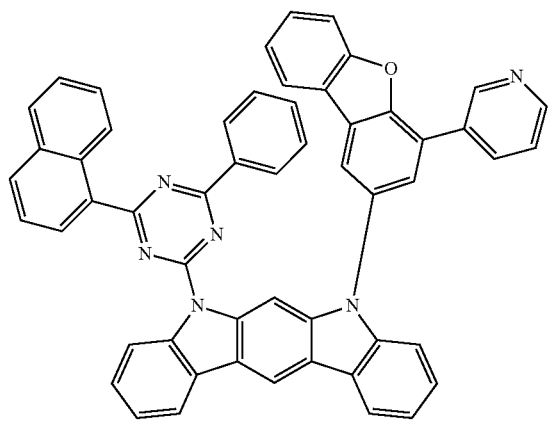 [SMILES: c1ccc(-c2nc(-c3cccc4ccccc34)nc(-n3c4ccccc4c4cc5c6ccccc6n(-c6cc(-c7cccnc7)c7oc8ccccc8c7c6)c5cc43)n2)cc1] 38%
B31 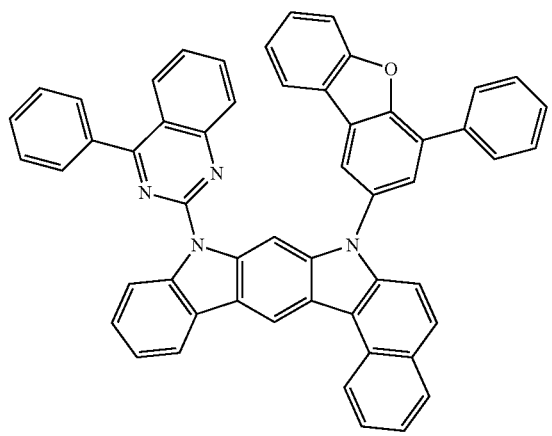 [SMILES: c1ccc(-c2nc(-n3c4ccccc4c4cc5c6c7ccccc7ccc6n(-c6cc(-c7ccccc7)c7oc8ccccc8c7c6)c5cc43)nc3ccccc23)cc1] 59%
B32 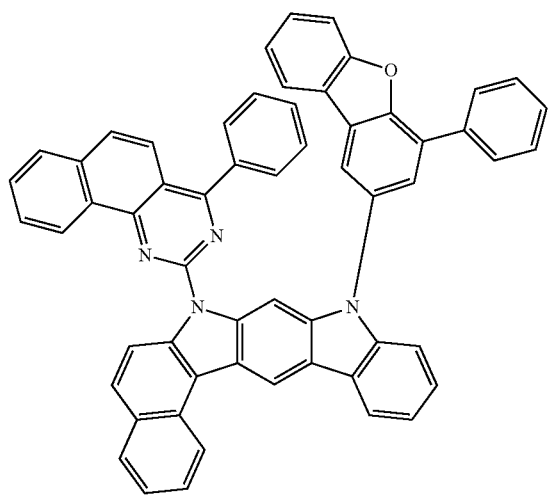 [SMILES: c1ccc(-c2nc(-n3c4cc5c(cc4c4c6ccccc6ccc43)c3ccccc3n5-c3cc(-c4ccccc4)c4oc5ccccc5c4c3)nc3c2ccc2ccccc23)cc1] 67%

TABLE 7-continued
| B33 | 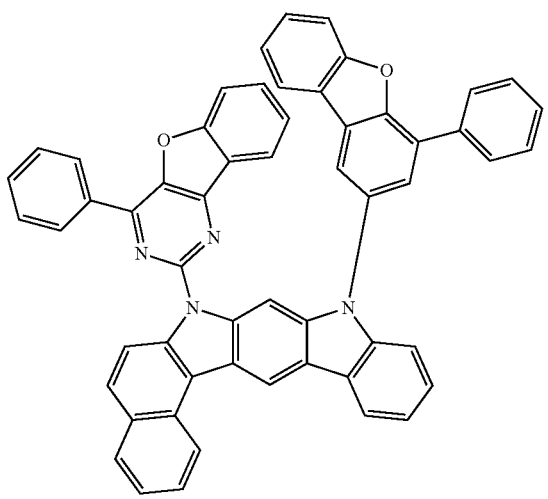 [SMILES: c1ccc(-c2cc(-n3c4ccccc4c4cc5c6c7ccccc7ccc6n(-c6nc(-c7ccccc7)c7oc8ccccc8c7n6)c5cc43)cc3c2oc2ccccc23)cc1] | 52% |
| D1 | 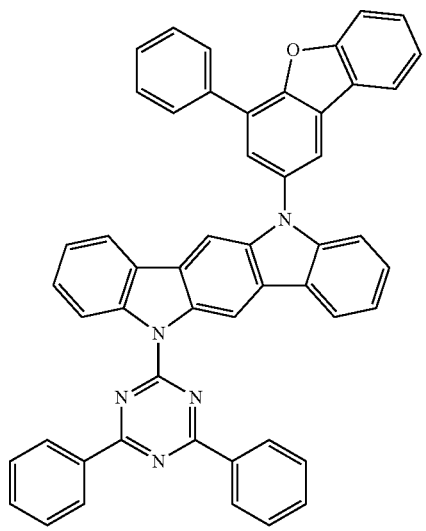 [SMILES: c1ccc(-c2nc(-c3ccccc3)nc(-n3c4ccccc4c4cc5c(cc43)c3ccccc3n5-c3cc(-c4ccccc4)c4oc5ccccc5c4c3)n2)cc1] | 50% |
| D9 | 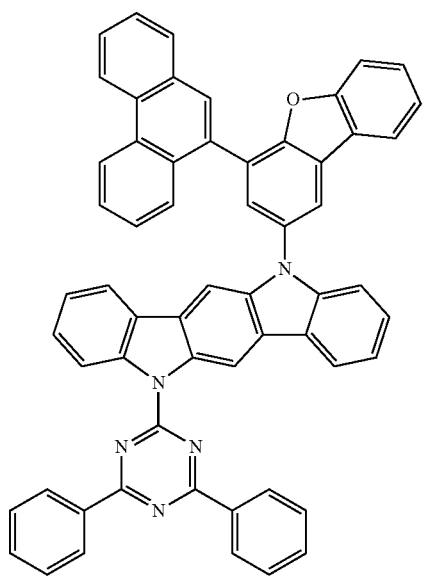 [SMILES: c1ccc(-c2nc(-c3ccccc3)nc(-n3c4ccccc4c4cc5c(cc43)c3ccccc3n5-c3cc(-c4cc5ccccc5c5ccccc45)c4oc5ccccc5c4c3)n2)cc1] | 65% |

TABLE 7-continued

D10 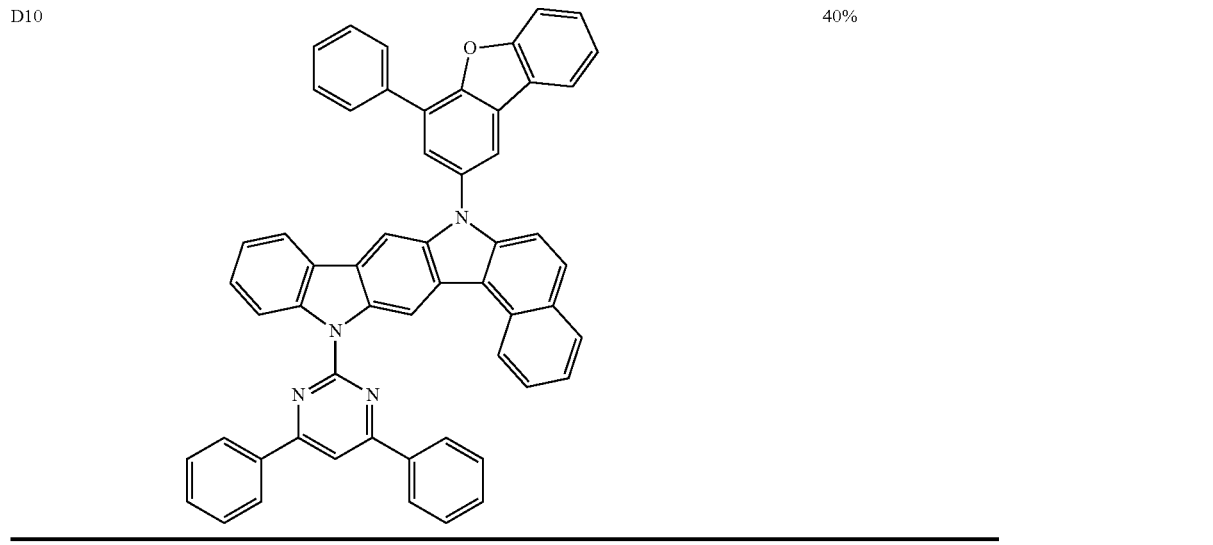 40%

Mass spectrum data of the above compounds are as shown in Table 8 below.

TABLE 8

| Compound B16 | m/z = 806.3 [M + H]+ | Compound B32 | m/z = 803.3 [M + H]+ |
| Compound B3 | m/z = 755.3 [M + H]+ | Compound B33 | m/z = 793.3 [M + H]+ |
| Compound B12 | m/z = 806.3 [M + H]+ | Compound D1 | m/z = 730.3 [M + H]+ |
| Compound B26 | m/z = 781.3 [M + H]+ | Compound D9 | m/z = 830.3 [M + H]+ |
| Compound B31 | m/z = 753.3 [M + H]+ | Compound D10 | m/z = 779.3 [M + H]+ |

Mass spectrum data of the above partial compounds are as shown in Table 9 below.

TABLE 9

| Compound | Nuclear magnetism data |
|---|---|
| B16 | $^1$H-NMR (400 MHz, Cl$_2$D$_2$):<br>9.11 (s, 1H), 9.05 (s, 1H), 8.99 (d, 1H), 8.54 (d, 2H),<br>8.45 (d, 2H),8.23 (d, 1H), 8.17 (d, 1H), 7.90 (s, 1H),<br>7.70 (d, 1H), 7.67 (s, 1H),7.59-7.54 (m, 3H),<br>7.51-7.49 (m, 3H), 7.46-7.42 (m, 6H),<br>7.38-7.36 (m, 2H),7.32-7.28 (m, 6H),<br>7.24-7.21 (m, 2H), 7.15 (t, 1H). |

Preparation and Evaluation of Organic Electroluminescent Device

Example 1: Green Organic Electroluminescent Device

An anode was prepared by the following processes: an ITO substrate (manufactured by Corning) with a thickness of 1500 Å was cut into a size of 40 mm×40 mm×0.7 mm to be prepared into an experimental substrate with a cathode, an anode and an insulating layer pattern by adopting a photoetching process, and surface treatment was performed by utilizing ultraviolet ozone and $O_2$:$N_2$ plasma to increase the work function of the anode (the experiment substrate), and remove scum.

HI-01 was vacuum-evaporated on the experiment substrate (the anode) to form a hole injection layer (HIL) with a thickness of 110 Å, and HT-01 was evaporated on the hole injection layer to form a first hole transport layer with a thickness of 940 Å.

HT-02 was vacuum-evaporated on the first hole transport layer to form a second hole transport layer with a thickness of 300 Å.

The compounds A1, GH-p and Ir(ppy)$_3$ was co-evaporated on the second hole transport layer in a film thickness ratio of 50%:45%:5% to form a green luminescent layer (EML) with a thickness of 410 Å.

ET-01 and LiQ were mixed at a weight ratio of 1:1 and evaporated to form an electron transport layer (ETL) with a thickness of 310 Å, LiQ was evaporated on the electron transport layer to form an electron injection layer (EIL) with a thickness of 20 Å, and then magnesium (Mg) and silver (Ag) were mixed at an evaporation rate of 1:9 and vacuum-evaporated on the electron injection layer to form a cathode with a thickness of 105 Å.

Furthermore, CP-01 with a thickness of 700 Å was evaporated on the cathode to form an organic capping layer (CPL), so that manufacturing of the organic luminescent device was completed, and the structure is as shown in FIG. 1.

In example 2 to example 28, except using the compounds shown in Table 11 instead of the compound A1 during forming an organic luminescent layer, an organic electroluminescent device is manufactured by using the same method as in example 1.

Comparative Examples 1 to 3

Organic electroluminescent devices were fabricated using the same method as in Example 1, except that Compound A1 was replaced by Compound I, Compound II, and Compound III in Table 10, respectively, when forming the organic light-emitting layer, for Comparative Examples 1 to 3

In examples 1 to 28 and comparative examples 1 to 3, a structural formula of each used material is shown in Table 10 below.
TABLE 10
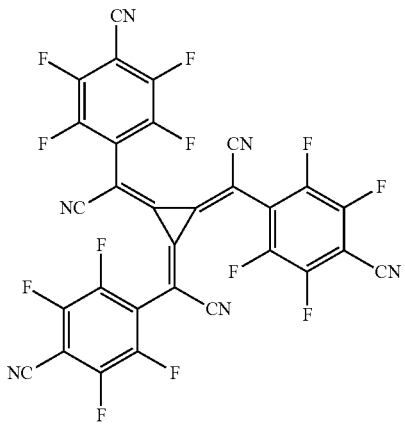 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F]
HI-01
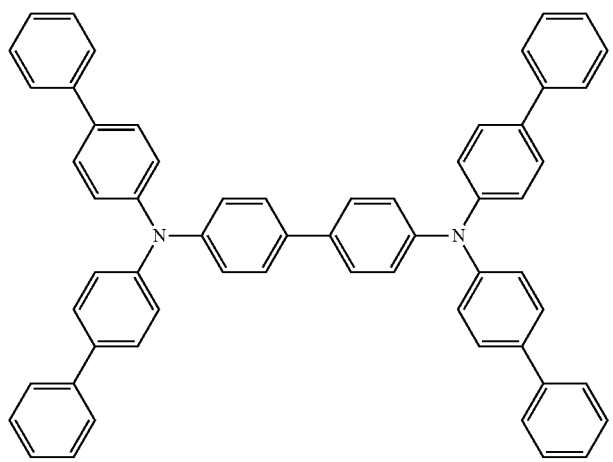 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
HT-01
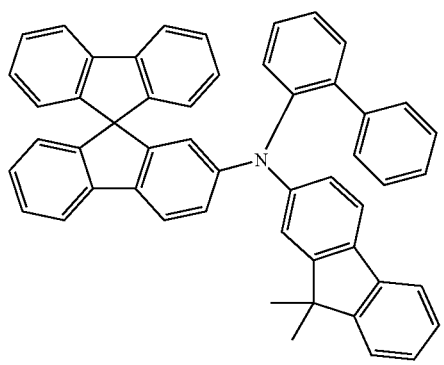 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
HT-02

TABLE 10-continued
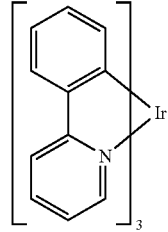
Ir(ppy)₃
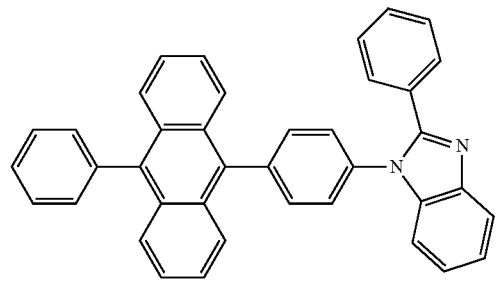 [SMILES: c1ccc(-c2c3ccccc3c(-c3ccc(-n4c(-c5ccccc5)nc5ccccc54)cc3)c3ccccc23)cc1]
ET-01
LiQ
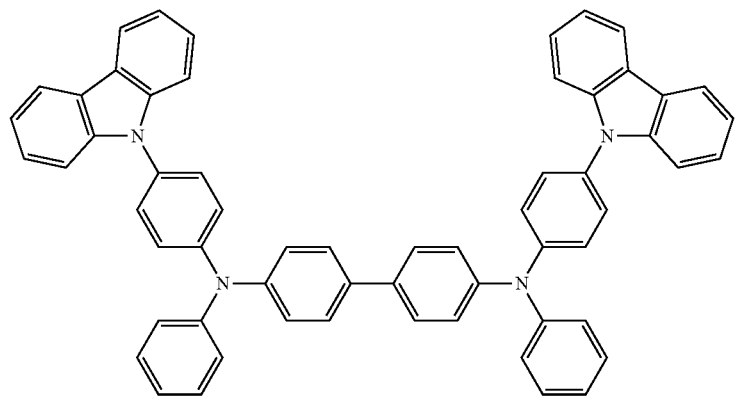 [SMILES: c1ccc(N(c2ccc(-c3ccc(N(c4ccccc4)c4ccc(-n5c6ccccc6c6ccccc65)cc4)cc3)cc2)c2ccc(-n3c4ccccc4c4ccccc43)cc2)cc1]
CP-01
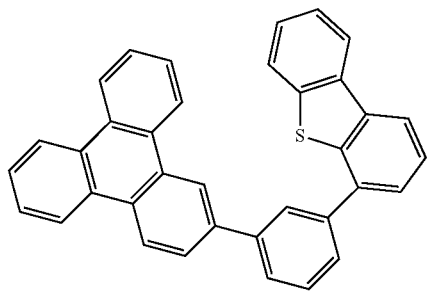 [SMILES: c1cc(-c2ccc3c4ccccc4c4ccccc4c3c2)cc(-c2cccc3c2sc2ccccc23)c1]
GH-p TABLE 10-continued
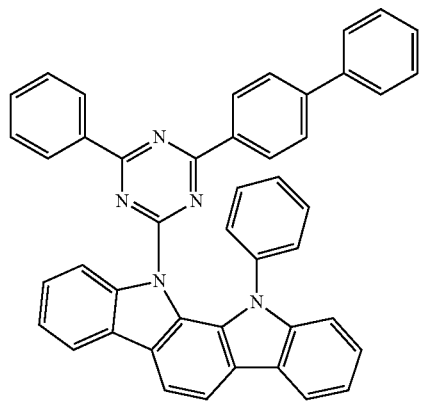 [SMILES: c1ccc(-c2ccc(-c3nc(-c4ccccc4)nc(-n4c5ccccc5c5ccc6c7ccccc7n(-c7ccccc7)c6c54)n3)cc2)cc1]
Compound I
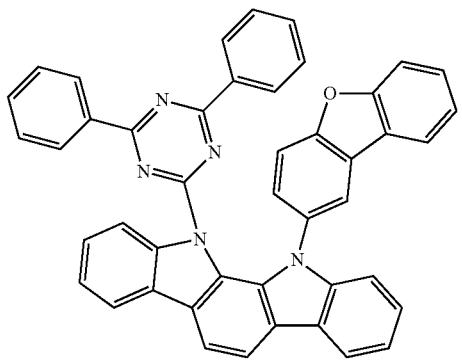 [SMILES: c1ccc(-c2nc(-c3ccccc3)nc(-n3c4ccccc4c4ccc5c6ccccc6n(-c6ccc7oc8ccccc8c7c6)c5c43)n2)cc1]
Compound II
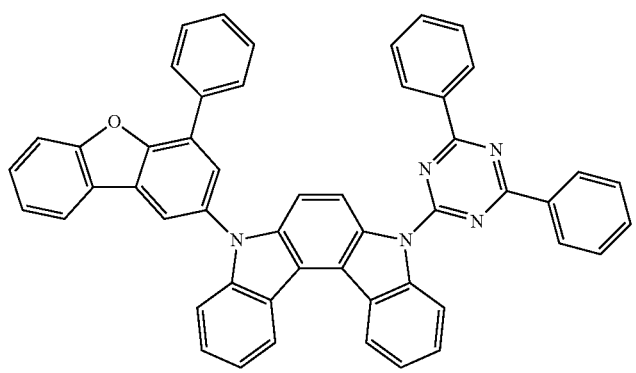 [SMILES: c1ccc(-c2nc(-c3ccccc3)nc(-n3c4ccccc4c4c5c6ccccc6n(-c6cc(-c7ccccc7)c7oc8ccccc8c7c6)c5ccc43)n2)cc1]
Compound III The performance of the manufactured organic electroluminescent device above is analyzed under a condition of 20 mA/cm$^2$, and the result is shown in Table 11 below.

TABLE 11

| Example No. | Luminescent layer compound | Driving voltage (V) | Current efficiency (Cd/A) | Power efficiency (1 m/W) | Chromaticity coordinate CIEx | Chromaticity coordinate CIEy | External quantum efficiency EQE (%) | T95 service life (h) 20 mA/cm$^2$ |
|---|---|---|---|---|---|---|---|---|
| Example 1 | Compound A1 | 3.92 | 97.0 | 77.8 | 0.22 | 0.73 | 23.3 | 324 |
| Example 2 | Compound A3 | 3.96 | 97.1 | 77.1 | 0.22 | 0.73 | 23.3 | 327 |
| Example 3 | Compound A6 | 3.97 | 96.3 | 76.2 | 0.22 | 0.73 | 23.1 | 313 |
| Example 4 | Compound A14 | 3.93 | 98.3 | 78.5 | 0.22 | 0.73 | 23.6 | 308 |
| Example 5 | Compound A16 | 3.88 | 97.4 | 78.8 | 0.22 | 0.73 | 23.4 | 313 |
| Example 6 | Compound A23 | 3.96 | 99.0 | 78.5 | 0.22 | 0.73 | 23.8 | 311 |
| Example 7 | Compound A34 | 3.95 | 98.9 | 78.7 | 0.22 | 0.73 | 23.7 | 328 |
| Example 8 | Compound A39 | 3.93 | 98.9 | 79.0 | 0.22 | 0.73 | 23.7 | 329 |
| Example 9 | Compound A45 | 3.90 | 96.0 | 77.3 | 0.22 | 0.73 | 23.0 | 304 |
| Example 10 | Compound A52 | 3.95 | 96.3 | 76.6 | 0.22 | 0.73 | 23.1 | 317 |
| Example 11 | Compound A57 | 3.95 | 98.2 | 78.1 | 0.22 | 0.73 | 23.6 | 312 |
| Example 12 | Compound A67 | 3.94 | 98.8 | 78.8 | 0.22 | 0.73 | 23.7 | 317 |
| Example 13 | Compound A74 | 3.98 | 96.9 | 76.5 | 0.22 | 0.73 | 23.2 | 316 |
| Example 14 | Compound A76 | 3.89 | 98.7 | 79.7 | 0.22 | 0.73 | 23.7 | 326 |
| Example 15 | Compound F5 | 4.00 | 95.1 | 74.7 | 0.22 | 0.73 | 22.8 | 275 |
| Example 16 | Compound F10 | 3.93 | 92.8 | 74.1 | 0.22 | 0.73 | 22.3 | 262 |
| Example 17 | Compound A79 | 3.94 | 97.0 | 77.4 | 0.22 | 0.73 | 23.3 | 324 |
| Example 18 | Compound A85 | 3.94 | 98.5 | 78.6 | 0.22 | 0.73 | 23.6 | 317 |
| Example 18 | Compound A86 | 3.93 | 96.5 | 77.1 | 0.22 | 0.73 | 23.2 | 325 |
| Example 20 | Compound A87 | 3.95 | 98.0 | 77.9 | 0.22 | 0.73 | 23.5 | 317 |
| Example 21 | Compound A88 | 3.95 | 98.7 | 78.5 | 0.22 | 0.73 | 23.7 | 324 |
| Example 22 | Compound A11 | 3.91 | 98.0 | 78.7 | 0.22 | 0.73 | 23.5 | 318 |
| Example 23 | Compound A43 | 3.91 | 97.9 | 78.6 | 0.22 | 0.73 | 23.5 | 313 |
| Example 24 | Compound A89 | 3.92 | 96.9 | 77.6 | 0.22 | 0.73 | 23.3 | 328 |
| Example 25 | Compound A91 | 3.98 | 97.0 | 76.5 | 0.22 | 0.73 | 23.3 | 316 |
| Example 26 | Compound A69 | 3.94 | 97.1 | 77.5 | 0.22 | 0.73 | 23.3 | 313 |
| Example 27 | Compound A70 | 3.95 | 97.6 | 77.6 | 0.22 | 0.73 | 23.4 | 321 |
| Example 28 | Compound A109 | 3.95 | 96.8 | 77.0 | 0.22 | 0.73 | 23.2 | 316 |
| Comparative example 1 | Compound I | 4.40 | 78.7 | 57.6 | 0.22 | 0.73 | 15.4 | 152 |
| Comparative example 2 | Compound II | 4.38 | 80.5 | 58.4 | 0.22 | 0.73 | 17.6 | 173 |
| Comparative example 3 | Compound III | 4.27 | 83.3 | 62.4 | 0.22 | 0.73 | 19.3 | 184 |

It can be seen from Table 11 above that the compound of the present disclosure is used as an electronic host material in the mixed host material of the green organic luminescent layer in examples 1 to 28, compared with comparative examples 1 to 3, the luminous efficiency and the service life of the device are apparently improved, the driving voltage is also reduced to a certain extent, the luminous efficiency Cd/A is at least improved by 11.400, the external quantum efficiency is at least improved by 15.5%, and the service life is at least increased by 42.4%.

Compared with comparative example 2, in the compound of the present disclosure, aryl or heteroaryl substituents are added on the 4-position of dibenzofuran, which can not only improve the carrier mobility and the energy transfer efficiency of the material, but also effectively improve the stability of a molecular structure, thus effectively reducing the driving voltage of the device and increasing the device lifetime.

Compared with comparative example 3, in the compound of the present disclosure, the service life and efficiency are both improved, the reason is that in the structure of the compound of the present disclosure, a parent core of indolocarbazole is different from a fused position of indolocarbazole in the compound of comparative example 3. In the indolocarbazole referenced in the compound of the present disclosure, a steric distance between two N atoms is smaller, such that the steric positions between dibenzofuranyl and triazinyl connected to the two N atoms are also closer. Thus, $\Delta E_{ST}$ (an energy level difference between a first excited singlet state and a first excited triplet state, $\Delta E_{ST}=S_1-T_1$) is small, a characteristic of thermally activated delayed fluorescence (TADF) is realized, when the indolocarbazole is used as the green host material (especially an electronic host) of the organic electroluminescent device, the utilization rate of excitons can be improved, and the luminous efficiency is improved. Secondly, the compound of the present disclosure has a large steric hindrance, reduces the intermolecular force of the compound, inhibits the mutual aggregation between molecules, and has a good film-forming property, thus having an effect of increasing the service life.

The above experimental results prove that the compound of the present disclosure has a structure formed by the combination of an electron-deficient aza-aryl group, an indolocarbazole group in a specific fusing mode and substituted dibenzofuran, when being used for preparing the green organic electroluminescent device, the luminous efficiency of the organic electroluminescent device can be effectively improved, the driving voltage is reduced, and the service life of the device is increased.

Example 29: Red Organic Electroluminescent Device

An anode was prepared by the following processes: an ITO substrate (manufactured by Corning) with a thickness of 1500 Å was cut into a size of 40 mm×40 mm×0.7 mm to be prepared into an experimental substrate with a cathode, an anode and an insulating layer pattern by adopting a photoetching process, and surface treatment was performed by utilizing ultraviolet ozone and $O_2:N_2$ plasma to increase the work function of the anode (the experiment substrate), and remove scum.

F4-TCNQ was vacuum-evaporated on the experiment substrate (the anode) to form a hole injection layer (HIL) with a thickness of 100 Å, and HT-01 was evaporated on the hole injection layer to form a first hole transport layer with a thickness of 950 Å.

HT-03 was vacuum-evaporated on the first hole transport layer to form a second hole transport layer with a thickness of 700 Å.

The compounds A82 and Ir(piq)$_2$(acac) was co-evaporated on the second hole transport layer in a ratio of 95%:5% (an evaporation rate) to form a red luminescent layer (EML) with a thickness of 380 Å.

ET-01 and LiQ were mixed at a weight ratio of 1:1 and evaporated to form an electron transport layer (ETL) with a thickness of 310 Å, LiQ was evaporated on the electron transport layer to form an electron injection layer (EIL) with a thickness of 10 Å, and then magnesium (Mg) and silver (Ag) were mixed at an evaporation rate of 1:9 and vacuum-evaporated on the electron injection layer to form a cathode with a thickness of 105 Å.

Furthermore, CP-01 with a thickness of 680 Å was evaporated on the cathode to form an organic capping layer (CPL), thus completing manufacturing of the organic luminescent device.

Example 30

Organic electroluminescent elements are prepared in the same way as in Example 29, except for the substitution of compounds shown in Table 13 for compound A82 in Example 29.

Comparative Examples 4 to 5

Organic electroluminescence devices were prepared by the same method as in Example 29, except for compounds 4 and 5 shown in Table 12 instead of compounds A82 in Example 29.

In examples 29 to 30 and comparative examples 4 to 5, a structural formula of each used material is shown in Table 12 below.

TABLE 12

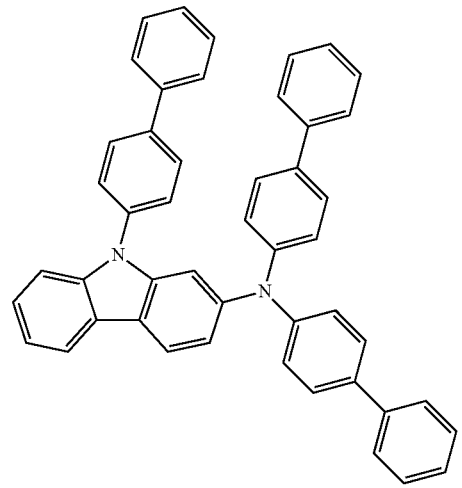 [SMILES: c1ccc(-c2ccc(N(c3ccc(-c4ccccc4)cc3)c3ccc4c5ccccc5n(-c5ccc(-c6ccccc6)cc5)c4c3)cc2)cc1]

HT-03

TABLE 12-continued

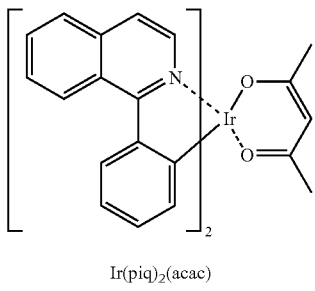

Ir(piq)₂(acac)

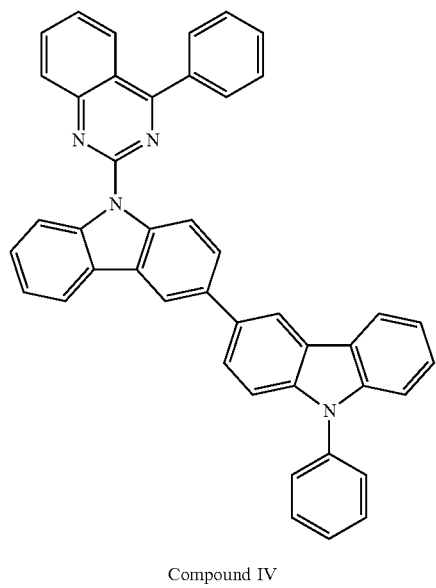

Compound IV

TABLE 12-continued

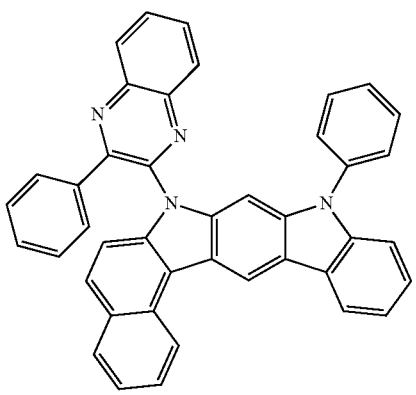 [SMILES: c1ccc(-c2nc3ccccc3nc2-n2c3cc4c(cc3c3c5ccccc5ccc32)c2ccccc2n4-c2ccccc2)cc1]

Compound V

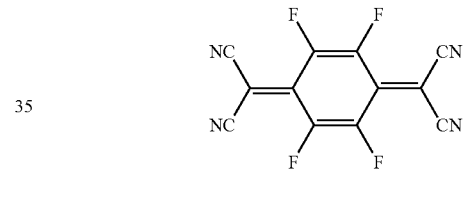

F4-TCNQ

The organic electroluminescent devices prepared in examples 29 to 30 and comparative examples 4 to 5 were tested for performance under a condition of 20 mA/cm², and the test results are shown in Table 13.

TABLE 13

| Example No. | Luminescent layer compound | Driving voltage (V) | Current efficiency (cd/A) | Power efficiency (1 m/W) | Chromaticity coordinate CIE-x | Chromaticity coordinate CIE-y | External quantum efficiency EQE (%) | T95 service life (h) 20 mA/cm² |
|---|---|---|---|---|---|---|---|---|
| Example 29 | Compound A82 | 3.62 | 45.4 | 39.4 | 0.68 | 0.32 | 30.9 | 375 |
| Example 30 | Compound A84 | 3.55 | 46.3 | 41.0 | 0.68 | 0.32 | 31.5 | 355 |
| Comparative example 4 | Compound IV | 3.86 | 39.6 | 32.2 | 0.68 | 0.32 | 26.9 | 291 |
| Comparative example 5 | Compound V | 3.79 | 39.3 | 32.6 | 0.68 | 0.32 | 26.7 | 304 |

It can be seen from data shown in Table 13 above, compared with the organic electroluminescent devices prepared in comparative examples 4 to 5, the voltage, luminous efficiency and device life of the organic electroluminescent devices prepared in examples 29 to 30 are improved to varying degrees. The reason may be that indolocarbazole is combined with the substituted dibenzofuran in a specific position, such that the material has the high carrier mobility, and good energy transfer efficiency and structural stability.

Preparation and Evaluation of Organic Electroluminescent Device

Example 31: Green Organic Electroluminescent Device

An anode was prepared by the following processes: an ITO substrate (manufactured by Corning) with a thickness of 1300 Å was cut into a size of 40 mm×40 mm×0.7 mm to be prepared into an experimental substrate with a cathode, an anode and an insulating layer pattern by adopting a photoetching process, and surface treatment was performed by utilizing ultraviolet ozone and $O_2:N_2$ plasma to increase the work function of the anode (the experiment substrate), and remove scum.

HT-01 was vacuum-evaporated on the experiment substrate (the anode) to form a hole injection layer (HIL) with a thickness of 110 Å, and HT-01 was evaporated on the hole injection layer to form a first hole transport layer with a thickness of 960 Å.

HT-02 was vacuum-evaporated on the first hole transport layer to form a second hole transport layer with a thickness of 310 Å.

Compounds B16, GH-p and Ir(ppy)$_2$(acac) were co-evaporated on the second hole transport layer in a film thickness ratio of 50%:45%:5% (an evaporation rate) to form a green luminescent layer (EML) with a thickness of 400 Å.

ET-01 and LiQ were mixed at a weight ratio of 1:1 and evaporated to form an electron transport layer (ETL) with a thickness of 310 Å, LiQ was evaporated on the electron transport layer to form an electron injection layer (EIL) with a thickness of 15 Å, and then magnesium (Mg) and silver (Ag) were mixed at an evaporation rate of 1:9 and vacuum-evaporated on the electron injection layer to form a cathode with a thickness of 115 Å.

Furthermore, CP-01 with a thickness of 710 Å was evaporated on the cathode to form an organic capping layer (CPL), thus completing manufacturing of the organic luminescent device, and the structure is as shown in FIG. 1.

In examples 32 to 36, except using the compounds shown in Table 15 11 instead of the compound B16 during forming an organic luminescent layer, an organic electroluminescent device was manufactured by using the same method as in example 31.

Comparative Examples 6 to 8

Except for the substitution of compounds BI, BII and BIII in Table 14, organic electroluminescence devices are made by the same method as in Example 1, as in Example 6 to 8.

In examples 31 to 36 and comparative examples 6 to 8, a structural formula of each used material is shown in Table 14 below.

TABLE 14

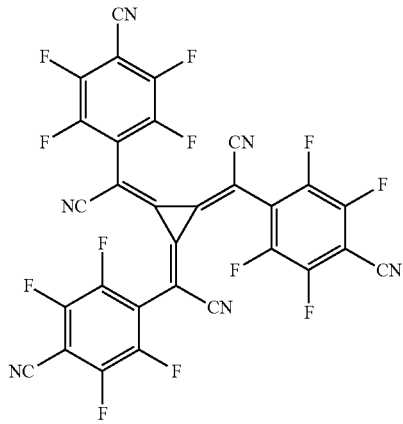 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F]

HI-01

TABLE 14-continued
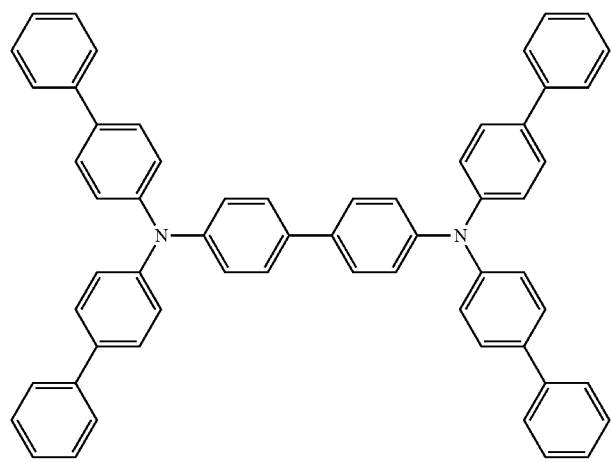 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
HT-01
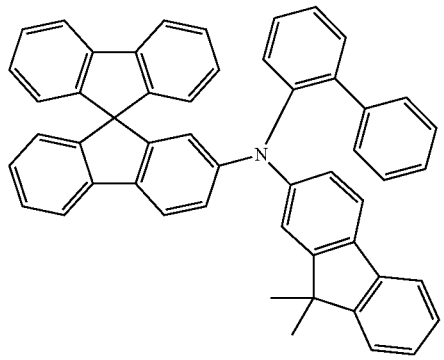 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
HT-02
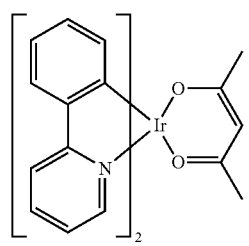
Ir(ppy)$_2$(acac)
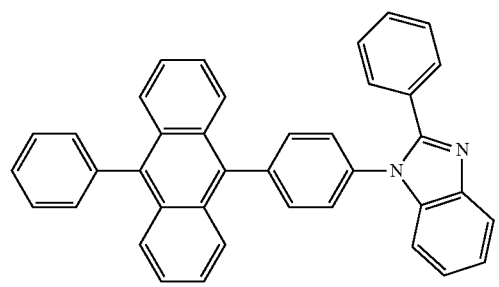 [SMILES: c1ccc(-c2c3ccccc3c(-c3ccc(-n4c(-c5ccccc5)nc5ccccc54)cc3)c3ccccc23)cc1]
ET-01

TABLE 14-continued
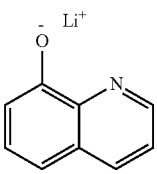 [SMILES: [Li+] ; Oc1cccc2cccnc12]
LiQ
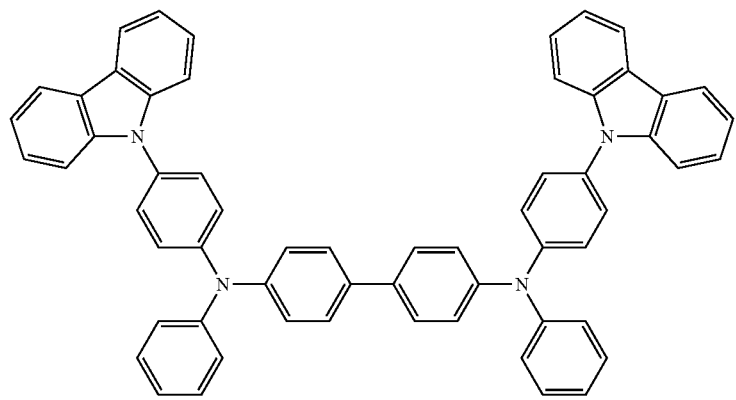 [SMILES: c1ccc(N(c2ccc(-c3ccc(N(c4ccccc4)c4ccc(-n5c6ccccc6c6ccccc65)cc4)cc3)cc2)c2ccc(-n3c4ccccc4c4ccccc43)cc2)cc1]
CP-01
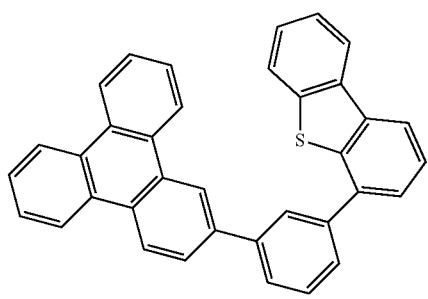 [SMILES: c1cc(-c2ccc3c4ccccc4c4ccccc4c3c2)cc(-c2cccc3c2sc2ccccc23)c1]
GH-p
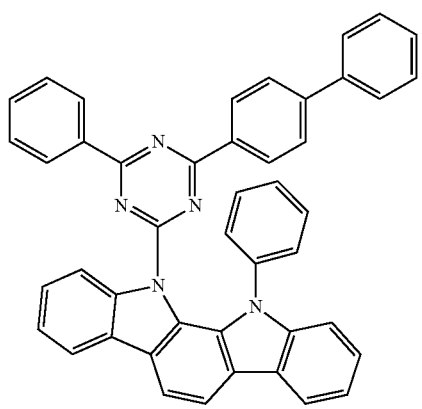 [SMILES: c1ccc(-c2ccc(-c3nc(-c4ccccc4)nc(-n4c5ccccc5c5ccc6c7ccccc7n(-c7ccccc7)c6c54)n3)cc2)cc1]
Compound BI TABLE 14-continued

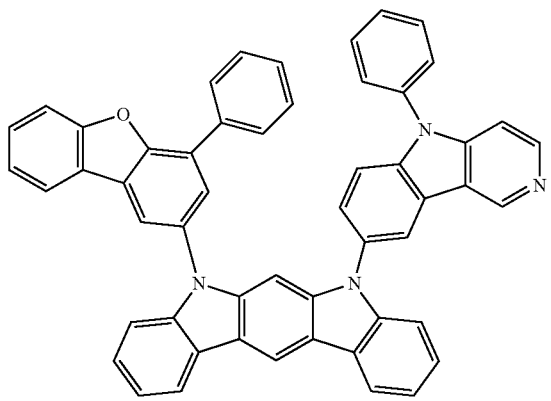 [SMILES: c1ccc(-c2cc(-n3c4ccccc4c4cc5c6ccccc6n(-c6ccc7c(c6)c6cnccc6n7-c6ccccc6)c5cc43)cc3c2oc2ccccc23)cc1]

Compound BII

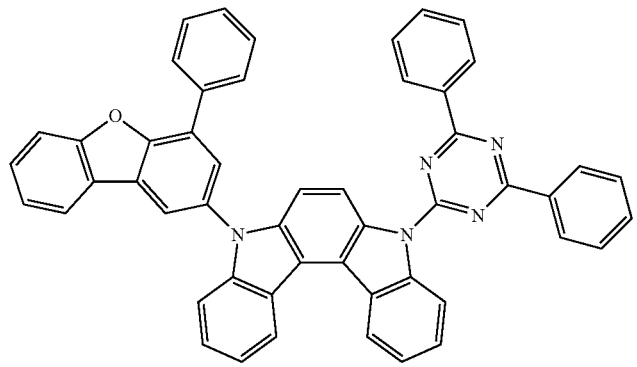 [SMILES: c1ccc(-c2nc(-c3ccccc3)nc(-n3c4ccccc4c4c5c6ccccc6n(-c6cc(-c7ccccc7)c7oc8ccccc8c7c6)c5ccc43)n2)cc1]

Compound BIII

The performance of the manufactured organic electroluminescent device above was analyzed under a condition of 20 mA/cm², and the result is shown in Table 15 below.

TABLE 15

| Example No. | Luminescent layer compound | Driving voltage (V) | Current efficiency (Cd/A) | Power efficiency (1 m/W) | Chromaticity coordinate CIEx | Chromaticity coordinate CIEy | External quantum efficiency EQE (%) | T95 service life (h) 20 mA/cm² |
|---|---|---|---|---|---|---|---|---|
| Example 31 | Compound B16 | 4.05 | 101.4 | 80.6 | 0.22 | 0.73 | 24.3 | 286 |
| Example 32 | Compound B3 | 4.02 | 105.4 | 82.4 | 0.22 | 0.73 | 25.3 | 295 |
| Example 33 | Compound B12 | 3.98 | 103.7 | 81.8 | 0.22 | 0.73 | 24.9 | 298 |
| Example 34 | Compound B26 | 3.98 | 105.7 | 83.4 | 0.22 | 0.73 | 25.4 | 299 |
| Example 35 | Compound D1 | 3.99 | 92.6 | 71.3 | 0.22 | 0.73 | 21.7 | 285 |
| Example 36 | Compound D9 | 4.00 | 92.8 | 71.1 | 0.22 | 0.73 | 21.7 | 275 |
| Comparative example 6 | Compound BI | 4.58 | 69.5 | 47.7 | 0.22 | 0.73 | 13.4 | 120 |
| Comparative example 7 | Compound BII | 4.41 | 75.5 | 55.3 | 0.22 | 0.73 | 16.6 | 172 |
| Comparative example 8 | Compound BIII | 4.31 | 80.1 | 60.4 | 0.22 | 0.73 | 17.7 | 167 |

It can be seen from Table 15 above that the compound of the present disclosure is used as an electronic host material in the mixed host material of the green organic luminescent layer in examples 31 to 36, compared with the organic electroluminescent devices in comparative examples 6 to 8, in the organic electroluminescent devices prepared by the compound of the present disclosure, the external quantum efficiency is at least improved by 22.6%, and the service life is at least increased by 59.900. It can be seen that when the novel compound of the present disclosure is used for preparing the green organic electroluminescent device, the luminous efficiency of the organic electroluminescent device can be effectively improved, the voltage is reduced, and the service life of the device is increased.

Compared with comparative example 6, the luminous efficiency and service life of the device of the example of the present disclosure are apparently improved, and the driving voltage is also reduced to a certain extent.

Compared with comparative example 7, the device of the example of the present disclosure has a lower working voltage and a higher luminous efficiency, the reason may be that the nitrogen-containing heteroaryl used in the compound of the present disclosure is different from the nitrogen-containing heteroaryl used in the compound BII, the nitrogen-containing heteroaryl used in the compound of the present disclosure has higher electron mobility than 5-phenyl-5H-pyrido[4,3-b]indole of comparative example 7.

Compared with comparative example 8, a patent core of indolocarbazole used in the compound of the present disclosure is different from a fusing position of indolocarbazole in the compound of comparative example 8, the indolocarbazole used in the present disclosure has a larger steric hindrance, reduces the intermolecular force, inhibits the mutual aggregation between molecules, and has a better film-forming property, thus having an effect of increasing the service life.

To sum up, when the compound of the present disclosure is used as the electronic host of the organic electroluminescent green light device, the luminous efficiency of the organic electroluminescent device can be effectively improved, the driving voltage is reduced, and the service life of the device is prolonged.

Example 37: Red Organic Electroluminescent Device

An anode was prepared by the following processes: an ITO substrate (manufactured by Corning) with a thickness of 1500 Å was cut into a size of 40 mm×40 mm×0.7 mm to be prepared into an experimental substrate with a cathode, an anode and an insulating layer pattern by adopting a photoetching process, and surface treatment was performed by utilizing ultraviolet ozone and $O_2$:$N_2$ plasma to increase the work function of the anode (the experiment substrate), and remove scum.

F4-TCNQ was vacuum-evaporated on the experiment substrate (the anode) to form a hole injection layer (HIL) with a thickness of 100 Å, and HT-01 was evaporated on the hole injection layer to form a first hole transport layer with a thickness of 950 Å.

HT-03 was vacuum-evaporated on the first hole transport layer to form a second hole transport layer with a thickness of 700 Å.

The compounds B31 and Ir(piq)$_2$(acac) were co-evaporated on the second hole transport layer in a ratio of 95%:5% (an evaporation rate) to form a red luminescent layer (EML) with a thickness of 380 Å.

ET-01 and LiQ were mixed at a weight ratio of 1:1 and evaporated to form an electron transport layer (ETL) with a thickness of 310 Å, LiQ was evaporated on the electron transport layer to form an electron injection layer (EIL) with a thickness of 10 Å, and then magnesium (Mg) and silver (Ag) were mixed at an evaporation rate of 1:9 and vacuum-evaporated on the electron injection layer to form a cathode with a thickness of 105 Å.

Furthermore, CP-01 with a thickness of 680 Å was evaporated on the cathode to form an organic capping layer (CPL), thus completing manufacturing of the organic luminescent device.

Example 38 to Example 40

Except using the compounds shown in Table 17 instead of the compound B31 during forming the forming an organic luminescent layer, an organic electroluminescent device is prepared by using the same method as in example 37.

Comparative Examples 9 to 10

Organic electroluminescence devices are prepared by the same method as in Example 37 except for the substitution of compounds BIV and BV respectively in the formation of organic luminescence layers.

In examples 37 to 40 and comparative examples 9 to 10, a structural formula of each used material is shown in Table 16 below.

TABLE 16

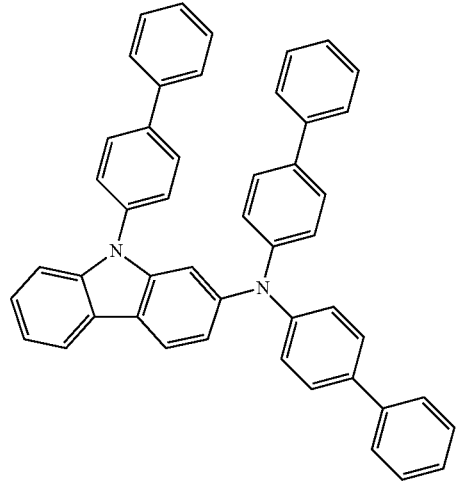 [SMILES: c1ccc(-c2ccc(N(c3ccc(-c4ccccc4)cc3)c3ccc4c5ccccc5n(-c5ccc(-c6ccccc6)cc5)c4c3)cc2)cc1]

HT-03

TABLE 16-continued

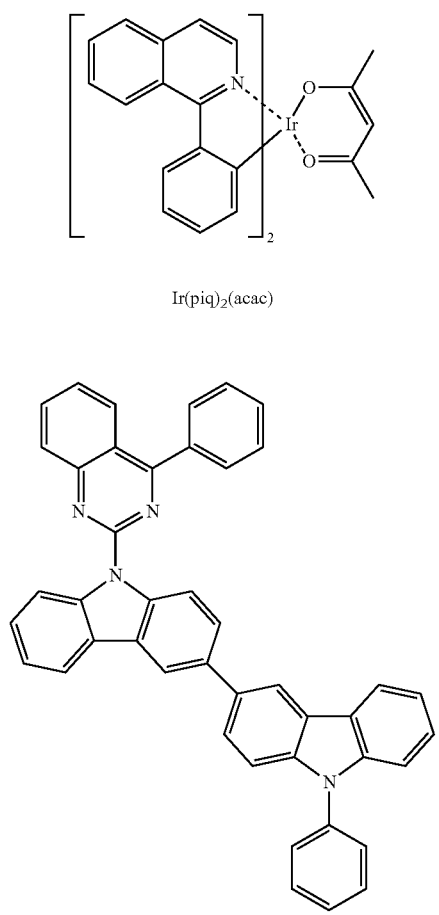

Ir(piq)₂(acac)

Compound BIV

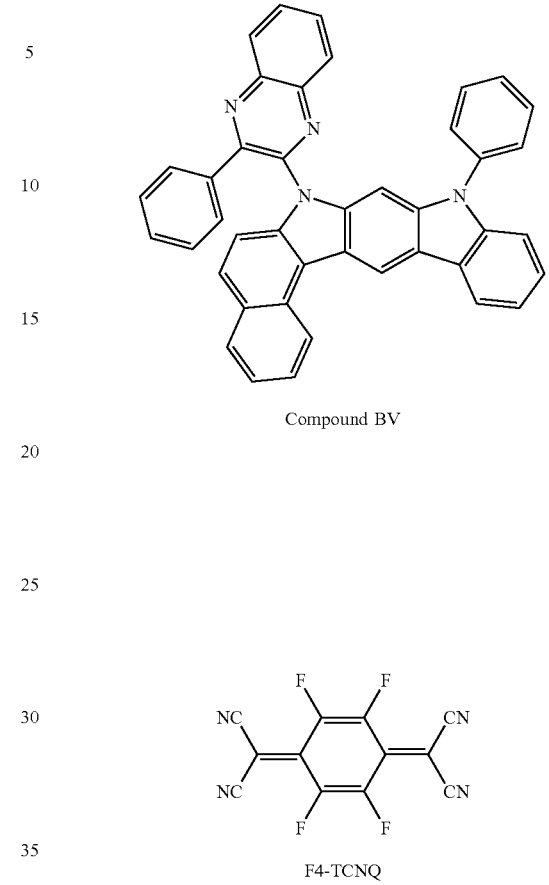

Compound BV

F4-TCNQ

The organic electroluminescent devices prepared in examples 37 to 40 and comparative examples 9 to 10 were tested for performance under a condition of 20 mA/cm², and the test results are shown in Table 17.

TABLE 17

| Example No. | Luminescent layer compound | Driving voltage (V) | Current efficiency (Cd/A) | Power efficiency (1 m/W) | Chromaticity coordinate CIE-x | Chromaticity coordinate CIE-y | External quantum efficiency EQE (%) | T95 service life (h) 20 mA/cm² |
|---|---|---|---|---|---|---|---|---|
| Example 37 | Compound B31 | 3.55 | 48.8 | 43.1 | 0.68 | 0.32 | 33.2 | 352 |
| Example 38 | Compound B32 | 3.60 | 46.8 | 40.8 | 0.68 | 0.32 | 31.8 | 357 |
| Example 39 | Compound B33 | 3.59 | 47.3 | 41.4 | 0.68 | 0.32 | 32.1 | 351 |
| Example 40 | Compound D10 | 3.54 | 48.6 | 43.1 | 0.68 | 0.32 | 33.0 | 361 |
| Comparative example 9 | Compound BIV | 3.86 | 39.6 | 32.2 | 0.68 | 0.32 | 26.9 | 291 |
| Comparative example 10 | Compound BV | 3.79 | 39.3 | 32.6 | 0.68 | 0.32 | 26.7 | 304 |

It can be seen from data shown in Table 17 above, compared with the organic electroluminescent devices prepared in comparative examples 9 to 10, the voltage, luminous efficiency and device life of the organic electroluminescent devices prepared in examples 37 to 40 are improved to varying degrees. The reason may be that indolocarbazole is combined with the substituted dibenzofuran in a specific position, such that the material has the higher carrier mobility, and better energy transfer efficiency and structural stability.

Compared with the organic electroluminescent devices in comparative examples, in the organic electroluminescent devices prepared by the compound of the present disclosure, the service life is at least increased by 15.46%, and the external quantum efficiency is at least improved by 18.22%.

The preferable implementations of the present disclosure are described in detail above in combination with the drawings, however, the present disclosure is not limited to the specific details in the above implementations, in the technical concept range of the present disclosure, the technical solutions of the present disclosure can be subjected to various simple variations, and these simple variations all belong to the protection range of the present disclosure.

In addition, it needs to be noted that all the specific technical features described in the above specific implementations can be combined in any appropriate mode without contradiction, and in order to avoid unnecessary repetition, various possible combinations are not separately illustrated any more in the present disclosure.

In addition, various different implementations of the present disclosure can also be combined at will, and as long as the implementations do not violate the idea of the present disclosure, the implementations also should be regarded as the contents disclosed by the present disclosure.

What is claimed is:

1. An organic compound, having a structure as shown in a formula A or a formula F:

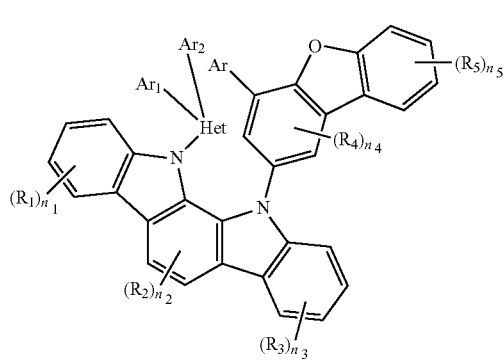

Formula A

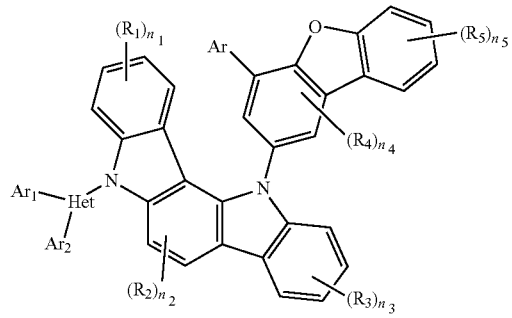

Formula F wherein, Ar is selected from substituted or unsubstituted phenyl, substituted or unsubstituted biphenyl, substituted or unsubstituted naphthyl;

Het is selected from substituted or unsubstituted nitrogen-containing heteroaryl with 3 to 12 carbon atoms, and the nitrogen-containing heteroaryl at least contains two N atoms;

$Ar_1$ is selected from hydrogen, substituted or unsubstituted aryl with 6 to 20 carbon atoms, and substituted or unsubstituted heteroaryl with 5 to 20 carbon atoms;

$Ar_2$ is selected from substituted or unsubstituted aryl with 6 to 20 carbon atoms, and substituted or unsubstituted heteroaryl with 5 to 20 carbon atoms;

$R_1$, $R_2$, $R_3$, $R_4$ and $R_5$ are the same or different, and are each independently selected from deuterium, fluorine, cyano, alkyl with 1 to 5 carbon atoms, aryl with 6 to 12 carbon atoms;

$n_1$ represents the number of $R_1$ and is selected from 0, 1, 2, 3 or 4, when $n_1$ is greater than 1, any two $R_1$ are the same or different, and alternatively, two adjacent $R_1$ form a ring;

$n_2$ represents the number of $R_2$ and is selected from 0, 1 or 2, when $n_2$ is greater than 1, any two $R_2$ are the same or different, and alternatively, two adjacent $R_2$ form a ring;

$n_3$ represents the number of $R_3$ and is selected from 0, 1, 2, 3 or 4, when $n_3$ is greater than 1, any two $R_3$ are the same or different, and alternatively, two adjacent $R_3$ form a ring;

$n_4$ represents the number of $R_4$ and is selected from 0;

$n_5$ represents the number of $R_5$ and is selected from 0; and substituents in the $Ar_1$ and $Ar_2$ are each independently selected from deuterium, a halogen group, cyano, heteroaryl with 5 to 12 carbon atoms, aryl with 6 to 12 carbon atoms, and alkyl with 1 to 5 carbon atoms; and substituents in the Ar are selected from deuterium, a halogen group, cyano, deuterated alkyl with 1 to 5 carbon atoms, aryl with 6 to 12 carbon atoms, and alkyl with 1 to 5 carbon atoms.

2. The organic compound according to claim 1, wherein substituent in the Ar is selected from deuterium, fluorine, cyano, methyl, ethyl, n-propyl, isopropyl, tert-butyl, trideuteromethyl, phenyl, naphthyl and biphenyl.

3. The organic compound according to claim 1, wherein Het is selected from triazinylene, pyrimidylene, quinoxalinylene, quinazolinylene, or the group consisting of the following groups:

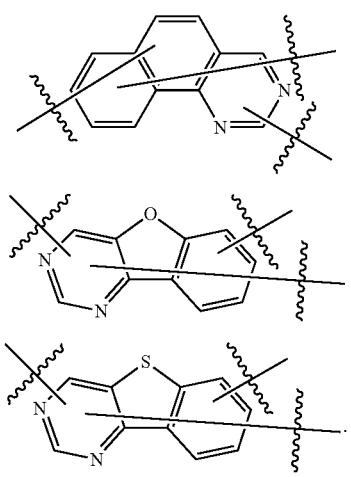

4. The organic compound according to claim 1, wherein Ar$_1$ is and selected from hydrogen, substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted carbazolyl, substituted or unsubstituted dibenzofuranyl, and substituted or unsubstituted dibenzothienyl; and Ar$_2$ is selected from substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted carbazolyl, substituted or unsubstituted dibenzofuranyl, and substituted or unsubstituted dibenzothienyl.

5. The organic compound according to claim 4, wherein substituents in the Ar$_1$ and Ar$_2$ are respectively and independently selected from deuterium, fluorine, cyano, methyl, ethyl, n-propyl, isopropyl, tert-butyl, phenyl, naphthyl, biphenyl and carbazolyl.

6. The organic compound according to claim 1, wherein

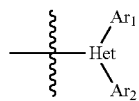

is selected from the group consisting of the following groups:

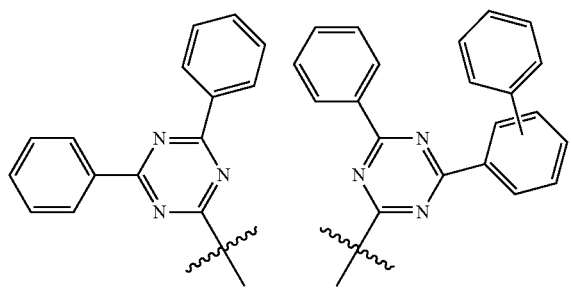

-continued

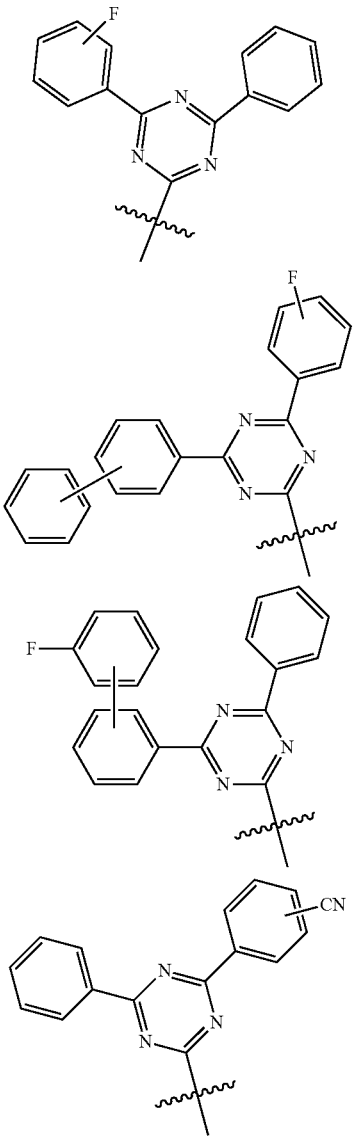

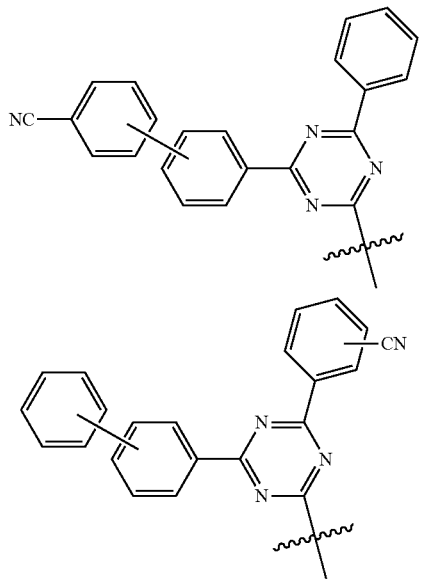

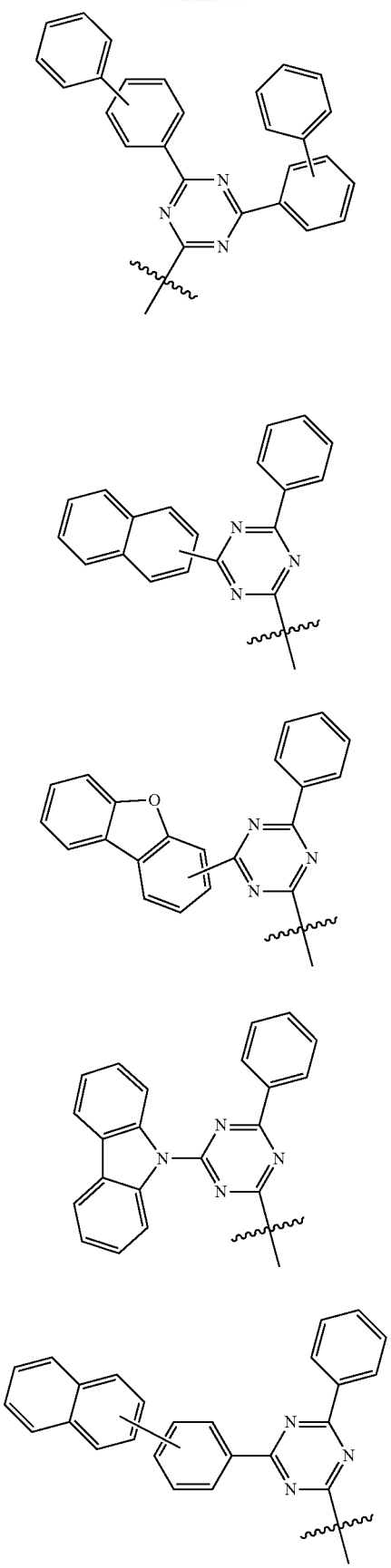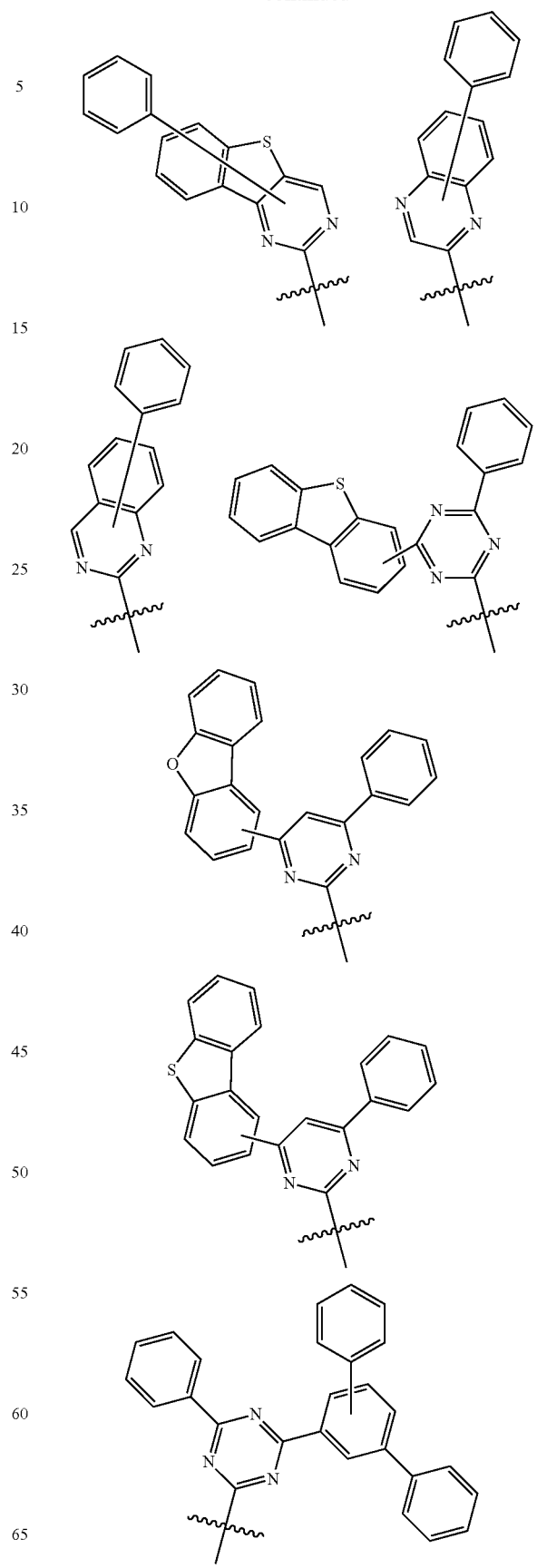

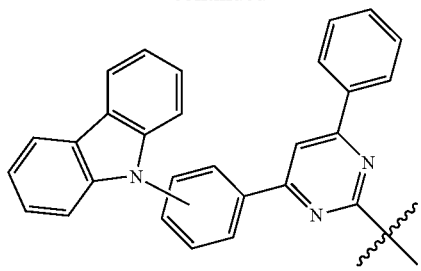
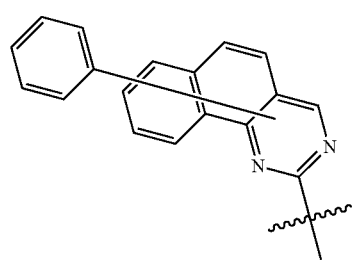
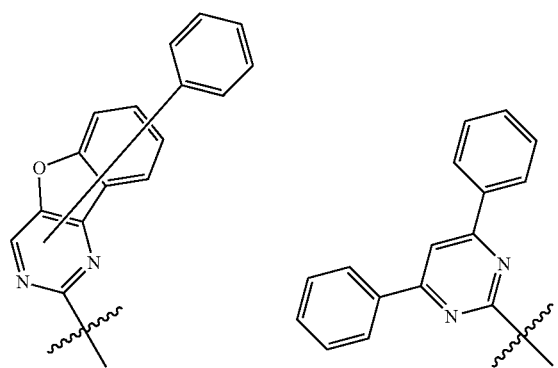
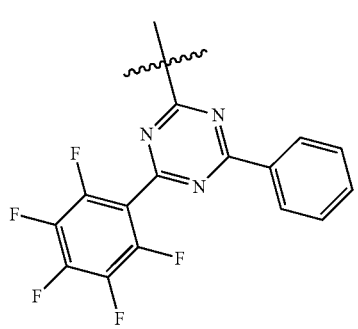
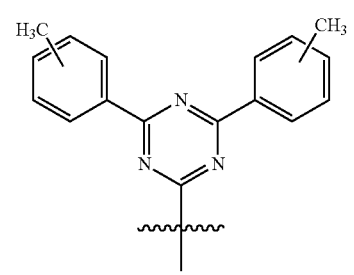
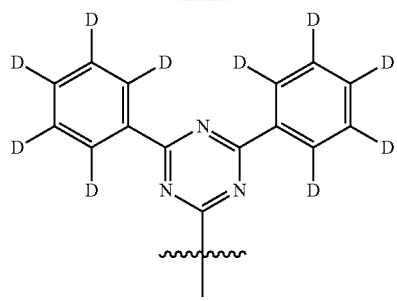
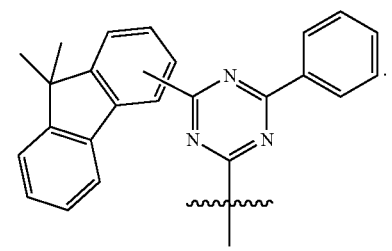
7. The organic compound according to claim 1, wherein two adjacent $R_1$ form a benzene ring, or two adjacent $R_2$ form a benzene ring, or two adjacent $R_3$ form a benzene ring.
8. The organic compound according to claim 1, wherein the organic compound is selected from the group consisting of the following compounds:
A1
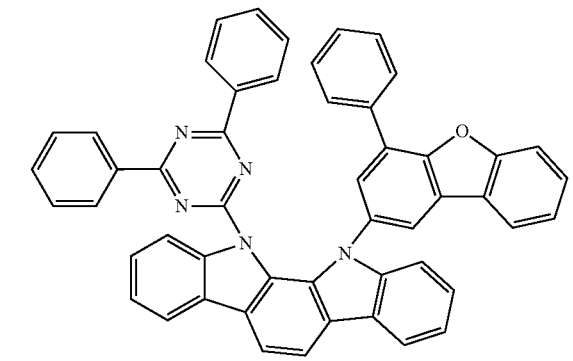
A2
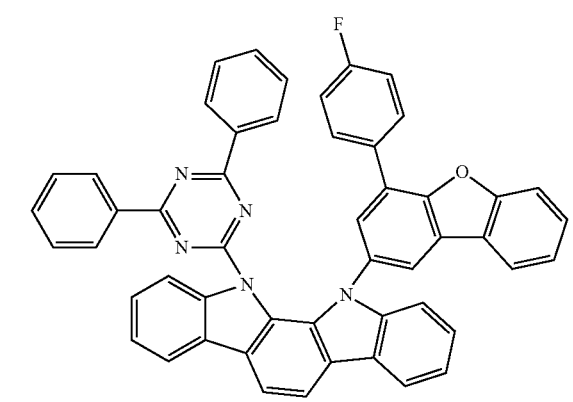

-continued
A3
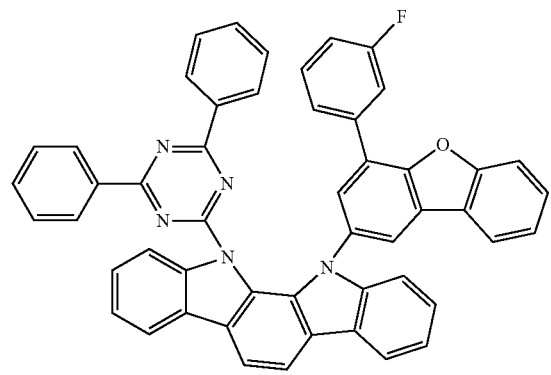
A4
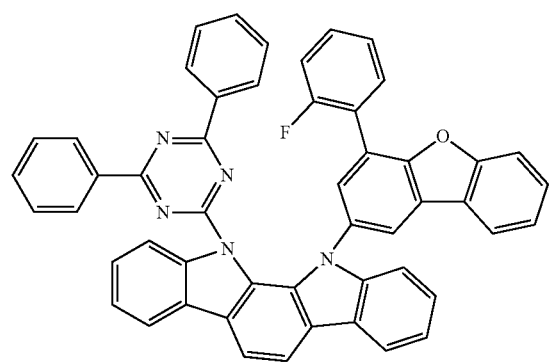
A5
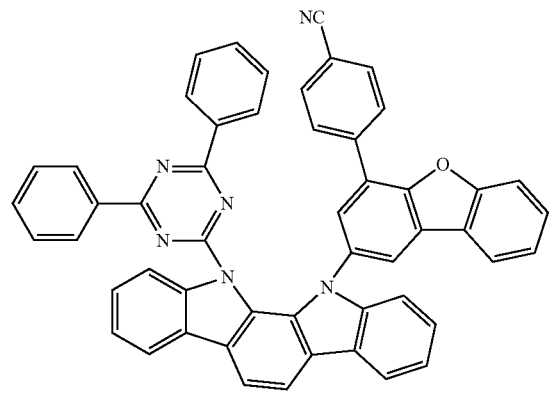
A6
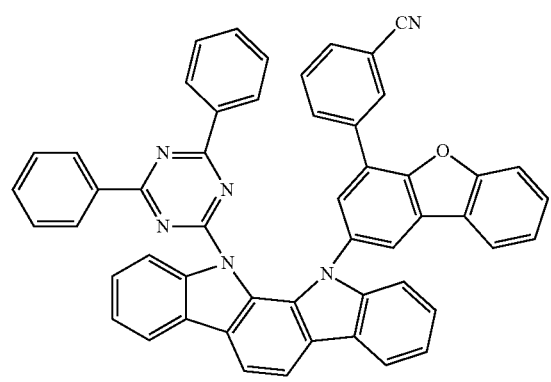
-continued
A7
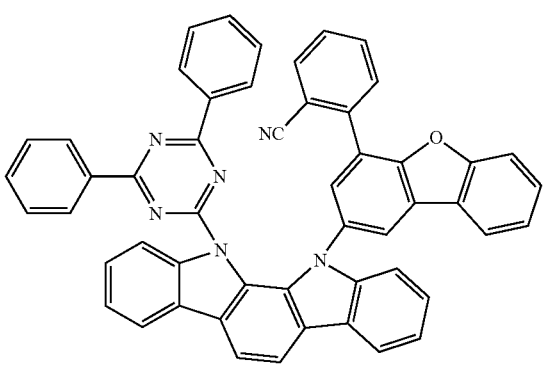
A8
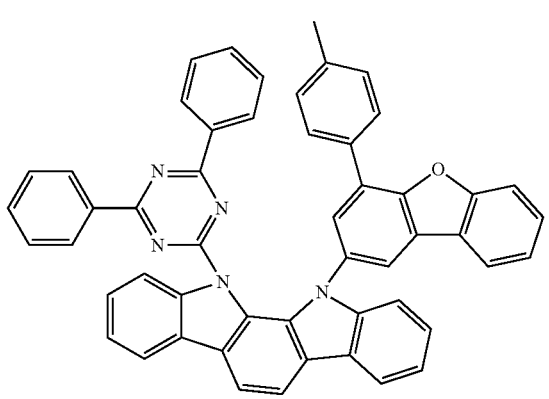
A9
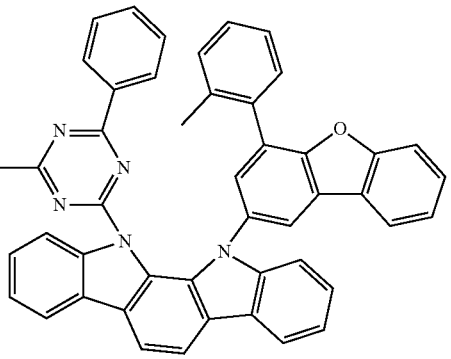
A10
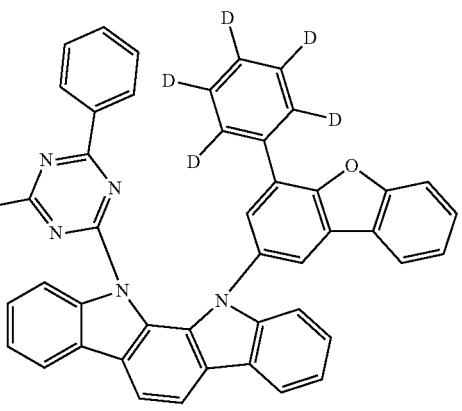

A11
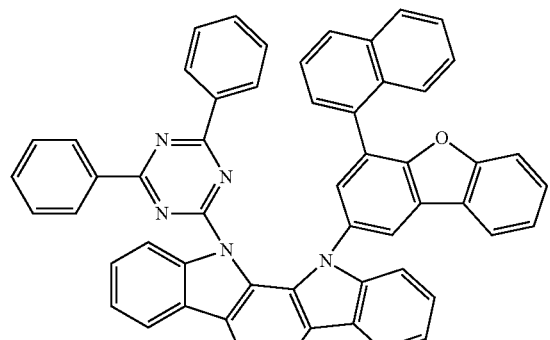
A12
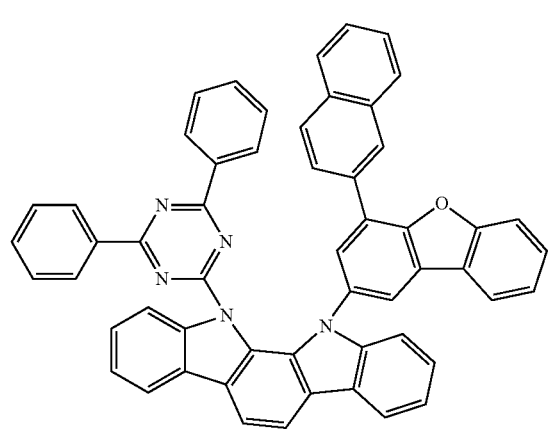
A13
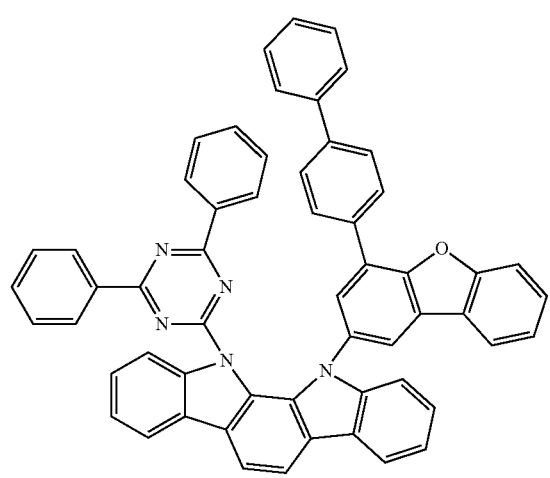
A14
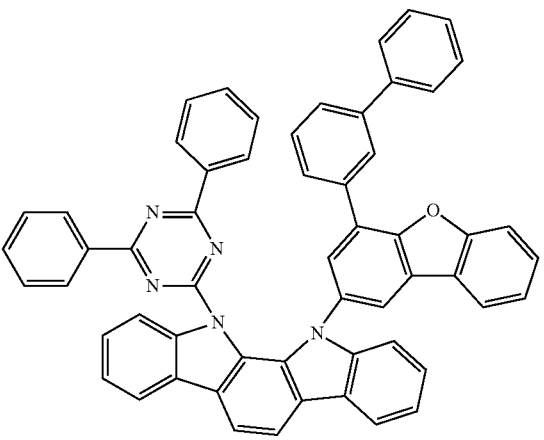
A15
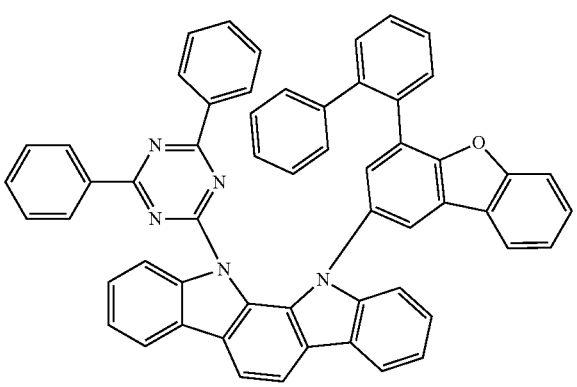
A16
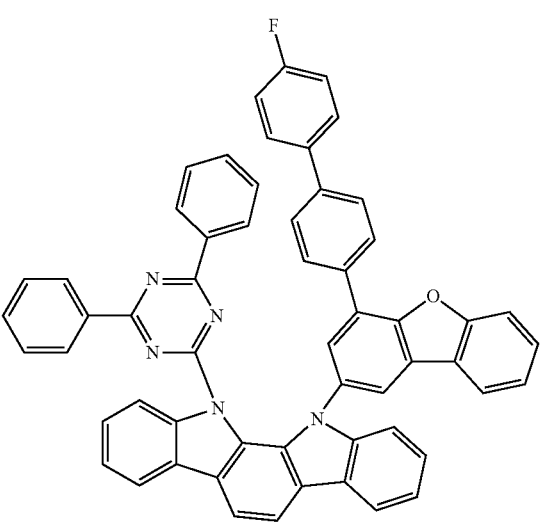

-continued
A17
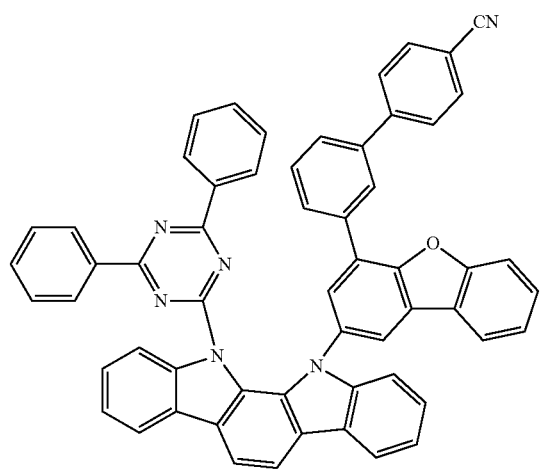
A21
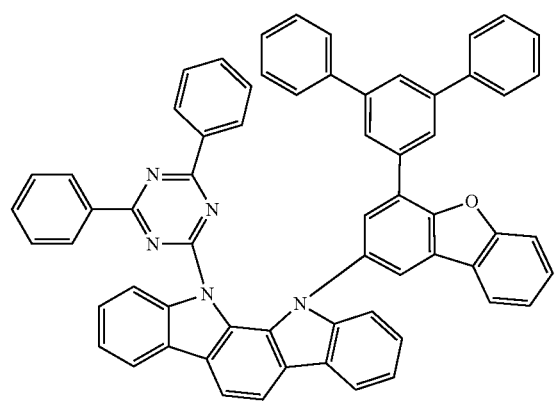
A22
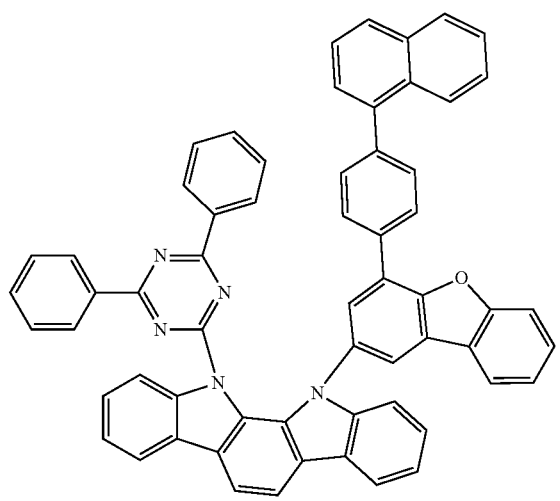
-continued
A23
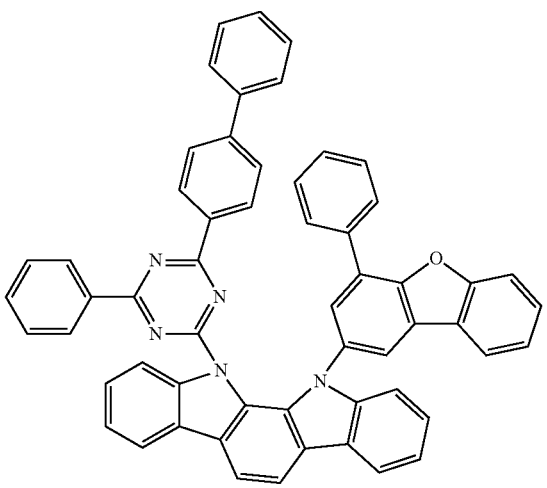
A24
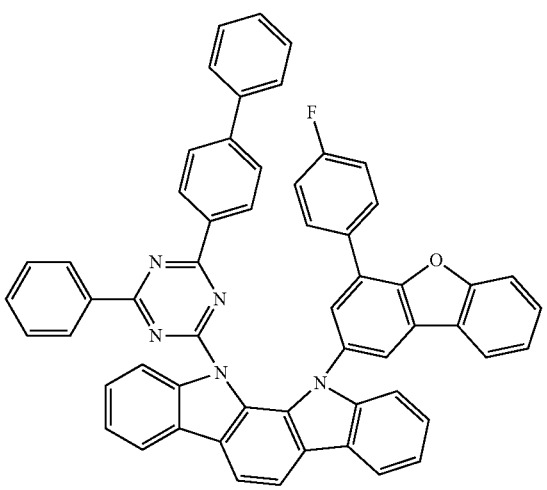
A25
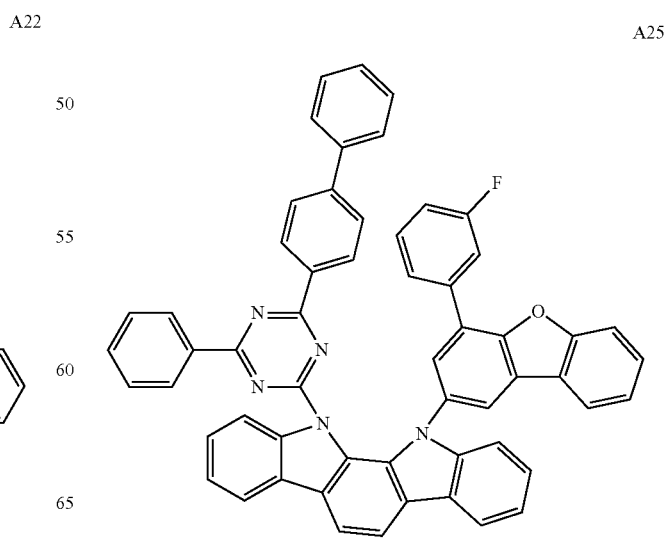

A26
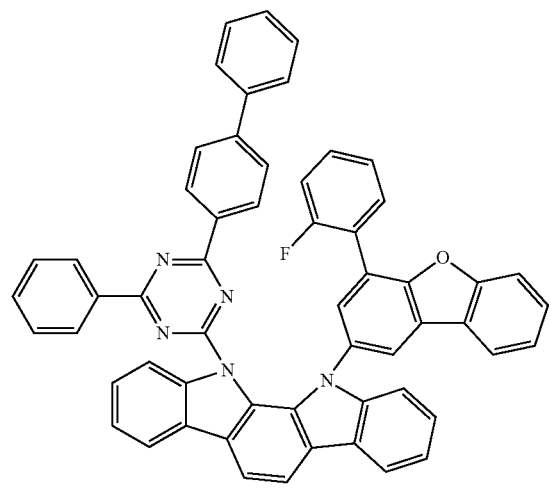
A29
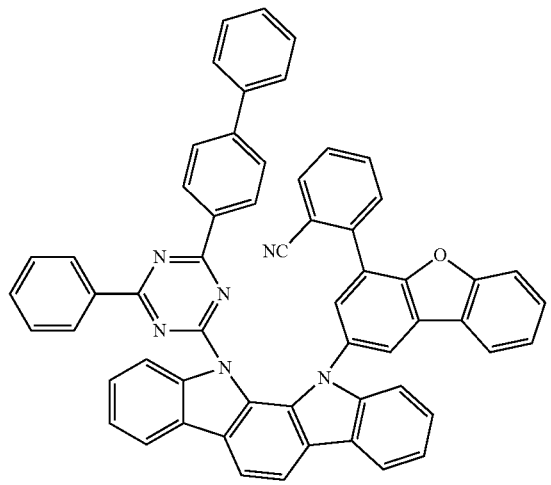
A27
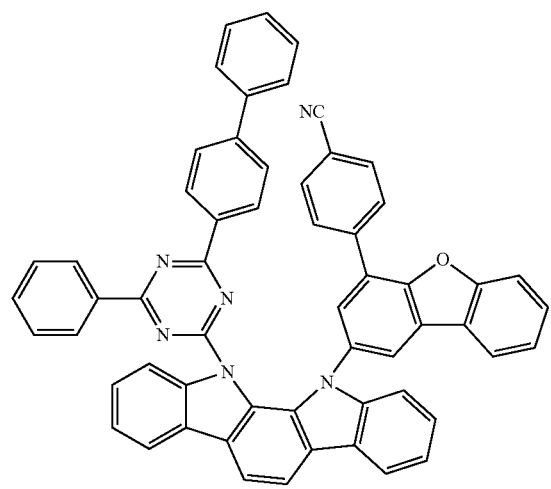
A30
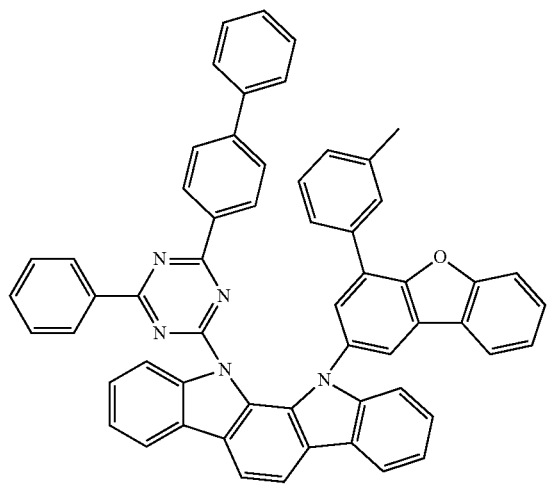
A28
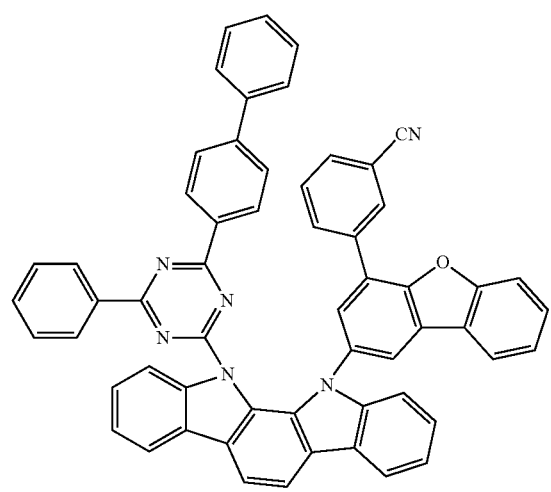
A31
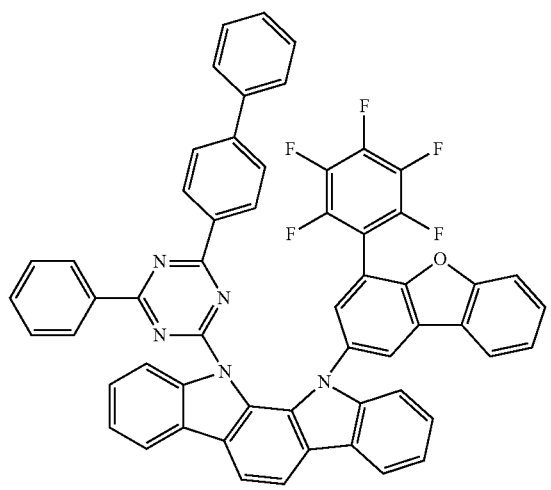

A32
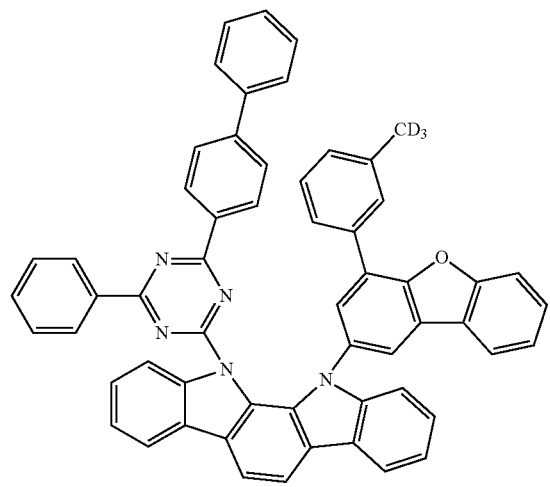
A35
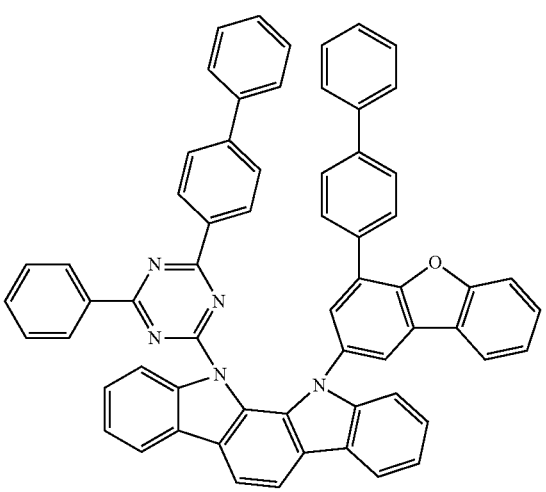
A33
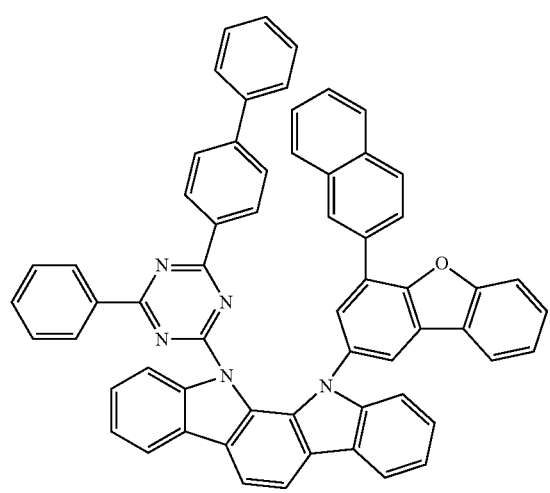
A36
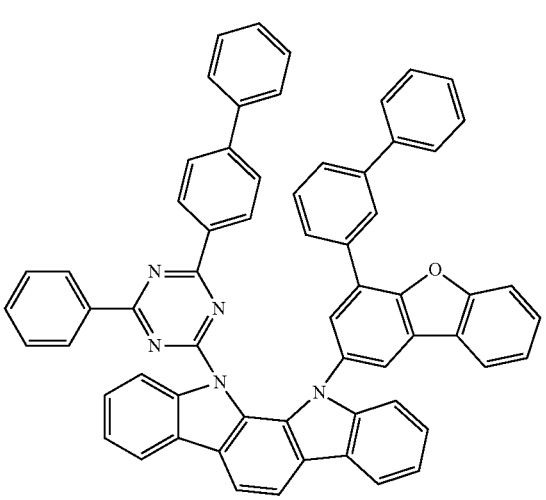
A34
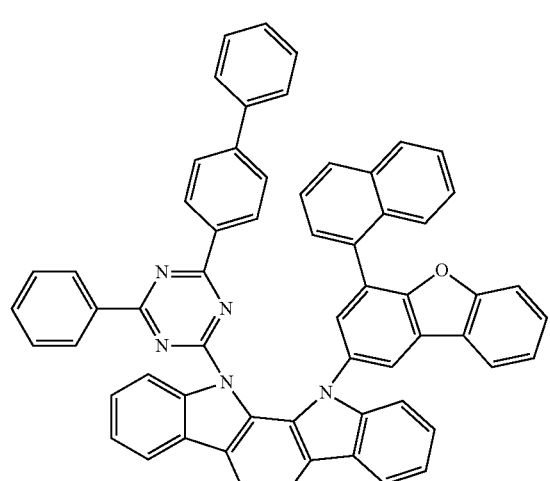
A39
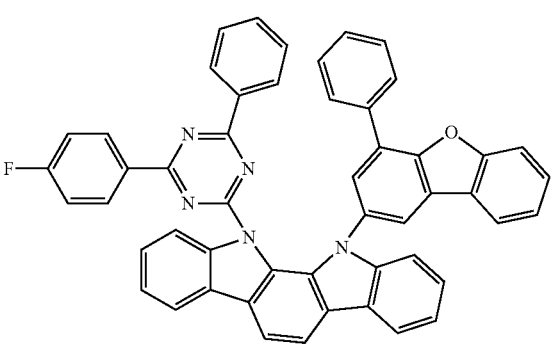

A40
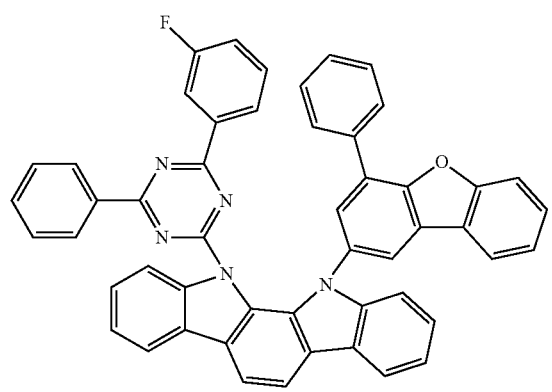
A41
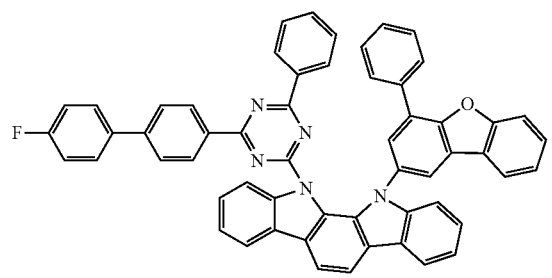
A42
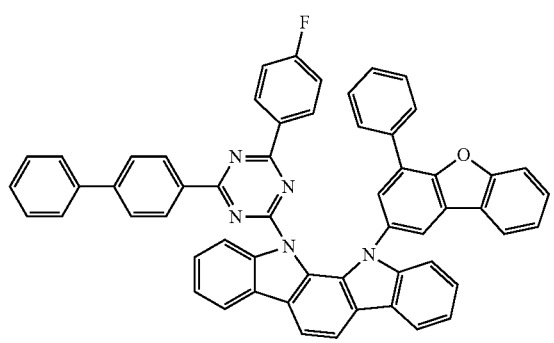
A43
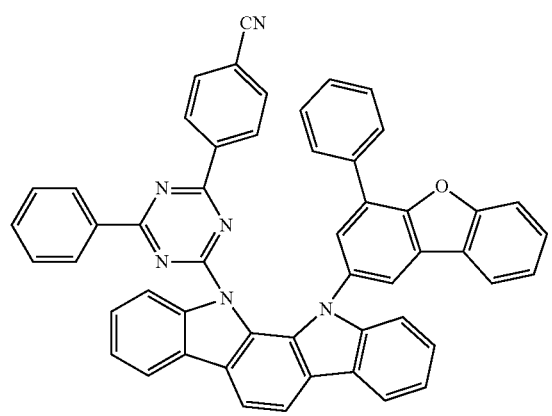
A44
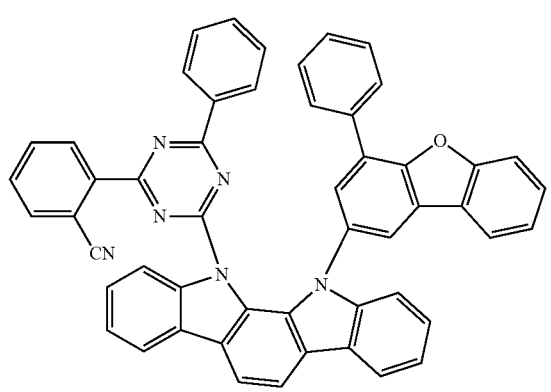
A45
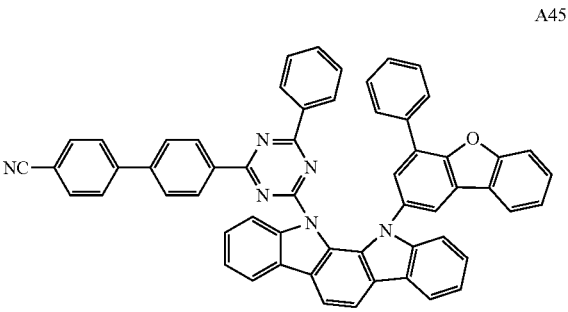
A46
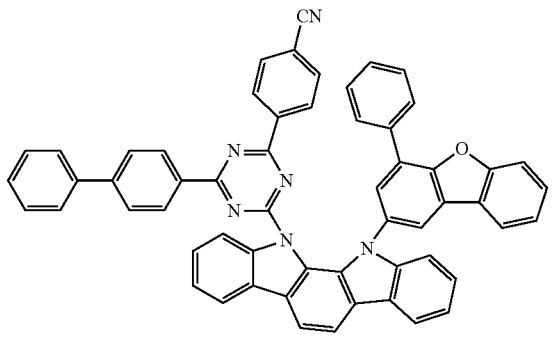
A47
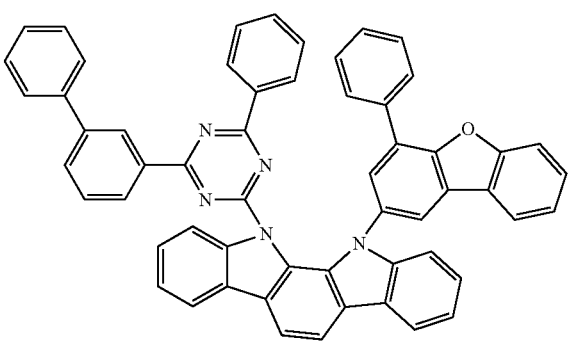

A48
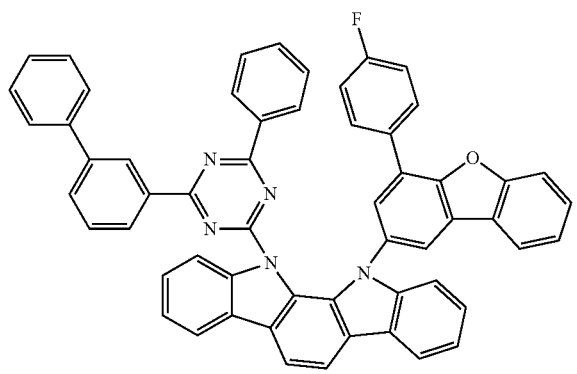
A49
A50
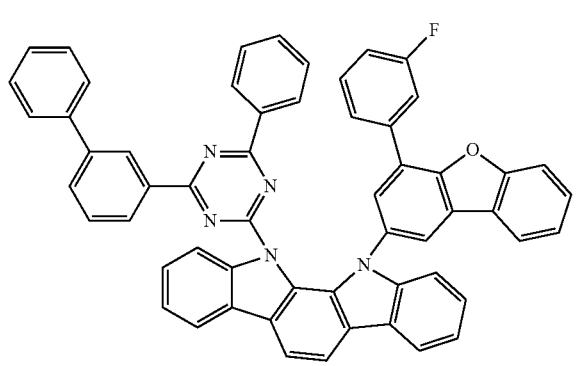
A51
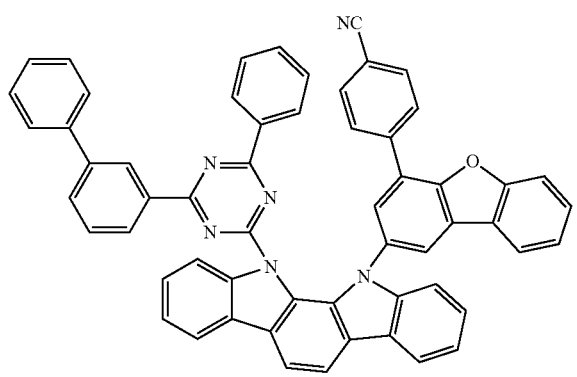
A52
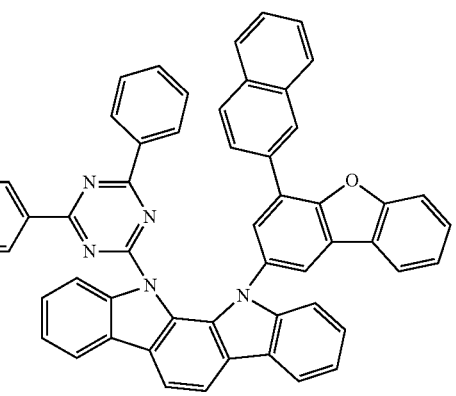
A55
A56
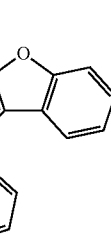
A57
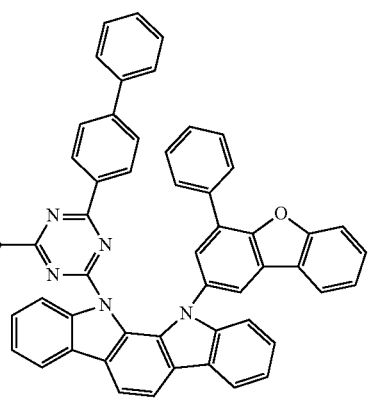

A58
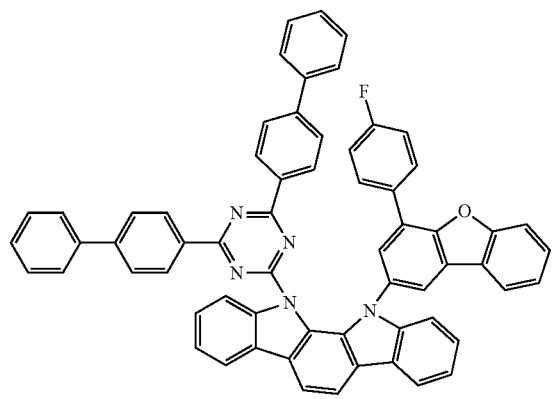
A59
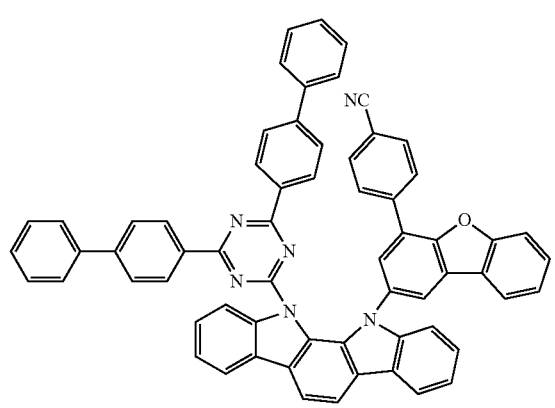
A60
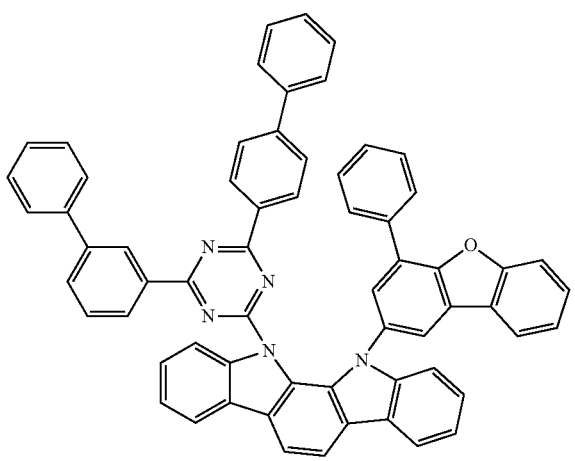
A61
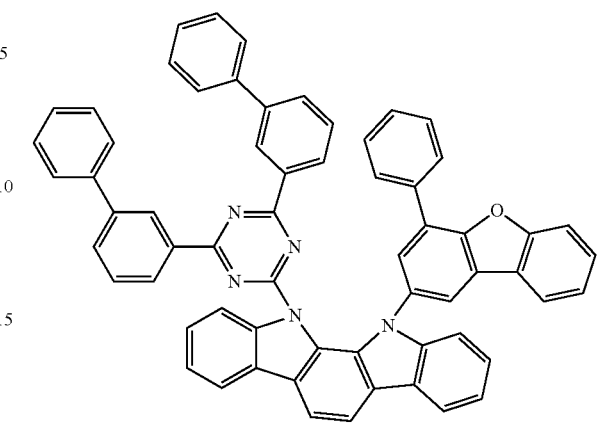
A62
A63
A64
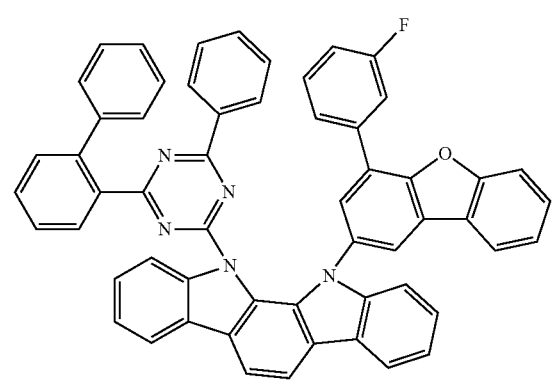

A65
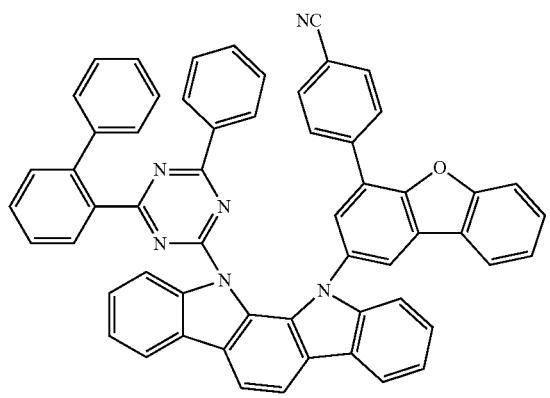
A66
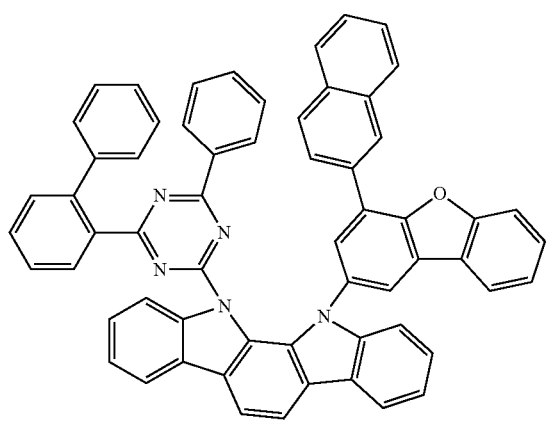
A67
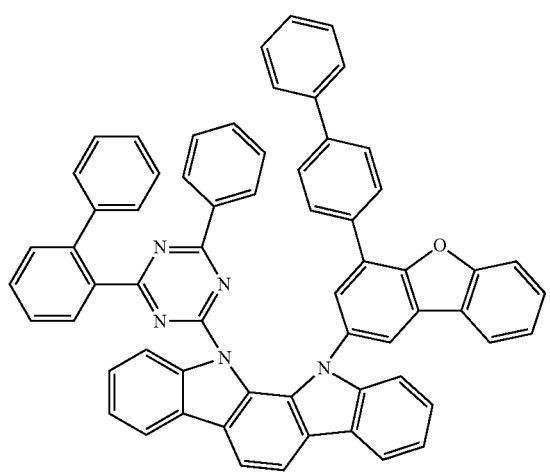
A68
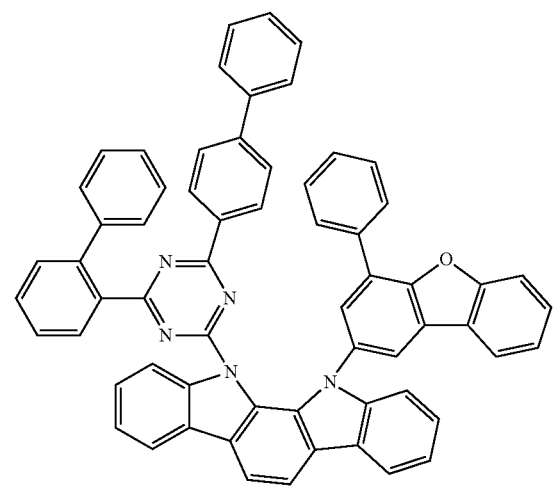
A69
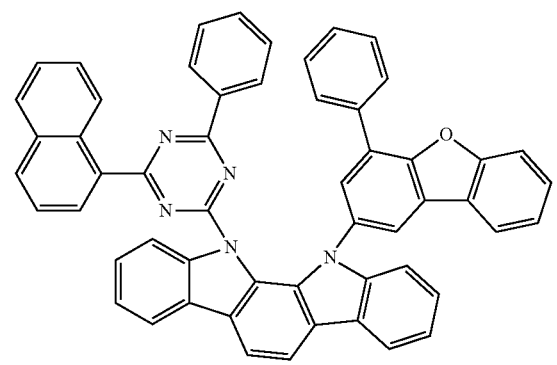
A70
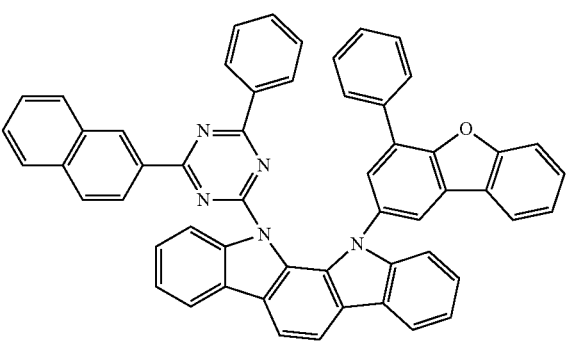
A71
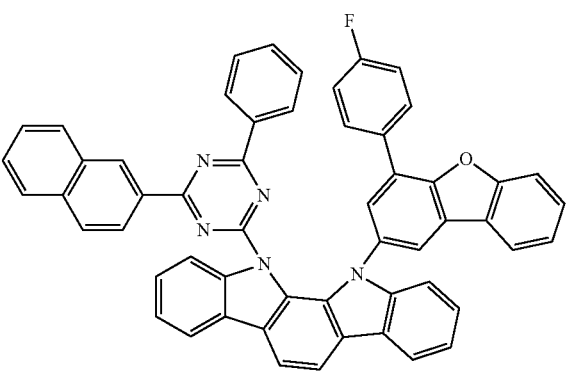

A72
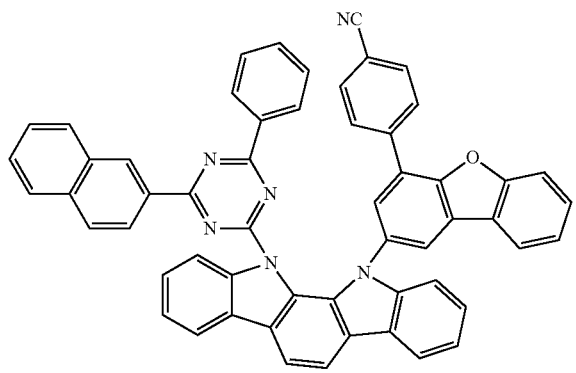
A77
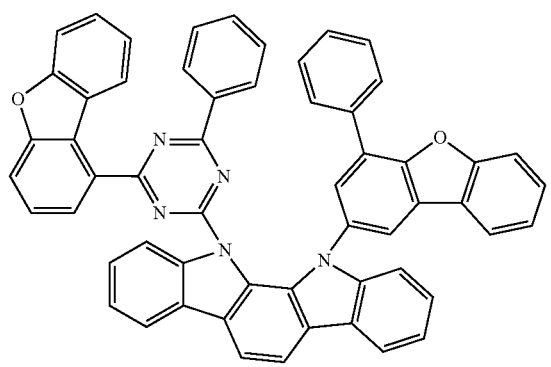
A74
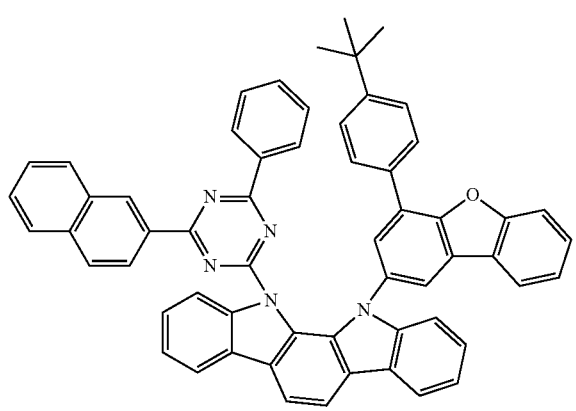
A78
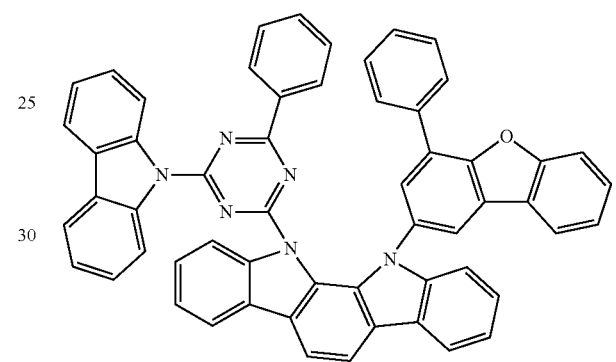
A75
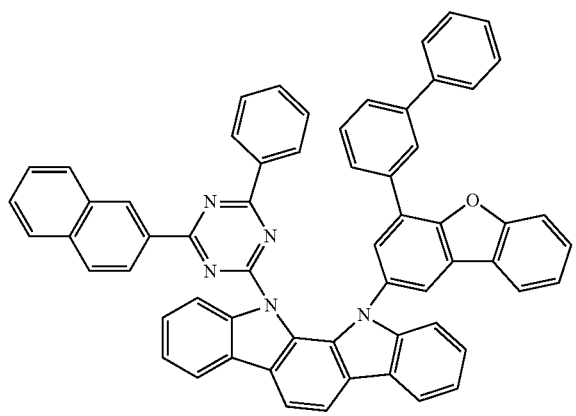
A79
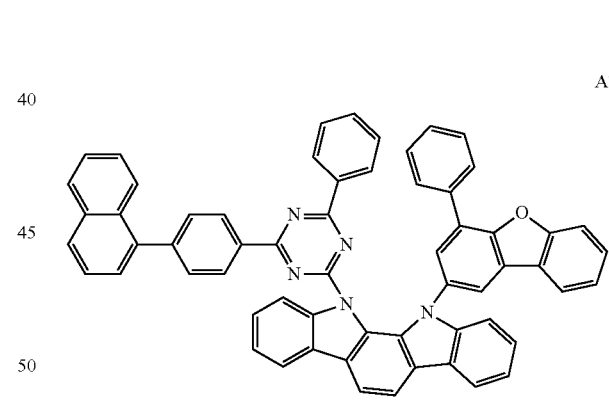
A76
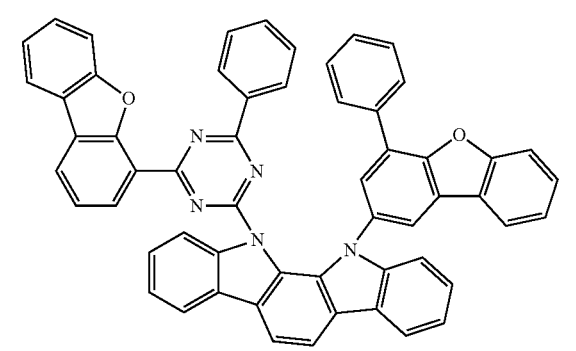
A80
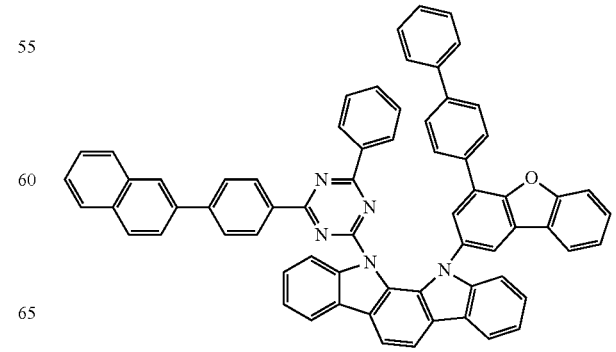

211
-continued
A81
A82
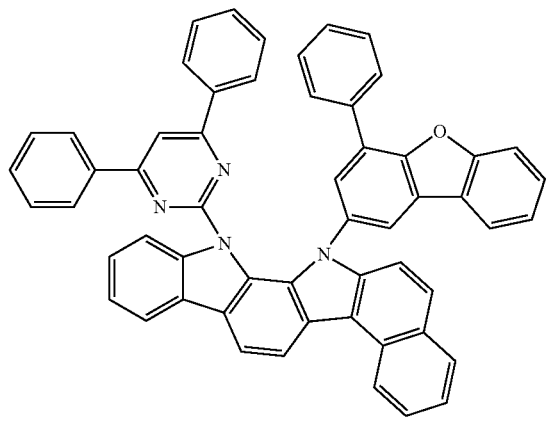
212
-continued
A84
A85
A86
A83
A87
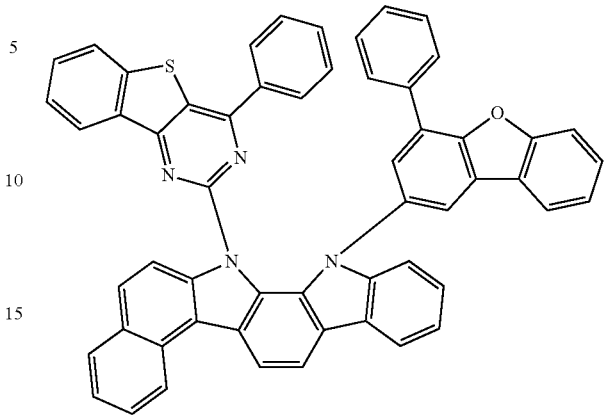
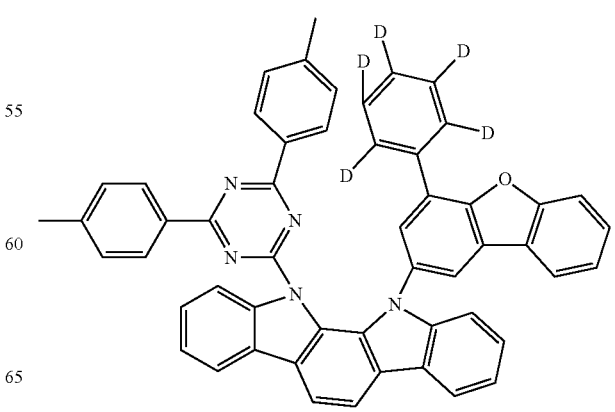

A88
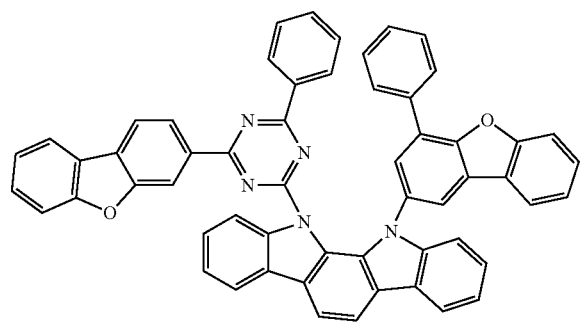
A89
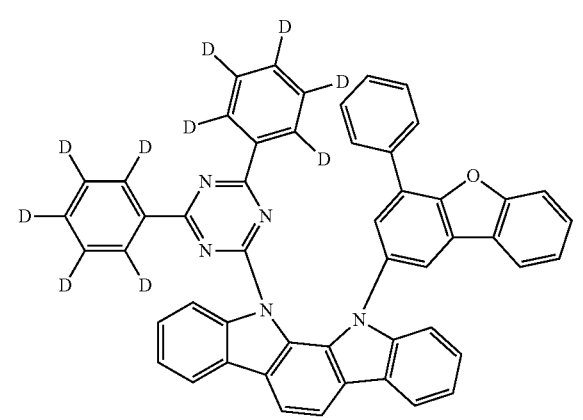
A90
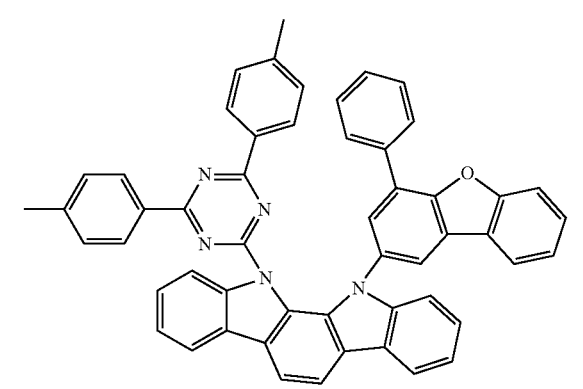
A91
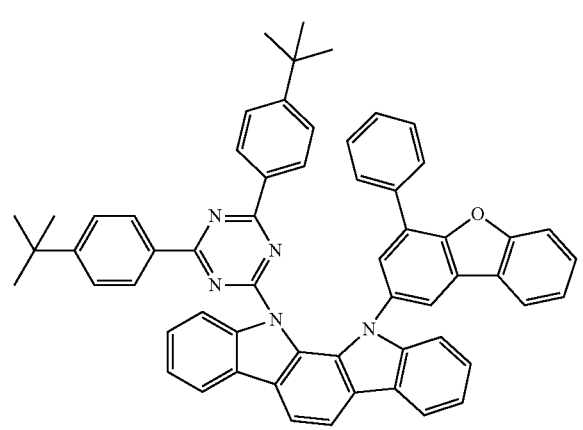
A92
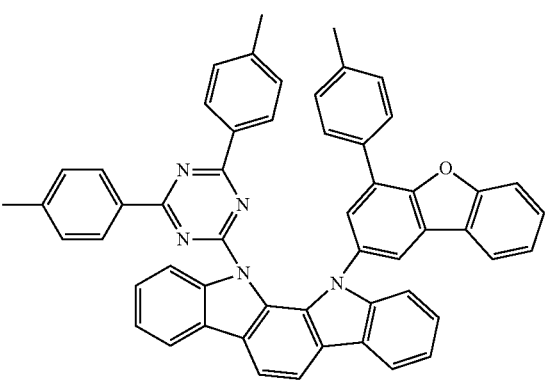
A93
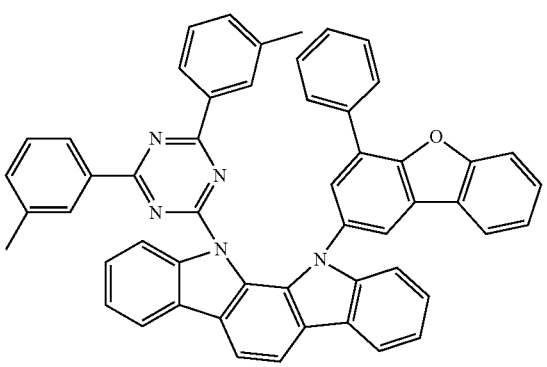
A94
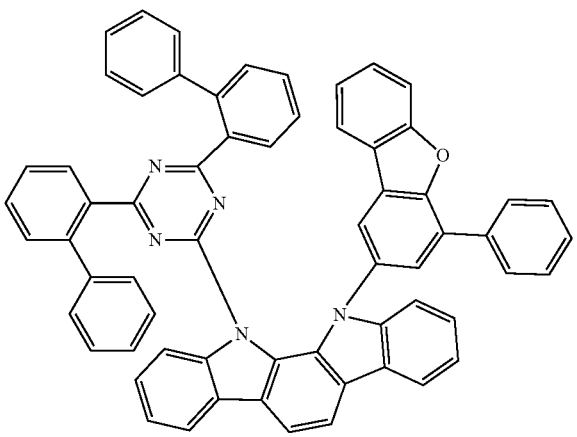

A95
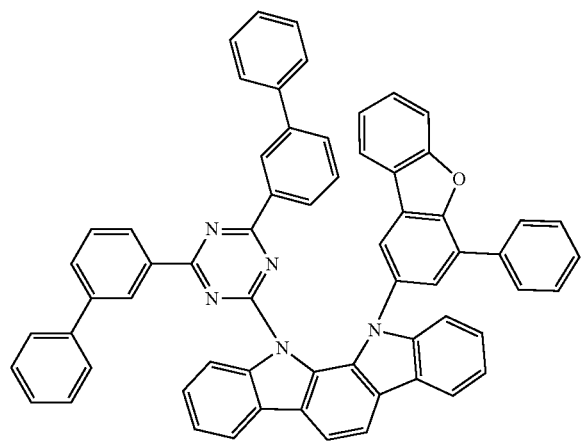
A96
A97
A98
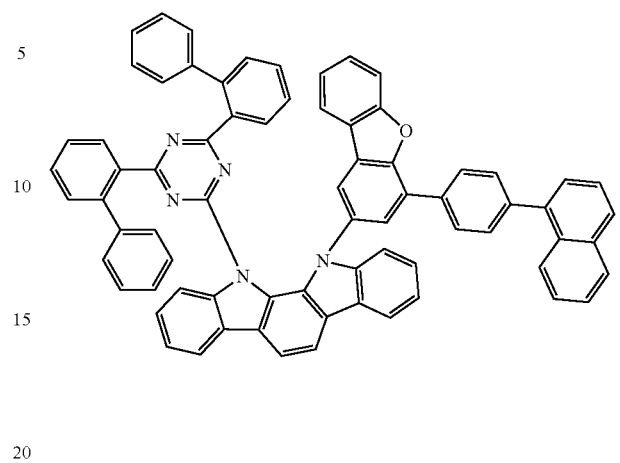
A99
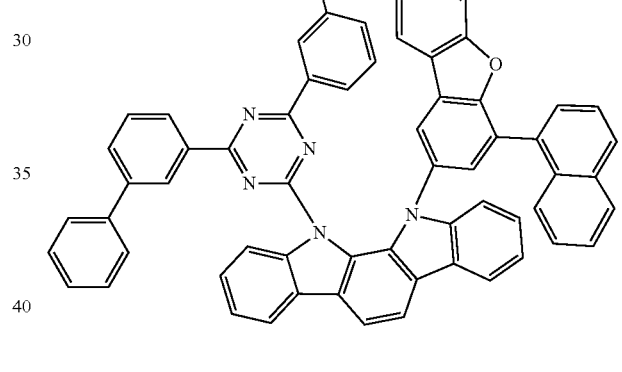
A100
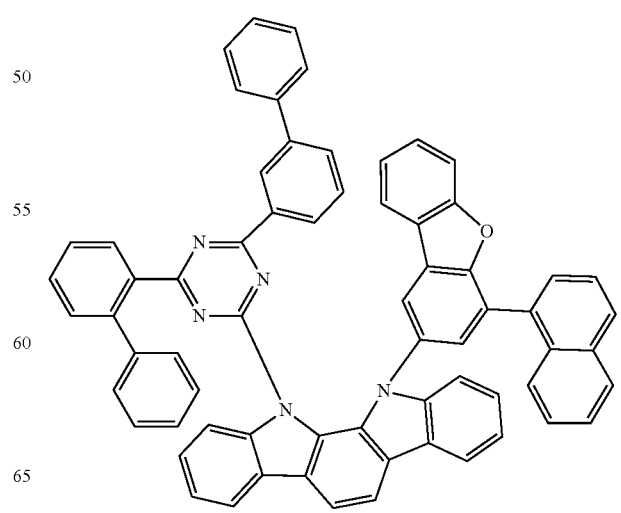

-continued
A101
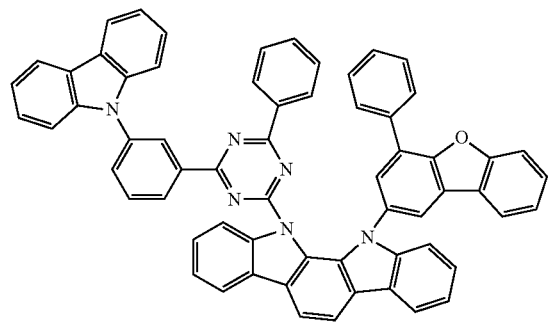
A102
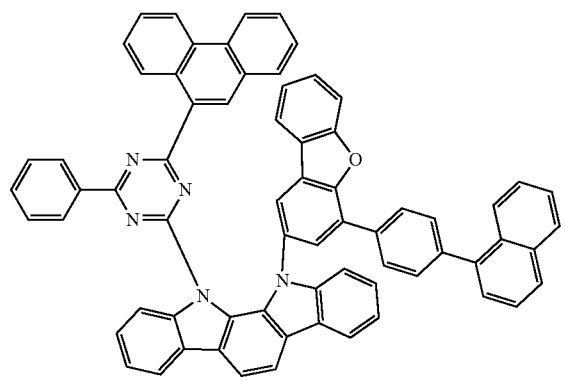
A103
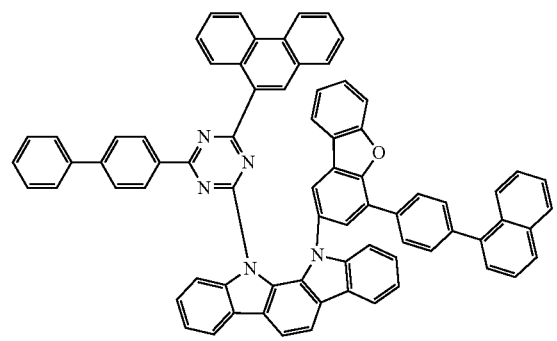
A104
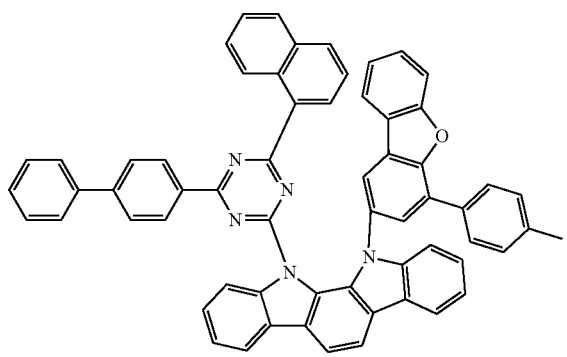
-continued
A105
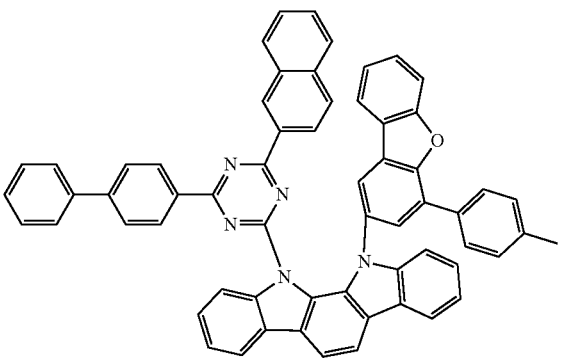
A106
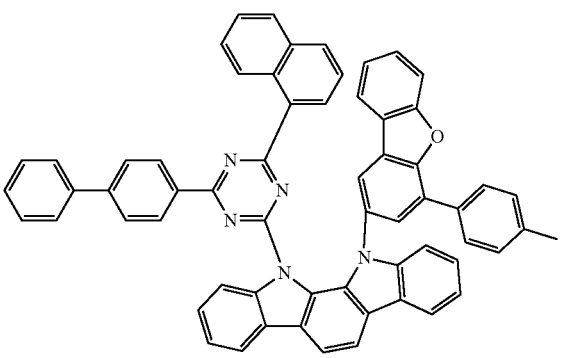
A107
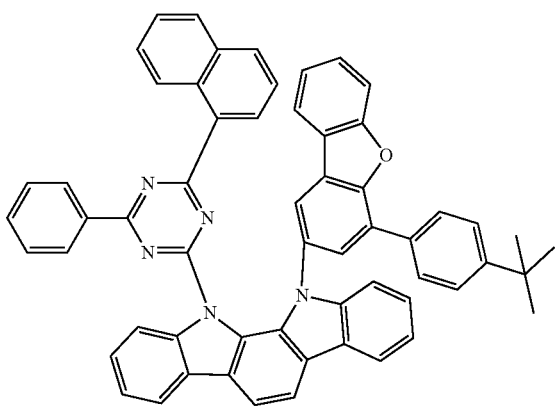
A108
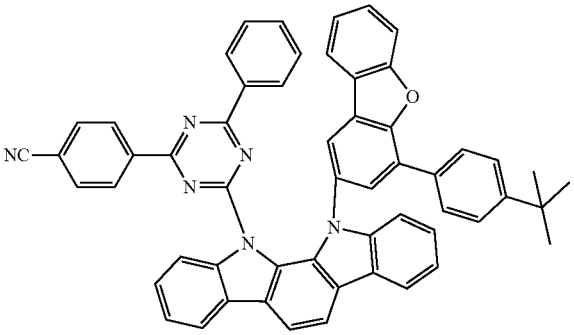

A109
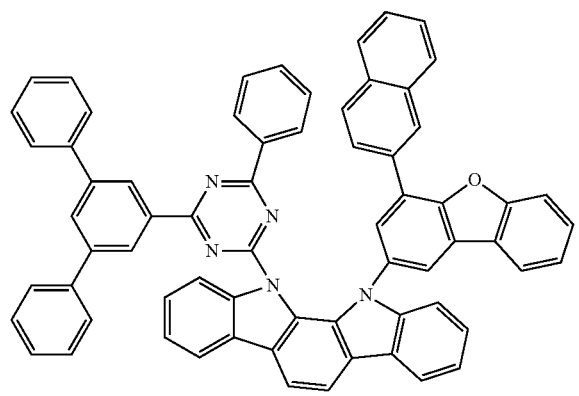
A110
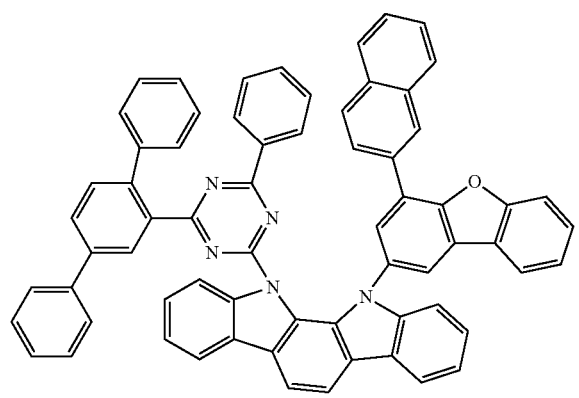
A111
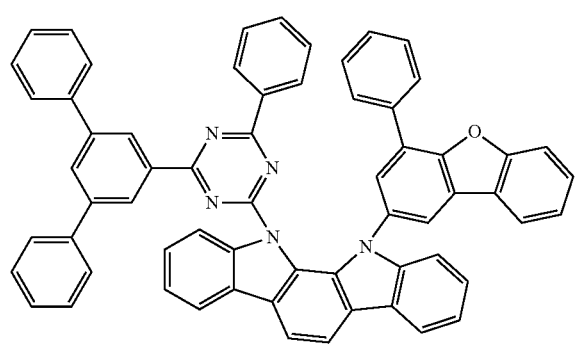
A112
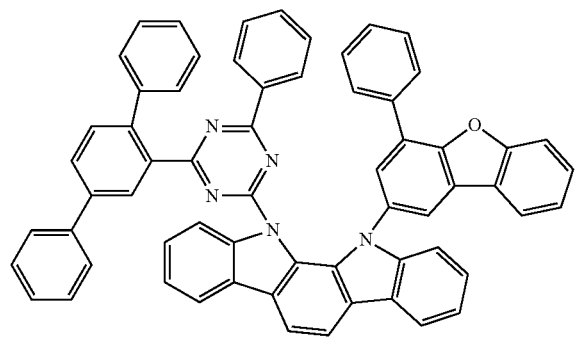
F1
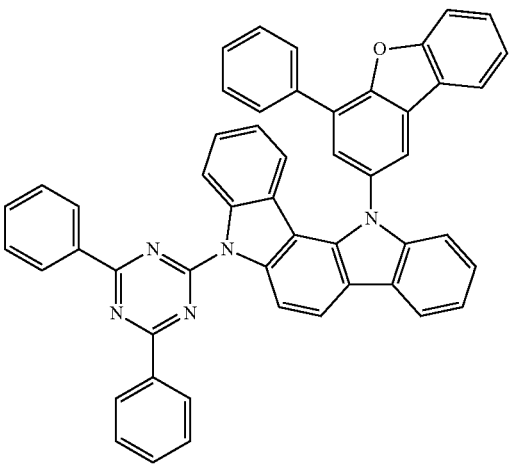
F2
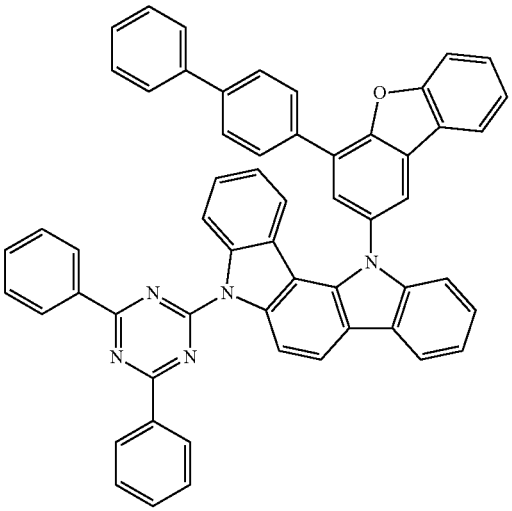
F3
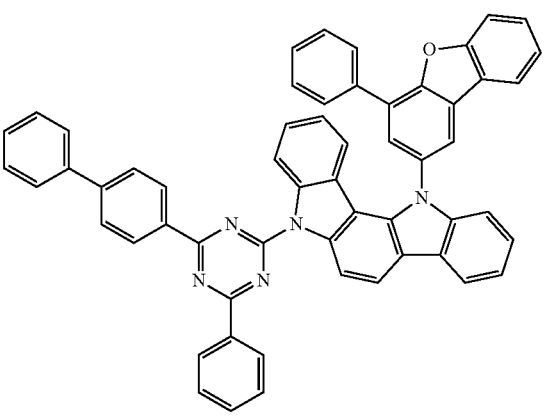

-continued
F4
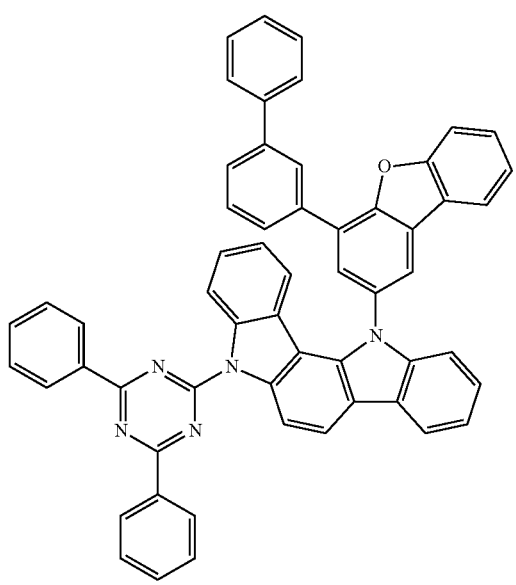
F5
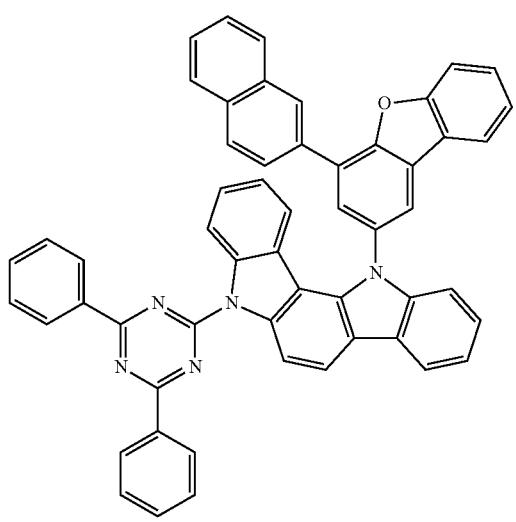
F6
-continued
F7
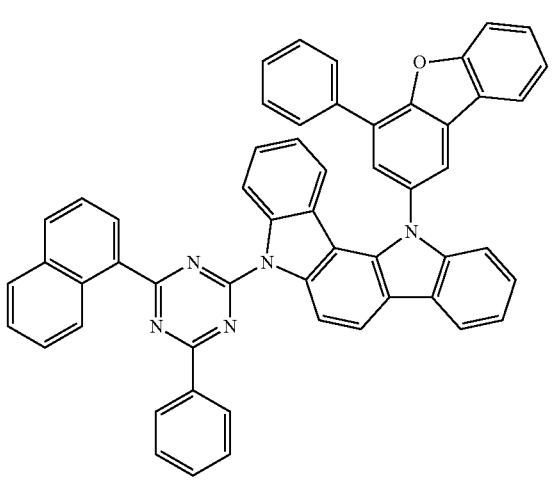
F8
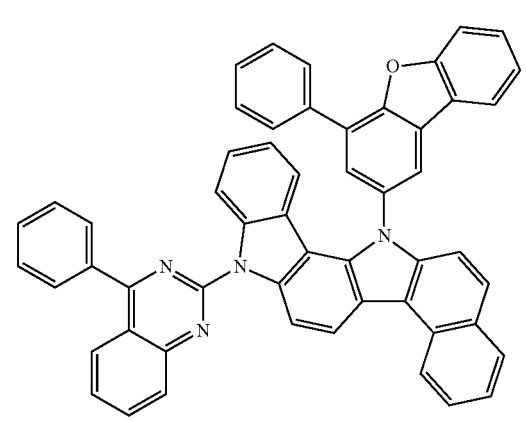
F9

F10

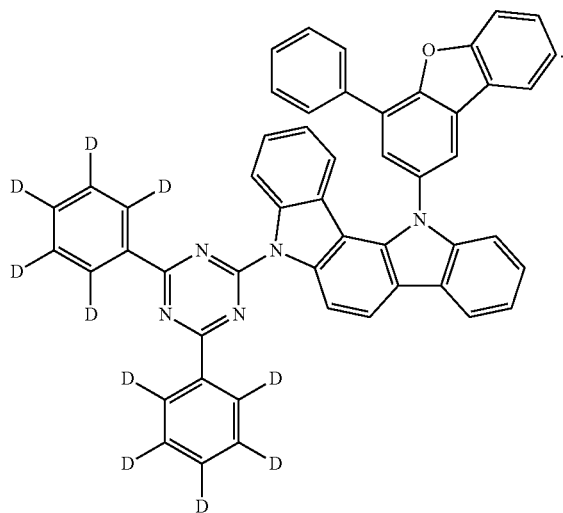

9. An electronic component, comprising an anode and a cathode which are oppositely arranged, and a functional layer arranged between the anode and the cathode; wherein
the functional layer contains the organic compound according to claim lany one of claims 1.

10. The electronic component according to claim 9, wherein the electronic component is an organic electroluminescent device.

11. The electronic component according to claim 10, the organic electroluminescent device is a green light device or a red light device.

12. An electronic device, comprising the electronic component according to claim 9.

13. The electronic component according to claim 9, the functional layer comprises an organic luminescent layer, and the organic luminescent layer contains the organic compound.

14. The organic compound according to claim 1, wherein

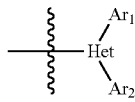

is selected from the group:

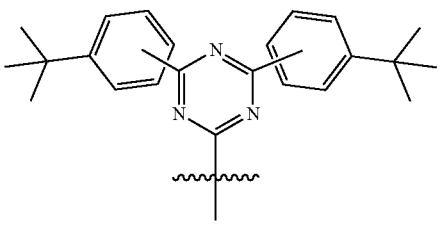

* * * * *

UNITED STATES PATENT AND TRADEMARK OFFICE
CERTIFICATE OF CORRECTION

Page 1 of 2

PATENT NO. : 11,723,271 B2
APPLICATION NO. : 18/011941
DATED : August 8, 2023
INVENTOR(S) : Tiantian Ma, Lei Yang and Linlin Hu It is certified that error appears in the above-identified patent and that said Letters Patent is hereby corrected as shown below:

In the Specification

Column 23, Lines 5-10 " 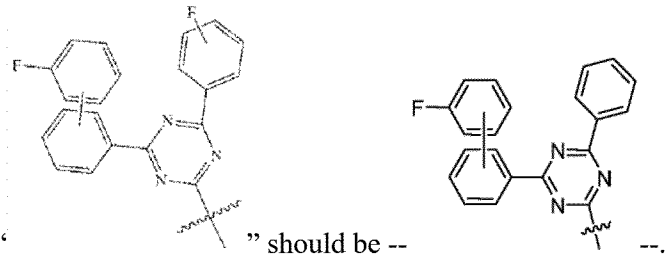 " should be --   --.

Column 26, Lines 30-40 " 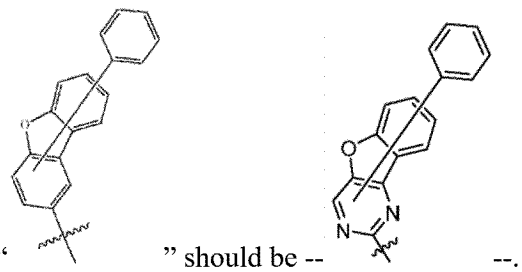 " should be --   --.

Column 58, Lines 30-45 " 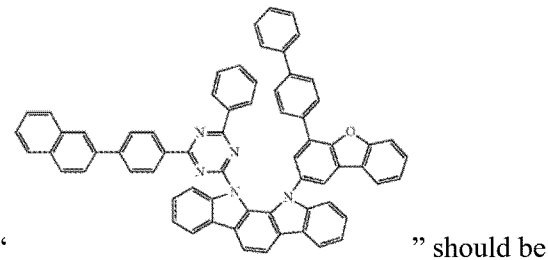 " should be

Signed and Sealed this
Thirty-first Day of October, 2023

Katherine Kelly Vidal
Katherine Kelly Vidal
*Director of the United States Patent and Trademark Office*

-- 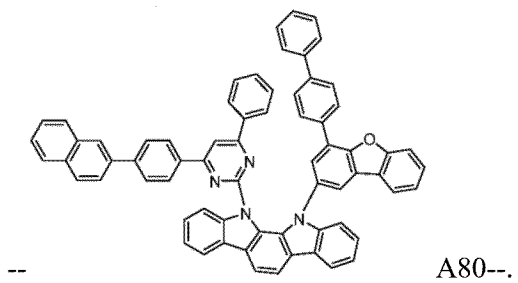 A80--.